US006897227B2

(12) United States Patent
Garst et al.

(10) Patent No.: US 6,897,227 B2
(45) Date of Patent: May 24, 2005

(54) PRODRUGS OF PROTON PUMP INHIBITORS

(75) Inventors: Michael Garst, Newport Beach, CA (US); George Sachs, Encino, CA (US); Jai M. Shin, Chatsworth, CA (US)

(73) Assignees: Winston Pharmaceuticals, Inc., Newport Beach, CA (US); The United States of America as represented by the Department of Veteran Affairs, Washington, DC (US); The Reagents of the University of California, Oakland, CA (US)

( * ) Notice: Subject to any disclaimer, the term of this patent is extended or adjusted under 35 U.S.C. 154(b) by 3 days.

(21) Appl. No.: 10/620,252

(22) Filed: Jul. 15, 2003

(65) Prior Publication Data

US 2004/0102484 A1 May 27, 2004

Related U.S. Application Data

(60) Provisional application No. 60/397,459, filed on Jul. 19, 2002.

(51) Int. Cl.$^7$ .................. A61K 31/4439; C07D 401/12
(52) U.S. Cl. ..................................... 514/341; 546/273.7
(58) Field of Search ........................ 546/273.7; 514/341

(56) References Cited

U.S. PATENT DOCUMENTS

| | | | |
|---|---|---|---|
| 4,045,563 | A | 8/1977 | Berntsson et al. |
| 4,255,431 | A | 3/1981 | Junggren et al. |
| 4,628,098 | A | 12/1986 | Nohara et al. |
| 4,686,230 | A | 8/1987 | Rainer et al. |
| 4,758,597 | A | 7/1988 | Martin et al. |
| 4,965,269 | A | 10/1990 | Brandstrom et al. |
| 5,021,433 | A | 6/1991 | Alminger et al. |
| 5,045,522 | A | 9/1991 | Kidd |
| 5,430,042 | A | 7/1995 | Lindberg et al. |
| 5,693,818 | A | 12/1997 | Von Unge |
| 5,708,017 | A | 1/1998 | Dave et al. |
| 6,093,734 | A | 7/2000 | Garst et al. |
| 6,599,167 | B2 | 7/2003 | Waltz |

FOREIGN PATENT DOCUMENTS

| | | |
|---|---|---|
| WO | WO 00/09498 | 2/2000 |
| WO | WO 02/00166 | 1/2002 |
| WO | WO 02/30920 | 4/2002 |

OTHER PUBLICATIONS

Bundgaard, H., Design of Prodrugs, 1985, chapter 1, Elsevier Science Publishers B.V., not available.
Bundgaard, et al., Int. J. of Pharmaceutics, 1984, 45–56, 22, Elsevier.
Bundgaard, et al., Int. J. of Pharmaceutics, 1986, 19–28, 29, Elsevier.
Bundgaard, et al., J. Med. Chem, 1989, 2503–2507, 32.
Bundgaard, et al., Chem. Abstracts, 1980, vol. 93, abst. # 137935y.
Bundgaard, et al., Chem. Abstracts, 1981, vol. 95, abst. # 138493f.
Bundgaard, et al. Chem. Abstracts, 1981, vol. 95, abst. # 138592n.
Alminger, et al., Chem. Abstracts, 1989, vol. 110, abst. # 57664p.
Buur, et al., Chem. Abstracts, 1991, vol. 115, abst. # 64029s.
Hansen, et al., Chem. Abstracts,1991, vol. 115, abst. # 189582y.
Bundgaard, et al., Chem. Abstract, 1992, vol. 117, abst. # 14347q.
Jensen, et al., Chem. Abstract, 1992, vol. 117, abst. # 55790x.
Thomsen et al., Chem. Abstract, 1995, vol. 123, abst. # 17593b.
Sih, et al., Journal of Medicinal Chemistry, 1991, 1049–1062, 34.

*Primary Examiner*—Patricia L. Morris
(74) *Attorney, Agent, or Firm*—Gabor L. Szekeres

(57) ABSTRACT

Prodrugs of proton pump inhibitors of Formulas 1 through 4,

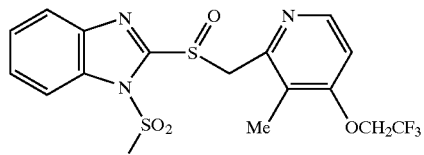

Formula 1

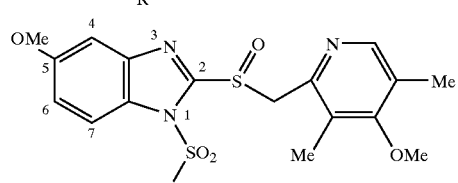

Formula 2

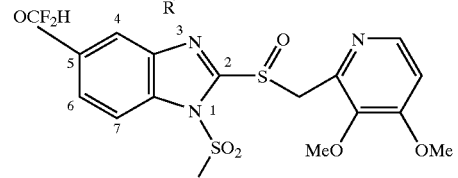

Formula 3

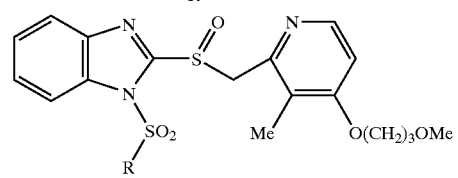

Formula 4 where the symbols are as defined in the specification, and the R group includes at least one acidic group or its pharmaceutically acceptable salt, have improved aqueous solubility and bioavailability.

34 Claims, No Drawings

PRODRUGS OF PROTON PUMP INHIBITORS

This application claims the benefit of 60/397,459 filed Jul. 19, 2002.

BACKGROUND OF THE INVENTION

1. Field of the Invention

The present invention is directed to improved prodrugs of proton pump inhibitors, which are useful as anti-ulcer agents. More particularly, the present invention is directed to prodrugs that slowly hydrolyze to provide benzimidazole-type proton pump inhibitors which inhibit exogenously or endogenously gastric acid secretion, have improved solubility in physiological fluids and can be used in the prevention and treatment of gastrointestinal inflammatory diseases in mammals, including humans.

2. Brief Description of the Prior Art

Benzimidazole derivatives intended for inhibiting gastric acid secretion are disclosed in U.S. Pat. Nos. 4,045,563; 4,255,431; 4,628,098; 4,686,230; 4,758,579; 4,965,269; 5,021,433; 5,430,042, 5,708,017, 6,093,734 and 6,599,167. Generally speaking, the benzimidazole-type inhibitors of gastric acid secretion work by undergoing a rearrangement to form a thiophilic species which then covalently binds to gastric H,K-ATPase, the enzyme involved in the final step of proton production in the parietal cells, and thereby inhibits the enzyme. Compounds which inhibit the gastric H,K-ATPase enzyme are generally known in the field as "proton pump inhibitors" (PPI).

Some of the benzimidazole compounds capable of inhibiting the gastric H,K-ATPase enzyme have found substantial use as drugs in human medicine and are known under such names as LANSOPRAZOLE (U.S. Pat. No. 4,628,098), OMEPRAZOLE (U.S. Pat. Nos. 4,255,431 and 5,693,818), PANTOPRAZOLE (U.S. Pat. No. 4,758,579), and RABEPRAZOLE (U.S. Pat. No. 5,045,552). The diseases treated by proton pump inhibitors and specifically by the four above-mentioned drugs include peptic ulcer, heart burn, reflux esophagitis errosive esophagitis, non-ulcer dispepsia, infection by *Helicobacter pylori*, laryngitis and asthma among others.

Whereas the proton pump inhibitor type drugs represent substantial advance in the field of human and veterinary medicine, they are not totally without shortcomings or disadvantages. The shortcomings of the presently used proton pump inhibitor (PPI) type drugs can be best explained by a more detailed description of the mode of their action, the diseases or condition against which they are employed and the circumstances of their application. Thus, acid related diseases include but are not limited to erosive esophagitis, esophageal reflux, gastric and duodenal ulcer, non-ulcer dyspepsia and infection by *Helicobacter pylori*. Current therapy of all but the infection by *H. pylori* bacteria involves treatment with drugs designed to suppress acid secretion, one type of which are the above-mentioned proton pump inhibitors.

The presently used proton pump inhibitors are pyridyl methyl sulfinyl benzimidazoles (or compounds of closely related structure) with a stated $pK_a$ of 4.0 to 5.0. Their mechanism of action requires accumulation in the acidic space of the parietal cell (secretory canaliculus, pH ca. 1.0) and subsequently hydrogen ion catalyzed conversion to the reactive thiophilic species that is capable of inhibiting the gastric ATPase, enzyme resulting in effective inhibition of gastric secretion with a large therapeutic index. Because of this mechanism the presently used PPI type drugs require specialized gastro protection to remain active for duodenal absorption. For this reason, and due to sensitivity to degradation in the acid milieu of the stomach, oral formulations of the PPI drugs are enteric coated. The need for enteric coating is a shortcoming because enteric coating is expensive and moisture sensitive.

Because of the requirement for accumulation in the acid space of the parietal cell, acid secretion is necessary for the efficacy of the PPI type drugs. It was found that the plasma half life of these drugs is between 60 to 90 minutes. All acid pumps are not active at any one time, rather only about 75% are active on the average during the time the drug is present in the blood following oral administration. It was also found in medical experience that on a currently used once-a-day oral administration therapy the maximal inhibition of stimulated acid output is approximately 66%. This is due to a combination of the short plasma half life of the drug, to the limited number of acid pumps active during presentation of the drug and to the turn-over of acid pumps. In present practice it is often not possible to properly control night time acid secretion by evening therapy with oral administration because the drug is dissipated from the plasma by the time acid secretion is established after midnight. The ideal target for healing in acid related diseases and for treatment of *H. pylori* infection (in conjunction with antibiotics), as well as for relief of symptoms of non-ulcer dyspepsia would be full inhibition of acid secretion. With the currently used PPI type drugs this is achieved only by intravenous infusion; in case of the drug OMEPRAZOLE this requires intravenous infusion of 8 mg per hour. Clearly, there is a need in the art for a drug or drugs acting through the mechanism of PPI-type drugs which can attain or approach full inhibition of acid secretion through oral therapy.

Because of the less than full inhibition of acid secretion and less than 24 hour inhibition through oral administration that is attained by the current dosage forms of currently used PPI-type drugs, therapy for healing of gastric and duodenal ulcerations is 4 to 8 weeks. This is in spite of the fact that the generation time of surface cells of the esophagus, stomach and duodenum is approximately 72 hours. Undoubtedly the presently observed prolonged healing times with these drugs is due to inadequate acid suppression and acid related damage. The foregoing underscores the need in the art for a drug or drugs acting through the mechanism of PPI-type drugs that can attain or approach full inhibition of acid secretion through oral therapy.

As further pertinent background to the present invention, applicants note the concept of prodrugs that is well known in the art. Generally speaking, prodrugs are derivatives of per se drugs, which after administration undergo conversion to the physiologically active species. The conversion may be spontaneous, such as hydrolysis in the physiological environment, or may be enzyme catalyzed. From among the voluminous scientific literature devoted to prodrugs in general, the foregoing examples are cited: Design of Prodrugs (Bundgaard H. ed.) 1985 Elsevier Science Publishers B. V. (Biomedical Division), Chapter 1; Design of Prodrugs: Bioreversible derivatives for various functional groups and chemical entities (Hans Bundgaard); Bundgaard et al. Int. J. of Pharmaceutics 22 (1984)45–56 (Elsevier); Bundgaardet al. Int. J. of Pharmaceutics 29 (1986) 19–28 (Elsevier); Bundgaard et al. J. Med. Chem. 32 (1989) 2503–2507 Chem. Abstracts 93, 137935y (Bundgaard et al.); Chem. Abstracts 95, 138493f (Bundgaardet al.); Chem. Abstracts 95, 138592n (Bundgaard et al.); Chem. Abstracts 110, 57664p (Alminger et al.); Chem. Abstracts 115, 64029s (Buur et al.); Chem. Abstracts 115, 189582y (Hansen et al.); Chem. Abstracts 117, 14347q (Bundgaard et al.); Chem. Abstracts 117, 55790x (Jensen et al.); and Chem. Abstracts 123, 17593b (Thomsen et al.).

As far as the present inventors are aware, there are no prodrugs of the proton pump inhibitors presently in use. However, several United States patents describe compounds that can act as prodrugs of certain proton pump inhibitors. Specifically, U.S. Pat. No. 4,686,230 (Rainer et al.) describes derivatives of pyridyl methyl sulfinyl benzimidazoles which include a group designated "$R_5$" on one of the benzimidazole nitrogens. The "$R_5$" group is expected to cleave under physiological condition, or under the influence of an enzyme to provide the corresponding compound with a free N—H bond (see column 3 of U.S. Pat. No. 4,686,230). U.S. Pat. No. 5,021,433 (Alminger et al.), U.S. Pat. No. 4,045,563 (Berntsson et al.), U.S. Pat. No. 4,965,269 and (Brändström et al) also describe pyridyl methyl sulfinyl benzimidazoles where one of the nitrogens of the benzimidazole moiety bears a substituent that cleaves under physiological or enzymatic conditions. U.S. Pat. No. 4,045,563 (Berntsson et al.) describes N-alkoxycarbonyl benzimidazole derivates.

A publication by Sih., et al. Journal of Medicinal Chemistry, 1991, vol. 34, pp 1049–1062, describes N-acyloxyalkyl, N-alkoxycarbonyl, N-(aminoethyl), and N-alkoxyalkyl derivatives of benzimidazole sulfoxide as prodrugs of proton-pump inhibitors. According to this article these prodrugs exhibited improved chemical stability in the solid state and in aqueous solutions, but had similar activity or less activity than the corresponding parent compounds having a free imidazole N—H group. This publication does not provide data regarding the duration of the inhibitory activity of these prodrugs.

U.S. Pat. No. 6,093,734 and PCT Publication WO 00109498 (published on Feb. 24, 2000) describe prodrugs of proton pump inhibitors which include a substituted arylsulfonyl moiety attached to one of the benzimidazole nitrogens of proton pump inhibitors having the structure identical with or related to proton pump inhibitor drugs known by the names LANSOPRAZOLE, OMEPRAZOLE, PANTOPRAZOLE and RABEPRAZOLE.

PCT Publication WO 02/30920 describes benzimidazole compounds which are said to have gastric acid secretion inhibitory and anti *H. pylori* effects. PCT Publication WO 02/00166 describes compounds that are said to be nitric oxide (NO) releasing derivatives of proton pump inhibitors of the benzimidazole structure.

The present invention represents further advance in the art in that it provides prodrugs of the proton pump inhibitor type drugs of improved solubility in physiological fluids and improved cell penetration, and provides proof of the suitability of the prodrugs of the invention for use as prodrug of proton pump inhibitors, with improved efficacy in therapy of acid related diseases due to prolongation of the presence of the proton pump inhibitors in the body.

SUMMARY OF THE INVENTION

The present invention relates to compounds of Formula 1, Formula 2, Formula 3 and Formula 4

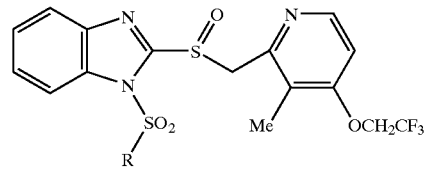

Formula 1

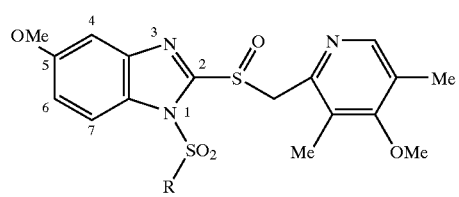

Formula 2

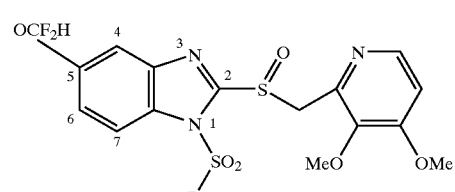

Formula 3

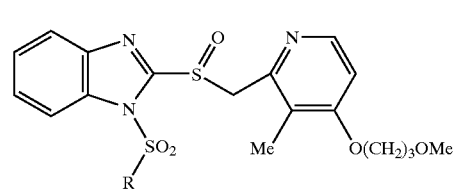

Formula 4 and to isomers of the compounds of Formulas 2 and 3 where the $OCH_3$, and $HF_2CO$ groups, respectively are linked to the 6 position of the benzimidazole ring, and wherein R represents the groups selected from Formulas (i) through (viii); the dashed line represents the bond connecting the R group with the $SO_2$ group,

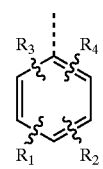

(i)

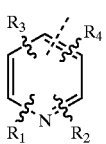

(ii)

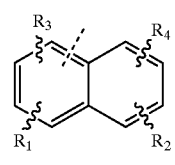

(iii)

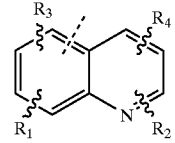

(iv)

-continued

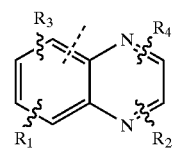
(v)

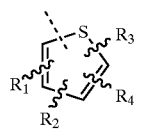
(vi)

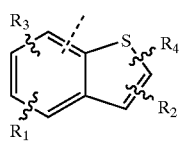
(vii)

(viii)

Y is a straight chained or branch-chained disubstituted alkyl group of 1 to 8 carbons, or Y is N;

$R_1$ and $R_2$ independently are H, a straight chained or branch-chained di- or trisubstituted alkyl group of 1 to 12 carbons including 1 or two $R_5$ groups, or a straight chained or branch-chained saturated hydrocarbon skeleton having no more than 12 carbons including 1 or two $R_5$ groups and optionally further including one to three X groups where X is independently selected from the group consisting of —O—, —S—, —$NR_6$—, —NHCO—, —CONH—, —CONHCO—, —COO—, —OCO— and a disubstituted phenyl group which can optionally be substituted with one or two halogen atoms or with one or two $R_3$ groups; or the $R_5$ group is directly attached without an intervening $R_1$ or $R_2$ group to the aromatic or heteroaromatic ring or to the Y group of formulas (i) through (viii);

$R_3$ and $R_4$ independently are H, alkyl of 1 to 3 carbons, fluoroalkyl of 1 to 3 carbons, O-alkyl of 1 to 3 carbons, O-fluoroalkyl of 1 to 3 carbons, S-alkyl of 1 to 3 carbons, S-fluoroalkyl of 1 to 3 carbons;

$R_5$ is independently H, COOH or a tetrazole moiety;

$R_6$ is H or alkyl of 1 to 3 carbons;

with the provisos that at least one the $R_1$ and $R_2$ groups is not H, and at least one $R_5$ is not H and no more than two $R_5$ groups are COOH or tetrazole whereby the compound includes at least one but no more than two COOH or tetrazole groups;

when Y is —N then neither of the $R_1$ and $R_2$ groups is H, or a pharmaceutically acceptable salt of said compound.

DETAILED DESCRIPTION OF THE INVENTION

Definitions

The term alkyl refers to and covers any and all groups which are known as normal alkyl, branched-chain alkyl, cycloalkyl and also cycloalkyl-alkyl.

A pharmaceutically acceptable salt may be prepared for any compound in this invention having a functionality capable of forming a salt, such as the carboxylic acid, tetrazole or a basic (for example an amine) functionality of the compounds of the present invention. A pharmaceutically acceptable salt is any salt that retains the activity of the parent compound and does not impart any deleterious or untoward effect on the subject to which it is administered and in the context in which it is administered.

Pharmaceutically acceptable salts may be derived from organic or inorganic bases. The salt may be a mono or polyvalent ion. Of particular interest are the inorganic ions, lithium, sodium, potassium, calcium, and magnesium. Organic salts may be made with amines, particularly ammonium salts such as mono-, di- and trialkyl amines or ethanol amines. Salts may also be formed with caffeine, tromethamine and similar molecules. Hydrochloric acid or some other pharmaceutically acceptable acid may form a salt with a compound of the invention when the compound includes a basic group, such as an amine or a pyridine ring.

Some of the compounds of the present invention may contain one or more chiral centers and therefore may exist in enantiomeric and diastereomeric forms. The scope of the present invention is intended to cover all isomers per se, mixtures of diastereomers and racemic mixtures of enantiomers (optical isomers) as well.

General Embodiments

The chemical structure of the compounds of the invention is shown and described in broad terms in the Summary of the Invention in connection with Formulas 1 through 4. As it can be seen in these formulas, the compounds of the invention are pyridyl methyl sulfinyl benzimidazoles substituted in the pyridine and benzimidazole moieties in the same manner as in the well known proton pump inhibitor drugs LANSOPRAZOLE (U.S. Pat. No. 4,628,098), OMEPRAZOLE (U.S. Pat. Nos. 4,255,431 and 5,693,818), PANTOPRAZOLE (U.S. Pat. No. 4,758,579), and RABEPRAZOLE (U.S. Pat. No. 5,045,552). The specifications of U.S. Pat. Nos. 4,628,098, 4,255,431, 5,693,818, 4,758,579 and 5,045,552 are expressly incorporated herein by reference.

Moreover, as it can be seen in connection with Formulas 1 through 4, in the compounds of the invention one of the benzimidazole nitrogens is substituted with a group (designated R in Formulas 1 through 4) that gradually cleaves under physiological conditions and thereby provides the pyridyl methyl sulfinyl benzimidazole compound which has a free NH function in the benzimidazole moiety. The compound thus obtained by cleavage of the R group then undergoes the acid catalyzed rearrangement and provides the thiophilic species which inhibits the H,K-ATPase enzyme involved in gastric acid production. Thus, the novel compounds of the present invention bearing the R group are prodrugs of the proton pump inhibitor compounds which could also be depicted by Formulas 1 through 4 where, however the R group would be designated hydrogen. For further description of prodrugs of pyridyl methyl sulfinyl benzimidazoles type proton pump inhibitor drugs which include a substituted arylsulfonyl or substituted arylsulfonyl moiety attached to one of the benzimidazole nitrogens reference is made to U.S. Pat. No. 6,093,734, 6,599,167 and PCT Publication WO 00109498, the specifications of which are expressly incorporated herein. As it is demonstrated by the solubility and related data provided below, the compounds of the present invention represent a significant improvement over these compounds of the prior art because they are significantly more soluble in physiological media, and therefore are expected to be significantly more bioavailable.

Referring now to the group designated R and shown by structural formulas (i) through (viii), compounds are preferred where R represents a substituted phenyl (formula (i)), substituted pyridyl (formula (ii)), substituted naphthyl (formula (iii)) or substituted thienyl (formula (vi)). Presently still more preferred are compounds where R represents substituted phenyl (formula (i)).

Referring now to the variables designated $R_3$ and $R_4$ in formulas (i) through (vii), compounds of the invention are presently preferred where these variables are independently selected from H, methyl, ethyl, iso-propyl, methoxy, ethoxy, $CF_3$, $CH_3O$ and $OCF_3$. Preferably at least one of these substituents are not hydrogen, and preferably these substituents are on the carbon or carbons which is or are located adjacent to the carbon linked to the sulfonyl group. In many of the presently most preferred compounds of the invention where R is phenyl, these carbons are in ortho position relative to the sulfonyl group. As it will be recognized by those skilled in the art, the $R_3$ and $R_4$ substituents can electronically and sterically influence the rate of cleavage or hydrolysis of the sulfonyl group from the benzimidazole nucleus, and thereby influence the bio-availabilty of the prodrugs of the present invention. When, as in several preferred embodiments, the $R_3$ and $R_4$ substituents are in ortho (or comparable) position relative to the sulfonyl group, then the steric bulk or lack of steric bulk of these substituents are especially significant in influencing the rate of hydrolysis of the sulfonyl group from the benzimidazole moiety. In several of the presently preferred compounds of the invention R is phenyl (formula (i)) and $R_3$ and $R_4$ are both methyl and occupy the ortho and ortho' positions on the phenyl ring. In other examples of the preferred compounds of the invention R is phenyl, one of the $R_3$ and $R_4$ groups is H, and the other is isopropyl. The ortho and ortho' methyl and the ortho iso-propyl substituents slow down the rate of hydrolysis relative to a compound of otherwise comparable structure that lacks these ortho and ortho' substituents.

Referring now to the variables $R_1$ and $R_2$ it is an important feature of the compounds of the present invention that one or both of these groups include a carboxylic acid (or like-wise acidic tetrazole) function. The purpose of function of the carboxylic acid moiety included in these variables in the compounds of the invention is to render the compounds more soluble in aqueous physiological fluids at physiological pH than the prodrugs of pyridyl-methyl-sulfinyl-benzimidazole proton pump inhibitors of the prior art. Generally speaking it is desired within the scope of the present invention that the pKa of the carboxylic acid (or tetrazole) moiety of the compounds of the invention be in the range of 2 to 6, even more preferable the pKa should be in the range of 2 to 4, and still more preferably the pKa is approximately 3. One or two carboxylic acid moieties attached to the $R_1$ and/or to the $R_2$ substituents provide the desired pKa and therefore the desired solubility to the compounds of the invention. Those skilled in the art will recognize that the acidity of the carboxylic acid moiety is influenced by the electronic effects of other groups in its vicinity, particularly so when the carboxylic acid moiety is attached directly to an aromatic ring. It will also be recognized that tetrazole ring may substitute for one or both carboxylic acid moieties, and further that physiologically acceptable salts of the compounds of the present invention may have the same or even better solubility in physiological fluids than the corresponding free acids.

The requirement of the present invention that one or both of the $R_1$ and $R_2$ groups include at least one but no more than a total of two carboxylic acid (or tetrazole) moieties (or its pharmaceutically acceptable salt) can be satisfied with a large variety or combination of $R_1$ and $R_2$ groups. For example, one of these two groups may represent H, in which case the other group includes one or two carboxylic acid (or tetrazole) function (or its pharmaceutically acceptable salt). Alternatively, each of the $R_1$ and $R_2$ may include one carboxylic acid (or tetrazole) function (or their pharmaceutically acceptable salt). The carboxylic acid (or tetrazole) functions, designated $R_5$ in connection with formulas (i) through (viii), may be directly attached to the aromatic or heteroaromatic rings (formulas (i) through (vii)) or to the Y group (formula (viii)), or one or both of the $R_1$ and $R_2$ groups may include a hydrocarbon "skeleton" or "frame" which is attached directly to the aromatic rings (formulas (i) through (vii)), or to the Y group (formula (viii)). Alternatively, the hydrocarbon "skeleton" or "frame" itself may be attached to the aromatic or heteroaromatic rings (formulas (i) through (vii)) or to the Y group (formula (viii)) through an intermediate ether, thioether, amino, ester or amide function. These functions are represented by the variable X in the description of the compounds in the Summary Section of this application for patent.

Moreover, the ether, thioether, amino, ester or amide function or functions may be included at one or more places in the hydrocarbon "skeleton" or "frame" in which case the carboxylic acid (or tetrazole) moiety or moieties are attached to or are "carried by" $R_1$ and/or $R_2$ groups which themselves include ether, thioether, amino, ester or amide linkages. Any combination of these linkages may be suitable for providing compounds within the scope of the invention. Moreover, the "skeleton" or "frame" itself may be straight chained or branch chained, and branching may be due to carbon-to-carbon or to carbon-to-X group linkages.

With the understanding that the $R_1$ and $R_2$ groups may be independently selected and in such a manner that at least one but no more than two carboxylic acid (or tetrazole) function is present in the compounds of the invention, the following serve as examples for preferred embodiments of the $R_1$ and $R_2$ groups:

(1) H,
(2) $(CH_2)_m R_5$,
(3) $(CH_2)_m CH(R_5)(CH_2)_n [CH(R_5)]_q (CH_2)_o CH_3$,
(4) $X(CH_2)_m R_5$,
(5) $X(CH_2)_m CH(R_5)[(CH_2)_n CH(R_5)]_q (CH_2)_o CH_3$,
(6) $(CH_2)_m X(CH_2)_p CH(R_5)[(CH_2)_n CH(R_5)]_q (CH_2)_o CH_3$,
(7) $(CH_2)_m CH(R_5)(CH_2)_n X[(CH_2)_p CH(R_5)]_q (CH_2)_o CH_3$,
(8) $(CH_2)_m X[(CH_2)_p CH(R_5)]_q (CH_2)_n CH(R_5)(CH_2)_o CH_3$,
(9) $(CH_2)_m [CH(R_5)(CH_2)_n]_q X(CH_2)_p CH(R_5)(CH_2)_o CH_3$,
(10) $X(CH_2)_m XCH(R_5)[(CH_2)_n CH(R_5)]_q (CH_2)_o CH_3$,
(11) $(CH_2)_m [CH(CH_2)_s(R_5)](CH_2)_n [CH(CH_2)_s(R_5)]_q (CH_2)_o CH_3$,
(12) $X[CH(CH_2)_s(R_5)]_m R_5$,
(13) $X(CH_2)_m [CH(CH_2)_s(R_5)][CH(CH_2)_s(R_5)]_q (CH_2)_o CH_3$,
(14) $(CH_2)_m X(CH_2)_p [CH(CH_2)_s(R_5)][CH(CH_2)_s(R_5)]_q (CH_2)_o CH_3$,
(15) $(CH_2)_m [CH(CH_2)_s(R_5)](CH_2)_n X[CH(CH_2)_s(R_5)]_q (CH_2)_o CH_3$,
(16) $(CH_2)_m X[(CH_2)_p [CH(CH_2)_s(R_5)]]_q (CH_2)_n [CH(CH_2)_s(R_5)](CH_2)_o CH_3$,
(17) $(CH_2)_m [[CH(CH_2)_s(R_5)](CH_2)_n]_q X(CH_2)_p [CH(CH_2)_s(R_5)](CH_2)_o CH_3$,
(18) $X(CH_2)_m X[CH(CH_2)_s(R_5)][(CH_2)_n [CH(CH_2)_s(R_5)]]_q (CH_2)_o CH_3$
(19) $X(CH_2)_m C(CH_3)_2 R_5$
(20) $X(CH_2)_m X(CH_2)_n R_5$ where m is an integer having the values 0 to 6;
n is an integer having the values 0 to 5;
q is an integer having the values 0 or 1, and
o is an integer having the values 0 to 5,
s is an integer having the values 0 to 5,
the sum of the integers m, n, q, o and s does not exceed 12, and
where the other variables have the meaning defined above in connection with Formulas 1 through 4, the provisos set forth in connection with Formulas 1 through 4 apply with the further proviso that the $R_5$ group is not directly linked to O, S, $NR_6$, NHCO, CONH, COO or OCO group.

Utilizing the substituted phenylsulfonyl group and COOH (for $R_5$) as preferred moieties in the compounds of the present invention, the following are the structural formulas showing not as a limitation but for illustration and exemplary purposes, the preferred $R_1$ or $R_2$ groups designated (2), (3), (4), (5), (10), (11), (12), (19) and (20) above.

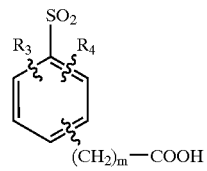
(2)

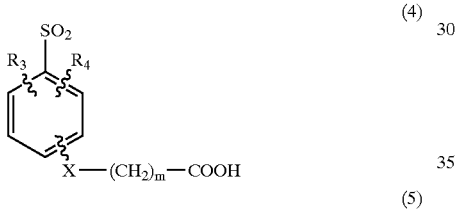
(3)

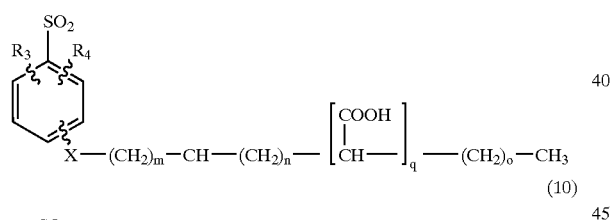
(4)

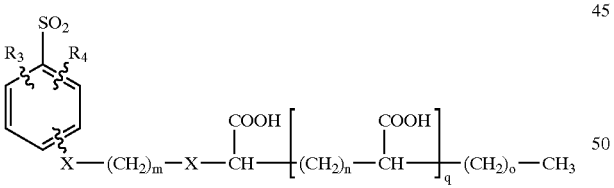
(5)

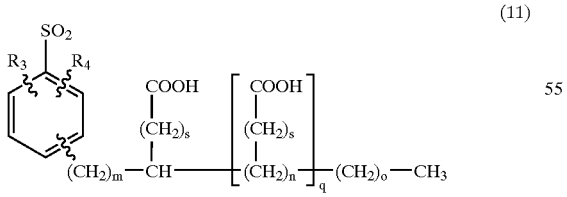
(10)

(11)

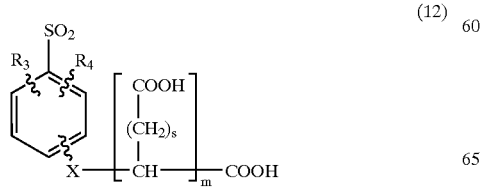
(12)

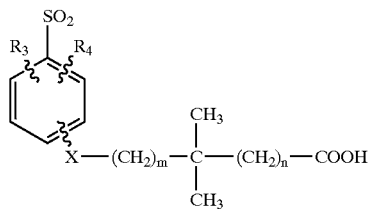
(19)

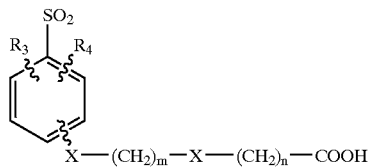
(20)

The presently most preferred R groups included within the compounds of the invention are shown below. For ease of reference these preferred groups are identified with an R designation bearing a subscript, such as "$R_{11}$, $R_{12}$ etc."

($R_{11}$)

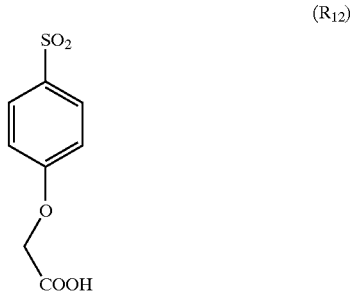
($R_{12}$)

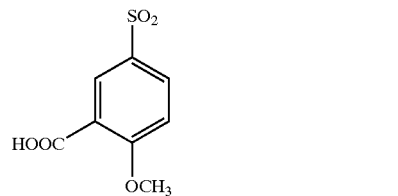
($R_{13}$)

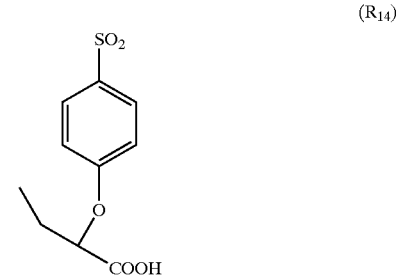
($R_{14}$)

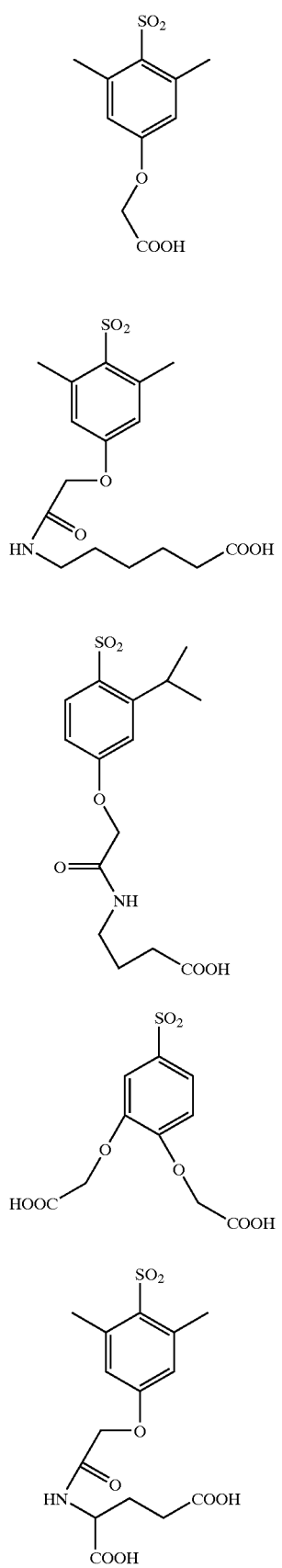
(R15)
(R16)
(R17)
(R18)
(R19)
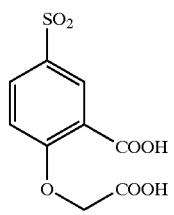
(R20)
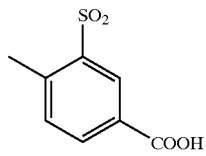
(R21)
(R22)
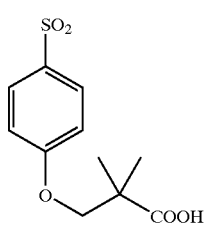
(R23)
(R24)
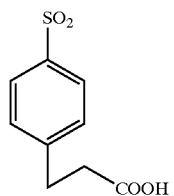
(R25)
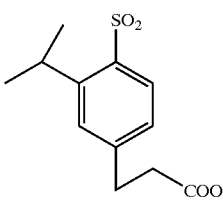
(R26)
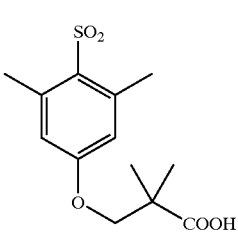
(R27)

(R28)
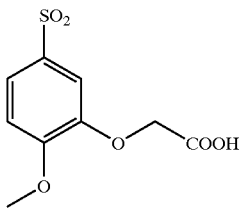

(R29)
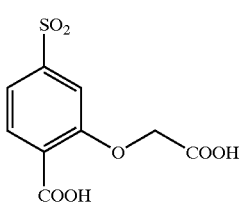

(R30)
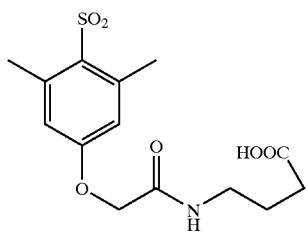

(R31)
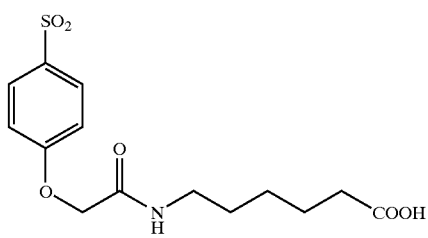

(R32)
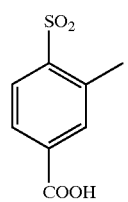

(R33)
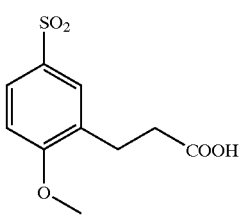

(R34)
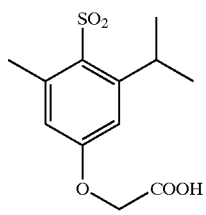

The presently most preferred compounds of the invention are those where one of the $R_{11}$ through $R_{34}$ groups is attached to the benzimidazole moiety shown in Formulas 1 through 4. Structures of specific examples of the most preferred compounds of the invention are provided below together with the experimental description of the preparation of the specific examples.

Synthetic Methodology

Generally speaking the compounds of the invention can be prepared by base catalyzed hydrolysis of substituted or unsubstituted phenyl sulfonyl-ethyl esters of the mono or dicarboxylic acids which constitute the compounds of the invention. The general method of the presently preferred synthetic process is shown in Reaction Scheme 1, where for the sake of simplicity of illustration the pyridyl methyl sulfinyl benzimidazole moieties corresponding to Formulas 1 through 4 are jointly shown by Formula 5, the aryl, heteroaryl or alkyl moieties of formulas (i) through (viii) are illustrated by a phenyl group, only the $R_1$ group (as defined above) and only a monocarboxylic acid are shown. However those skilled in the art will readily understand that the herein described synthetic procedure can be applied to the preparation of all compounds within the scope of the invention with only such modifications which are readily apparent to those skilled in the art in view of the present disclosure.

Referring now specifically to Formula 5 in Reaction Scheme 1, this formula represents the pyridyl methyl sulfinyl benzimidazole compounds known as LANSOPRAZOLE, OMEPRAZOLE, PANTOPRAZOLE and RABEPRAZOLE. The variable Z represents H or such substituent which may be present in the benzimidazole moiety in any of these compounds, and Z' represents the substituent or substituents which are present in the pyridine moiety of these proton pump inhibitor drugs. The compound of Formula 5 is reacted with a chlorosulfonyl compound of Formula 6 in the presence of base such as sodium hydride, triethylamine, and di(isopropyl)methylamine or other suitable base, in an aprotic solvent such as $CH_2Cl_2$. The compound of Formula 6 includes a substituted or unsubstituted phenylsulfonylethyl ester of the carboxylic acid moiety that is included in the compounds of the invention.

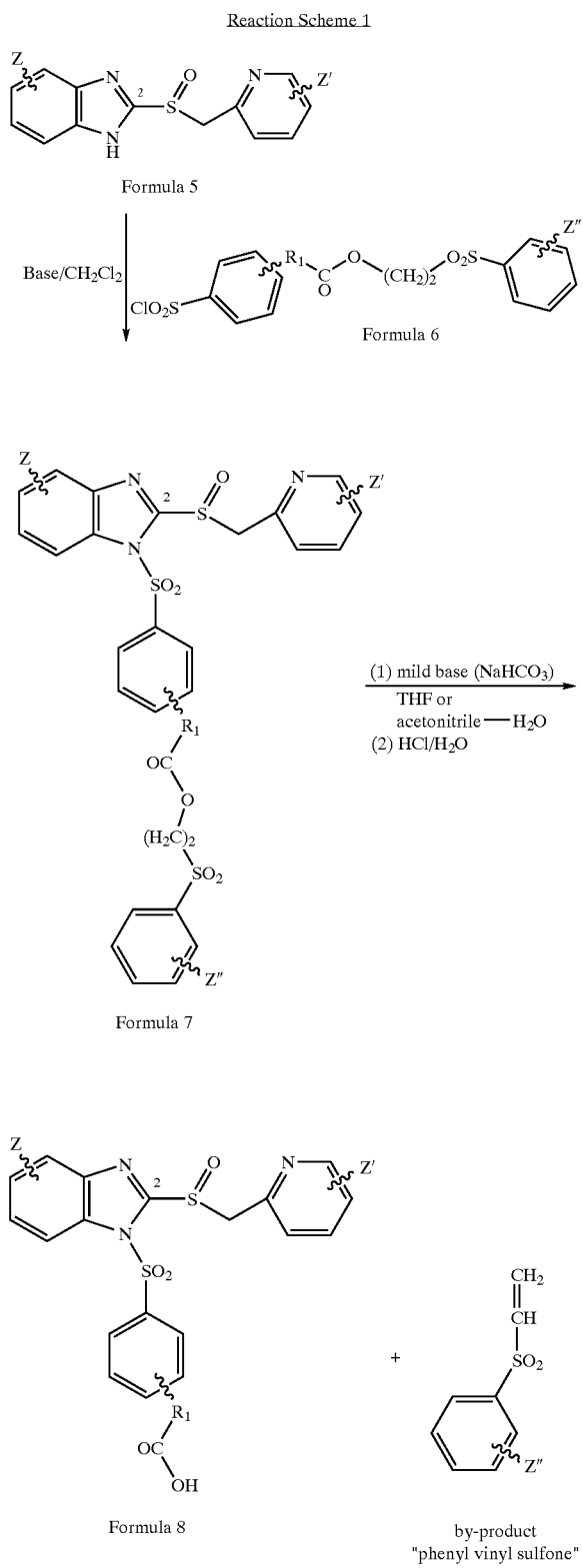

The substituent of the phenylsulfonylethyl moiety is indicated with the symbol Z″, which in many preferred examples is a methyl group in the para position or a nitro group in the meta position of the phenyl ring. The preferred methods of synthesizing the chlorosulfonyl compounds of Formula 6 are illustrated in the reaction schemes below and are also described in detail in connection with the Specific Examples. Still further and generally speaking chlorosulfonyl compounds within the scope of Formula 6 can be obtained by such modifications of the reactions shown here which will be readily apparent to those skilled in the art in light of widely available chemical patent and scientific literature.

Reaction of the pyridyl methyl sulfinyl benzimidazole compounds of Formula 5 with the chlorosulfonyl compounds of Formula 6 results in the formation of the intermediates of Formula 7. The intermediates of Formula 7 are hydrolyzed in the presence of mild base, such as $NaHCO_3$, to provide the sodium salt of the compounds of the invention. A by-product of this reaction is a substituted or unsubstituted phenyl vinyl sulfone that is shown in Reaction Scheme 1. The sodium salt can be readily converted to the free acid compounds of the invention which are represented (in their simplified form) by Formula 8.

Compounds of the invention which are depicted by Formulas 2 and 3 include a substituent in the benzimidazole moiety, namely a $CH_3O$— group (Formula 2, OMEPRAZOLE derivatives) or a $HF_2CO$— group (Formula 3, PANTOPRAZOLE derivatives). For this reason reaction of OMEPRAZOLE and PANTOPRAZOLE (depicted in a simplified form in Formula 5) with the chlorosulfonyl compounds of Formula 6 gives rise to 2 isomeric compounds, both of which are, generally speaking, within the scope of the invention. The two isomers are usually but not necessarily formed approximately in 1 to 1 ratios in the reaction, and it was found in accordance with the invention that the biological activity, solubility and particularly the stability of the isomers may also differ, in some cases significantly. Although, when desired, the isomers can be separated from one another by state-of-the-art separation techniques, such as high pressure liquid chromatography (HPLC), a more efficient synthetic route to synthesize single isomers of these compounds has been developed also. Reaction Schemes 1A and 1B disclose general synthetic routes to obtain the two single isomers of the OMEPRAZOLE derivatives of the invention. Specific synthetic schemes for making preferred single isomers of the OMEPRAZOLE derivatives of the invention are shown and described in the specific examples.

Reaction Scheme 1A
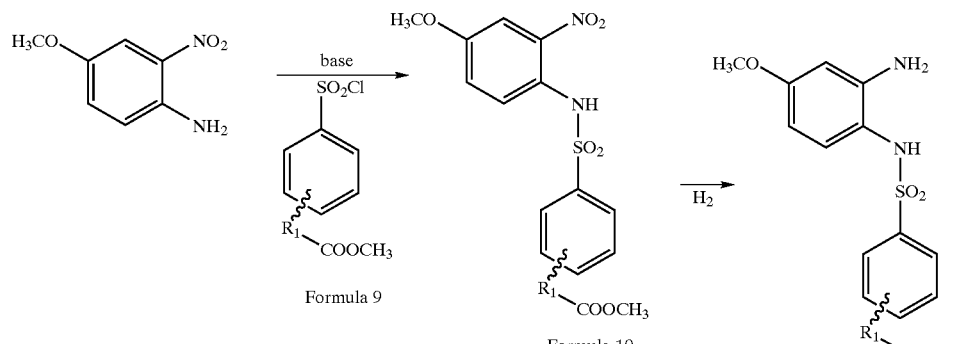
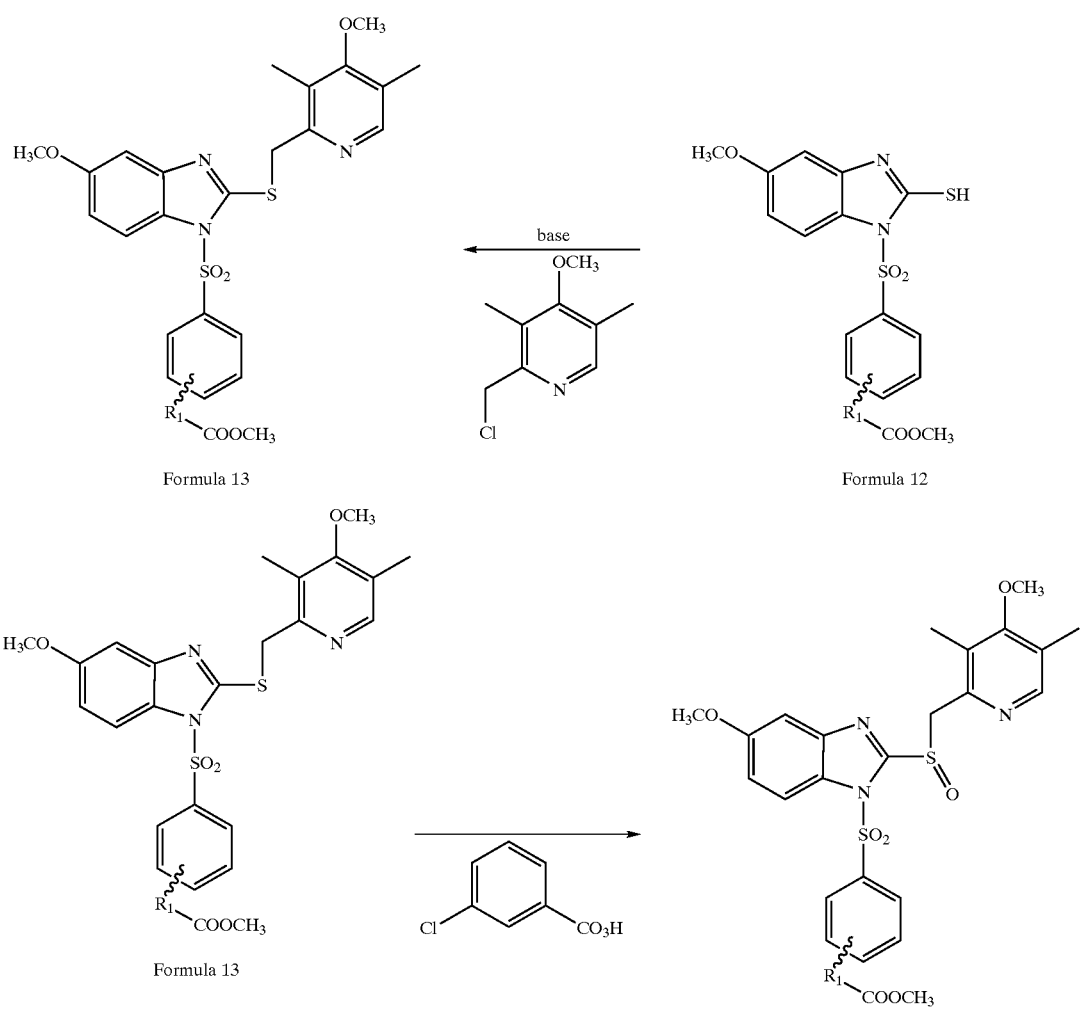

-continued
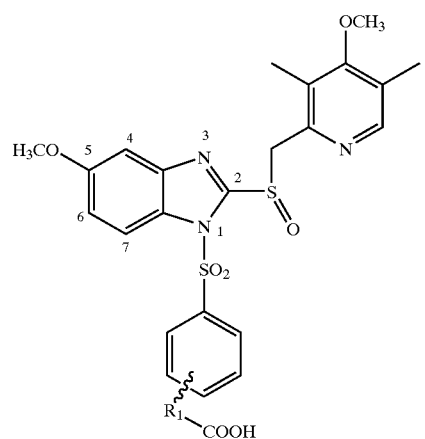
Formula 15
Reaction Scheme 1B
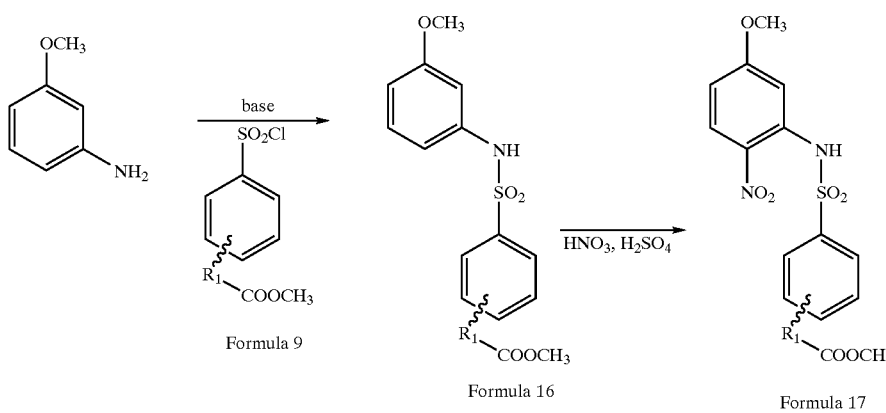
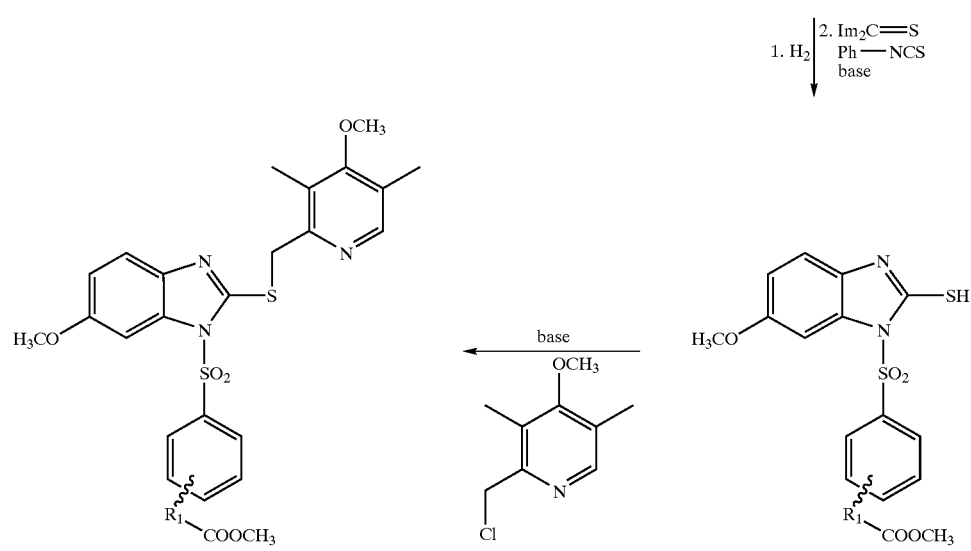

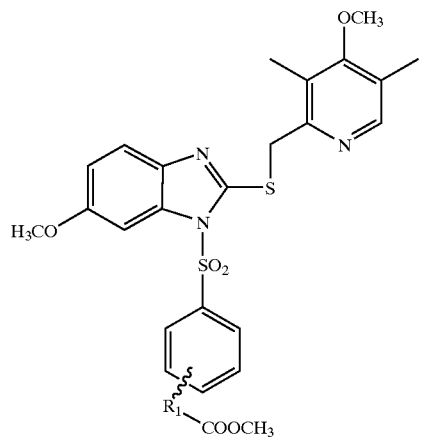

Formula 19

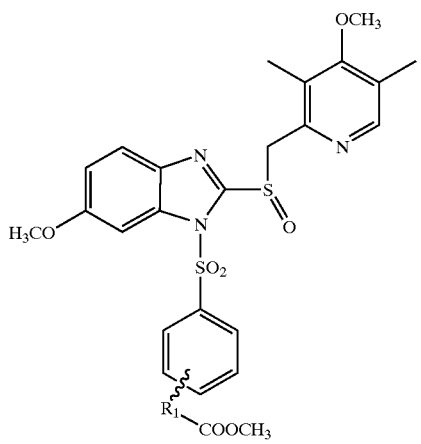

Formula 20

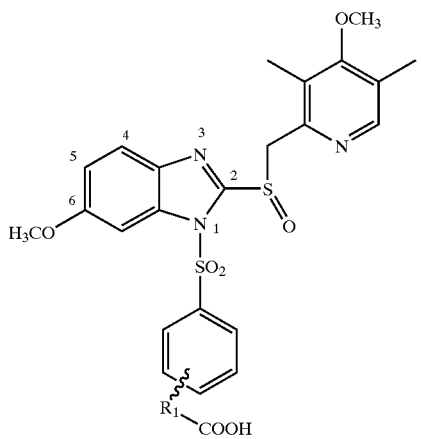

Formula 21

Referring now to Reaction Scheme 1A 2-nitro-4-methoxy-aniline (available from Aldrich) is reacted with a chlorosulfonyl compound of Formula 9. As in connection with Reaction Scheme 1 in Reaction Schemes 1A and 1B also, for the sake of simplicity of illustration the reagent of Formula 9 illustrates the aryl, heteroaryl or alkyl moieties of formulas (i) through (viii) only by an exemplary phenyl group, and shows only the $R_1$ group (as defined above) and an ester leading to a monocarboxylic acid. However those skilled in the art will readily understand that the herein described synthetic procedures can be applied to the preparation of single isomers of the OMEPRAZOLE derivatives of the present invention having the full scope of the R groups, as that group is defined in connection with Formulas 1–4.

The reaction of 2-nitro-4-methoxy-aniline with the chlorosulfonyl compound of Formula 9 provides the chlorosulfonyl-2-nitro-4-methoxy-aniline derivative of Formula 10. The nitro group of the latter compound is reduced in the next reaction step to yield a chlorosulfonyl-2-amino-4-methoxy-aniline derivative of Formula 11. The chlorosulfonyl-2-amino-4-methoxy-aniline derivative of Formula 11 is then ring closed by treatment with thiocarbonyldiimidazole ($Im_2C=S$) (or by treatment with phenylisocyanate, or with thiophosgene) to provide a 2-thiobenzimidazole derivative of Formula 12 where the methoxy group is in the 5-position of the imidazole ring and the chlorosulfonyl group is attached to the nitrogen in the 1-position. The compound of Formula 12 is reacted with 2-chloromethyl-4-methoxy-3,5-dimethylpyridine to give rise to a N-1-sulfonyl-5-methoxy-2-[(4-methoxy-3,5-dimethyl(2-pyridyl))methylthio]-benzimidazol derivative of Formula 13. The reagent 2-chloromethyl-4-methoxy-3,5-dimethylpyridine or its hydrochloride salt can be obtained by treatment of 4-methoxy-3,5-dimethylpyridine-methanol with thionyl chloride. The thioether linkage of the compound of Formula 13 is oxidized to the sulfoxide level by treatment with 3-chloroperoxybenzoic acid (meta-chloroperbenzoic acid, m-CPBA) or with other suitable oxidizing agent to yield a N-1-sulfonyl-5-methoxy-2-[(4-methoxy-3,5-dimethyl(2-pyridyl))methylsulfinyl]-benzimidazol derivative of Formula 14. Treatment of the compounds of Formula 14 with base saponifies the carboxylic acid ester function attached to the aryl ring of the chlorosulfonyl moiety and gives rise to the OMEPRAZOLE derivative compounds of the invention of Formula 15 where the methoxy group is attached to the 5-position of the benzimidazole moiety (pure positional isomers).

Reaction Scheme 1B illustrates a synthetic route to the "other isomer" where the methoxy group is attached to the 6-position of the benzimidazole moiety. In this scheme 3-methoxyaniline (available from Aldrich) is reacted with the reagent of Formula 9 to provide a chlorosulfonyl-3-methoxy-aniline derivative of Formula 16. The chlorosulfonyl-3-methoxy-aniline derivative of Formula 16 is treated with nitric acid in the presence of sulfuric acid to yield a chlorosulfonyl-3-methoxy-6-nitro-aniline derivative of Formula 17. The nitro group of the compound of Formula 17 is reduced to an amino group and the resulting chlorosulfonyl-3-methoxy-6-amino-aniline derivative is ring-closed by treatment with thiocarbonyldiimidazole to give a 2-thiobenzimidazole derivative of Formula 18 where the methoxy group is in the 6-position of the imidazole ring and the chlorosulfonyl group is attached to the nitrogen in the 1-position. The compound of Formula 18 is then subjected to the same sequence of reaction as the compound of Formula 12 in Reaction Scheme 1A, to give rise to the OMEPRAZOLE derivative compounds of the invention of Formula 21 where the methoxy group is attached to the 6-position of the benzimidazole moiety (pure positional isomers). It was found in accordance with the present invention that the positional isomers of Formula 21 tend to be less stable than the positional isomers of Formula 15.

Reaction Schemes 2 to 44 incorporated in the section titled Specific Examples below, disclose the presently preferred synthetic routes to exemplary preferred compounds of the invention.

Biological Activity, Modes of Administration

A significant advantage of the compounds of the present invention is that they can release the active forms of the proton pump inhibitors spontaneously by hydrolysis in the mammalian (including human) body. Hydrolysis can occur chemically or enzymatically. Because the compounds of this invention spontaneously release the active form of the proton pump inhibitor drugs by in vivo hydrolysis, they can attain longer duration of effective drug concentration in the body. Thus, the compounds of the present invention are prodrugs which are converted to active drugs by hydrolysis in the body, providing long duration of effective concentration. The long duration of inhibitory activity by spontaneous hydrolysis of the compounds of this invention allows more effective inhibition of gastric acid secretion, which enables better therapy of acid related disease defined above. Compounds of this invention can be administered for inhibiting gastric acid secretion orally. The typical daily dose of the compounds will depend on various factors such as the individual requirement of each patient. In general, oral and parenteral dosages will be in the range of 5 to 300 mg per day.

Those skilled in the art will readily understand that for oral administration the compounds of the invention are admixed with pharmaceutically acceptable excipients which per se are well known in the art. Specifically, a drug to be administered systemically, it may be confected as a powder, pill, tablet or the like or as a syrup or elixir suitable for oral administration. Description of the substances normally used to prepare tablets, powders, pills, syrups and elixirs can be found in several books and treatise well known in the art, for example in Remington's Pharmaceutical Science, Edition 17, Mack Publishing Company, Easton, Pa.

Compounds of the present invention can be combined with certain amounts of known proton pump inhibitors, e.g LANSOPRAZOLE, OMEPRAZOLE, PANTOPRAZOLE, or RABEPRAZOLE, to provide a drug-prodrug combination, and the combination administered for inhibition of gastric acid secretion. Thus, initially the proton pump inhibitor (drug) inhibits gastric acid secretion of the patient. The aforesaid known and widely used proton pump inhibitors have 60–90 minutes of plasma half-life. As the effective concentration of the proton pump inhibitor (drug) is decreased by metabolism, the compound of the present invention (prodrug) continuously undergoes hydrolysis and provides and maintains new active inhibitor concentration in the mammalian, including human body for much longer periods of time than the unmodified proton pump inhibitor. This results in more rapid and effective inhibition of acid secretion.

A disadvantage of many of the presently used proton pump inhibitors is that for therapy by injection in a liquid form they must be reconstituted from a lyophilized powder in a medium having the high pH of approximately 9.5 to 10.5. The prodrugs of the present invention overcome the disadvantage of requiring a reconstituting medium having such high pH, because the compounds of the present invention can be reconstituted to form an injectable liquid in a medium of approximately pH 7 to 8. It will be readily appreciated by those skilled in the art that for administration in liquid form by injection the liquid that reconstitutes the drug is a pharmaceutically acceptable aqueous solution that per se is known in the art. Such pharmaceutically acceptable solutions utilized for administration of drugs in injectable form are described for example in the treatise PHARMACEUTICAL DOSAGE FORMS (Parenteral Medications, Volume 1, Edited by K. E. Avis, H. A. Lieberman and L. Lachman (1992).

Among the benefits of the pre-proton pump inhibitor (P-PPI) type of drugs of the present invention is their ability to provide more effective treatment of erosive esophagitis and of less severe reflux diseases as well. This is because effective treatment of erosive esophagitis (and to a lesser extent of lesser reflux diseases) requires prevention of the reflux of gastric contents at pH 3.0 or still lower pH. The current PPI drugs allow several acidic excursions to pH<2.0 per day, resulting in often a moderate to weak amelioration of symptoms. However, healing would require elevation to pH>4.0 for about 16 hours per day or longer. When, as in current usual treatment by PPIs, the other 8 hours contain episodic acidity to pH 3.0 or less, the patients tend to continue to complain of pain. The more effective and more continues acid suppression by the drugs of the present invention is likely to result in substantially better treatment of this disease, as well as faster healing of all acid related erosions or ulcers.

The pre-proton pump inhibitor (P-PPI) type of drugs of the present invention provide improved dual therapy for H.

pylori eradication. This is because the PPI's synergize with cell division dependent antibiotics such as amoxicillin (cell wall biosynthesis) and clarithromycin (protein synthesis) by elevating gastric surface pH to enable a larger fraction of the bacterial population to be in dividing or growth phase during presentation of the antibiotic to the gastric lumen. However, their effect on intragastric pH is limited by their dwell time in the plasma. The pre-proton pump inhibitor (P-PPI) type of drugs of the present invention can continuously elevate intra gastric pH close to neutrality on current once a day therapy. Therefore, 100% eradication of the bacteria is expected in dual therapy with the prodrugs of the invention (for example a prodrug of OMEPRAZOLE in accordance with the invention) plus an effective antibiotic, such as amoxicillin.

Even monotherapy for *H. pylori* eradication is likely to be successful with the pre-proton pump inhibitor (P-PPI) type of drugs of the present invention. This is because in the absence of acid, the enzyme *H. pylori* urease elevates environmental pH to >8.3, which is toxic to the organism. PPI's in current formulation inhibit growth or present of the organism in the antrum, due to elevation of antral pH to close to neutrality. Elevation of 24 hour pH to neutrality, as it can be accomplished with the drugs of the present invention, is likely to result in "self eradication" of the bacteria.

Approximately 30% of patients with gastrointestinal distress appear with symptoms without quantitative underlying disease (non-ulcer dyspepsia). The most likely cause for these symptoms is upper gastrointestinal afferent nerve sensitivity to gastric acid. Only highly effective inhibition of acid secretion or even acid ablation can ameliorate these symptoms and this can be attained with the drugs of the present invention.

Solubility and Stability

Solubility

A further significant advantage of the proton pump inhibitor prodrugs of the present invention relative to the proton pump inhibitor prodrugs disclosed in U.S. Pat. No. 6,093,734, 6,559,167 and PCT Publication WO 00109498 and to all other prior art is their increased solubility. To illustrate this, the aqueous solubility of each of the prior art compounds (a) through (f) shown below is less than 0.01 µg per milliliter (<0.01 µg/mL) when these prior art compounds are prodrugs of the drug LANSOPRAZOLE (compounds (a) through (c), and between 5 to 8 µg per milliliter (5 to 8 µg/mL) when these prior art compounds are prodrugs of the drug OMEPRAZOLE (compounds (d) through (f). In contrast, the solubility in distilled water of the free carboxylic acids of Compounds 2 and 9 of the invention is greater than 100 µg per milliliter (>100 µg/mL).

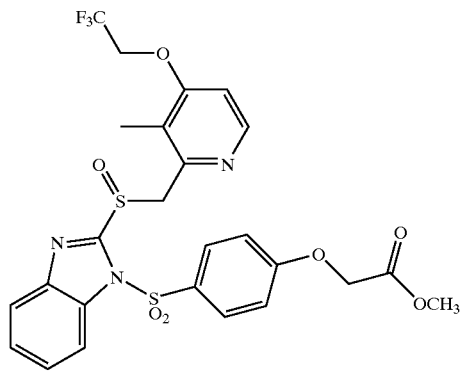
compound (a)

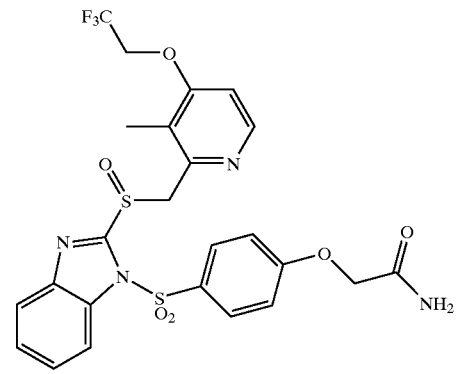
compound (b)

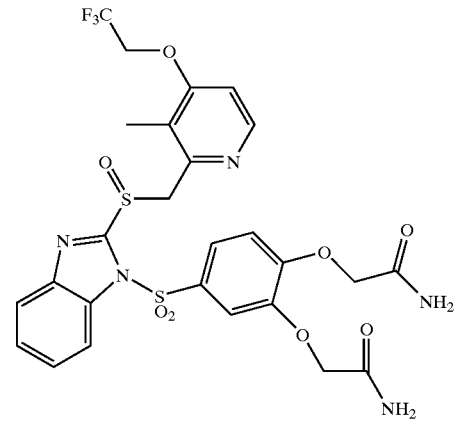
compound (c)

(<0.01 µg/mL)

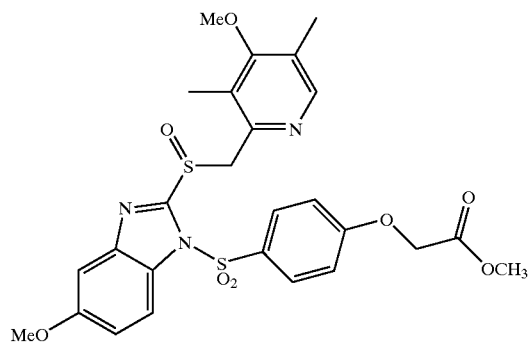
compound (d)

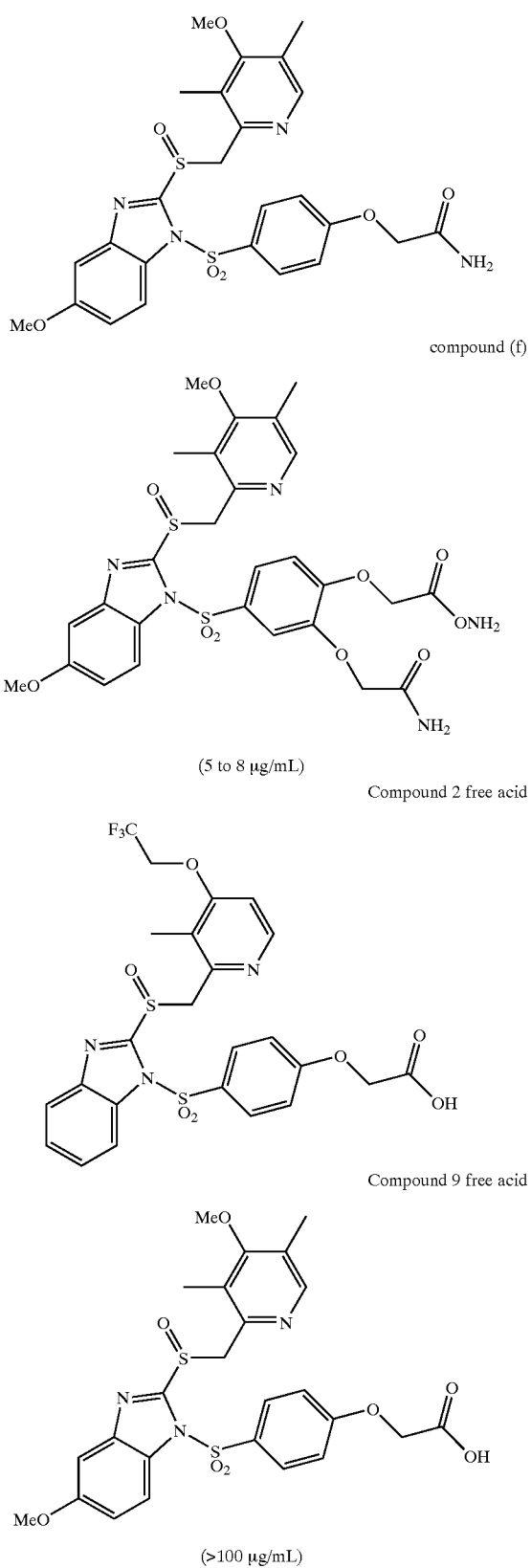

saline buffer of pH 7.4 (50 mM sodium phosphate, 10 mM KCl, 0.1 M NaCl) and also in a more acidic Britton Robinson buffer of pH 3 (40 mM acetic acid, 40 mM phosphoric acid, 40 mM boric acid, 36 mM NaOH, and 19.6 mg/ml KCl) was also evaluated. The results in the buffer of pH 7.4 are shown in Table 1. As it can be seen in Table 1, the compounds tested were found to be highly soluble in the phosphate buffered saline buffer at pH 7.4. The tested compounds were much less soluble little in the Britton Robinson buffer of pH 3, but still more soluble than the prior art compounds (a) through (f). This is understandable in view of the fact that in the buffer of pH 7.4 the compounds of the invention form a sodium salt, whereas in the buffer of pH 3 the compounds are less soluble free carboxylic acids. Thus, a solution of a sodium or other pharmaceutically acceptable salt of the compounds of the invention, or stated in an other way the compounds of the invention at pH 7 or above are highly soluble and therefore suitable for administration by intravenous injection.

TABLE 1

Solubility at 37° C.

| Compound | Conc. (mg/mL at pH 7.4) |
|---|---|
| Compound 1 | >30 |
| Compound 2 | >50 |
| Compound 3 | >50 |
| Compound 5 | >30 |
| Compound 8 | >30 |
| Compound 9 | >30 |
| Compound 12 | >50 |

Stability in Buffers

The stability of Compounds 1, 2, 3, 4 and 5 of the invention in aqueous solution (0.1 mg/mL) was investigated in Britton Robinson buffers of pH 3, pH 7, and pH 9, respectively. A solution of 0.1 mg/mL concentration of each compound in each buffer was prepared and the solutions were stored at 37° C. for 1 h and then the concentrations of test compounds were determined by HPLC. It was found that the test compounds are stable in aqueous solution under neutral conditions. Half-life of hydrolysis at pH 7 of the prodrug to yield the corresponding proton pump inhibitory drug was over 50 hours. This demonstrates that the prodrugs per se are stable enough for intravenous injection.

Stability in Plasma

Exemplary test compounds (prodrugs) of the invention were incubated in plasma at 37° C., and the concentration of the compounds and also of the corresponding proton pump inhibitor compounds (PPI) were determined by a gradient HPLC-UV method. The results are shown in Table 2. Although the half-lives of test compounds in plasma varies depending on their structure, nevertheless it is apparent that in plasma the compounds of the invention are converted into the corresponding proton pump inhibitor at a rate faster than the hydrolysis rate of the compound at neutral or near neutral pH. This demonstrates that the prodrugs of the invention can be used as prodrugs in intravenous injection and that they release the active proton pump inhibitor in vivo.

TABLE 2

Half-life of Exemplary Compounds in Plasma

| Compound # | Rat plasma | Human plasma |
|---|---|---|
| Compound 1 | 14 min | 12 min |
| Compound 2 | 18 min | (ND) |
| Compound 3 | 81 min | 10 min |
| Compound 4 Na salt | 98 min | 60 min |

The solubility of the sodium salts of certain exemplary compounds of the present invention in a phosphate buffered TABLE 2-continued Half-life of Exemplary Compounds in Plasma

| Compound # | Rat plasma | Human plasma |
|---|---|---|
| Compound 5 | 31 min | (ND) |
| Compound 6 | 52 min | 60 min |
| Compound 11 | 53 min | 14 min |
| Compound 12 | 78 min | 51 min |
| Mixture of Compound 16 and 17 (1:1) | 71 min | 58 min |
| Compound 27 | 14 min | (ND) |
| Mixture of compound 31 and 32 (1:1) | 62 min | 40 min |
| Compound 36 | 19 min | (ND) |
| Compound 39 | 317 min | (ND) |

*(ND); the half-life was not determined.

Inhibitory Effect of the Compounds of the Invention on Gastric Acid Secretion of the Conscious Male Rat at Timed Intervals Oral Administration Male rats (the Sprague-Dawley strain) were used in this experiment. OMEPRAZOLE sodium salt or LANSOPRAZOLE sodium salt (20 mg) was suspended in 10 ml of 0.1 N NaHCO$_3$. 40 mg of each of the sodium salts of Compound 1, Compound 2, Compound 3, Compound 4, Compound 6 Compound 9, Compound 12, mixture (1:1) of Compound 16 and 17, mixture (1:1) of Compound 18 and 19, mixture (1:1) of Compound 20 and 21, mixture (1:1) of Compound 22 and 23, Compound 27, mixture (1:1) of Compound 34 and 35, and Compound 36 were dissolved in 10 ml of 50 mM sodium phosphate buffer, pH 7.4. The doses administered to the rats were as follows (μmole per kg body weight of the rat): OMEPRAZOLE (10 μmole/kg), LANSOPRAZOLE (10 μmole/kg), Compound 1 20 μmole/kg, Compound 2 40 μmole/kg, Compound 3 20 μmole/kg, Compound 4 20 μmole/kg, Compound 6 20 μmole/kg, Compound 9 40 μmole/kg, Compound 12 40 μmole/kg, mixture (1:1) of Compound 16 and 17 40 μmole/kg, mixture (1:1) of Compound 18 and 19 40 μmole/kg, mixture (1:1) of Compound 20 and 21 40 μmole/kg, mixture (1:1) of Compound 22 and 23 40 μmole/kg, Compound 27 40 μmole/kg, mixture (1:1) of Compound 34 and 35 40 μmole/kg, and Compound 36 40 μmole/kg. These drug solutions were orally administered.

3 hours after administration the abdomen of the rat was incised and the pylorus was ligated under light ether anethesia. Histamine (30 mg/kg) and carbachol (30 μg/kg) were subcutaneously injected for acid stimulation. Immediately the abdomen was closed. Two hours later, the esophagus was ligated and the stomach was removed. The gastric juice was collected and acid output was quantified by titration using 0.1 N NaOH solution. As a control experiment, 1 ml of 50 mM phosphate buffer (pH 7.4) solution was orally administrated without any prodrug or proton pump inhibitory drug. Acid output was quantified by same method as described above, showing maximum histamine and carbachol-stimulated gastric acid secretion. Percentage inhibition was calculated from the fractional responses elicited by the test compound and a control experiment.

TABLE 3

Inhibition of gastric acid secretion between 3–5 hours after administration of the prodrugs of the invention

| Compound # | Dosage per kg of rat weight | % inhibition |
|---|---|---|
| Compound 1 | 20 μmole/kg | 81.9 ± 7.1 |
| Compound 2 | 40 μmole/kg | 64.2 ± 11.3 |
| Compound 3 | 20 μmole/kg | 84.9 ± 13.6 |
| Compound 4 | 20 μmole/kg | 60.9 ± 25.5 |
| Compound 6 | 20 μmole/kg | 53.5 ± 18.3 |
| Compound 9 | 40 μmole/kg | 74.4 ± 25.1 |
| Compound 12 | 40 μmole/kg | 82.8 ± 9.6 |
| Mixture of compound 16 and 17 (1:1) | 40 μmole/kg | 80.5 ± 4.5 |
| Mixture of Compound 18 and 19 (1:1) | 40 μmole/kg | 94.3 ± 2.7 |
| Mixture of Compound 20 and 21 (1:1) | 40 μmole/kg | 87.7 ± 10.8 |
| Mixture of Compound 22 and 23 (1:1) | 40 μmole/kg | 96.4 ± 0.6 |
| Compound 27 | 40 μmole/kg | 96.7 ± 1.3 |
| Mixture of Compound 34 and 35 (1:1) | 40 μmole/kg | 75.4 ± 14.3 |
| Compound 36 | 40 μmole/kg | 89.8 ± 6.8 |
| OMEPRAZOLE | 10 μmole/kg | 54.6 ± 10.4 |
| LANSOPRAZOLE | 10 μmole/kg | 67.6 ± 14.7 |

Intravenous Administration

Inhibition of gastric acid secretion after intravenous administration of compounds of the invention was also examined. Lansoprazole sodium salt (20 mg) was dissolved in 40% hydroxypropyl-beta-cyclodextrin. The compounds of the invention used in this experiment were dissolved in phosphate buffered saline solution of pH 7.4. Each compound was injected intravenously at a dose of 5 μmole/kg or 10 μmole/kg (μmole per kg body weight of rat) as indicated in Table 4 below. Between 2 to 4 hours after injection gastric juice was collected, and the percentage of inhibition was determined as described above.

TABLE 4

Inhibition of gastric acid secretion between 2–4 hours after i.v. administration

| Compound # | Dosage per kg of rat | % inhibition |
|---|---|---|
| Compound 1 | 5 μmole/kg | 83.7 ± 10.1 |
| Compound 1 | 10 μmole/kg | 90.6 ± 2.1 |
| Compound 2 | 5 μmole/kg | 63.1 ± 31.7 |
| Compound 10 | 5 μmole/kg | 18.3 ± 11.9 |
| Compound 12 | 5 μmole/kg | 89.2 ± 6.8 |
| Compound 12 | 10 μmole/kg | 92.6 ± 2.9 |
| LANSOPRAZOLE | 5 μmole/kg | 91.5 ± 5.0 |

Reaction Scheme 2

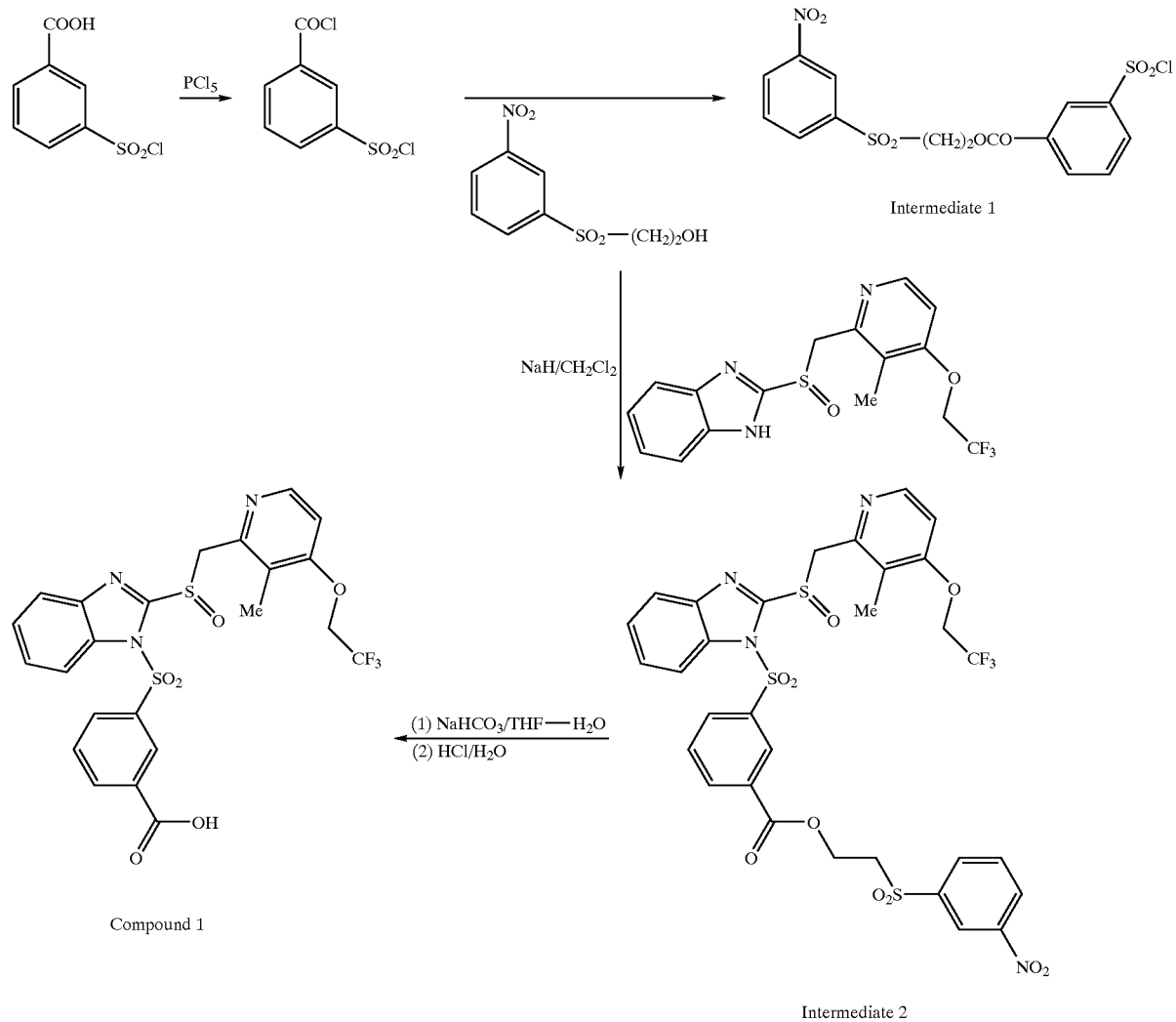

3-Chlorosulfonyl-benzoic acid 2-(3-nitro-benzenesulfonyl)ethyl ester (Intermediate 1)

To solid 3-chlorosulfonylbenzoic acid (3.2 g, 14.4 mmol) was added solid PCl$_5$ (3.0 g, 14.4 mmol) at room temperature with mixing. The mixture was heated to 70° C. forming a brown liquid that was heated for an additional 2 h. POCl$_3$ side product was removed by vacuum distillation and the residual brown oil was dissolved in 15 mL of CH$_3$CN, and then 2-(3-nitrobenzenesulfonyl)ethanol (2.8 g, 12.0 mmol) was added. The mixture was heated to reflux temperature for 36 h. Thereafter water was added and the mixture was extracted with CH$_2$Cl$_2$. The resulting oil was purified by short column chromatography (eluent: CH$_2$Cl$_2$ to 1% MeOH in CH$_2$Cl$_2$) to give a brown semisolid, which became a white solid by treatment with ether-EtOAc (yield 2.75 g (53%)).

$^1$H NMR (DMSO-d$_6$, 400 MHz) δ 4.08 (t, 2H), 4.58 (t, 2H), 7.33 (t, 1H), 7.40 (d, 1H), 7.77 (d, 1H), 7.84 (m, 2H), 8.32 (d, 1H), 8.40 (d, 1H), 8.56 (s, 1H).

3-{2-[3-Methyl-4-(2,2,2-trifluoro-ethoxy)-pyridin-2-ylmethanesulfinyl]-benzimidazole-1-sulfonyl}benzoic acid 2-(3-nitro-benzenesulfonyl) ethyl ester (Intermediate 2)

To a heterogeneous mixture of 2-[3-methyl-4-(2,2,2-trifluoroethoxy)pyridin-2-ylmethanesulfinyl]-1H-benzimidazole (600 mg, 1.62 mmol) in CH$_2$Cl (10 mL) was added NaH (45 mg, 1.95 mmol) at room temperature, resulting in a clear solution. To this clear mixture was added the sulfonyl chloride (Intermediate 1, 845 mg, 1.95 mmol, 1.2 eq), in CH$_2$Cl$_2$ at room temperature, and then the mixture was stirred for 2 h. Thereafter water was added and the mixture was extracted with CH$_2$Cl$_2$, and the organic layers were dried and concentrated. The residual oil was purified by column chromatography (3% MeOH in CH$_2$Cl$_2$) to yield 1.0 g (80%) of yellow foam.

$^1$H NMR (CDCl$_3$, 400 MHz) δ 2.33 (s, 3H), 3.73 (m, 2H), 4.54 (m, 2H), 4.75 (m, 2H), 5.22 (dd, 2H), 6.95 (m, 1H), 7.43 (t, 1H), 7.52 (t, 1H), 7.62 (t, 1H), 7.71 (t, 1H), 7.80 (d, 1H), 7.99 (d, 1H), 8.11 (d, 1H), 8.25 (m, 4H), 8.55 (s, 1H), 8.71 (s, 1H).

3-{2-[3-Methyl-4-(2,2,2-trifluoro-ethoxy)-pyridin-2-yl methanesulfinyl]-benzimidazole-1-sulfonyl}benzoic acid (Compound 1) and its sodium salt A solution of 3-{2-[3-methyl-4-(2,2,2-trifluoro-ethoxy)-pyridin-2-ylmethanesulfinyl]-benzimidazole-1-sulfonyl}-benzoic acid 2-(3-nitro-benzenesulfonyl)ethyl ester (Intermediate 2, 900 mg, 1.17 mmol) and NaHCO$_3$ (118 mg, 1.41 mmol, 1.2 eq.) in THF-H$_2$O (6 mL-3 mL) was heated to 70° C. for 20 min, during which time the heterogeneous mixture became clear. Thereafter all the volatile materials were removed in vacuo, the residual gummy material was dissolved in CH$_2$Cl$_2$, and the mixture was filtered to remove solids. The filtrate was evaporated to dryness in vacuo, and the residual yellow foam was treated with ether-EtOAc (5:1) to precipitate a solid. This solid was collected by filtration to give 630 mg (94%) of 3-{2-[3-methyl-4-(2,2,2-trifluoro-ethoxy)pyridin-2-yl methanesulfinyl]-benzimidazole-1-sulfonyl}benzoic acid sodium salt (sodium salt of Compound 1).

3-{2-[3-Methyl-4-(2,2,2-trifluoro-ethoxy)-pyridin-2-ylmethanesulfinyl]-benzimidazole-1-sulfonyl}benzoic acid (Compound 1)

3-{2-[3-Methyl-4-(2,2,2-trifluoro-ethoxy)-pyridin-2-ylmethanesulfinyl]-benzimidazole-1-sulfonyl}benzoic acid sodium salt (100 mg) was dissolved in 10 ml of water and acidified to pH 3 using 1 N HCl solution, and extracted with dichloromethane. The dichloromethane layer was dried over anhydrous magnesium sulfate, and evaporated to dryness to give the free acid (Compound 1, 76 mg).

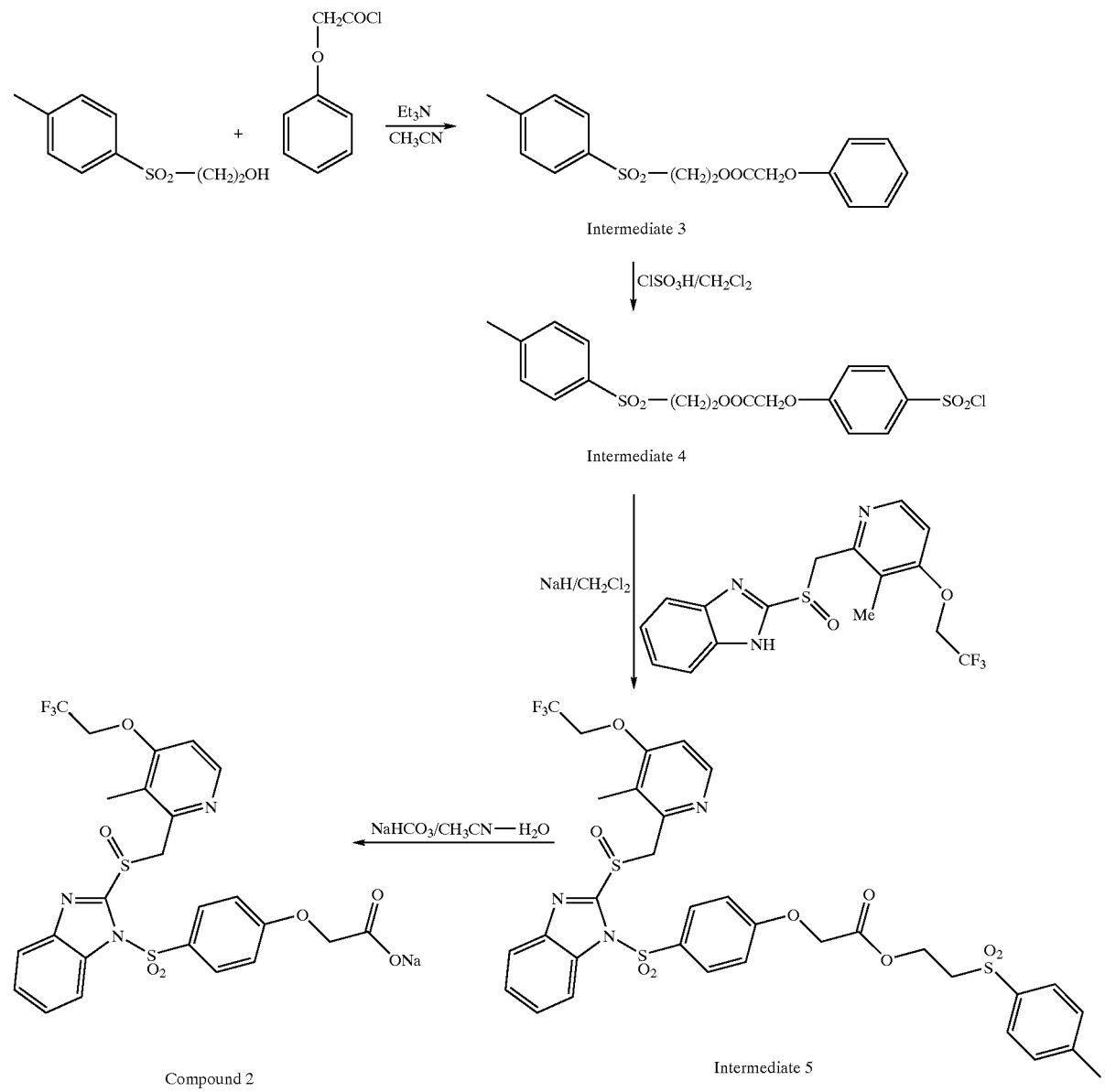

Reaction Scheme 3

$^1$H NMR (DMSO-d$_6$, 400 MHz) δ 2.23 (s, 3H), 4.86 (m, 3H), 5.15 (d, 1H), 6.99 (d, 1H), 7.30 (m, 1H), 7.47 (t, 1H), 7.60 (m, 2H), 7.81 (m, 1H), 7.93 (d, 1H), 8.00 (d, 1H), 8.22 (m, 1H), 8.58 (s, 1H).

Phenoxyacetic acid 2-(toluene-4-sulfonyl)ethyl ester (Intermediate 3)

To a solution of phenoxyacetyl chloride (available from Aldrich 5.0 g) and triethylamine (Et$_3$N) (3 g) in 50 mL of CH$_3$CN was added a solution of the 2-(p-tolylsulfonyl) ethanol (5.0 g) at 0° C. Thereafter water was added and the reaction mixture was extracted with CH$_2$Cl$_2$. The combined organic layers were washed with 1 N HCl and with saturated NaHCO$_3$ solution, dried over anhydrous MgSO$_4$, and concentrated to give 8.0 g (97%) of the ester (Intermediate 3) as a light-yellow solid.

$^1$H NMR (CDCl$_3$, 400 MHz) δ 2.41 (s, 3H), 3.47 (t, 2H), 4.40 (s, 2H), 4.53 (t, 2H), 6.83 (d, 2H), 7.01 (m, 1H), 7.29 (d, 2H), 7.36 (d, 2H), 7.81 (d, 2H).

(4-Chlorosulfonylphenoxy)acetic acid 2-(toluene-4-sulfonyl)ethyl ester (Intermediate 4)

To an ice-bath cooled mixture of phenoxyacetic acid 2-(toluene-4-sulfonyl)ethyl ester (Intermediate 3, 3.0 g) and 1 mL of CH$_2$Cl$_2$ was added drop-wise 3.0 mL of chlorosulfonic acid (5.2 g, 5.0 eq). After the addition of the chlorosulfonic acid was complete the ice bath was removed. The mixture was continued to stir at room temperature for 3 h. Thereafter the thick syrupy mixture was poured onto the crushed ice with vigorous stirring. White precipitates were collected by filtration, were washed with methanol and cold benzene, and dried overnight under high vacuum to yield 3.4 g (87%) of Intermediate 4 as white powder.

$^1$H NMR (CDCl$_3$, 400 MHz) δ 2.44 (s, 3H), 2.47 (t, 2H), 4.59 (t, 2H), 4.63 (s, 2H), 7.03 (d, 2H), 7.40 (d, 2H), 7.80 (d, 2H), 7.98 (d, 2H).

(4-{2-[3-Methyl-4-(2,2,2-trifluoro-ethoxy)-pyridin-2-ylmethanesulfinyl]-benzimidazole-1-sulfonyl}phenoxy)acetic acid 2-(toluene-4-sulfonyl) ethyl ester (Intermediate 5)

To a heterogeneous solution of 2-[3-methyl-4-(2,2,2-trifluoroethoxy)pyridin-2-ylmethanesulfinyl]-1H-benzimidazole (900 mg, 2.44 mmol) in 30 mL of CH$_2$Cl$_2$ was added 70 mg of NaH (2.92 mmol) at room temperature, during which time the mixture became homogeneous. To this clear reaction mixture was added the 4-chlorosulfonylphenoxy)acetic acid 2-(toluene-4-sulfonyl) ethyl ester (Intermediate 4, 1.26 g, 2.92 mmol, 1.2 eq). About 1 g of solid NaHCO$_3$ was added after the chlorosulfonate has dissolved completely in the reaction mixture. (Without addition of NaHCO$_3$ the mixture became black when the reaction was complete.) Thereafter the solvent was removed by evaporation and the residual oil was purified by column chromatography (silica gel, CH$_2$Cl$_2$ to 4% MeOH in CH$_2$Cl$_2$) to give 1.75 g (94%) of the desired product (Intermediate 5) as an off-white foam.

$^1$H NMR (CDCl$_3$, 400 MHz) δ 2.24 (s, 3H), 2.39 (s, 3H), 3.46 (m, 2H), 4.50–4.63 (m, 6H), 5.15–5.27 (dd, 2H), 6.97 (m, 3H), 7.35 (d, 2H), 7.41 (t, 1H), 7.49 (t, 1H), 7.76 (d, 2H), 7.82 (d, 1H), 7.99 (d, 1H), 8.10 (d, 2H), 8.37 (d, 1H).

(4-{2-[3-Methyl-4-(2,2,2-trifluoro-ethoxy)-pyridin-2-ylmethanesulfinyl]-benzimidazole-1-sulfonyl}-phenoxy)acetic acid sodium salt (Compound 2)

(4-{2-[3-Methyl-4-(2,2,2-trifluoro-ethoxy)-pyridin-2-ylmethanesulfinyl]-benzimidazole-1-sulfonyl}phenoxy) acetic acid 2-(toluene-4-sulfonyl)ethyl ester (Intermediate 5, 400 mg, 0.54 mmol) was dissolved in 4 mL of CH$_3$CN and 2 mL of isopropanol, and then a solution of NaHCO$_3$ (48 mg, 0.57 mmol, 1.1 eq) in 3 mL of H$_2$O was added. The mixture was heated to 70° C. for 2 h. Thereafter all volatile materials were removed by evaporation in vacuo and the residual oil was re-dissolved in EtOAc, and the resulting mixture was filtered to remove undissolved solids. The filtrate was concentrated and dried under vacuum to give an off-white foam. The foam was washed with ethyl ether to remove by-product (vinyl toluene sulfone) to yield 300 mg Compound 2 (sodium salt) as an off-white foam.

$^1$H NMR (DMSO-d$_6$, 400 MHz) δ 2.18 (s, 3H), 4.28 (s, 2H), 4.88 (m, 3H), 5.16 (d, 1H), 7.01 (m, 3H), 7.46 (m, 1H), 7.54 (m, 1H), 7.80 (d, 1H), 8.00 (m, 2H), 8.08 (d, 2H).

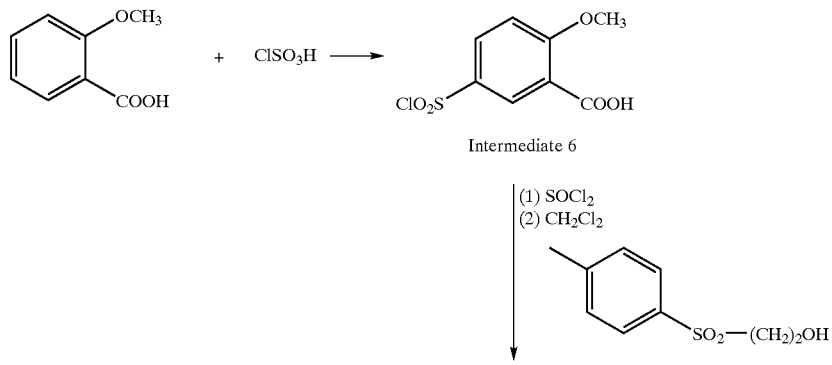

Reaction Scheme 4

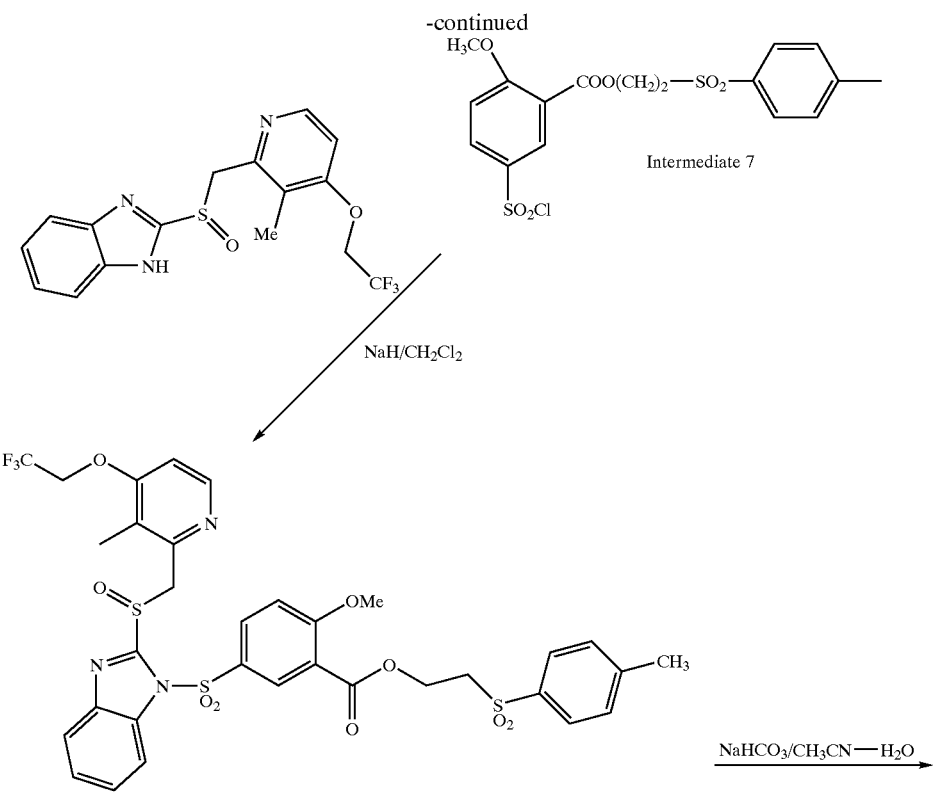

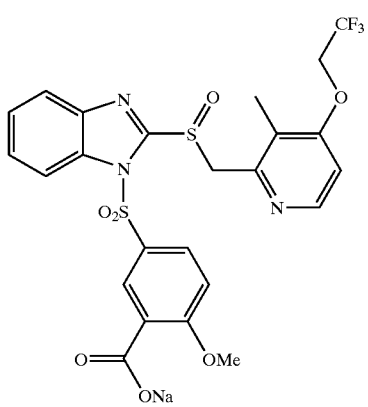

Compound 3

5-Chlorosulfonyl-2-methoxybenzoic acid (Intermediate 6)

2-Methoxybenzoic acid (available from Aldrich, 5.0 g, 32.9 mmol) was warmed with chlorosulfuric acid (164 mmol, 5.0 eq., 19.1 g, 11.0 mmol) at 50° C. for 2 h. The resulting thick brown liquid was poured on crushed ice with vigorous stirring. The resulting white precipitates were filtered, washed with $H_2O$, and dried overnight under high vacuum to give Intermediate 6 (4.8 g, 58%) as a white powder.

$^1$H NMR (DMSO-$d_6$, 400 MHz) δ 3.77 (s, 3H), 7.03 (d, 1H), 7.65 (dd, 1H), 7.84 (s, 1H).

2-(p-Toluenesulfonyl)ethyl 5-chlorosulfonyl-2-methoxybenzoate (Intermediate 7)

A mixture of 5-chlorosulfonyl-2-methoxybenzoic acid (Intermediate 6, 3.0 g, 12.0 mmol) and $SOCl_2$ (6 mL) was heated to reflux temperature for 2 h. Then excess $SOCl_2$ was removed by distillation. The resulting residual oil was dissolved in 20 mL of $CH_2Cl_2$ and 2-(p-toluenesulfonyl) ethanol (available from Aldrich 2.0 g, 10 mmol) in 10 mL of $CH_2Cl_2$ was added at room temperature. The resulting mixture was heated to reflux temperature for 3 h. Thereafter volatile materials were removed under reduced pressure and the residual oil was purified by column chromatography (silica gel, hexane:$CH_2C_2$=1:1 to $CH_2Cl_2$) to give 3.5 g (81%) of 2-(p-toluenesulfonyl)ethyl 5-chlorosulfonyl-2-methoxybenzoate (Intermediate 7) as clear thick oil.

$^1$H NMR (CDCl$_3$, 400 MHz) δ 2.51 (s, 3H), 3.76 (t, 2H), 4.17 (s, 3H), 4.83 (t, 2H), 7.29 (d, 1H), 7.46 (m, 2H), 7.97 (m, 2H), 8.29 (dd, 1H), 8.42 (d, 1H).

2-Methoxy-5-{2-[3-methyl-4-(2,2,2-trifluoro-ethoxy)-pyridin-2-ylmethanesulfinyl]-benzimidazol-1-sulfonyl}benzoic acid 2-(toluene-4-sulfonyl)ethyl ester (Intermediate 8)

To a clear solution of 2-[3-methyl-4-(2,2,2-trifluoroethoxy)pyridin-2-ylmethanesulfinyl]-1H-benzimidazole (740 mg, 2.0 mmol) and NaH (60 mg, 2.5 mmol) in 10 mL of $CH_2Cl_2$ was added 2-(p-toluenesulfonyl)ethyl 5-chlorosulfonyl-2-methoxybenzoate (Intermediate 7, 1.0 g, 2.3 mmol). The resulting mixture was stirred at room temperature for 1.5 h. Thereafter water was added and the mixture was extracted with $CH_2Cl_2$. The dichloromethane layer was dried over anhydrous magnesium sulfate, and evaporated under reduced pressure to give a thick oil. The oil was purified by column chromatography (silica gel, $CH_2Cl_2$ to 2% MeOH in $CH_2Cl_2$) to give 1.0 g (65%) of 2-methoxy-5-{2-[3-methyl-4-(2,2,2-trifluoro-ethoxy)-pyridin-2-ylmethanesulfinyl]-benzimidazole-1-sulfonyl}benzoic acid 2-(toluene-4-sulfonyl)ethyl ester (Intermediate 8).

$^1$H NMR (CDCl$_3$, 400 MHz) δ 2.28 (s, 3H), 2.31 (s, 3H), 3.54 (m, 2H), 3.92 (s, 3H), 4.58 (m, 4H), 5.22 (dd, 2H), 6.95 (m, 1H), 7.09 (d, 1H), 7.22 (d, 2H), 7.42 (t, 1H), 7.51 (t, 1H), 7.78 (m, 3H), 8.03 (d, 1H), 8.30 (dd, 1H), 8.36 (dd, 1H), 8.52 (d, 1H).

2-methoxy-5-{2-[3-methyl-4-(2,2,2-trifluoro-ethoxy)-pyridin-2-ylmethanesulfinyl]benzimidazole-1-sulfonyl}-benzoic acid sodium salt (Compound 3)

A mixture of 2-methoxy-5-{2-[3-methyl-4-(2,2,2-trifluoro-ethoxy)-pyridin-2-ylmethanesulfinyl]-benzimidazole-1-sulfonyl}benzoic acid 2-(toluene-4-sulfonyl)ethyl ester (Intermediate 8, 400 mg, 0.52 mmol) and NaHCO$_3$ (52 mg, 0.62 mmol, 1.2 eq) in CH$_3$CN (3 mL)-H2O (2 mL)-i-PrOH (1 mL) was heated to 70° C. for 1.5 h. Then volatile materials were removed by evaporation and the residual oil was dissolved in $CH_2Cl_2$-MeOH, the mixture was filtered to remove insoluble solids. The filtrate was concentrated by evaporation. The residual syrup was dissolved in H$_2$O, and the mixture was extracted with $CH_2Cl_2$ (2 times) to remove the starting material, lansoprazole and tolyl vinyl sulfone. The water solution was freeze-dried to yield 200 mg (65%) Compound 3 sodium salt as a light yellow solid.

$^1$H NMR (DMSO-d$_6$, 400 MHz) δ 2.24 (s, 3H), 3.78 (s, 3H), 4.88 (m, 3H), 5.14 (d, 1H), 7.01 (d, 1H), 7.14 (d, 1H), 7.46 (d, 1H), 7.55 (t, 1H), 7.81 (d, 1H), 7.88 (s, 1H), 7.97 (d, 1H), 8.02 (d, 1H), 8.10 (d, 1H).

Reaction Scheme 5

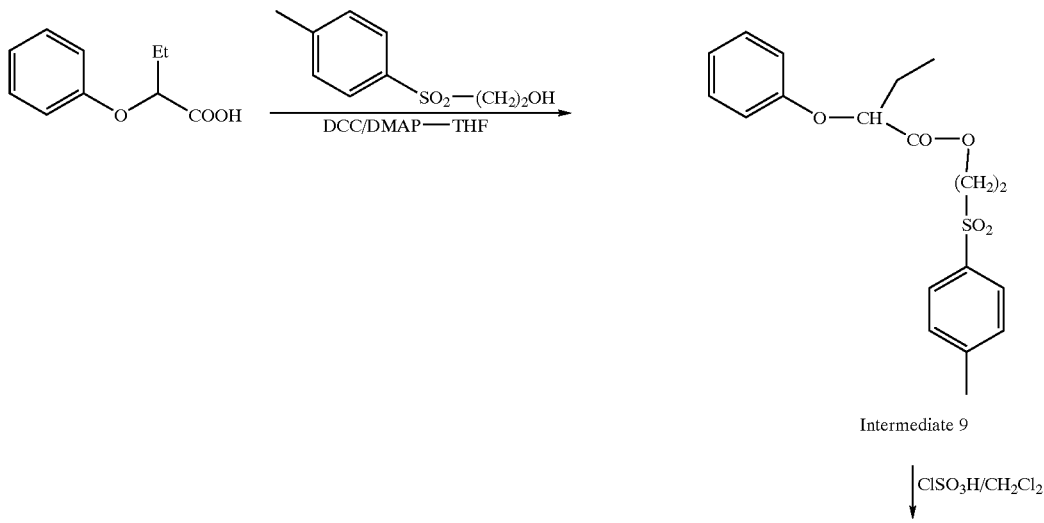

Intermediate 9

ClSO$_3$H/CH$_2$Cl$_2$

-continued

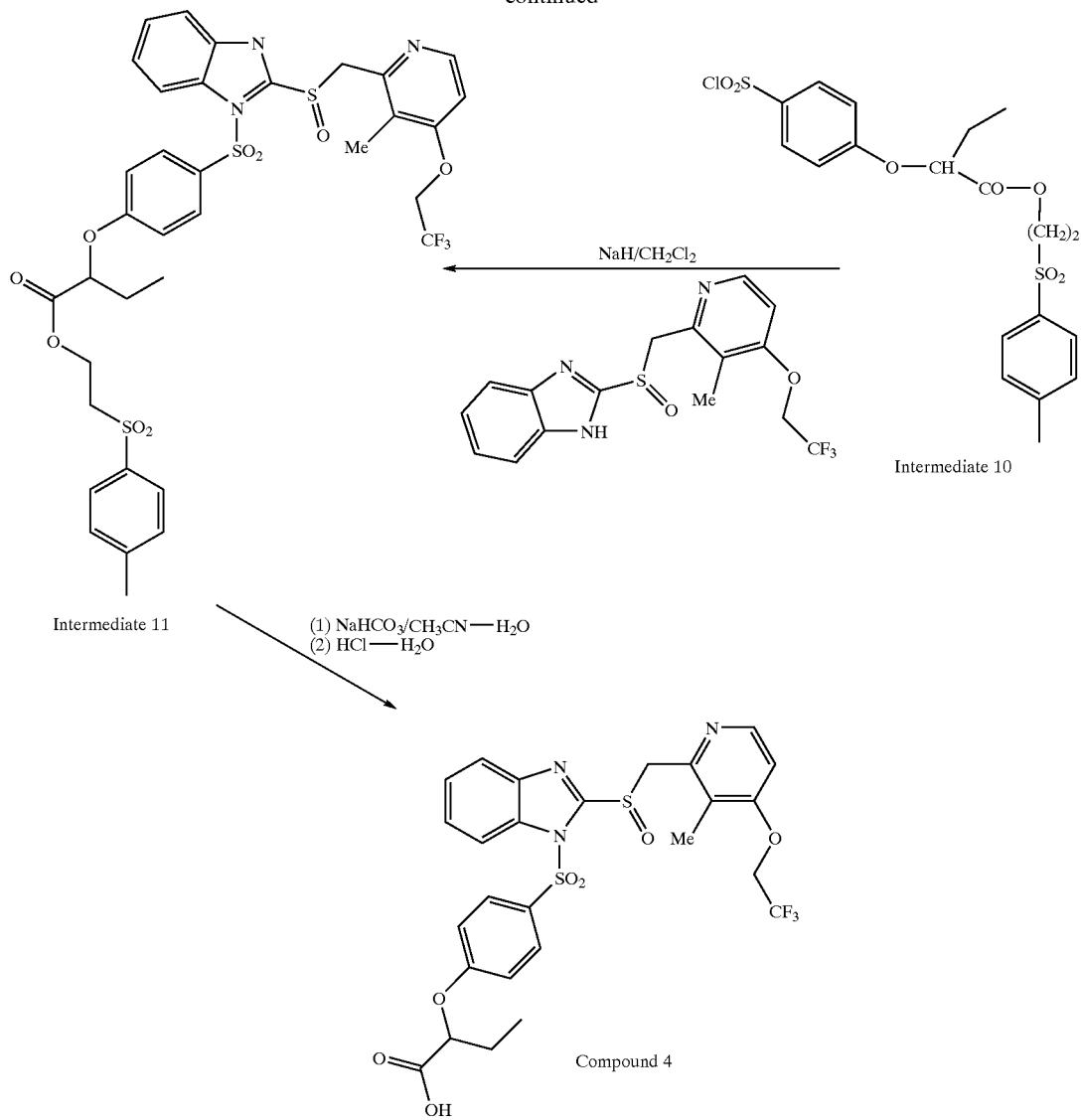

Intermediate 10

Intermediate 11

(1) NaHCO₃/CH₃CN—H₂O
(2) HCl—H₂O

Compound 4

Phenoxy-2-butyric acid 2-(p-toluenesulfonyl)ethyl ester (Intermediate 9)

To a mixture of phenoxy-2-butyric acid (available from Aldrich, 2.51 g, 13.8 mmol), 2-(p-toluenesulfonyl)ethanol (2.8 g, 13.8 mmol), and 0.5 g of p-dimethyaminopyridine (DMAP) in 50 mL of tetrahydrofuran (THF) was added N,N'-dicyclohexyl carbodiimide (DCC) (3.14 g, 15.2 mmol, 1.1 eq) in 15 mL of THF at 0° C. The resulting mixture was stirred overnight at room temperature. Then a white solid was removed from the reaction mixture by filtration and the filtrate was concentrated by evaporation. The resulting residual oil was purified by column chromatography (hexane-CH₂Cl₂ to CH₂Cl₂) to yield Intermediate 9, (4.1 g, 82%) as a clear oil.

$^1$H NMR (CDCl₃, 400 MHz) δ 1.02 (t, 3H), 1.86 (m, 2H), 2.45 (s, 3H), 3.40 (m, 2H), 4.45 (m, 3H), 6.82 (d, 2H), 6.97 (t, 1H), 7.26 (t, 2H), 7.37 (d, 2H), 7.77 (d, 2H).

4-Chlorosulfonylphenoxy-2-butyric acid 2-(p-toluenesulfonyl)ethyl ester (Intermediate 10)

To an ice-bath cooled mixture of phenoxy-2-butyric acid 2-(p-toluenesulfonyl)ethyl ester (Intermediate 9, 4.0 g, 11.0 mmol) and 1 mL of CH₂Cl₂ chlorosulfonic acid (3.7 mL, 6.4 g, 5.0 eq) was added slowly. After the addition of chlorosulfonic acid was complete the ice bath was removed. The resulting mixture was stirred at room temperature for 3 h. Then the thick syrupy mixture was poured onto crushed ice with vigorous stirring to give a gummy precipitate. The mixture of the precipitate, ice and water was extracted with CH₂Cl₂, and the organic layers were dried over MgSO₄, and concentrated by evaporation to yield 4.1 g (81%) of 4-chlorosulfonylphenoxy-2-butyric acid 2-p-toluenesulfonyl)ethyl ester (Intermediate 10).

$^1$H NMR (CDCl₃, 400 MHz) δ 1.06 (t, 3H), 1.97 (m, 2H), 2.45 (2 s, 3H), 3.41 (m, 2H), 4.46 (m, 1H), 4.63 (m, 2H), 7.01 (dd, 2H), 7.38 (d, 2H), 7.78 (d, 2H), 7.96 (dd, 2H).

2-(4-{2-[3-Methyl-4-(2,2,2-trifluoro-ethoxy)-pyridin-2-ylmethanesulfinyl]-benzimidazole-1-sulfonyl}phenoxy)butyric acid 2-(toluene-4-sulfonyl)ethyl ester (Intermediate 11)

To a heterogeneous mixture of 2-[3-methyl-4-(2,2,2-trifluoroethoxy)pyridin-2-ylmethanesulfinyl]-1H- benzimidazole (500 mg, 1.36 mmol) in $CH_2Cl_2$ (10 mL) was added NaH (35 mg, 1.45 mmol) at room temperature resulting in a clear solution. To this clear mixture was added 4-chlorosulfonylphenoxy-2-butyric acid 2-(p-toluenesulfonyl)ethyl ester (Intermediate 10, 700 mg, 1.52 mmol, 1.12 eq) in $CH_2Cl_2$ at room temperature, and the resulting mixture was stirred for 2 h.

Thereafter water was added and the mixture was extracted with $CH_2Cl_2$. The organic layers were dried and concentrated by evaporation. The residual oil was purified by column chromatography (3% MeOH in $CH_2Cl_2$) to yield Intermediate 11 (1.0 g, 93%) as a white foam.

$^1$H NMR ($CDCl_3$, 400 MHz) δ 0.99 (m, 3H), 1.89 (m, 2H), 2.28 (s, 3H), 2.42 (2 s, 3H), 3.38 (m, 2H), 4.43–4.53 (m, 5H), 5.01 (m, 1H), 5.14 (d, 1H), 6.81 (m, 1H), 6.92 (dd, 2H), 7.33–7.50 (m, 4H), 7.76 (m, 3H), 8.00 (d, 1H), 8.06 (d, 2H), 8.29 (d, 1H).

2-(4-{2-[3-Methyl-4-(2,2,2-trifluoro-ethoxy)-pyridin-2-ylmethanesulfinyl]-benzimidazole-1-sulfonyl}phenoxy)butric acid (Compound 4)

A solution of 2-(4-{2-[3-methyl-4-(2,2,2-trifluoro-ethoxy)-pyridin-2-ylmethanesulfinyl]-benzoimidazole-1-sulfonyl}phenoxy)butyric acid 2-(toluene-4-sulfonyl)ethyl ester (Intermediate 11, 400 mg, 0.50 mmol) and $NaHCO_3$ (47 mg, 0.55 mmol, 1.1 eq) in $CH_3CN-H_2O$ (7 mL-3 mL) was heated to 70° C. for 3 h. Then volatile materials were removed by evaporation and the residual gummy oil was dissolved in $CH_3CN$. The $CH_3CN$ solution was filtered to remove un-dissolved solids. The filtrate was dried and the residual yellow foam was treated with ether-EtOAc (5:1) to precipitate a solid. The solid was again treated with $CH_3CN$, and the $CH_3CN$ solution was filtered to give 180 mg (58%) of 2-(4-{2-[3-methyl-4-(2,2,2-trifluoro-ethoxy)-pyridin-2-ylmethanesulfinyl]-benzimidazole-1-sulfonyl}phenoxy) butyric acid sodium salt (Compound 4 sodium salt). The sodium salt was dissolved in water, and acidified to pH 3 by 1 N HCl solution, and extracted with dichloromethane. The dichloromethane layer was evaporated to give Compound 4 as a free acid, which was further purified on a short silica gel column to yield 125 mg of 2-(4-{2-[3-methyl-4-(2,2,2-trifluoro-ethoxy)-pyridin-2-ylmethanesulfinyl] benzimidazole-1-sulfonyl}phenoxy)butyric acid (Compound 4).

$^1$H NMR (DMSO-$d_6$, 400 MHz) δ 0.88 (t, 3H), 1.83 (m, 2H), 2.20 (s, 3H), 4.75 (m, 1H), 4.84 (m, 3H), 5.11 (m, 1H), 6.96 (d, 1H), 7.06 (d, 2H), 7.42 (t, 1H), 7.51 (t, 1H), 7.77 (d, 1H), 7.95 (m, 2H), 8.10 (d, 2H).

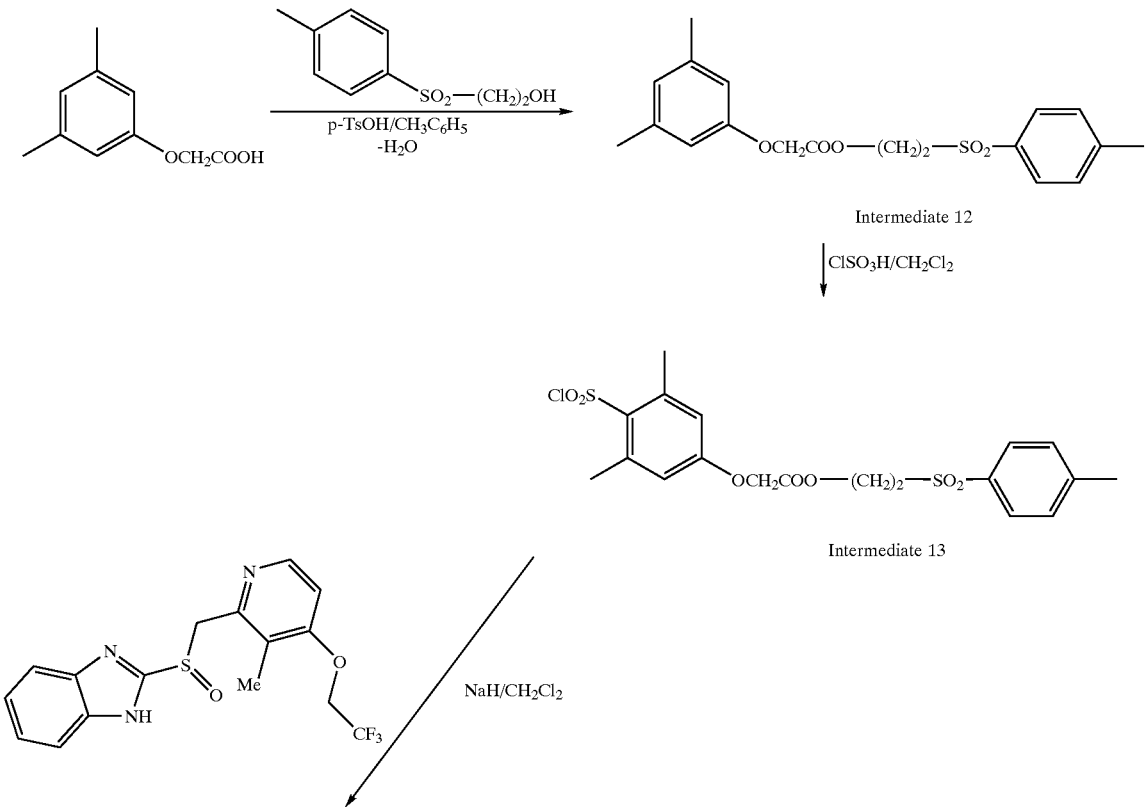

Reaction Scheme 6

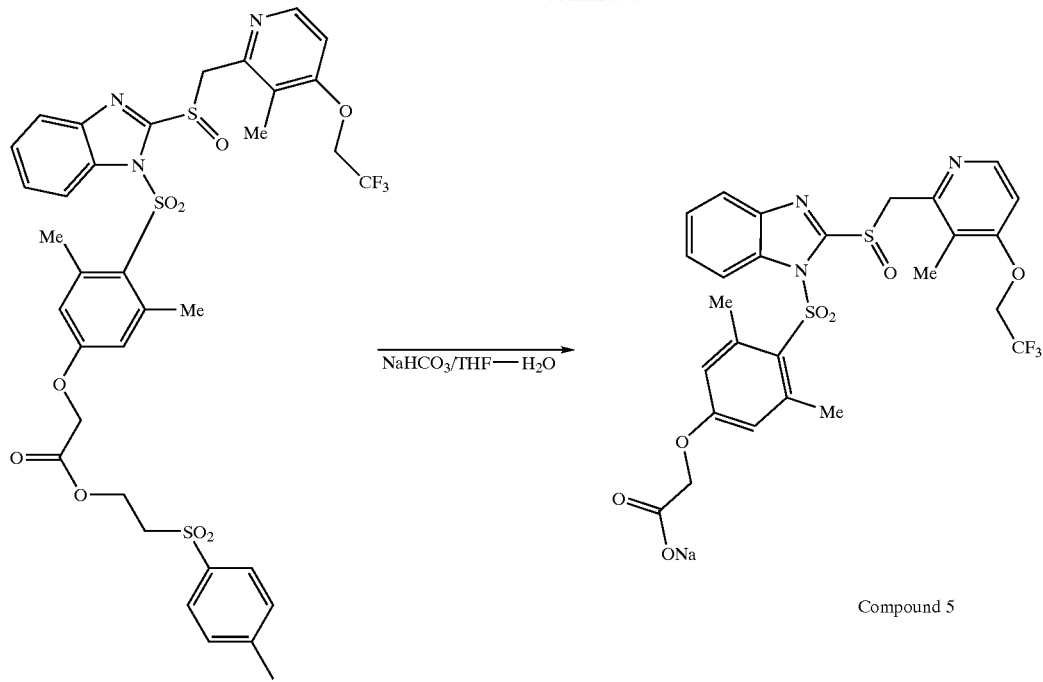

Intermediate 14

Compound 5

3,5-Dimethyl phenoxyacetic acid 2-(p-toluenesulfonyl)ethyl ester (Intermediate 12)

3,5-dimethyl phenoxyacetic acid was prepared, following a known method, as follows:

3,5-dimethylphenol (12.2 g, 0.1 mole) and chloroacetic acid (18.9 g, 0.2 mole) was dissolved in 50% aqueous isopropanol (300 ml), and 3-equimolar NaOH (12 g, 0.3 mole) was added slowly. The reaction mixture was refluxed overnight and thereafter concentrated by distillation. The residue was diluted to 300 ml by adding water and acidified to pH 1. The mixture was extracted with dichloromethane (500 ml). The dichloromethane layer was concentrated under reduced pressure to give the product and small amounts of unreacted phenol. The solids were crystallized from benzene-hexane to give pure product, 15.6 g (86.6%).

A mixture of 3,5-dimethyl phenoxyacetic acid (prepared as described above, 2.3 g, 12.6 mmol), 2-(p-toluenesulfonyl) ethanol (2.3 g, 11.5 mmol), and p-toluenesulfonic acid hydrate (pTsOH.H$_2$O) (0.5 g) in 100 mL of toluene was refluxed with Dean-Stark trap for 4 h. Then water was added and the mixture was extracted with CH$_2$Cl$_2$. The combined organic layers were washed with saturated NaHCO$_3$ solution (2×), dried over MgSO$_4$, and concentrated to give Intermediate 12 (4.4 g, 97%) as a yellowish thick oil.

$^1$H NMR (CDCl$_3$, 400 MHz) δ 2.29 (s, 6H), 2.42 (s, 3H), 4.37 (s, 2H), 4.53 (t, 2H), 6.64 (s, 1H), 7.36 (m, 2H), 7.81 (d, 2H).

4-Chlorosulfonyl-3,5-dimethyl phenoxyacetic acid 2-(p-toluenesulfonyl)ethyl ester (Intermediate 13)

To a mixture of 3,5-dimethyl phenoxyacetic acid 2-(p-toluenesulfonyl)ethyl ester (Intermediate 12, 4.0 g, 11.0 mmol) and CH$_2$Cl$_2$ (1.5 mL) was added drop-wise ClSO$_3$H with cooling, and then the mixture was stirred vigorously at 0° C. for 2 h. The resulting thick oil was poured onto the crushed ice with vigorous stirring. The mixture was extracted with CH$_2$Cl$_2$. The organic layer was dried over MgSO$_4$, and concentrated by evaporation to give a thick oil. Upon treatment with diethyl ether (2 mL) and hexane (2 mL), the oil solidified. The solid was dried under vacuum to give 4-chlorosulfonyl-3,5-dimethyl phenoxyacetic acid 2-p-toluenesulfonyl)ethyl ester (Intermediate 13, 4.7 g 94%) as an off-white solid.

$^1$H NMR (CDCl$_3$, 400 MHz) δ 2.44 (s, 3H), 2.73 (s, 6H), 3.46 (t, 2H), 4.57 (t, 2H), 4.60 (s, 2H), 6.80 (s, 2H), 7.38 (d, 2H), 7.80 (d, 2H).

(3,5-Dimethyl-4-{2-[3-methyl-4-(2,2,2-trifluoro-ethoxy)-pyridin-2-ylmethanesulfinyl]-benzimidazole-1-sulfonyl}phenoxy)acetic acid 2-(toluene-4-sulfonyl)ethyl ester (Intermediate 14)

To a heterogeneous mixture of 2-[3-methyl-4-(2,2,2-trifluoroethoxy)pyridin-2-ylmethanesulfinyl]-1H-benzimidazo[500 mg, 1.36 mmol) in CH$_2$Cl$_2$ (10 mL) was added NaH (40 mg, 1.65 mmol) at room temperature resulting in a clear solution. To this clear mixture was added 4-chlorosulfonyl-3,5-dimethyl phenoxyacetic acid 2-(p-toluenesulfonyl)ethyl ester (Intermediate 13, 760 mg, 1.65 mmol, 1.2 eq) in CH$_2$Cl$_2$ (5 mL) at room temperature and the mixture was stirred for 4 h. Thereafter water was added, the mixture was extracted with CH$_2$Cl$_2$, and the organic layers were dried and concentrated by evaporation. The residual oil was purified by column chromatography (3% MeOH in CH$_2$Cl$_2$) to yield (3,5-dimethyl-4-{2-[3-methyl-4-(2,2,2-trifluoro-ethoxy)-pyridin-2-ylmethanesulfinyl]- benzimidazole-1-sulfonyl}phenoxy)acetic acid 2-(toluene-4-sulfonyl)ethyl ester (Intermediate 14, 700 mg 65%) as an off-white foam.

$^1$H NMR (CDCl$_3$, 400 MHz) δ 2.04 (s, 3H), 2.43 (s, 3H), 2.56 (s, 6H), 3.44 (t, 2H), 4.55 (t, 6H), 4.92 (d, 1H), 5.04 (d, 1H), 6.71 (s, 2H), 7.38 (m, 5H), 7.77 (m, 3H), 7.88 (d, 1H), 8.33 (d, 1H).

(3,5-Dimethyl-4-{2-[3-methyl-4-(2,2,2-trifluoro-ethoxy-pyridin-2-ylmethanesulfinyl]-benzimidazole-1-sulfonyl}phenoxy)acetic acid sodium salt (Compound 5)

A solution of (3,5-dimethyl-4-{2-[3-methyl-4-(2,2,2-trifluoro-ethoxy)-pyridin-2-ylmethanesulfinyl]-benzimidazole-1-sulfonyl}phenoxy)acetic acid 2-(toluene-4-sulfonyl)ethyl ester (Intermediate 14, 400 mg, 0.50 mmol) and NaHCO$_3$ (51 mg, 0.60 mmol, 1.2 eq) in THF-H$_2$O (6 mL-3 mL) was heated to 70° C. for 3 h. Then volatile materials were removed, the residual gummy oil was dissolved in THF and the mixture was filtered to remove un-dissolved solid. The filtrate was dried, the solvent was removed by evaporation to give a yellow foam which was treated with ether-EtOAc (5:1) to precipitate a solid. The solid was treated with CH$_3$CN, and then collected by filtration to give Compound 5 (230 mg, 72%) as a light yellow solid.

$^1$H NMR (DMSO-d$_6$, 400 MHz) δ 2.12 (s, 3H), 2.39 (s, 6H), 4.20 (s, 2H), 4.84 (m, 4H), 6.72 (s, 2H), 6.98 (d, 1H), 7.46 (m, 3H), 7.84 (d, 1H), 8.04 (d, 1H).

Reaction Scheme 7

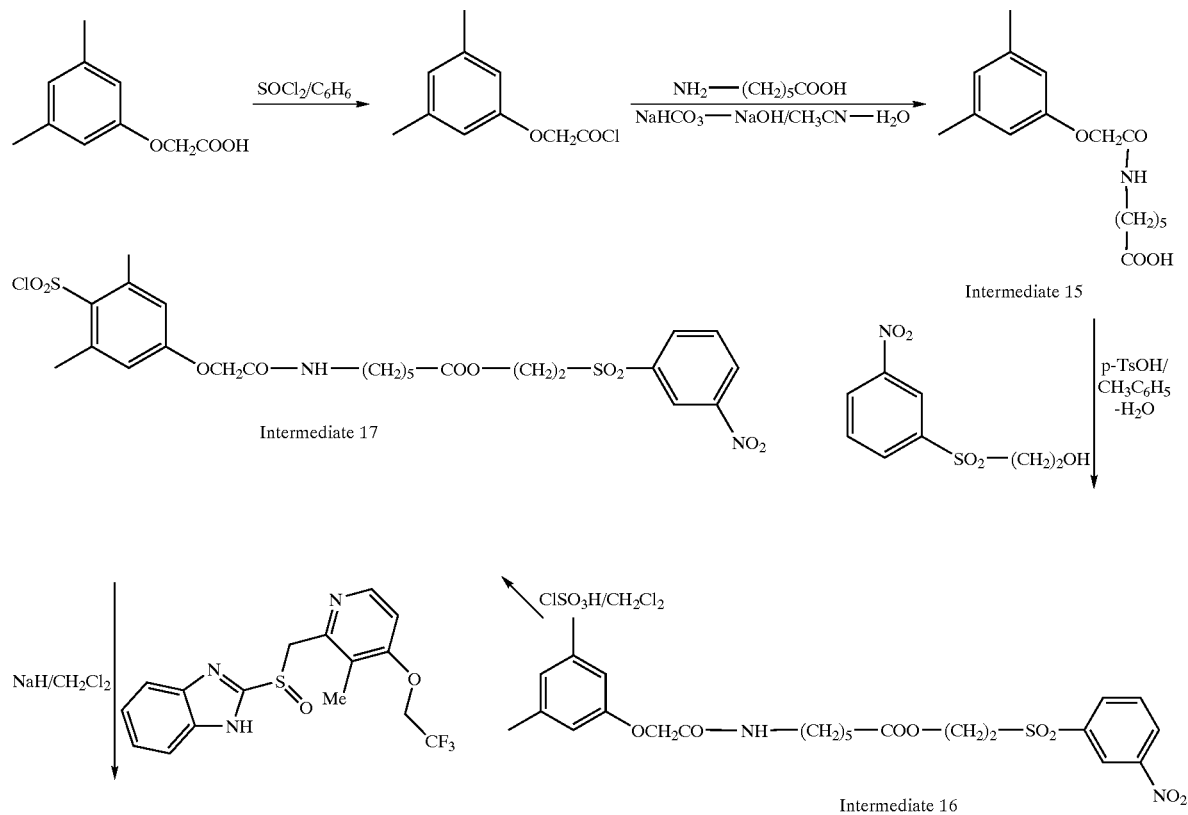

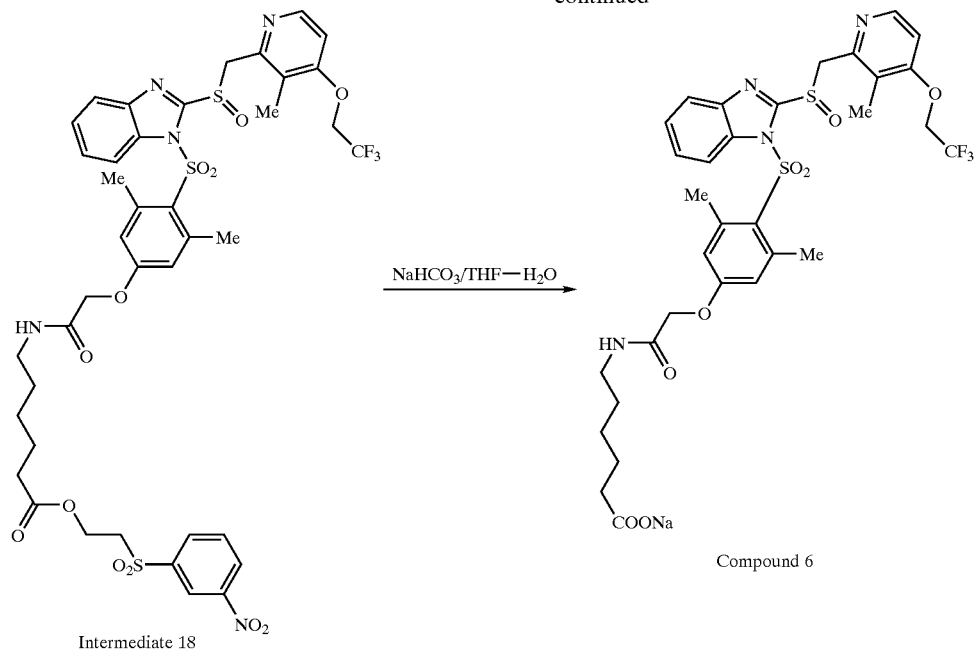

Compound 6

6-[2-(3,5-Dimethyl-phenoxy)acetylamino]hexanoic acid (Intermediate 15)

A mixture of the 3,5-dimethylphenoxyacetic acid (prepared as described above, 9.3 g, 51.6 mmol) and $SOCl_2$ (11.3 mL, 18.5 g, 156 mmol, 3.0 eq) in 10 mL of benzene was refluxed for 2 h. Then volatile materials were removed by vacuum distillation to give 3,5-dimethylphenoxyacetic acid chloride as a light brown oil. To an ice-bath cooled solution of 6-amino-n-caproic acid (13.5 g, 103 mmol, 2.0 eq) and NaOH (4.2 g, 105 mmol) in 100 mL of $H_2O$ and 130 mL of $CH_3CN$ were added drop-wise a solution of the acid chloride (prepared in previous step) in 100 mL of $CH_3CN$ and a solution of $NaHCO_3$ (6.5 g, 77.0 mmol, 1.5 eq) in 80 mL of $H_2O$. The mixture was stirred vigorously overnight. Then most of the $CH_3CN$ was removed under reduced pressure and the mixture was acidified to pH 2 at room temperature with conc-HCl. The resulting white precipitates were collected by filtration, washed with $H_2O$, followed by hexane, and thereafter dried under high vacuum to yield Intermediate 15 (14.5 g, 95%) as a white solid.

$^1$H NMR ($CDCl_3$, 400 MHz) δ 1.35 (m, 2H), 1.56 (m, 2H), 1.64 (m, 2H), 2.29 (s, 6H), 2.35 (m, 2H), 3.34 (m, 2H), 4.44 (s, 2H), 6.47 (s, 2H), 6.70 (s, 1H).

6-[2-(3,5-Dimethyl-phenoxy)acetylamino]hexanoic acid 2-(3-nitrobenzenesulfonyl)ethyl ester (Intermediate 16)

A mixture of 6-[2-(3,5-dimethyl-phenoxy)acetylamino]hexanoic acid (Intermediate 15, 3.0 g, 10.2 mmol), 2-(m-nitrobenzenesulfonyl)ethanol (available from Aldrich 2.3 g, 10.0 mmol), and p-toluenesulfonic acid hydrate (0.5 g) in 100 mL of toluene was refluxed overnight with Dean-Stark trap. Then water was added and the mixture was extracted with $CH_2Cl_2$. The combined organic layers were washed with saturated $NaHCO_3$ solution two times, dried over anhydrous $MgSO_4$, and concentrated under reduced pressure. The resulting residual oil was purified by column chromatography (1% MeOH in $CH_2Cl_2$) to give Intermediate 16 (4.8 g, 89%) as a yellowish thick oil.

$^1$H NMR ($CDCl_3$, 400 MHz) δ 1.25 (m, 2H), 1.51 (m, 4H), 2.07 (t, 2H), 2.27 (s, 6H), 2.31 (m, 2H), 3.53 (t, 2H), 4.45 (m, 4H), 6.53 (s, 2H), 6.65 (s, 1H), 7.82 (t, 1H), 8.26 (d, 1H), 8.52 (m, 1H), 8.77 (s, 1H).

6-[2-(4-Chlorosulfonyl-3,5-dimethyl-phenoxy)acetylamino]hexanoic acid 2-(3-nitro-benzenesulfonyl)ethyl ester (Intermediate 17)

To a cooled solution of 6-[2-(3,5-dimethyl-phenoxy)acetylamino]hexanoic acid 2-(3-nitrobenzenesulfonyl)ethyl ester (Intermediate 16, 4.6 g, 9.1 mmol) in 3 mL of $CH_2Cl_2$ was added drop-wise $ClSO_3H$ (3 mL, 5 eq., 45.5 mmol)) at 0° C. During the reaction small aliquots of the reaction mixture were taken out as samples, treated with ice, extracted with ethyl acetate, and the ethyl acetate layers were analyzed by thin layer chromatography (TLC). TLC analysis showed that the reaction was complete after 30 min. Then the resulting thick reaction mixture was poured onto the crushed ice with vigorous stirring to give a yellow gummy material mostly in the bottom of the flask. This mixture was extracted with $CH_2Cl_2$, the organic layers were dried over anhydrous $MgSO_4$, and concentrated under reduced pressure to give Intermediate 17 (2.2 g, 40%) as a white foam.

$^1$H NMR ($CDCl_3$, 400 MHz) δ 1.26 (m, 2H), 1.50 (m, 4H), 2.08 (t, 2H), 2.73 (s, 6H), 2.30 (m, 2H), 3.52 (t, 2H), 4.44 (t, 2H), 4.63 (s, 2H), 6.80 (s, 2H), 7.82 (t, 1H), 8.26 (d, 1H), 8.52 (m, 1H), 8.77 (s, 1H).

6-[2-(3,5-Dimethyl-4-{2-[3-methyl-4-(2,2,2-trifluoro-ethoxy)-pyridin-2-ylmethanesulfinyl]-benzimdazole-1-sulfonyl{phenoxy)acetylamino]hexanoic acid 2-(3-nitro-benzenesulfonyl)ethyl ester (Intermediate 18)

To a heterogeneous mixture of 2-[3-methyl-4-(2,2,2-trifluoroethoxy)pyridin-2-ylmethanesulfinyl]-1H-benzimidazo (500 mg, 1.35 mmol) in $CH_2Cl_2$ was added NaH (40 mg, 1.65 mmol) at room temperature resulting in a clear solution. To this clear mixture was added 6-[2-(4- chlorosulfonyl-3,5-dimethyl-phenoxy)acetylamino]hexanoic acid 2-(3-nitro-benzenesulfonyl)ethyl ester (Intermediate 17, 1.0 g, 1.65 mmol, 1.2 eq), in CH₂Cl₂ at room temperature, and the mixture was stirred for 4 h. Thereafter water was added, the mixture was extracted with CH₂Cl₂, and the organic layers were dried and concentrated under reduced pressure. The resulting oil was purified by column chromatography (3% MeOH in CH₂Cl₂) to yield Intermediate 18 (860 mg, 68%) as a white foam.

$^1$H NMR (CDCl$_3$, 400 MHz) δ 1.24 (m, 2H), 1.49 (m, 4H), 2.08 (t, 2H), 2.18 (s, 3H), 2.55 (s, 6H), 3.30 (m, 2H), 3.53 (t, 2H), 4.47 (m, 6H), 4.95 (dd, 2H), 6.73 (s, 2H), 6.85 (m, 1H), 7.40 (m, 2H), 7.55 (m, 1H), 7.85 (m, 2H), 8.26 (m, 1H), 8.35 (d, 1H), 8.52 (d, 1H), 8.75 (s, 1H).

6-[2-(3,5-Dimethyl-4-{2-[3-methyl-4-(2,2,2-trifluoro-ethoxy)-pyridin-2-ylmethanesulfinyl]-benzimidazole-1-sulfonyl}-phenoxy)acetylamino]hexanoic acid sodium salt (Compound 6)

A solution of 6-[2-(3,5-dimethyl-4-{2-[3-methyl-4-(2,2,2-trifluoroethoxy)-pyridin-2-ylmethanesulfinyl]-benzimdazole-1-sulfonyl}phenoxy)acetylamino]hexanoic acid 2-(3-nitro-benzenesulfonyl)ethyl ester (Intermediate 18, 420 mg, 0.45 mmol) and of NaHCO₃ (42 mg, 0.49 mmol) in THF-H₂O (6 mL-3 mL) was heated to 70° C. for 1 h. Then volatile materials were removed, the residual gummy oil was dissolved in CH₂Cl₂ and the mixture was filtered to remove un-dissolved solid. The filtrate was concentrated to dryness and the residual semi-solid was treated with diethyl ether to precipitate a solid which was briefly treated with CH₃CN. The solid was collected from CH₃CN suspension by filtration to give Compound 6 (170 mg 50%) as a white solid.

$^1$H NMR (DMSO-d$_6$, 400 MHz) δ 1.19 (m, 2H), 1.40 (m, 4H), 1.92 (t, 2H), 2.16 (s, 3H), 2.48 (s, 6H), 3.05 (m, 2H), 4.36 (s, 2H), 4.47 (d, 1H), 4.70 (d, 1H), 4.86 (q, 2H), 6.50 (s, 2H), 6.92 (m, 1H), 7.05 (d, 1H), 7.47 (m, 2H), 8.02 (m, 2H), 8.31 (d, 1H).

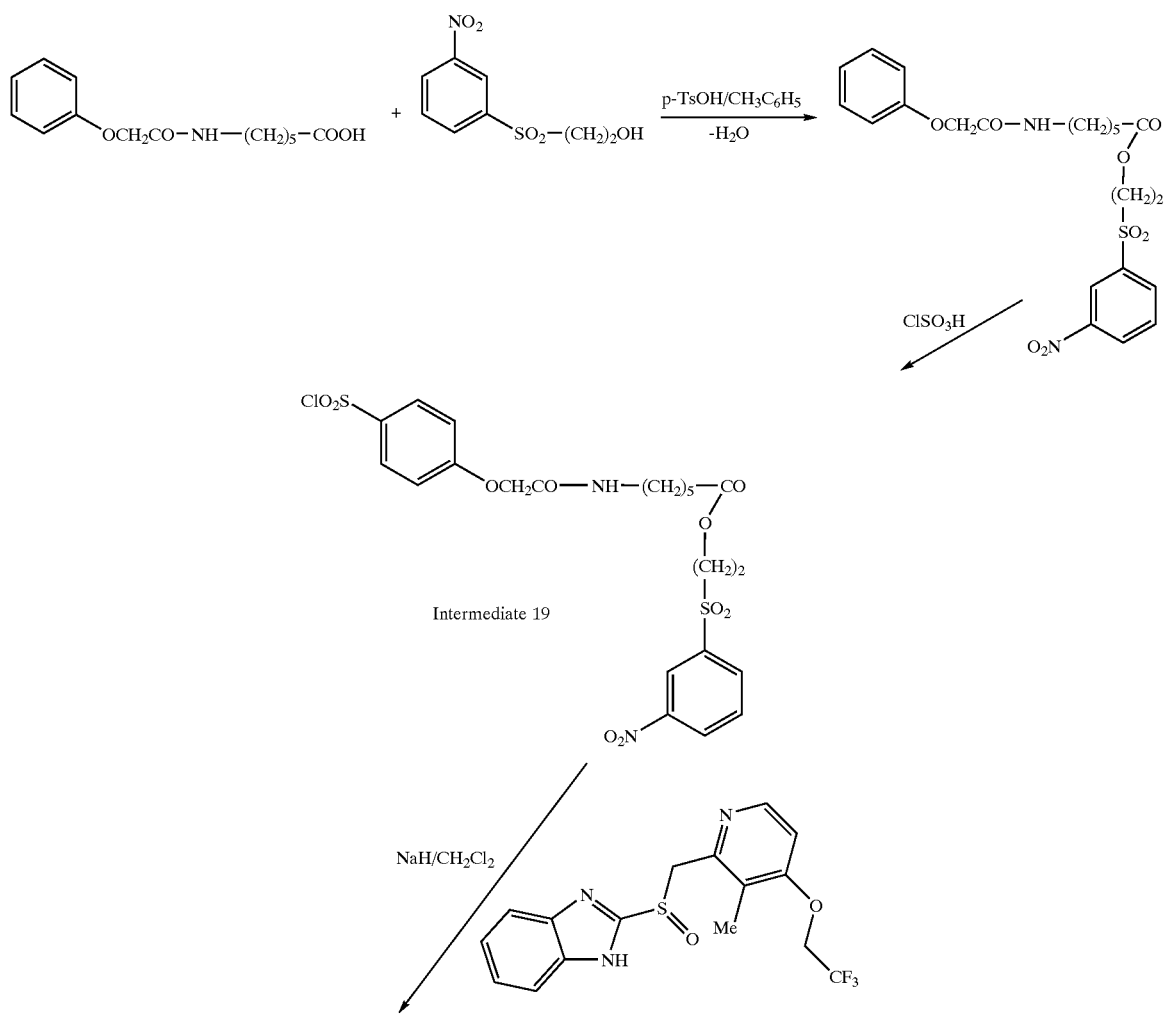

Reaction Scheme 8

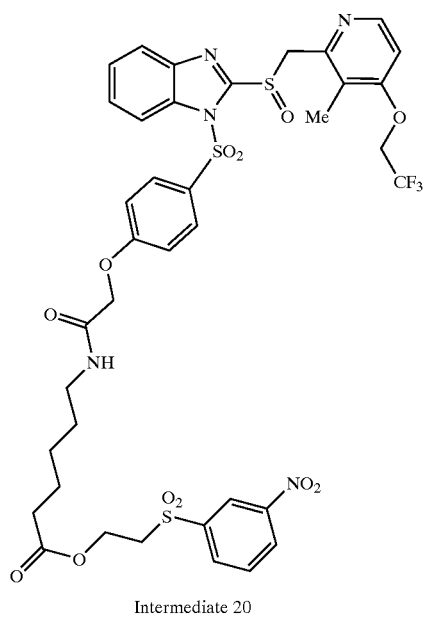

Intermediate 20

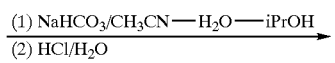

(1) NaHCO₃/CH₃CN—H₂O—iPrOH
(2) HCl/H₂O

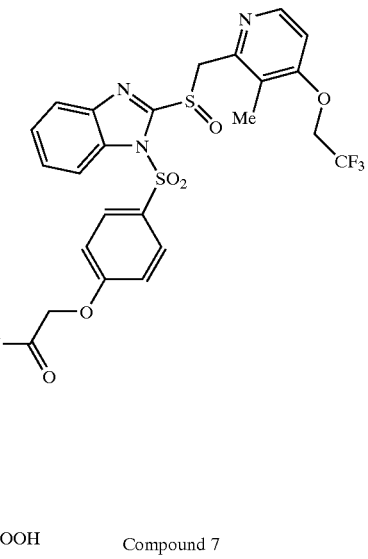

Compound 7

6-[2-(4-{2-[3-Methyl-4-(2,2,2-trifluoro-ethoxy)-pyridin-2-ylmethanesulfinyl]-benzimdazole-1-sulfonyl}phenoxy)acetylamino]hexanoic acid 2-(3-nitro-benzenesulfonyl)ethyl ester (Intermediate 20)

A mixture of 6-(2-phenoxyacetylamino)-n-hexanoic acid (made in analogy to Intermediate 15, 3.15 g, 11.9 mmol, 1.1 eq), 2-(m-nitrobenzenesulfonyl)ethanol (2.5 g, 10.8 mmol), and p-toluenesulfonic acid hydrate (0.5 g) in 100 mL of benzene was refluxed overnight with Dean-Stark trap. Thereafter water was added and the mixture was extracted with $CH_2Cl_2$. The combined organic layers were washed with saturated $NaHCO_3$ solution, dried over $MgSO_4$, and concentrated under reduced pressure. The residual oil was purified by column chromatography (1% MeOH in $CH_2Cl_2$) to give 4.6 g (89%) of 6-(2-phenoxy-acetylamino)-n-hexanoic acid 2-(3-nitrobenzenesulfonyl)ethyl ester.

To a cooled solution of 6-(2-phenoxy-acetylamino)-n-hexanoic acid 2-(3-nitro-benzenesulfonyl)ethyl ester (4.5 g, 9.4 mmol) in 10 mL of $CH_2Cl_2$ was added drop-wise $ClSO_3H$ (3.3 mL, 5.5 g, 5 eq., 47.0 mmol)) at 0° C. The chlorosulfonylation reaction was complete in 30 min. The thick reaction mixture was poured onto the crushed ice with vigorous stirring, resulting in a yellow gummy material mostly in the bottom of the flask. The mixture was extracted with $CH_2Cl_2$, the organic layers were dried over anhydrous magnesium sulfate and concentrated under reduced pressure to give a syrupy material, which was purified by column chromatography ($CH_2Cl_2$ to 1% MeOH in $CH_2Cl_2$) to give 6-[2-(4-chlorosulfonyl-phenoxy)-acetylamino]-n-hexanoic acid 2-(3-nitro-benzenesulfonyl)ethyl ester (Intermediate 19, 3.3 g, 60%) as a white foam.

6-[2-(4-chlorosulfonyl-phenoxy)-acetylamino]-n-hexanoic acid 2-(3-nitro-benzenesulfonyl)ethyl ester (Intermediate 19, 1.0 g, 1.73 mmol, 1.27 eq) in $CH_2Cl_2$ (5 mL) was added to a heterogeneous mixture of 2-[3-methyl-4-(2,2,2-trifluoroethoxy)pyridin-2-ylmethanesulfinyl]-1H-benzimidazole (500 mg, 1.36 mmol) in $CH_2Cl_2$ (10 mL) and NaH (40 mg, 1.65 mmol) at room temperature, and the mixture was stirred for 2 h. Thereafter water was added, the mixture was extracted with $CH_2Cl_2$, and the organic layers were dried and concentrated under reduced pressure. The residual oil was purified by column chromatography ($CH_2Cl_2$ to 3% MeOH in $CH_2Cl_2$) to yield 6-[2-(4-{2-[3-methyl-4-(2,2,2-trifluoro-ethoxy)-pyridin-2-ylmethanesulfinyl]-benzimidazole-1-sulfonyl}-phenoxy)acetylamino]hexanoic acid 2-(3-nitrobenzenesulfonyl)ethyl ester (Intermediate 20, 1.15 g, 94%) as an off-white foam.

$^1$H NMR (CDCl$_3$, 400 MHz) δ 1.23 (m, 2H), 1.45 (m, 4H), 2.05 (t, 2H), 2.26 (s, 3H), 3.28 (m, 2H), 3.54 (t, 2H), 4.43 (t, 2H), 4.45 (s, 2H), 4.59 (m, 2H), 5.25 (dd, 2H), 6.61 (m, 1H), 7.05 (d, 2H), 7.42 (t, 1H), 7.50 (t, 1H), 7.80 (m, 2H), 7.99 (d, 1H), 8.11 (d, 2H), 8.45 (d, 1H), 8.50 (d, 1H), 8.74 (s, 1H).

6-[2-(4-{2-[3-Methyl-4-(2,2,2-trifluoro-ethoxy)-pyridin-2-ylmethanesulfinyl]-benzimdazole-1-sulfonyl}phenoxy)acetylamino]hexanoic acid (Compound 7)

A solution of 6-[2-(4-{2-[3-methyl-4-(2,2,2-trifluoro-ethoxy)-pyridin-2-ylmethanesulfinyl]-benzimidazole-1-sulfonyl}-phenoxy)acetylamino]hexanoic acid 2-(3-nitro-benzenesulfonyl)ethyl ester (Intermediate 20, 450 mg, 0.50 mmol) and of NaHCO$_3$ (50 mg, 0.60 mmol, 1.2 eq) in CH$_3$CN-H$_2$O-iPrOH (2 mL:1 mL:1 mL) was heated to 70° C. for 1.5 h. Thereafter volatile materials were removed by evaporation, the residual gummy oil was dissolved in $CH_2Cl_2$, and the mixture was filtered to remove undissolved solid. The filtrate was dried and concentrated under reduced pressure. The residual oil was purified by silica gel column to yield 150 mg of Compound 7 as a light brown foam.

$^1$H NMR (DMSO-d$_6$, 400 MHz) δ 1.19 (m, 2H), 1.40 (m, 4H), 1.92 (t, 2H), 2.16 (s, 3H), 3.05 (m, 2H), 4.36 (s, 2H), 4.47 (d, 1H), 4.70 (d, 1H), 4.86 (q, 2H), 6.50 (s, 2H), 6.92 (m, 1H), 7.05 (d, 1H), 7.47 (m, 2H), 8.02 (m, 2H), 8.31 (d, 1H).

Reaction Scheme 9

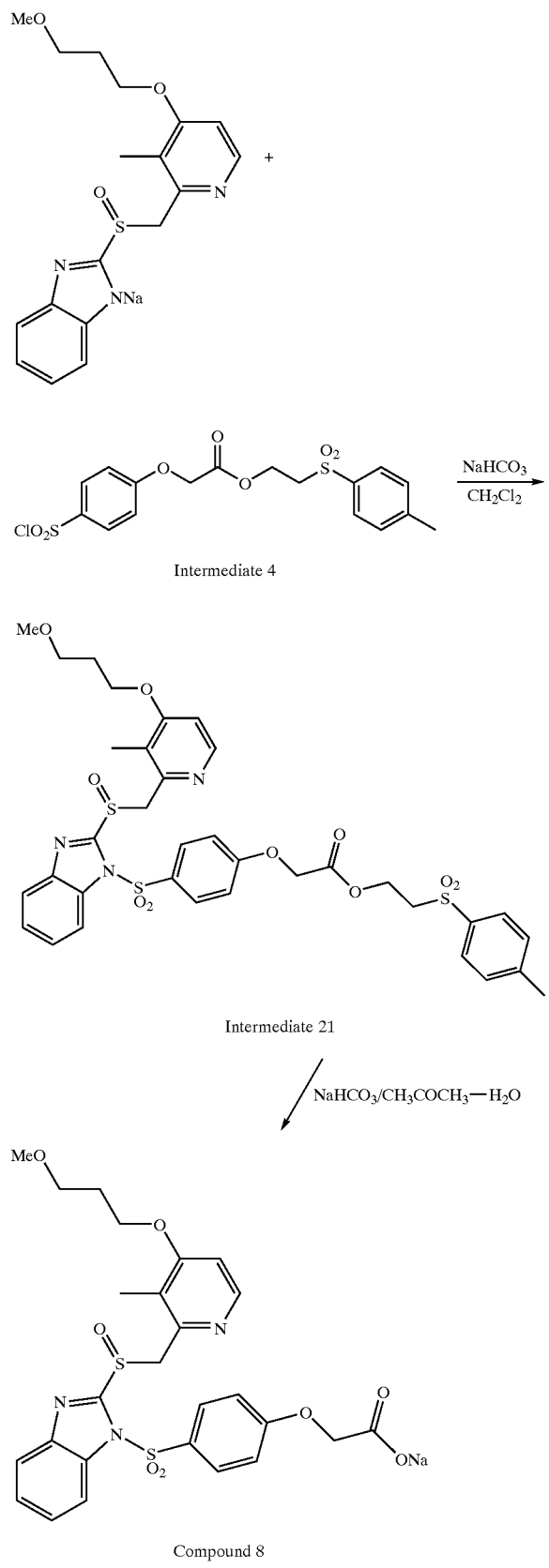

Intermediate 4

Intermediate 21

Compound 8

(4-{2-[4-(3-Methoxy-propoxy)-3-methyl-pyridin-2-ylmethanesulfinyl]-benzimidazole-1-sulfonyl phenoxy)acetic acid 2-(toluene-4-sulfonyl)ethyl ester (Intermediate 21)

To a solution of 2-[4-(3-methoxy-propoxy)-3-methyl-pyridin-2-ylmethanesulfinyl]-1H-benzimidazole sodium salt (760 mg, 2.0 mmol) in 10 mL of $CH_2Cl_2$ was added (4-chlorosulfonylphenoxy)acetic acid 2-(toluene-4-sulfonyl)ethyl ester (Intermediate 4, 1.04 g, 2.4 mmol, 1.2 eq). Solid $NaHCO_3$ (~1 g) was also added to the reaction mixture. The reaction mixture was stirred for 8 hr at room temperature, and the solid $NaHCO_3$ was re moved by filtration. The dichloromethane layer was evaporated under reduced pressure to give a residual oil, which was purified by column chromatography (silica gel, $CH_2Cl_2$ to 3% MeOH in $CH_2Cl_2$) to give Intermediate 21 (1.4 g, 92%) as an off-white foam.

$^1$H NMR ($CDCl_3$, 400 MHz) δ 2.09 (m, 2H), 2.26 (s, 3H), 2.38 (s, 3H), 3.35 (s, 3H), 3.43 (t, 2H), 3.55 (t, 2H), 4.16 (t, 2H), 4.50 (m, 4H), 5.13 (dd, 2H), 6.82 (m, 1H), 6.95 (d, 2H), 7.34 (d, 2H), 7.40 (t, 1H), 7.47 (t, 1H), 7.76 (d, 2H), 7.81 (d, 1H), 7.99 (d, 1H), 8.11 (d, 2H), 8.26 (d, 1H).

(4-{2-[4-(3-Methoxy-propoxy)-3-methyl-pyridin-2-ylmethanesulfinyl]-benzimidazole-1-sulfonyl}-phenoxy)-acetic acid sodium salt (Compound 8)

(4-{2-[4-(3-Methoxy-propoxy)-3-methyl-pyridin-2-ylmethanesulfinyl]-benzimidazole-1-sulfonyl}phenoxy)acetic acid 2-(toluene-4-sulfonyl)ethyl ester (Intermediate 21, 400 mg, 0.53 mmol) was dissolved in 6 mL of acetone and a solution of $NaHCO_3$ (50 mg, 0.597 mmol, 1.1 eq) in 4 mL of $H_2O$ was added. The mixture was heated to 70° C. for 2 h. Thereafter volatile materials were removed under vacuum, the residual oil was dissolved in EtOAc-iPrOH (5:1) and the mixture was filtered to remove un-dissolved material. The filtrate was concentrated and the residue dried under vacuum to give an off-white foam. The foam was washed with ethyl acetate to remove by-product (vinyl toluene sulfone) and to yield (4-{2-[4-(3-methoxy-propoxy)-3-methyl-pyridin-2-ylmethanesulfinyl]-benzimidazole-1-sulfonyl}-phenoxy)-acetic acid sodium salt (Compound 8, 300 mg) as an off-white solid.

$^1$H NMR (DMSO-$d_6$, 400 MHz) δ 1.98 (m, 2H), 2.20 (s, 3H), 3.24 (s, 3H), 3.48 (t, 2H), 4.08 (t, 2H), 4.27 (s, 3H), 4.86 (d, 1H), 5.12 (d, 1H), 6.87 (d, 1H), 7.02 (d, 2H), 7.45 (t, 1H), 7.54 (t, 1H), 7.81 (d, 1H), 7.93 (d, 1H), 8.02 (d, 1H), 8.09 (d, 2H).

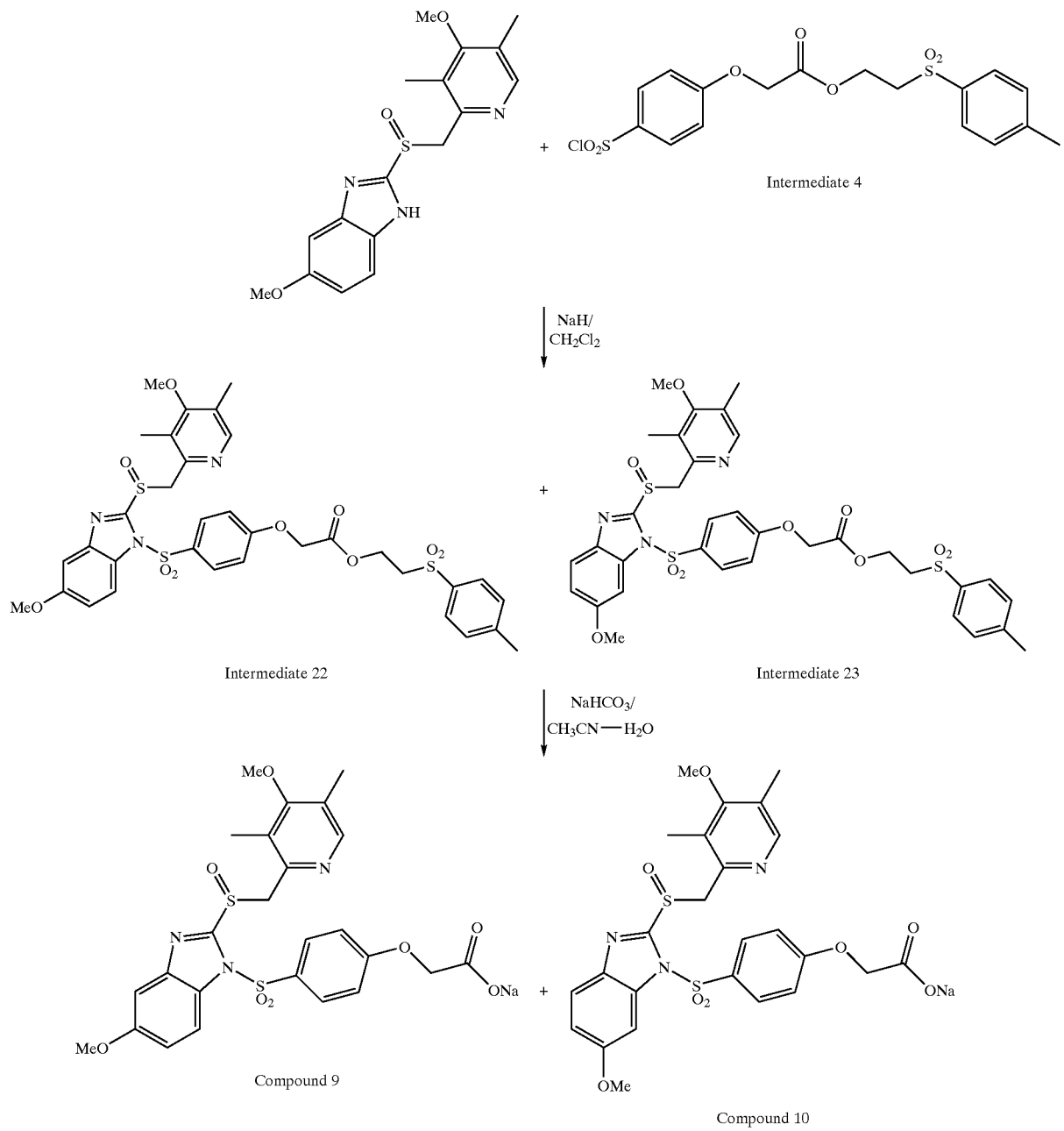

Reaction Scheme 10

Intermediate 4

Intermediate 22

Intermediate 23

Compound 9

Compound 10

Mixture of {4-[5-methoxy-2-(4-methoxy-3,5-dimethyl-pyridin-2-yl-methanesulfinyl)-benzimidazole-1-sulfonyl]phenoxy}acetic acid 2-(toluene-4-sulfonyl)ethyl ester (Intermediate 22) and {4-[6-methoxy-2-(4-methoxy-3,5-dimethyl-pyridin-2-yl-methanesulfinyl)-benzimidazole-1-sulfonyl]phenoxy}acetic acid 2-(toluene-4-sulfonyl) ethyl ester (Intermediate 23)

To a heterogeneous solution of 5-methoxy-2-(4-methoxy-3,5-dimethyl-pyridin-2-ylmethanesulfinyl)-1H-benzimidazole (840 mg, 2.44 mmol) in 20 mL of $CH_2Cl_2$ was added 90 mg of NaH (3.75 mmol, 1.5 eq) at room temperature resulting in a homogeneous mixture. To this clear reaction mixture was added powdered (4-chlorosulfonylphenoxy)acetic acid 2-(toluene-4-sulfonyl)ethyl ester (Intermediate 4, 1.26 g, 2.92 mmol, 1.2 eq.) Solid $NaHCO_3$ (~1 g) was also added to the reaction mixture. The reaction mixture was stirred for 8 hr at room temperature, and then the solid $NaHCO_3$ was removed by filtration. The dichloromethane layer was evaporated under reduced pressure to give a residual oil, which was purified by column chromatography (silica gel, $CH_2Cl_2$ to 4% MeOH in $CH_2Cl_2$) to give a mixture of Intermediate 22 and Intermediate 23 (1.6 g, 88%; 1:1 ratio of 5- and 6-isomer) as an off-white foam.

$^1$H NMR ($CDCl_3$, 400 MHz) δ 2.23 (s, 3H), 2.29 (s, 3H), 2.39 (s, 3H), 3.43 (t, 2H), 3.76 (s, 3H), 3.82 and 3.89 (2 s, 3H, 5-OMe and 6-OMe), 4.52 (m, 4H), 4.90 (m, 1H), 4.99

(m, 1H), 6.93 (dd, 2H), 7.00 and 7.10 (2 m, 1H), 7.24 and 7.43 (2 s, 1H), 7.34 (d, 2H), 7.67 and 7.84 (2 d, 1H), 7.75 (d, 2H), 8.06 (t, 2H), 8.17 (s, 1H).

Mixture of {4-[5-methoxy-2-(4-methoxy-3,5-dimethyl-pyridin-2-ylmethanesulfinyl)-benzimidazole-1-sulfonyl]-phenoxy}-acetic acid sodium salt (Compound 9) and {4-[6-methoxy-2-(4-methoxy-3,5-dimethyl-pyridin-2-ylmethanesulfinyl)-benzimidazole-1-sulfonyl]-phenoxy}-acetic acid sodium salt (Compound 10)

A mixture of {4-[5-methoxy-2-(4-methoxy-3,5-dimethyl-pyridin-2-ylmethanesulfinyl)-benzimidazole-1-sulfonyl]phenoxy}acetic acid 2-(toluene-4-sulfonyl)ethyl ester (Intermediate 22) and {4-[6-methoxy-2-(4-methoxy-3,5-dimethyl-pyridin-2-ylmethanesulfinyl)-benzimidazole-1-sulfonyl]phenoxy}acetic acid 2-(toluene-4-sulfonyl)ethyl ester (Intermediate 23), 2.2 g (2.97 mmole) was dissolved in 20 mL of acetonitrile and a solution of NaHCO$_3$ (250 mg, 2.97 mmole) in 10 mL of H$_2$O was added. The resulting mixture was heated to 60° C. for 3 hr. Thereafter the reaction mixture was concentrated to about 10 mL under reduced pressure, then, the concentrate was washed with ethyl acetate to remove by-product (vinyl toluene sulphone). If necessary, 1 ml of concentrated NaCl was added to make clear separation between two layers. The aqueous layer was dried under high vacuum to give an off-white foam. The solid foam was extracted with chloroform. The chloroform extracts were concentrated under reduced pressure, and treated with ethyl acetate, and kept at 0° C. for 2 hr to give precipitates. The precipitated solids were collected and dried to yield 1.37 g of a isomeric mixture of Compound 9 (sodium salt) and Compound 10 (sodium salt) (1:1 ratio of 5- and 6-isomer) as a white solid.

$^1$H NMR (D$_2$O, 400 MHz) δ 1.77 and 1.80 (s, 3H), 1.83 (s, 3H), 3.33 and 3.34 (s, 3H), 3.51 and 3.54 (2 s, 3H; 5-OMe and 6-OMe), 4.19 and 4.20 (s, 2H), 4.54 (d, 1H), 4.66 (d, 1H), 6.70 (m, 3H), 6.99 (m, 1H), 7.32 (d, 1H), 7.68 (m, 3H).

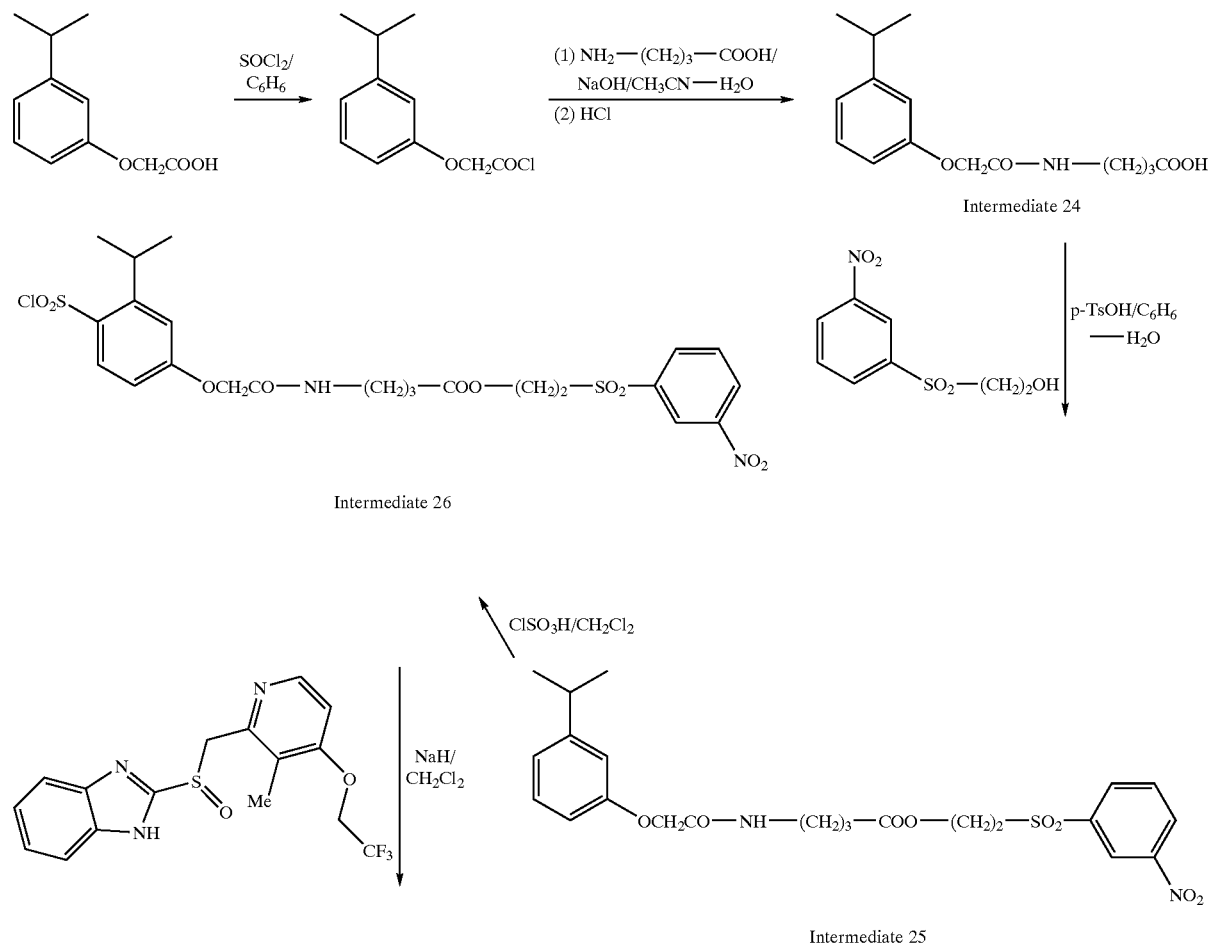

Reaction Scheme 11

-continued

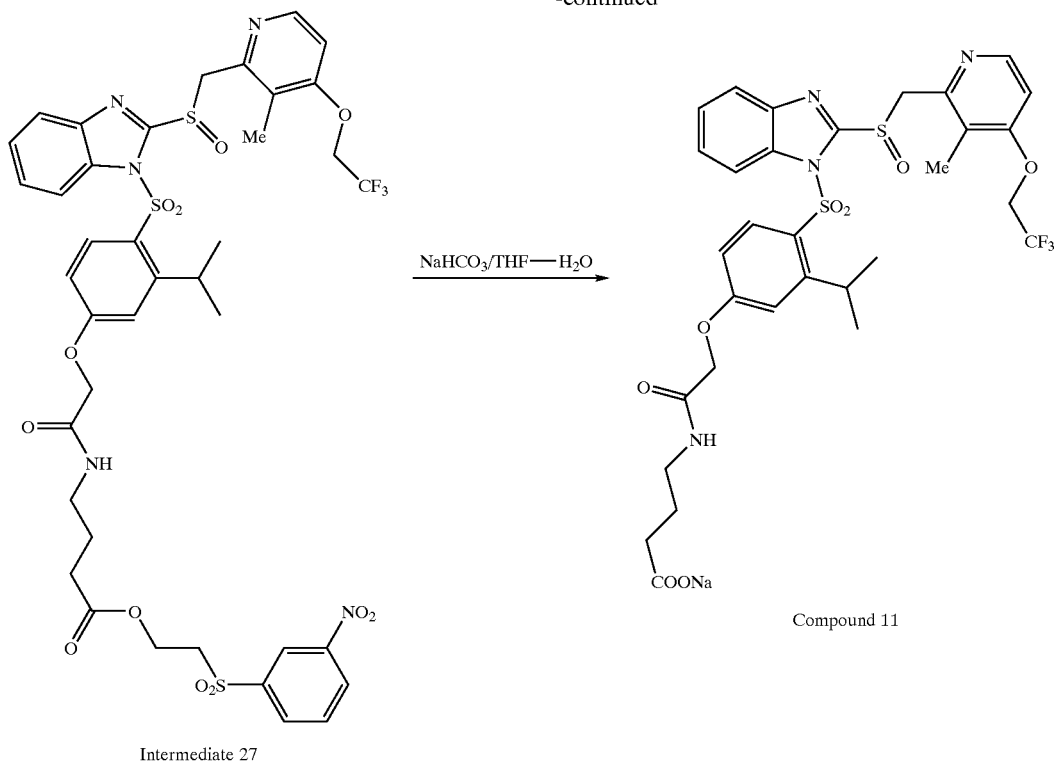

Intermediate 27

Compound 11

4-(3-Isopropylphenoxyactamido)butyric acid (Intermediate 24)

A mixture of 3-isopropylphenoxyacetic acid (prepared by the reaction of 3-isopropylphenol with chloroacetic acid in the presence of sodium hydroxide, 5.0 g, 25.8 mmol) and $SOCl_2$ (5.0 mL, 8.2 g, 68.8 mmol) in 10 mL of benzene was refluxed for 2 h. Thereafter volatile materials were removed by vacuum distillation to give 3-isopropylphenoxyacetic acid chloride as a light brown oil. To an ice-bath cooled solution of 4-aminobutyric acid (5.3 g, 51.6 mmol, 2.0 eq) and NaOH (2.0 g, 51.6 mmol) in 60 mL of $H_2O$ and 80 mL of $CH_3CN$ were added drop-wise the acid chloride in 40 mL of $CH_3CN$ and $NaHCO_3$ (3.3 g, 38.7 mmol, 1.5 eq) in 50 mL of $H_2O$. The resulting mixture was stirred vigorously for 5 h.

Thereafter most of $CH_3CN$ was removed under reduced pressure, the mixture was acidified at room temperature with conc-HCl to pH 2. The resulting white precipitates were collected by filtration, washed with $H_2O$ followed by hexane, and dried under high vacuum to yield Intermediate 24 (6.6 g, 92%) as a white solid.

$^1$H NMR ($CDCl_3$, 400 MHz) δ 1.23 (d, 6H), 1.88 (m, 2H), 2.37 (t, 2H), 2.88 (m, 1H), 3.42 (m, 2H), 4.49 (s, 2H), 6.72 (dd, 1H), 6.80 (s, 1H), 6.89 (d, 1H), 7.23 (m, 1H).

4-(3-Isopropylphenoxyactamido)butyric acid 2-(3-nitrobenzenesulfonyl)ethyl ester (Intermediate 25)

A mixture of 4-(3-isopropylphenoxyactamido)butyric acid (Intermediate 24, 3.1 g, 11.1 mmol, 1.1 eq), 2-(3-nitrobenzenesulfonyl)ethanol (2.3 g, 10.0 mmol), and $TsOH.H_2O$ (0.5 g) in 100 mL of benzene was heated overnight to reflux temperature with a Dean-Stark trap. Thereafter the mixture was concentrated by evaporation and the resulting residual oil was purified by column chromatography ($CH_2Cl_2$ to 1% MeOH in $CH_2Cl_2$) to give Intermediate 25 (4.8 g, 97%) as a light yellow oil which solidified on standing.

$^1$H NMR ($CDCl_3$, 400 MHz) δ 1.22 (d, 6H), 1.79 (m, 2H), 2.18 (t, 2H), 2.88 (m, 1H), 3.33 (m, 2H), 3.53 (m, 2H), 4.46 (m, 4H), 6.73 (m, 1H), 6.80 (m, 1H), 6.89 (d, 1H), 7.21 (d, 1H), 7.82 (t, 1H), 8.26 (dd, 1H), 8.50 (d, 1H), 8.78 (s, 1H).

4-(4-Chlorosulfonyl-3-isopropylphenoxyactamido)-butyric acid 2-(3-nitrobenzenesulfonyl)ethyl ester (Intermediate 26).

To a mixture of 4-(3-isopropylphenoxyactamido)butyric acid 2-(3-nitrobenzenesulfonyl)ethyl ester (Intermediate 25, 4.8 g, 9.75 mmol) and 2 mL of $CH_2Cl_2$ was added drop-wise $ClSO_3H$ (3.3 mL, 5.8 g, 50 mmol) at 0° C. with vigorous stirring. The mixture was stirred at 0° C. for 40 min. and then was poured onto crushed ice with vigorous stirring resulting in a thick mass. This was extracted with $CH_2Cl_2$. The organic layers were dried, and concentrated under reduced pressure. The residual oil was passed through a short silica gel column to remove material that was not moving on TLC. The eluent was concentrated to give Intermediate 26 (3.3 g, 57%) as a light brown foam.

4-[2-(3-Isopropyl-4-{2-[3-methyl-4-(2,2,2-trifluoroethoxy)-pyridin-2-ylmethanesulfinyl]benzimidazole-1-sulfonyl}phenoxy)acetylamino]butyric acid 2-(3-nitro-benzenesulfonyl)ethyl ester (Intermediate 27)

To a heterogeneous mixture of 2-[3-methyl-4-(2,2,2-trifluoroethoxy)pyridin-2-ylmethanesulfinyl]-1H-benzimidazole (500 mg, 1.36 mmol) in $CH_2Cl_2$ (10 mL) was added NaH (40 mg, 1.65 mmol) at room temperature resulting in a clear solution. To this clear mixture was added 4-(4-chlorosulfonyl-3-Isopropylphenoxyactamido)-butyric acid 2-(3-nitrobenzenesulfonyl)ethyl ester (Intermediate 26, 1.0 g, 1.70 mmol, 1.25 eq) in $CH_2Cl_2$ (5 mL) at room temperature, and then the mixture was stirred for 2 h. Thereafter water was added, the mixture was extracted with $CH_2Cl_2$, the organic layers were dried and concentrated under reduced pressure. The residual oil was purified by column chromatography (CH$_2$Cl$_2$ to 3% MeOH in CH$_2$Cl$_2$) to yield Intermediate 27 (1.0 g, 80%) as an off-white foam.

$^1$H NMR (CDCl$_3$, 400 MHz) δ 0.90 (d, 3H), 0.98 (d, 3H), 1.79 (m, 2H), 2.12 (s, 3H), 2.19 (t, 2H), 3.33 (t, 2H), 3.54 (t, 2H), 3.70 (m, 1H), 4.46 (t, 2H), 4.55 (m, 4H), 5.17 (d, 1H), 5.29 (d, 1H), 6.9–7.1 (m, 4H), 7.43 (m, 2H), 7.83 (m, 3H), 8.07 (d, 1H), 8.27 (d, 1H), 8.41 (d, 1H), 8.52 (d, 1H), 8.75 (s, 1H).

4-[2-(3-Isopropyl-4-{2-[3-methyl-4-(2,2,2-trifluoroethoxy)-pyridin-2-ylmethanesulfinyl]benzimidazole-1-sulfonyl 1-phenoxy)-acetylamino]-butyric acid sodium salt (Compound 11)

A solution of 4-[2-(3-isopropyl-4-{2-[3-methyl-4-(2,2,2-trifluoroethoxy)-pyridin-2-ylmethanesulfinyl]-benzimidazole-1-sulfonyl}phenoxy)acetylamino]butyric acid 2-(3-nitro-benzenesulfonyl)ethyl ester (Intermediate 27, 1.0 g, 1.08 mmol) and NaHCO$_3$ (109 mg, 1.30 mmol, 1.2 eq) in THF-H$_2$O (6 mL-3 mL) was heated to 70° C. for 0.5 h. Thereafter volatile materials were removed by evaporation, the residual oil was dissolved in CH$_2$Cl$_2$ and the mixture was filtered to remove un-dissolved solid. The filtrate was evaporated under reduced pressure, and the residual semi-solid was treated with ether-EtOAc (10:1) to precipitate the solid, which was briefly treated with CH$_3$CN. The solid was collected from the CH$_3$CN suspension by filtration to give Compound 11 (550 mg, 69%) as an off-white solid.

$^1$H NMR (CDCl$_3$, 400 MHz) δ 0.80 (d, 3H), 0.88 (d, 3H), 1.58 (m, 2H), 2.21 (s, 3H), 2.28 (m, 1H), 3.12 (m, 2H), 4.36–4.50 (m, 6H), 4.73 (d, 1H), 4.89 (d, 1H), 6.62 (d, 1H), 6.80 (m, 1H), 6.91 (s, 1H), 7.39 (m, 3H), 7.76–7.91 (m, 3H), 8.14 (m, 1H).

Reaction Scheme 12

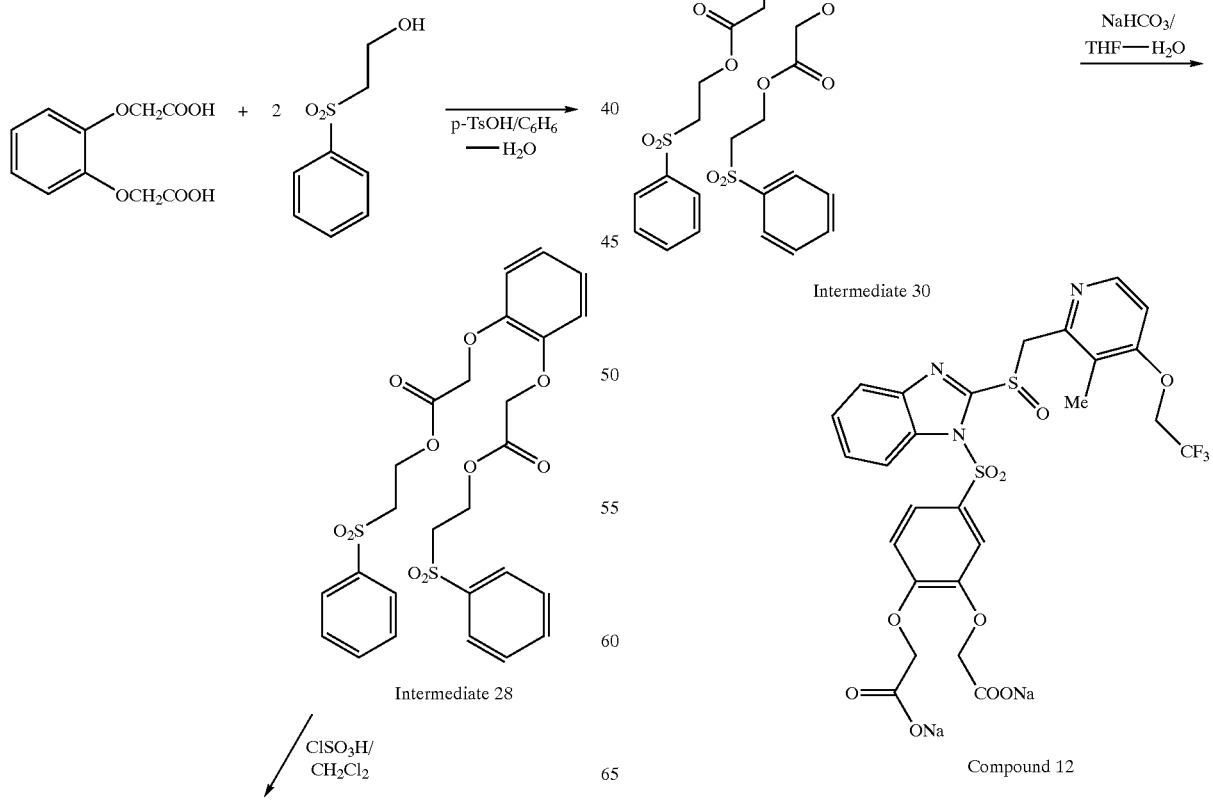

Intermediate 28

Intermediate 29

Intermediate 30

Compound 12

[2-(2-Benzenesulfonyl-ethoxycarbonylmethoxy)-phenoxy]acetic acid 2-benzenesulfonyl-ethyl ester (Intermediate 28)

A mixture of 1,2-phenylenedioxydiacetic acid (available from Aldrich, 3.0 g, 13.3 mmol), 2-(phenylsulfonyl)ethanol (5.0 g, 26.5 mmol), and p-TsOH.H$_2$O (0.5 g) in 100 mL of benzene was heated overnight to reflux temperature with a Dean-Stark trap. Thereafter the mixture was concentrated by evaporation under reduced pressure, water was added and the mixture was extracted with CH$_2$Cl$_2$. The combined organic layers were washed with saturated NaHCO$_3$ solution and water, dried, and concentrated under reduced pressure. The resulting residual oil was purified by short path column chromatography (silica gel, CH$_2$Cl$_2$) to give Intermediate 28 (7.4 g, 99%) as a light brown oil.

$^1$H NMR (CDCl$_3$, 400 MHz) δ 3.48 (t, 4H), 4.48 (s, 4H), 4.53 (t, 4H), 6.80 (t, 2H), 6.95 (m, 2H), 7.57 (m, 4H), 7.64 (m, 2H), 7.92 (m, 4H).

[2-(2-Benzenesulfonyl-ethoxycarbonylmethoxy)-4-chlorosulfonyl-phenoxy]acetic acid 2-benzenesulfonyl-ethyl ester (Intermediate 29)

To a solution of [2-(2-benzenesulfonyl-ethoxycarbonylmethoxy)phenoxy]acetic acid 2-benzenesulfonyl-ethyl ester (Intermediate 28, 7.4 g, 13.2 mmol) in 10 mL of CH$_2$Cl$_2$ was added drop-wise ClSO$_3$H (5.0 mL, 8.8 g, 75.8 mmol, 5.7 eq) at 0° C. with vigorous stirring. The mixture was stirred at 0° C. for 1.5 h. and then poured onto crushed ice with vigorous stirring, resulting in a thick mass. This was extracted with CH$_2$Cl$_2$. The organic layers were dried and concentrated under reduced pressure. The residual oil was dried under vacuum overnight to give Intermediate 29 (8.0 g, 92%) as an off-white foam.

$^1$H NMR (CDCl$_3$, 400 MHz) δ 3.48 (m, 4H), 4.57 (m, 6H), 4.69 (s, 2H), 6.96 (d, 1H), 7.39 (s, 1H), 7.59 (m, 4H), 7.67 (m, 3H), 7.92 (m, 4H).

(2-(2-Benzenesulfonyl-ethoxycarbonylmethoxy)-4-{2-[3-methyl-4-(2,2,2-trifluoro-ethoxy)-pyridin-2-ylmethanesulfinyl]-benzimidazole-1-sulfonyl}phenoxy)acetic acid 2-benzenesulfonyl-ethyl ester (Intermediate 30)

To a heterogeneous mixture of 2-[3-methyl-4-(2,2,2-trifluoro-ethoxy)pyridin-2-ylmethanesulfinyl]-benzimidazole, (LANSOPRAZOLE) (500 mg, 1.35 mmol) in CH$_2$Cl$_2$ (10 mL) was added NaH (40 mg, 1.63 mmol) at room temperature resulting in a clear solution. To this clear mixture was added [2-(2-benzenesulfonyl-ethoxycarbonylmethoxy)-4-chlorosulfonyl-phenoxy]-acetic acid 2-benzenesulfonyl-ethyl ester (Intermediate 29, 1.0 g, 1.63 mmol, 1.2 eq) in CH$_2$Cl$_2$ (5 mL) at room temperature, and the mixture was stirred for 3 h. Thereafter water was added, the mixture was extracted with CH$_2$Cl$_2$, and the organic layers were dried and concentrated under reduced pressure. The residual oil was purified by column chromatography (CH$_2$Cl$_2$ to 2% MeOH in CH$_2$Cl$_2$) to yield Intermediate 30 (1.05 g, 78%) as an off-white foam.

$^1$H NMR (CDCl$_3$, 400 MHz) δ 2.31 (s, 3H), 3.45 (m, 4H), 4.46–4.56 (m, 10H), 5.03 (d, 1H), 5.13 (d, 1H), 6.80 (m, 1H), 6.86 (d, 1H), 7.40 (t, 1H), 7.47 (t, 1H), 7.56 (m, 4H), 7.64 (m, 3H), 7.78 (dd, 2H), 7.88 (m, 4H), 7.98 (d, 1H), 8.28 (m, 1H).

(2-Carboxymethoxy-4-{2-[3-methyl-4-(2,2,2-trifluoro-ethoxy)-pyridin-2-ylmethanesulfinyl]-benzimidazole-1-sulfonyl}-phenoxy)-acetic acid di-sodium salt (Compound 12)

A solution of (2-(2-benzenesulfonyl-ethoxycarbonylmethoxy)-4-{2-[3-methyl-4-(2,2,2-trifluoro-ethoxy)-pyridin-2-ylmethanesulfinyl]-benzimidazole-1-sulfonyl}phenoxy)acetic acid 2-benzenesulfonyl-ethyl ester (Intermediate 30, 500 mg, 0.50 mmol) and NaHCO$_3$ (90 mg, 1.10 mmol, 2.2 eq) in THF-H$_2$O (6 mL-3 mL) was heated to 70° C. for 2 h. Thereafter volatile materials were removed by evaporation under reduced pressure and the residual semi-solid was briefly treated with MeOH-CH$_2$Cl$_2$ (1:1). The resulting solid was collected by filtration to give Compound 12 (300 mg, 74%) as an off-white solid.

$^1$H NMR (DMSO-d$_6$, 400 MHz) δ 2.20 (s, 3H), 4.14 (m, 4H), 4.86 (m, 3H), 5.10 (d, 1H), 6.99 (m, 1H), 7.05 (m, 1H), 7.34 (m, 1H), 7.50 (m, 1H), 7.61 (m, 1H), 7.72 (m, 2H), 8.02 (m, 2H).

Reaction Scheme 13

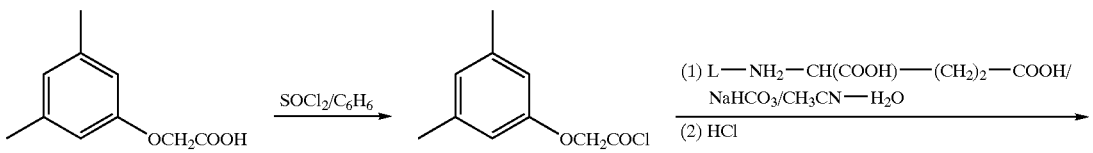

-continued
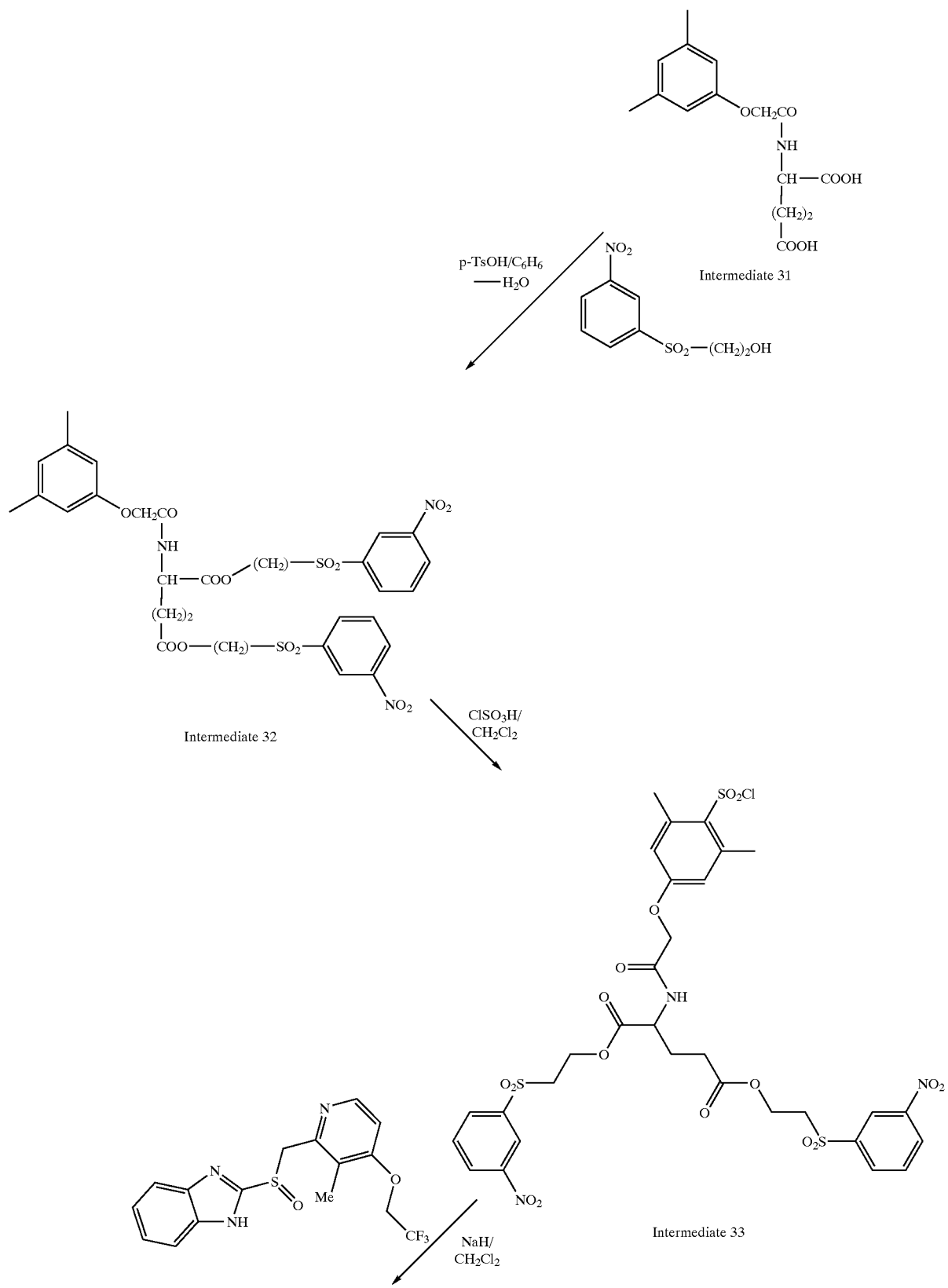

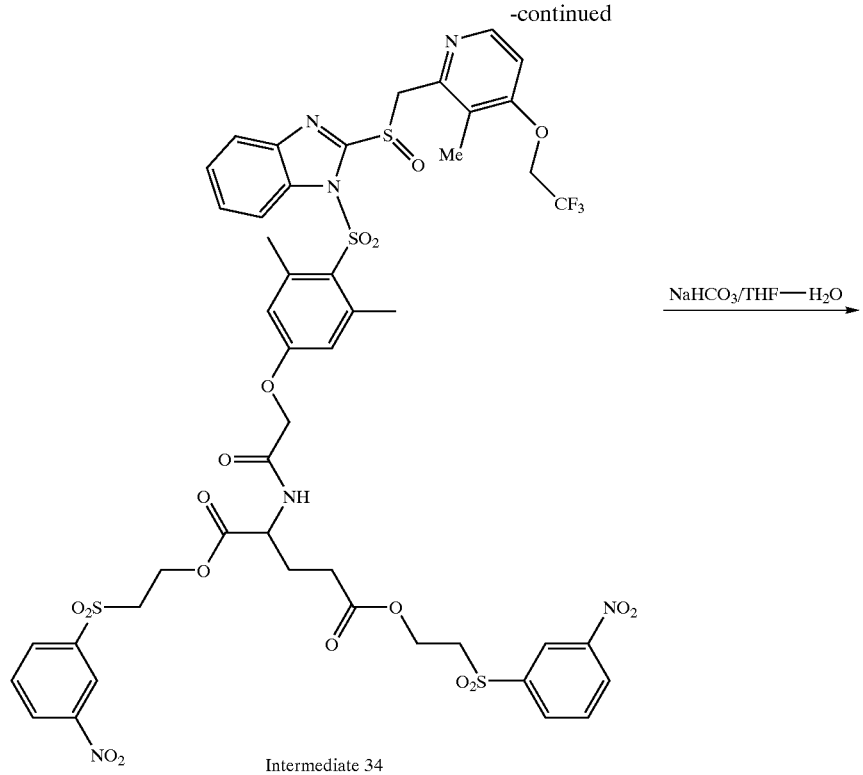

Intermediate 34

NaHCO₃/THF—H₂O →

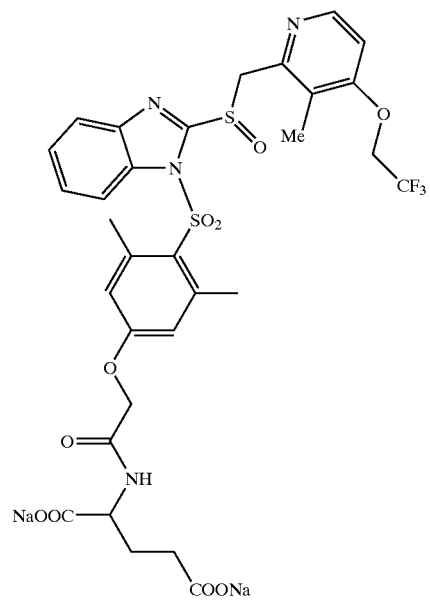

Compound 13

N-(3,5-Dimethylphenoxyacetyl)-L-glutamic acid (Intermediate 31)

To a solution of 3,5-dimethylphenoxyacetic acid (9.0 g, 50 mmole) in benzene (100 mL) was added thionyl chloride (10.89 mL). The resulting mixture was refluxed for 2 hr, then the benzene was removed by distillation. The residual material was dried in vacuo to give 3,5-dimethylphenoxyacetyl chloride, which was dissolved in 20 ml of acetonitrile and used in situ. L-Glutamic acid (8.8 g, 60 mmole) was dissolved in a solution of sodium carbonate (12.72 g, 150 mL, 120 mmole) and the 3,5-dimethylphenoxyacetyl chloride in the acetonitrile solution was slowly added while the pH 8 was adjusted from time-to-time by adding sodium carbonate solution. The reaction mixture was stirred at room temperature for 2 hr, and acidified to pH 2 to give a solid precipitate. The solid precipitate was collected by filtration, treated with hot benzene, filtered, again and washed again with benzene to give Intermediate 31 (9.2 g).

$^1$H NMR (DMSO-d$_6$, 400 MHz) δ 1.81 (m, 1H), 2.01 (m, 1H), 2.19 (m, 8H), 4.26 (m, 1H), 4.43 (dd, 2H), 6.54 (m, 3H), 8.22 (d, 1H, NH).

3,5-dimethylphenoxyacetyl glutamic acid bis[2-(3-nitrophenylsulphonyl)ethyl]ester (Intermediate 32)

A mixture of N-(3,5-dimethylphenoxyacetyl)-L-glutamic acid (Intermediate 31, 3.0 g, 10.0 mmol), 2-(3-nitrophenylsulfonyl)ethanol (4.6 g, 20.0 mmol), and p-TsOH.H$_2$O (0.5 g) in 100 mL of benzene was heated overnight to reflux temperature with a Dean-Stark trap. Thereafter the mixture was concentrated by evaporation, water was added and the mixture was extracted with CH$_2$Cl$_2$. The combined organic layers were washed with saturated NaHCO$_3$ solution and water, dried, and concentrated by evaporation under reduced pressure. The residual oil was purified by short path column chromatography (silica gel, CH$_2$Cl$_2$) to give Intermediate 32 (4.6 g, 62%) as a light brown oil.

$^1$H NMR (CDCl$_3$, 400 MHz) δ 1.82 (m, 1H), 2.05 (m, 1H), 2.18 (m, 2H), 2.28 (s, 6H), 3.54 (m, 4H), 4.48 (m, 7H), 6.55 (s, 2H), 6.66 (s, 1H), 7.10 (d, 1H, NH), 7.82 (m, 2H), 8.27 (d, 2H), 8.52 (m, 2H), 8.76 (s, 2H).

2-[2-(4-Chlorosulfonyl-3,5-dimethyl-phenoxy)-acetylamino]-pentanedioic acid bis-[2-(3-nitro-benzenesulfonyl)-ethyl]ester (Intermediate 33)

To a mixture of 3,5-dimethylphenoxyacetyl glutamic acid bis[2-(3-nitrophenylsulphonyl)ethyl]ester (Intermediate 32, 4.4 g, 5.99 mmol) and 10 mL of CH$_2$Cl$_2$ was added drop-wise ClSO$_3$H (2.0 mL, 3.5 g, 29.9 mmol, 5.0 eq) at 0° C. with vigorous stirring. The mixture was stirred at 0° C. for 1 h. and then was poured onto crushed ice with vigorous stirring, resulting in a thick mass. This was extracted with CH$_2$Cl$_2$. The organic layers were dried and concentrated under reduced pressure. The residual oil was dried under vacuum overnight to give Intermediate 33 (2.5 g, 44%) as an off-white foam.

$^1$H NMR (CDCl$_3$, 400 MHz), 1.87 (m, 1H), 2.09 (m, 1H), 2.23 (m, 2H), 2.72 (s, 6H), 3.55 (m, 4H), 4.46–4.64 (m, 7H), 6.79 (s, 2H), 7.20 (d, 1H, NH), 7.84 (m, 2H), 8.27 (m, 2H), 8.52 (m, 2H), 8.77 (m, 2H).

2-[2-(3,5-Dimethyl-4-42-3-methyl-4-(2,2,2-trifluoro-ethoxy)-pyridin-2-ylmethylsulfinyl]-benzimidazole-1-sulfonyl}-phenoxy)-acetylamino]-pentanedioic acid bis-[2-(3-nitro-benzenesulfonyl)-ethyl]ester (Intermediate 34)

To a heterogeneous mixture of 2-[3-methyl-4-(2,2,2-trifluoro-ethoxy)pyridin-2-ylmethanesulfinyl]-benzimidazole (LANSOPRAZOLE) (550 mg, 1.49 mmol) in CH$_2$Cl$_2$ (10 mL) was added NaH (43 mg, 1.80 mmol) at room temperature resulting in a clear solution. To this clear mixture was added 2-[2-(4-chlorosulfonyl-3,5-dimethyl-phenoxy)-acetylamino]-pentanedioic acid bis[2-(3-nitro-benzenesulfonyl)-ethyl]ester (Intermediate 33, 1.5 g, 1.80 mmol, 1.2 eq) in CH$_2$Cl$_2$ (5 mL) at room temperature, and the resulting mixture was stirred for 4 h. Thereafter water was added, the mixture was extracted with CH$_2$Cl$_2$, the organic layers were dried and concentrated by evaporation under reduced pressure. The oil was purified by column chromatography (CH$_2$Cl$_2$ to 2% MeOH in CH$_2$Cl$_2$) to yield Intermediate 34 (900 mg, 52%) as a light brown foam.

$^1$H NMR (CDCl$_3$, 400 MHz) δ 1.85 (m, 1H), 2.00 (m, 1H), 2.21 (m, 5H), 2.52 (s, 3H), 2.79 (s, 3H), 3.53 (m, 4H), 4.15 (m, 1H), 4.42 (m, 8H), 4.95 (m, 2H), 6.60 (m, 1H), 6.77 (s, 1H), 6.84 (s, 1H), 7.26 (m, 1H), 7.38 (m, 2H), 7.58 (m, 1H), 7.82 (m, 3H), 8.25 (m, 3H), 8.48 (m, 2H), 8.73 (m, 2H).

2-[2-(3,5-Dimethyl-4-{2-[3-methyl-4-(2,2,2-trifluoro-ethoxy)-pyridin-2-ylmethanesulfinyl]benzimidazole-1-sulfonyl}-phenoxy)-acetylamino]-pentanedioic acid sodium salt (Compound 13)

A solution of 2-[2-(3,5-dimethyl-4-{2-[3-methyl-4-(2,2,2-trifluoroethoxy)-pyridin-2-ylmethanesulfinyl]-benzimidazole-1-sulfonyl}-phenoxy)acetylamino]-pentanedioic acid bis-[2-(3-nitro-benzenesulfonyl)-ethyl]ester (Intermediate 34, 800 mg, 0.69 mmol) and NaHCO$_3$ (120 mg, 1.41 mmol, 2.05 eq) in THF-H$_2$O (6 mL-3 mL) was heated to 70° C. for 3 h. Thereafter volatile materials were removed by evaporation under reduced pressure, the residual semi-solid was treated with EtOAc, and the mixture was filtered to remove undissolved materials. The filtrate was concentrated to total volume of about 3 mL, and then diethyl ether was added to the mixture. A solid precipitate formed and was collected by filtration to give Compound 13 (400 mg, 73%) as an off-white solid.

$^1$H NMR (DMSO-d$_6$, 400 MHz) δ 1.81 (m, 1H), 2.01 (m, 1H), 2.16 (m+s, 5H), 2.47 (s, 6H), 4.40 (m, 1H), 4.47 (d, 1H), 4.75 (m, 2H), 4.85 (m, 3H), 6.62 (m, 1H), 6.92 (m, 2H), 7.04 (m, 2H), 7.46 (m, 3H), 8.31 (d, 1H).

Reaction Scheme 14

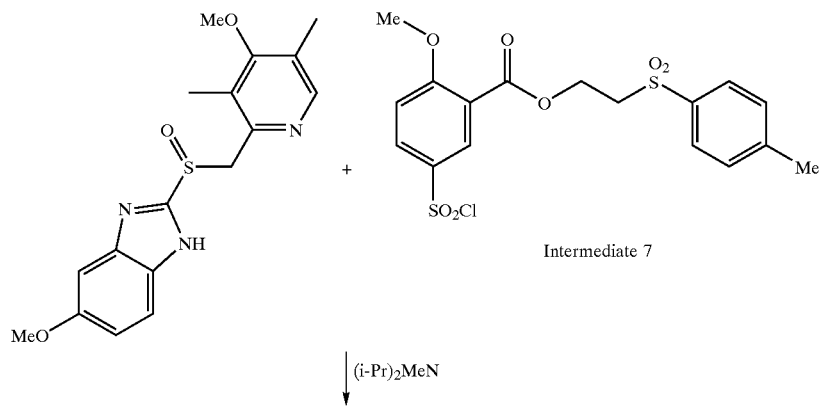

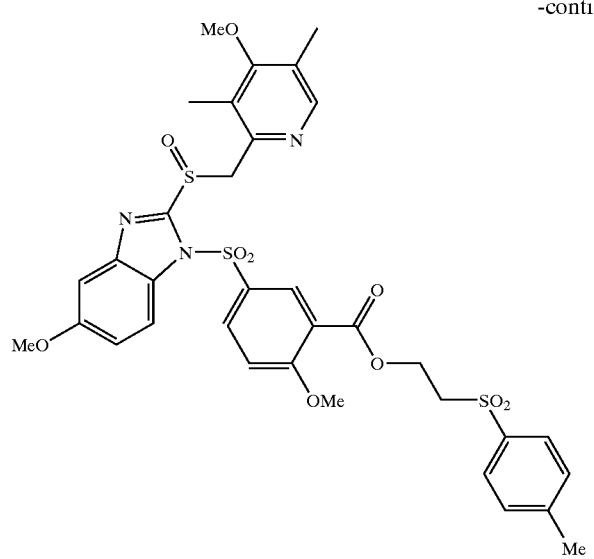

Intermediate 35

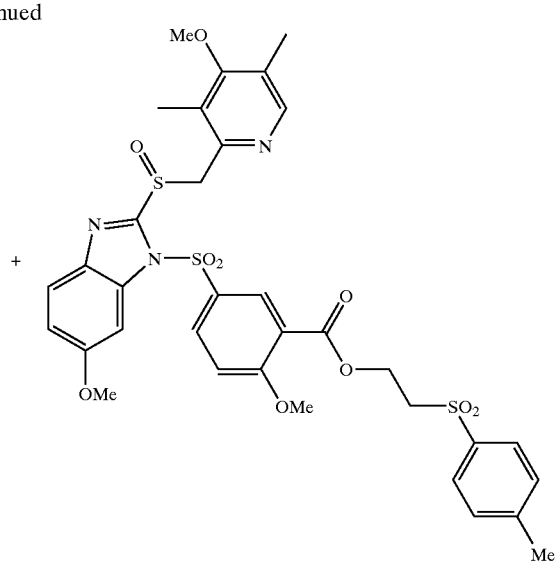

Intermediate 36

NaHCO₃/
CH₃CN—H₂O

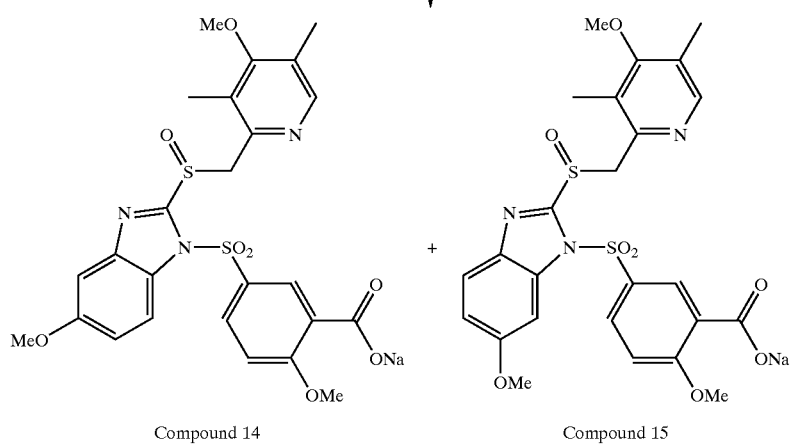

Compound 14    Compound 15

Mixture of 2-Methoxy-5-[5-methoxy-2-(4-methoxy-3,5-dimethyl-pyridin-2-ylmethanesulfinyl)-benzimidazole-1-sulfonyl]-benzoic acid 2-(toluene-4sulfonyl)ethyl ester (Intermediate 35) and 2-Methoxy-5-[6-methoxy-2-(4-methoxy-3,5-dimethyl-pyridin-2-ylmethanesulfinyl)-benzimidazole-1-sulfonyl]-benzoic acid 2-(toluene-4-sulfonyl)ethyl ester (Intermediate 36)

2-Methoxy-5-[5-methoxy-2-(4-methoxy-3,5-dimethyl-pyridin-2-ylmethanesulfinyl)-benzimidazole (1.5 g, 4.35 mmole) and 2-(p-toluenesulfonyl)ethyl 5-chlorosulfonyl-2-methoxybenzoate (Intermediate 7, 2.2 g, 5.09 mmole) were dissolved in di(isopropyl)methylamine (4 mL) and dichloromethane (20 mL). The reaction mixture was stirred at room temperature for 6 hr. Dichloromethane (100 mL) was added and the mixture was washed with water. The dichloromethane layer was dried over anhydrous magnesium sulfate and concentrated under reduced pressure to give a syrup, which was purified by silica gel column chromatography (eluent: 2% MeOH in dichloromethane). Isomeric mixture of 2-methoxy-5-[5-methoxy-2-(4-methoxy-3,5-dimethyl-pyridin-2-ylmethanesulfinyl)-benzimidazole-1-sulfonyl]-benzoic acid 2-(toluene-4-sulfonyl)ethyl ester (Intermediate 35) and 2-methoxy-5-[6-methoxy-2-(4-methoxy-3,5-dimethyl-pyridin-2-ylmethanesulfinyl)-benzimidazole-1-sulfonyl]-benzoic acid 2-(toluene-4-sulfonyl)ethyl ester (Intermediate 36), 2.96 g (92%), was obtained as a white foam.

¹H NMR (CDCl₃, 400 MHz) δ 2.21 (s, 3H), 2.28 (s, 3H), 2.32 (s, 3H), 3.54 (m, 2H), 3.74 (s, 3H), 3.81 and 3.91 (2 s, 6H), 4.58 (m, 2H), 4.83 (d, 1H), 4.97 (d, 1H), 7.02 (m, 1H), 7.17–7.30 (m, 2H), 7.66–7.89 (m, 2H), 8.25 (m, 1H), 8.15 and 8.45 (2 s, 1H).

2-Methoxy-5-[5-methoxy-2-(4-methoxy-3,5-dimethyl-pyridin-2-yl-methanesulfinyl)-benzimidazole-1-sulfonyl]-benzoic acid sodium salt (Compound 14) and 2-Methoxy-5-[6-methoxy-2-(4-methoxy-3,5-dimethyl-pyridin-2-ylmethanesulfinyl)-benzimidazole-1-sulfonyl]-benzoic acid sodium salt (Compound 15)

The mixture of 2-methoxy-5-[5-methoxy-2-(4-methoxy-3,5-dimethyl-pyridin-2-ylmethanesulfinyl)-benzimidazole-1-sulfonyl]-benzoic acid 2-(toluene-4-sulfonyl)-ethyl ester (Intermediate 35) and 2-methoxy-5-[6-methoxy-2-(4-methoxy-3,5-dimethyl-pyridin-2-ylmethanesulfinyl)benzimidazole-1-sulfonyl-benzoic acid 2-(toluene-4-sulfonyl)ethyl ester (Intermediate 36), (2.8 g, 3.78 mmole), was dissolved in acetonitrile (28 mL) and an aqueous solution of sodium bicarbonate (350 mg, 4.15 mmole, 1.1 eq.) in water (14 mL) was added. The reaction mixture was stirred at 60° C. for 2 hr, then, concentrated to about 14 mL under reduced pressure. The concentrate was extracted with ethyl acetate (25 mL), and aqueous layer was lyophilized in vacuo. The residual material was dissolved in dichloromethane and filtered. The filtrate was concentrated to about 5 mL, then, ethyl acetate (50 mL) was added. The mixture was kept at −20° C. for 2 hr, at which time white precipitates were collected by filtration. A mixture (1:1) of 2-methoxy-5-[5-methoxy-2-(4-methoxy-3,5-dimethyl-pyridin-2-ylmethanesulfinyl)-benzimidazole-1-sulfonyl]-benzoic acid sodium salt (Compound 14) and 2-methoxy-5-[6-methoxy-2-(4-methoxy-3,5-dimethyl-pyridin-2-ylmethanesulfinyl)-benzimidazole-1-sulfonyl]-benzoic acid sodium salt (Compound 15), 1.6 g (72%), was obtained. Second crop of the product, 0.15 g, was obtained from the filtrate after concentration and crystallization.

$^1$H NMR (D$_2$O, 400 MHz) δ 1.89 (m, 6H), 3.43 (2 s, 3H), 3.55–3.67 (4 s, 6H), 4.63 (m, 1H), 4.73 (m, 1H), 6.84–7.06 (m, 3H), 7.34 and 7.51 (d, 1H), 7.74 (m, 2H), 7.94 (d, 1H).

Reaction Scheme 15

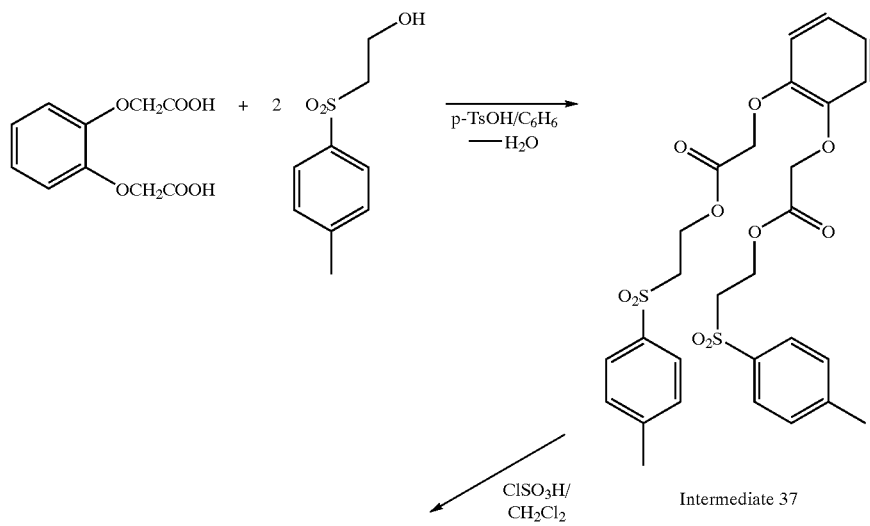

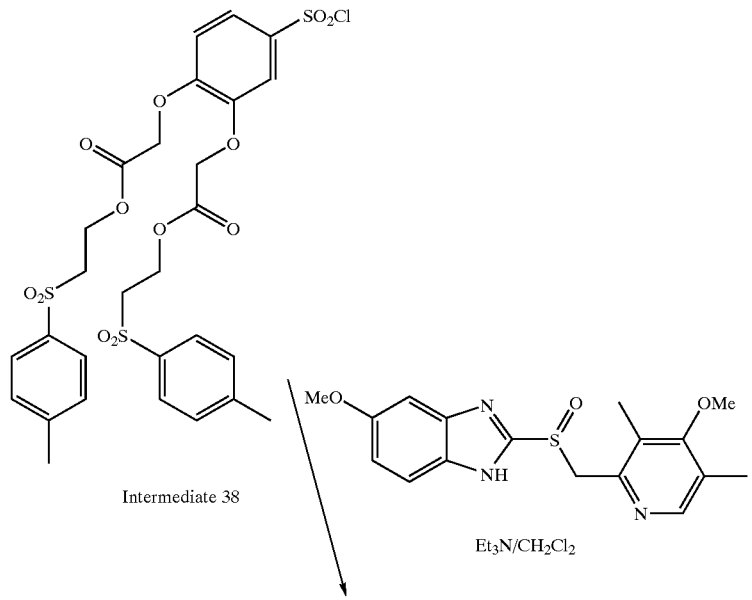

-continued

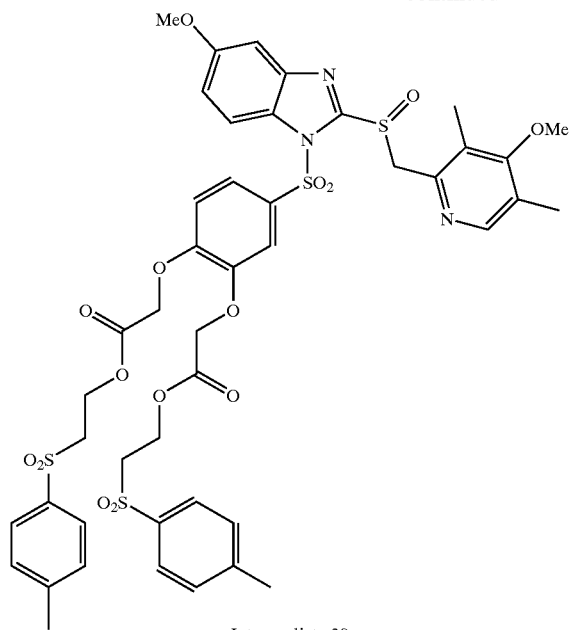

Intermediate 39

+

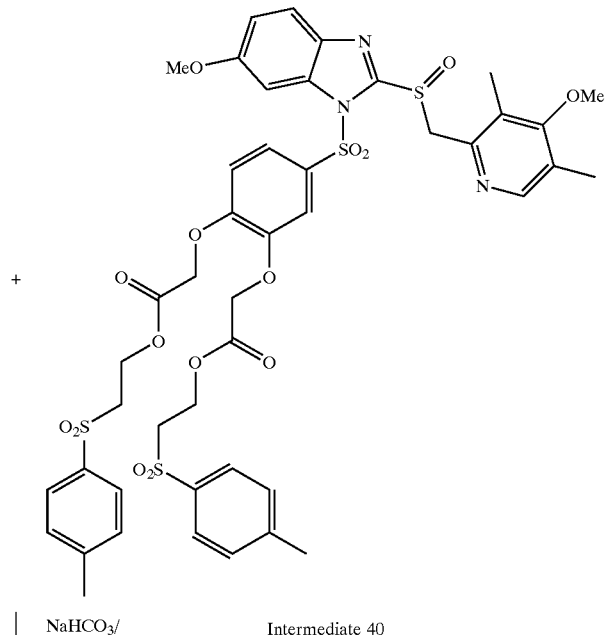

Intermediate 40

↓ NaHCO₃/ CH₃CN—H₂O

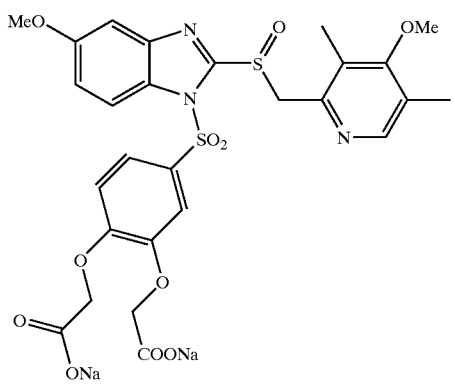

Compound 16

+

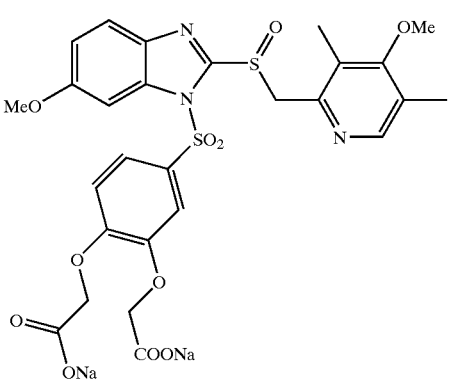

Compound 17

{2-[2-(Toluene-4-sulfonyl)-ethoxycarbonylmethoxy]-phenoxy}-acetic acid 2-(toluene-4-sulfonyl)ethyl ester (Intermediate 37)

1,2-Phenylenedioxydiacetic acid (available from Aldrich, 5 g, 22.1 mmole) and 2-(p-tolylsulfonyl)ethanol (available from Aldrich, 8.8 g, 44.2 mmole) were added to toluene (100 mL). Catalytic amounts of p-toluenesulfonic acid hydrate (0.5 g) were added and the reaction mixture was refluxed with removal of water, using Dean-Stark trap. After 6 hr of reflux, the toluene was distilled off. The residual material was dissolved in dichloromethane (250 mL) and washed with water (200 mL), and 6 N sodium bicarbonate solution (150 mL). The dichloromethane layer was dried over anhydrous magnesium sulfate, and concentrated under reduced pressure to yield 13 g (99%) of {2-[2-(toluene-4-sulfonyl)-ethoxycarbonylmethoxy]-phenoxy}-acetic acid 2-(toluene-4-sulfonyl)ethyl ester (Intermediate 37)

$^1$H NMR (CDCl₃, 400 MHz) δ 2.46 (s, 6H), 3.46 (t, 4H), 4.52 (m, 8H), 6.80 (m, 2H), 6.94 (m, 2H), 7.35 (d, 4H), 7.78 (d, 4H).

{4-Chlorosulfonyl-2-[2-(toluene-4-sulfonyl)-ethoxycarbonylmethoxy]-phenoxy}-acetic acid 2-(toluene-4-sulfonyl)ethyl ester (Intermediate 38)

{2-[2-(Toluene-4-sulfonyl)-ethoxycarbonylmethoxy]-phenoxy}-acetic acid 2-(toluene-4-sulfonyl)ethyl ester (Intermediate 37) (13 g, 22 mmole) was added to dichloromethane (30 mL), and cooled in an ice bath. Chlorosulfonic acid (10 mL) was slowly added, and the mixture was stirred at 0° C. for 2 hr., then at room temperature for 1 hr. Thereafter it was poured into crushed ice (200 g) with stirring. The precipitates were extracted with dichloromethane. The dichloromethane layer was dried over anhydrous magnesium sulfate and concentrated, the residue was dried in vacuo to yield 17.3 g of {4-chlorosulfonyl-2-[2-(toluene-4-sulfonyl)-ethoxycarbonylmethoxy]-phenoxy}-acetic acid 2-(toluene-4-sulfonyl)ethyl ester (Intermediate 38).

$^1$H NMR (CDCl₃, 400 MHz) δ 2.43 (2 s, 6H), 3.46 (m, 4H), 4.56 (m, 4H), 4.59 (s, 2H), 4.71 (s, 2H), 6.97 (d, 1H), 7.41 (m, 5H), 7.67 (d, 1H), 7.79 (m, 4H).

A mixture of {4-[5-methoxy-2-(4-methoxy-3,5-dimethyl-pyridin-2-ylmethanesulfinyl)-benzimidazole-1-sulfonyl]-2-[2-(toluene-4-sulfonyl)-ethoxycarbonylmethoxy]-phenoxy}-acetic acid 2-(toluene-4-sulfonyl)ethyl ester (Intermediate 39) and {4-[6-methoxy-2-(4-methoxy-3,5-dimethyl-pyridin-2-ylmethanesulfinyl)-benzimidazole-1-sulfonyl]-2-[2-(toluene-4-sulfonyl)-ethoxycarbonylmethoxy]-phenoxy}-acetic acid 2-(toluene-4-sulfonyl)ethyl ester (Intermediate 40)

{4-Chlorosulfonyl-2-[2-(toluene-4-sulfonyl)-ethoxycarbonylmethoxy]-phenoxy}-acetic acid 2-(toluene-4-sulfonyl)ethyl ester (Intermediate 38) (7.6 g, 11 mmole) and 5-methoxy-2-(4-methoxy-3,5-dimethyl-pyridin-2-ylmethanesulfinyl)-benzimidazole (3.5 g, 10 mmole) were added to a solution composed of dichloromethane (50 mL) and triethylamine (6 mL). The reaction mixture was stirred at room temperature for 6 hr. Dichloromethane (200 mL) was added and the dichloromethane layer was washed with water (200 mL). The dichloromethane layer was dried over anhydrous magnesium sulfate, and concentrated under reduced pressure. The concentrate was purified by chromatography on a silica gel column to give 6.7 g of a mixture of {4-[5-methoxy-2-(4-methoxy-3,5-dimethyl-pyridin-2-ylmethanesulfinyl)-benzimidazole-1-sulfonyl-2-[2-(toluene-4-sulfonyl)-ethoxycarbonylmethoxy]-phenoxy}-acetic acid 2-(toluene-4-sulfonyl)ethyl ester (Intermediate 39) and {4-[6-methoxy-2-(4-methoxy-3,5-dimethyl-pyridin-2-ylmethanesulfinyl)benzimidazole-1-sulfonyl]-2-[2-(toluene-4-sulfonyl)-ethoxycarbonylmethoxy]-phenoxy}-acetic acid 2-(toluene-4-sulfonyl)ethyl ester (Intermediate 40).

$^1$H NMR (CDCl$_3$, 400 MHz) δ 2.27 (s, 3H), 2.29 (s, 3H), 2.39 (s, 6H), 3.44 (m, 4H), 3.76–3.91 (3 s, 6H), 4.48 (m, 4H), 4.58 (m, 4H), 5.03 (d, 1H), 5.09 (d, 1H), 6.85 (m, 1H), 7.01–7.09 (m, 1H), 7.33 (m, 5H), 7.63–7.79 (m, 7H), 8.20 (s, 1H).

{2-Carboxymethoxy-4-[5-methoxy-2-(4-methoxy-3,5-dimethyl-pyridin-2-ylmethanesulfinyl)-benzimidazole-1-sulfonyl]-phenoxy}-acetic acid disodium salt (Compound 16) and {2-Carboxymethoxy-4-[6-methoxy-2-(4-methoxy-3,5-dimethyl-pyridin-2-ylmethanesulfinyl)-benzimidazole-1-sulfonyl]-phenoxy}-acetic acid disodium salt (Compound 17)

A mixture of {4-[5-methoxy-2-(4-methoxy-3,5-dimethyl-pyridin-2-ylmethanesulfinyl)-benzimidazole-1-sulfonyl]-2-[2-(toluene-4-sulfonyl)-ethoxycarbonylmethoxy]-phenoxy}-acetic acid 2-(toluene-4-sulfonyl)ethyl ester (Intermediate 39) and {4-[6-methoxy-2-(4-methoxy-3,5-dimethyl-pyridin-2-ylmethanesulfinyl)-benzimidazole-1-sulfonyl]-2-[2-(toluene-4-sulfonyl)-ethoxycarbonyl-methoxy]-phenoxy}-acetic acid 2-(toluene-4-sulfonyl)ethyl ester (Intermediate 40) (6.5 g, 6.5 mmole) was dissolved in acetonitrile (50 mL), and a solution of sodium bicarbonate (1.15 g, 13.7 mmole) in water (30 mL) was added. The reaction mixture was stirred at 60° C. for 5 hr. The reaction mixture was concentrated to about 30 mL under reduced pressure, and washed with ethyl acetate. The aqueous layer was lyophilized and the residue extracted with chloroform (200 mL). The chloroform extracts were filtered and concentrated to about 7 mL. Ethyl acetate was added to the concentrate to give white precipitates. The suspension was kept at 0° C. for 3 hr, and the solid was collected by filtration. A 1:1 mixture of {2-carboxymethoxy-4-[5-methoxy-2-(4-methoxy-3,5-dimethyl-pyridin-2-ylmethanesulfinyl)-benzimidazole-1-sulfonyl]-phenoxy]-acetic acid disodium salt (Compound 16) and {2-carboxymethoxy-4-[6-methoxy-2-(4-methoxy-3,5-dimethyl-pyridin-2-ylmethanesulfinyl)-benzimidazole-1-sulfonyl]-phenoxy}-acetic acid disodium salt (Compound 17), 3.1 g, was obtained.

$^1$H NMR (D$_2$O, 400 MHz) δ 1.92 (3 s, 6H), 3.48 (2 s, 3H), 3.64 and 3.73 (2 s, 3H; 5-OMe and 6-OMe), 4.32 (m, 4H), 4.62 (d, 1H), 4.74 (d, 1H), 6.74–6.84 (m, 2H), 6.97 (m, 1H), 7.17 (s, 1H), 7.30–7.60 (m, 2H), 7.71 (s, 1H).

Reaction Scheme 16

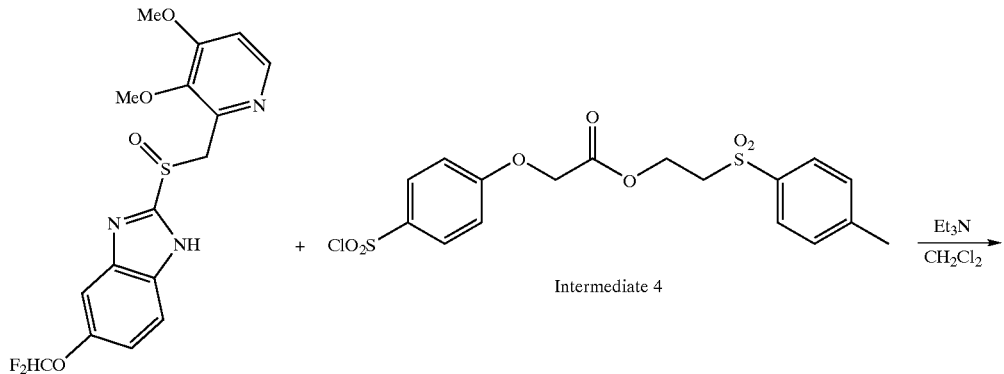

Intermediate 4

-continued

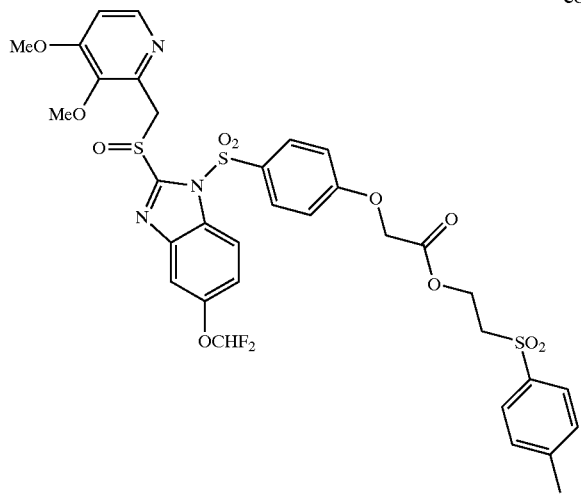

Intermediate 41

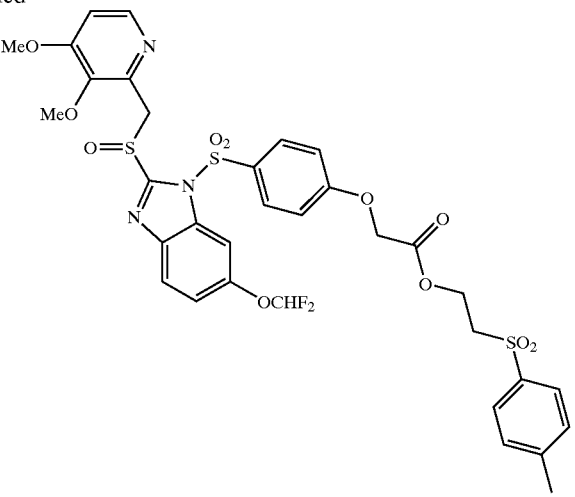

Intermediate 42

NaHCO₃/
CH₃CN—H₂O

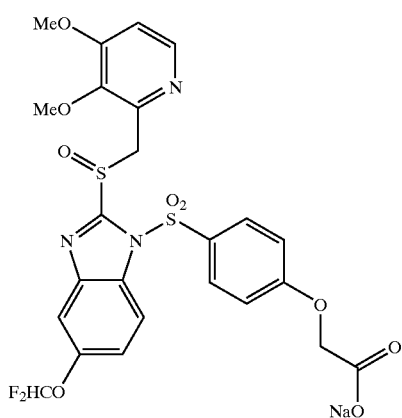

Compound 18

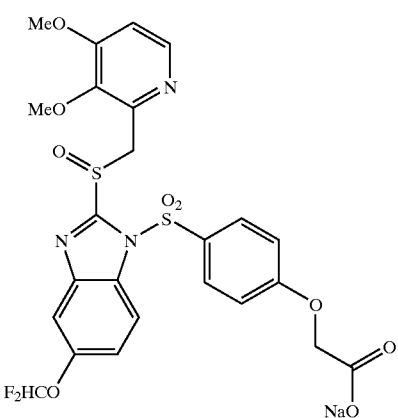

Compound 19

Mixture of 4-[5-difluoromethoxy-2-{(3,4-dimethoxy-pyridin-2-yl)-methanesulfinyl}-benzimidazole-1-sulfonyl]phenoxyacetic acid 2-(toluene-4-sulfonyl)ethyl ester (Intermediate 41) and 4-[6-difluoromethoxy-2-{(3,4-dimethoxy-pyridin-2-yl)-methanesulfinyl}-benzimidazole-1-sulfonyl]phenoxyacetic acid 2-(toluene-4-sulfonyl)ethyl ester (Intermediate 42)

To a heterogeneous solution of 5-difluoromethoxy-2-[(3,4-dimethoxy-pyridin-2-yl)-methanesulfinyl]-1H-benzimidazol sodium salt (4.3 g, 10.0 mmol) and 6 mL of Et₃N in 50 mL of CH₂Cl₂ was added the chlorosulfonyl ester (Intermediate 4, 5.0 g, 11.5 mmol, 1.15 eq). About 2 g of solid NaHCO₃ was added after the chlorosulfonyl ester has dissolved completely in the reaction mixture. (Without addition of NaHCO₃ the mixture became black when the reaction was complete.) Thereafter the solvent was removed by evaporation and the residual oil was purified by column chromatography (silica gel, CH₂Cl₂ to 2% MeOH in CH₂Cl₂) to give 7.8 g (99%) of a mixture of 4-[5-difluoromethoxy-2-{(3,4-dimethoxy-pyridin-2-yl)-methanesulfinyl}-benzimidazole-1-sulfonyl]phenoxyacetic acid 2-(toluene-4-sulfonyl)ethyl ester and 4-[6-difluoromethoxy-2-{(3,4-dimethoxy-pyridin-2-yl)-methanesulfinyl}-benzimidazole-1-sulfonyl]phenoxyacetic acid 2-(toluene-4-sulfonyl)ethyl ester (Intermediates 41 and 42; 1:1 ratio) as an off-white foam.

$^1$H NMR (CDCl₃, 400 MHz) δ 2.40 (s, 3H), 3.43 (m, 2H), 3.90 (s, 3H), 3.93 (s, 3H), 4.52 (m, 4H), 4.95 (dd, 2H), 6.55 (t, J=73.4, 5-OCHF₂ or 6-OCHF₂, 1/2H), 6.59 (t, J=73.4, 5-OCHF₂ or 6-OCHF₂, 1/2H), 6.78 (m, 1H), 6.95 (dd, 2H), 7.20–7.70 (m, 4H), 7.77 (m, 3H), 7.92–8.20 (m, 3H).

Mixture of 4-[5-difluoromethoxy-2-{(3,4-dimethoxy-pyridin-2-yl)methanesulfinyl}-benzimidazole-1-sulfonyl]phenoxyacetic acid sodium salt (Compound 18) and 4-[6-difluoromethoxy-2-{(3,4-dimethoxy-pyridin-2-yl)-methanesulfinyl}-benzimidazole-1-sulfonyl] phenoxyacetic acid sodium salt (Compound 19)

To a solution of a mixture of 4-[5-difluoromethoxy-2-{(3,4-dimethoxy-pyridin-2-yl)-methanesulfinyl}-benzimidazole-1-sulfonyl]phenoxyacetic acid 2-(toluene-4-sulfonyl)ethyl ester and 4-[6-difluoromethoxy-2-{(3,4-dimethoxy-pyridin-2-yl)-methanesulfinyl}-benzimidazole-1-sulfonyl]phenoxyacetic acid 2-(toluene-4-sulfonyl)ethyl ester (Intermediates 41 and 42, 7.7 g, 9.9 mmol) in 70 mL of $CH_3CN$ was added a solution of $NaHCO_3$ (0.94 g, 11.1 mmol, 1.2 eq) in 35 mL of $H_2O$. The mixture was heated to 65° C. for 5 h. Thereafter all the volatile materials were removed under vacuum, the mixture was washed with EtOAc, and then the aqueous layer was lyophilized overnight. The solid was dissolved in $CH_2Cl_2$, and then the mixture was filtered to remove the insoluble material. The filtrate was concentrated and the resulting oil was dissolved in 20 mL of EtOAc. Diethyl ether was added to the mixture to precipitate a white solid. The precipitate was collected by filtration, washed with ether, and dried under vacuum to yield 4.5 g (73%) of a mixture of 4-[5-difluoromethoxy-2-{(3,4-dimethoxy-pyridin-2-yl)-methanesulfinyl}-benzimidazole-1-sulfonyl]phenoxyacetic acid sodium salt and 4-[6-difluoromethoxy-2-{(3,4-dimethoxy-pyridin-2-yl)-methanesulfinyl}-benzimidazole-1-sulfonyl] phenoxyacetic acid sodium salt (1:1 ratio) as an off-white solid.

$^1$H NMR (DMSO-$d_6$, 400 MHz) δ 3.42 and 3.43 (2 s, 3H), 3.57 (s, 3H), 4.24 (s, 2H), 4.66 (m, 2H), 6.55 and 6.65 (t, J=73.4, 5-OCHF$_2$ or 6-OCHF$_2$, 1/2H), 6.69 (t, J=73.4, 5-OCHF$_2$ or 6-OCHF$_2$, 1/2H), 6.75 (m, 3H), 6.93 (m, 1H), 7.19 and 7.37 (2 s, 1H), 7.43 and 7.58 (2 d, 1H), 7.70 (t, 2H), 7.83 (d, 1H).

Reaction Scheme 17

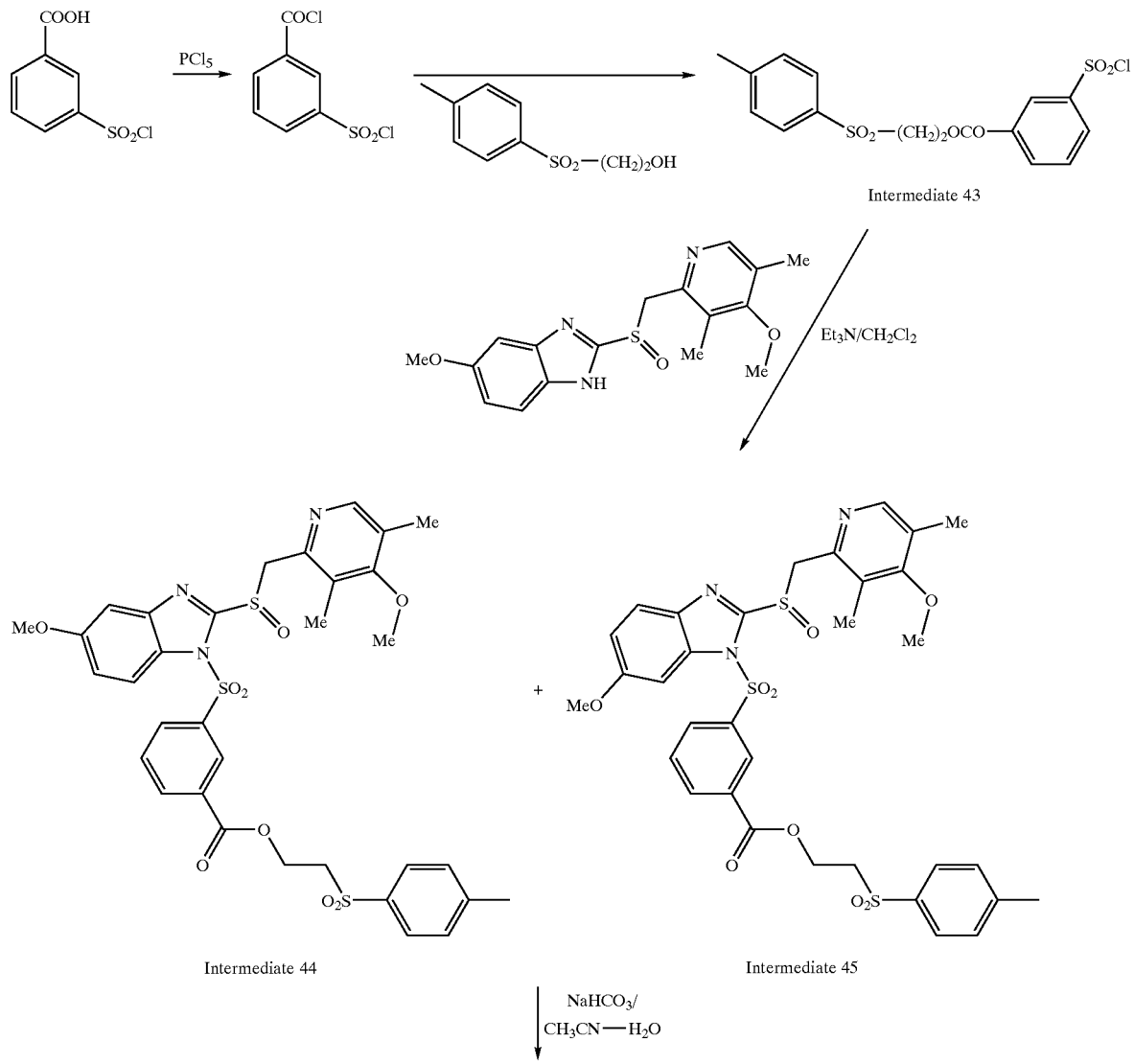

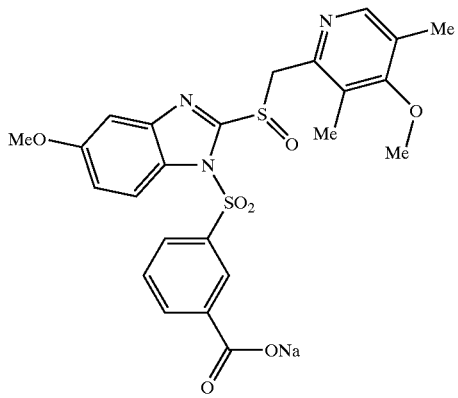

Compound 20

+

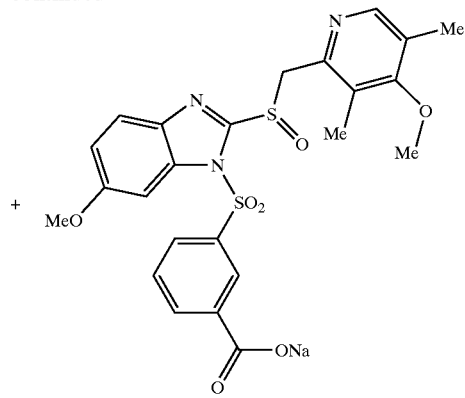

Compound 21

3-Chlorosulfonyl-benzoic acid 2-(toluene-4-sulfonyl)ethyl ester (Intermediate 43)

A heterogeneous mixture of 3-chlorosulfonyl-benzoic acid (11.0 g, 50.0 mmol) in 18 mL of $SOCl_2$ was refluxed for 3 h. Thereafter the excess of $SOCl_2$ was removed, the residual brown oil was dissolved in 60 mL of $CH_3CN$, and then 2-(p-tolylsulfonyl)ethanol (9.4 g, 47.0 mmol, 0.95 eq.) was added. The mixture was heated to reflux temperature for 20 h. Thereafter the most of $CH_3CN$ was removed, the resulting oil was purified by short column chromatography (silica gel, $CH_2Cl_2$) to give light brown oil, which was dried further under vacuum to yield 19.1 g (95%) of a light brown solid.

$^1$H NMR ($CDCl_3$, 400 MHz) δ 2.34 (s, 3H), 3.61 (t, 2H), 4.73 (t, 2H), 7.29 (d, 2H), 7.68 (t, 1H), 7.81 (d, 2H), 8.19 (m, 2H), 8.43 (s, 1H).

A mixture of 3-[5-methoxy-2-(4-methoxy-3,5-dimethyl-pyridin-2-yl-methanesulfinyl)-benzimidazole-1-sulfonyl]-benzoic acid 2-(toluene-4-sulfonyl)ethyl ester (Intermediate 44) and 3-[6-methoxy-2-(4-methoxy-3,5-dimethyl-pyridin-2-yl-methanesulfinyl)-benzimidazole-1-sulfonyl]-benzoic acid 2-(toluene-4-sulfonyl)ethyl ester (Intermediate 45)

To a heterogeneous mixture of 5-methoxy-2-(4-methoxy-3,5-dimethyl-pyridin-2-yl-methanesulfinyl)-1H-benzimidazole (OMEPRAZOLE, 1.0 g, 2.90 mmol), 5 mL of $Et_3N$, and about 1 g of $NaHCO_3$ in $CH_2Cl_2$ (20 mL) was added the sulfonyl chloride (Intermediate 43, 1.4 g, 3.48 mmol, 1.2 eq) in $CH_2Cl_2$ at room temperature, and then the mixture was stirred for 2 h. Thereafter water was added, the mixture was extracted with $CH_2Cl_2$, and the organic layers were dried, and concentrated. The oil was purified by column chromatography ($CH_2Cl$ to 1% MeOH in $CH_2Cl_2$) to yield 1.67 g (81%) of a mixture of 3-[5-methoxy-2-(4-methoxy-3,5-dimethoxy-pyridin-2-ylmethanesulfinyl)-benzimidazole-1-sulfonyl]-benzoic acid 2-(toluene-4-sulfonyl)ethyl ester (Intermediate 44) and 3-[6-methoxy-2-(4-methoxy-3,5-dimethyl-pyridin-2-ylmethanesulfinyl)-benzimidazole-1-sulfonyl]-benzoic acid 2-(toluene-4-sulfonyl)ethyl ester (Intermediate 45) as an off-white foam (1:1 ratio between 5- and 6-isomer).

$^1$H NMR ($CDCl_3$, 400 MHz) δ 2.25 (s, 3H), 2.27 (s, 3H), 2.33 and 2.43 (s, 3H, 5- and 6-isomers), 3.81 and 3.93 (s, 6H, 5- and 6-isomers), 4.66 (m, 2H), 5.07 (m, 2H), 7.0–8.6 (m, 12H, 5- and 6-isomers).

Mixture of 3-[5-methoxy-2-(4-methoxy-3,5-dimethyl-pyridin-2-yl-methanesulfinyl)-benzimidazole-1-sulfonyl]-benzoic acid sodium salt (Compound 20) and 3-[6-methoxy-2-(4-methoxy-3,5-dimethyl-pyridin-2-yl-ylmethanesulfinyl)-benzimidazole-1-sulfonyl]-benzoic acid sodium salt (Compound 21)

To the solution a mixture of 3-[5-methoxy-3,5-dimethyl-pyridin-2-ylmethanesulfinyl)-benzimidazole-1-sulfonyl]-benzoic acid 2-(toluene-4-sulfonyl)ethyl ester (Intermediate 44) and 3-[5-methoxy-2-(4-methoxy-3,5-dimethyl-pyridin-2-ylmethanesulfinyl)-benzimidazole-1-sulfonyl]-benzoic acid 2-(toluene-4-sulfonyl)ethyl ester (Intermediate 45) (1.6 g, 2.25 mmol) in 15 mL of $CH_3CN$ was added a solution of $NaHCO_3$ (225 mg, 2.7 mmol, 1.2 eq) in 8 mL of $H_2O$ at room temperature, and then the mixture was heated to 65° C. for 2 h. Thereafter most of $CH_3CN$ was removed, the mixture was extracted with EtOAc, and then the aqueous layer was lyophilized overnight. The resulting solid was dissolved in $CH_2Cl_2$, and then the mixture was filtered to remove insoluble solids. The filtrate was concentrated to near dryness. The resulting residual oil was dissolved in about 2 mL of $CH_2Cl_2$, and EtOAc was added to the mixture to precipitate a white solid. The white precipitate was collected by filtration, washed with EtOAc-ether (3:1), and dried under vacuum to give 900 mg (72%) of mixture of 3-[5-methoxy-2-(4-methoxy-3,5-dimethyl-pyridin-2-ylmethanesulfinyl)-benzimidazole-1-sulfonyl]-benzoic acid sodium salt (Compound 20) and 3-[6-methoxy-2-(4-methoxy-3,5-dimethyl-pyridin-2-ylmethanesulfinyl)-benzimidazole-1-sulfonyl]-benzoic acid sodium salt (Compound 21) as a white solid (1:1 ratio between 5- and 6-isomer).

$^1$H NMR ($D_2O$, 400 MHz) δ 1.77 (m, 6H, 5- and 6-isomers), 3.33–3.54 (m, 6H, 5- and 6-isomers), 4.57 (d, 1H), 4.76 (m, 1H), 6.6–8.3 (m, 8H, 5- and 6-isomers).

Reaction Scheme 18

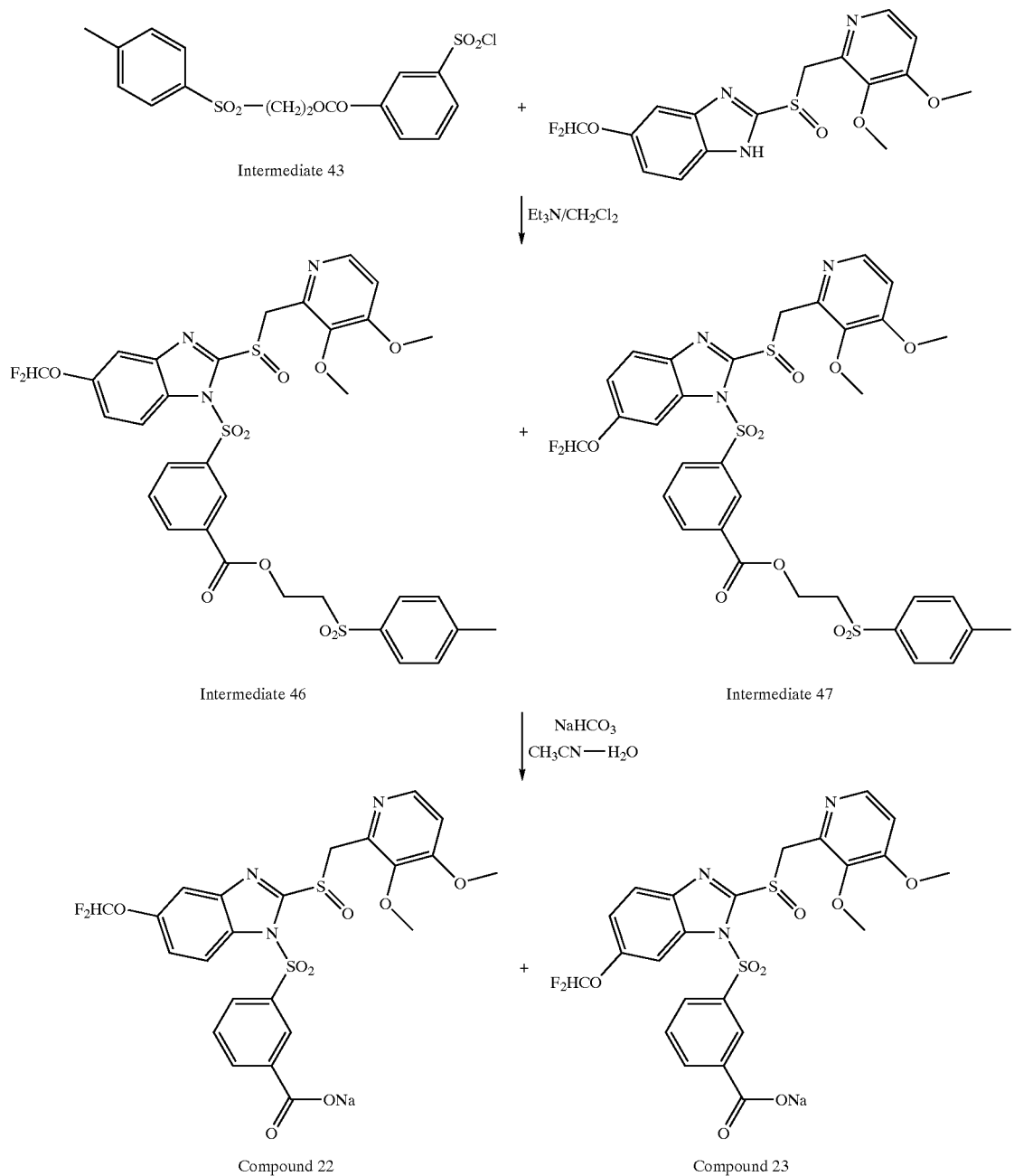

Compound 22 Compound 23

Mixture of 3-[5-difluoromethoxy-2-{(3,4-dimethoxy-pyridin-2-yl)-methanesulfinyl}-benzimidazole-1-sulfonyl]benzoic acid 2-(toluene-4-sulfonyl)ethyl ester (Intermediate 46) and 3-[6-difluoromethoxy-2-{(3,4-dimethoxy-pyridin-2-yl)-methanesulfinyl}-1-sulfonyl]benzoic acid 2-(toluene-4-sulfonyl)ethyl ester (Intermediate 47)

To a heterogeneous mixture of 5-difluoromethoxy-2-{(3,4-dimethoxy-pyridin-2-yl)-methanesulfinyl}-1H-benzimidazole sodium salt (PANTAPRAZOL sodium salt, 1.0 g, 2.3 mmol), 5 mL of $Et_3N$, and about 1 g of $NaHCO_3$ in $CH_2Cl_2$ (15 mL) was added the sulfonyl chloride (Intermediate 43, 1.12 g, 2.77 mmol, 1.2 eq) in $CH_2Cl_2$ at room temperature, and then the mixture was stirred for 1.5 h. Thereafter water was added, the mixture was extracted with $CH_2Cl_2$, and the organic layers were dried, and concentrated. The resulting residual oil was purified by column chromatography ($CH_2Cl_2$ to 1% MeOH in $CH_2Cl_2$) to yield 1.0 g (58%) of a mixture of 3-[5-difluoromethoxy-2-{(3,4-dimethoxy-pyridin-2-yl)-methanesulfinyl}-benzimidazole-1-sulfonyl]benzoic acid 2-(toluene-4-sulfonyl)ethyl ester (Intermediate 46) and 3-[6-difluoromethoxy-2-{(3,4-dimethoxy-pyridin-2-yl)-methanesulfinyl}-benzimidazole-1-sulfonyl]benzoic acid 2-(toluene-4-sulfonyl)ethyl ester (Intermediate 47) as an off-white foam (1:1 ratio between 5- and 6-isomer).

¹H NMR (CDCl₃, 400 MHz) δ 2.27 and 2.29 (2 s, 3H), 3.57 (m, 2H), 3.93 (s, 6H), 4.66 (m, 2H), 5.03 (dd, 2H), 6.53 (t, J=73.4, 5-OCHF₂ or 6-OCHF₂, 1/2H), 6.63 (t, J=73.4, 5-OCHF₂ or 6-OCHF₂, 1/2H), 6.86 (m, 1H), 7.25 (m, 3H), 7.59 (m, 1.5H), 7.77 (m, 3H), 8.05 (m, 1.5H), 8.12 (d, 1H), 8.32 (m, 1H), 8.58 (2 s, 1H).

Mixture of 3-[5-difluoromethoxy-2-{(3,4-dimethoxy-pyridin-2-yl)-methanesulfinyl}-benzimidazole-1-sulfonyl]benzoic acid sodium salt (Compound 22) and 3-[6-difluoromethoxy-2-{(3,4-dimethoxy-pyridin-2-yl)-methanesulfinyl}-benzimidazole-1-sulfonyl]benzoic acid sodium salt (Compound 23)

To the solution of mixture of 3-[5-difluoromethoxy-2-{(3,4-dimethoxy-pyridin-2-yl)-methanesulfinyl}-benzimidazole-1-sulfonyl]benzoic acid 2-(toluene-4-sulfonyl)ethyl ester (Intermediate 46) and 3-[6-difluoromethoxy-2-{(3,4-dimethoxy-pyridin-2-yl)-methanesulfinyl}-benzimidazole-1-sulfonyl]benzoic acid 2-(toluene-4-sulfonyl)ethyl ester (Intermediate 47) (1.0 g, 1.33 mmol) in 10 mL of CH₃CN was added a solution of NaHCO₃ (125 mg, 1.47 mmol, 1.2 eq) in 5 mL of H₂O at room temperature, and then the mixture was heated to 65° C. for 2.5 h. Thereafter most of the CH₃CN was removed, the mixture was extracted with EtOAc, and the aqueous layer was lyophilized overnight. The solid was dissolved in CH₂Cl₂, and then the mixture was filtered to remove insoluble solids. The filtrate was concentrated to near dryness to give an oil. The oil was dissolved in about 2 mL of CH₂Cl₂ and EtOAc-ether (2:1) was added to the mixture to precipitate a white solid. The precipitate was collected by filtration, washed with EtOAc-ether (2:1), and dried under vacuum to give 560 mg (71%) of mixture of 3-[5-difluoromethoxy-2-{(3,4-dimethoxy-pyridin-2-yl)-methanesulfinyl}-benzimidazole-1-sulfonyl]benzoic acid sodium salt (Compound 22) and 3-[6-difluoromethoxy-2-{(3,4-dimethoxy-pyridin-2-yl)-methanesulfinyl}-benzimidazole-1-sulfonyl]benzoic acid sodium salt (Compound 23) as a white solid (1:1 ratio between 5- and 6-isomer).

¹H NMR (D₂O, 400 MHz) δ 3.52 (s, 3H), 3.66 (s, 3H), 4.75 (dd, 2H), 6.61 (t, J=73.4, 5-OCHF₂ or 6-OCHF₂, 1/2H), 6.71 (t, J=73.4, 5-OCHF₂ and 6-OCHF₂, 1/2H; 5- and 6-isomers), 6.79–8.36 (m, 9H).

Reaction Scheme 19

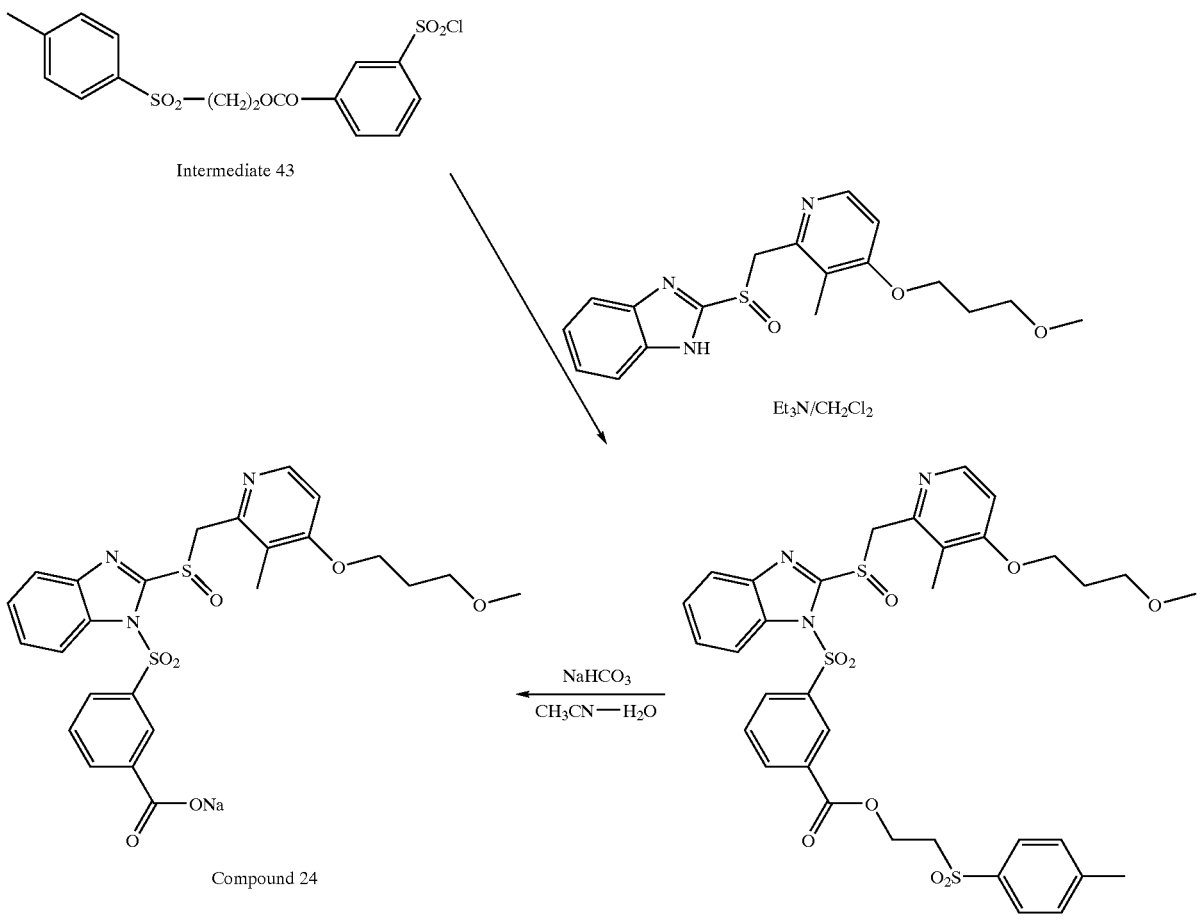

3-{2-[4-(3-Methoxy-propoxy)-3-methyl-pyridin-2-yl-methanesulfinyl]-benzimidazole-1-sulfonyl}benzoic acid 2-(toluene-4-sulfonyl)ethyl ester (Intermediate 48)

To a solution of 2-[4-(3-methoxy-propoxy)-3-methyl-pyridin-2-yl-methanesulfinyl]-1H-benzimidazole sodium salt (RABEPRAZOLE sodium salt, 1.0 g, 2.62 mmol), 5 mL of $Et_3N$, and about 1 g of $NaHCO_3$ in $CH_2Cl_2$ (15 mL) was added the sulfonyl chloride (Intermediate 43, 1.27 g, 3.15 mmol, 1.2 eq) in $CH_2Cl_2$ at room temperature, and then the mixture was stirred for 1.5 h. Thereafter water was added, the mixture was extracted with $CH_2Cl_2$, and the organic layers were dried, and concentrated. The resulting residual oil was purified by column chromatography ($CH_2Cl_2$ to 1% MeOH in $CH_2Cl_2$) to yield 1.5 g (76%) of 3-{2-[4-(3-methoxy-propoxy)-3-methyl-pyridin-2-yl-methanesulfinyl]-benzimidazole-1-sulfonyl}benzoic acid 2-(toluene-4-sulfonyl)ethyl ester (Intermediate 48) as an off-white foam.

$^1$H NMR (CDCl$_3$, 400 MHz) δ 2.09 (m, 2H), 2.24 (s, 3H), 2.29 (s, 3H), 3.34 (s, 3H), 3.57 (m, 4H), 4.13 (t, 2H), 4.65 (m, 2H), 5.05 (dd, 2H), 6.75 (d, 1H), 7.20 (d, 2H), 7.41 (t, 1H), 7.50 (t, 1H), 7.58 (t, 1H), 7.77 (m, 3H), 8.01 (t, 2H), 8.19 (d, 1H), 8.37 (d, 1H), 8.60 (s, 1H).

3-[2-[4-(3-Methoxy-propoxy)-3-methyl-pyridin-2-yl-methanesulfinyl]-benzimidazole-1-sulfonyl] benzoic acid sodium salt (Compound 24)

To the solution of the 3-[2-[4-(3-methoxy-propoxy)-3-methyl-pyridin-2-yl-methanesulfinyl]-benzimidazole-1-sulfonyl]benzoic acid 2-(toluene-4-sulfonyl)ethyl ester (Intermediate 48, 1.5 g, 2.0 mmol) in 15 mL of $CH_3CN$ was added a solution of $NaHCO_3$ (200 mg, 2.4 mmol, 1.2 eq) in 7 mL of $H_2O$ at room temperature, and then the mixture was heated to 65° C. for 2.5 h. Thereafter most of $CH_3CN$ was removed, the mixture was extracted with EtOAc, and the aqueous layer was lyophilized overnight. The solid was dissolved in $CH_2Cl_2$, and then the mixture was filtered to remove insoluble solids. The filtrate was concentrated to near dryness. The residual oil was dissolved in about 2 mL of $CH_2Cl_2$ and EtOAc-ether (1:1) was added to precipitate a white solid. The precipitate was collected by filtration, washed with EtOAc-ether (1:1), and dried under vacuum to give 700 mg (60%) of 3-[2-[4-(3-methoxy-propoxy)-3-methyl-pyridin-2-yl-methanesulfinyl]-benzimidazole-1-sulfonyl]benzoic acid sodium salt (Compound 24) as a white solid.

$^1$H NMR (D$_2$O, 400 MHz) δ 1.66 (m, 2H), 1.72 (s, 3H), 3.02 (s, 3H), 3.22 (t, 2H), 3.70 (m, 2H), 4.56 (d, 1H), 4.78 (d, 1H), 6.44 (d, 1H), 7.11 (t, 1H), 7.19 (t, 1H), 7.32 (t, 1H), 7.43 (d, 1H), 7.62 (d, 1H), 7.77 (m, 2H), 7.93 (d, 1H), 8.29 (s, 1H).

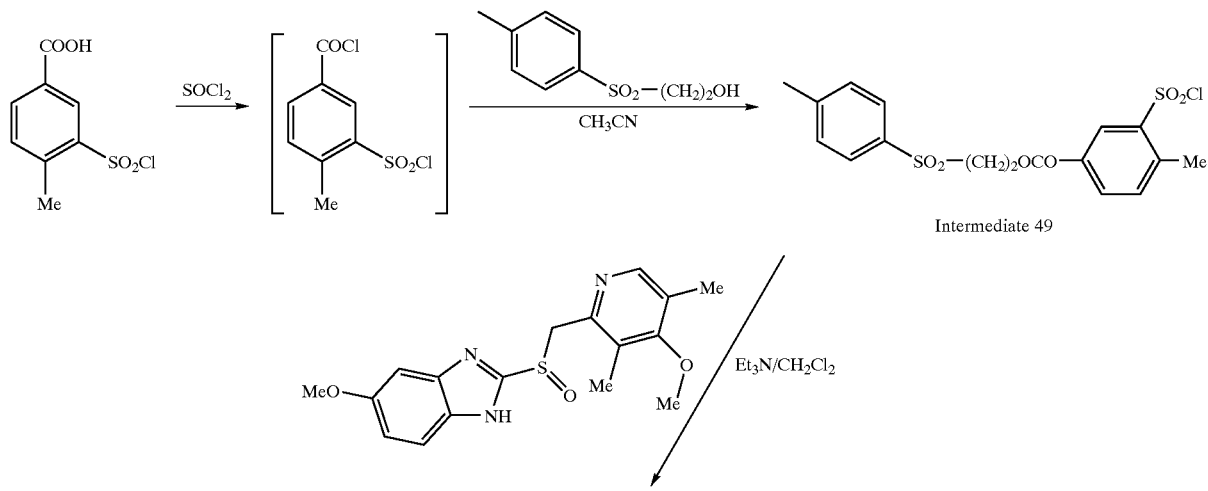

Reaction Scheme 20

-continued

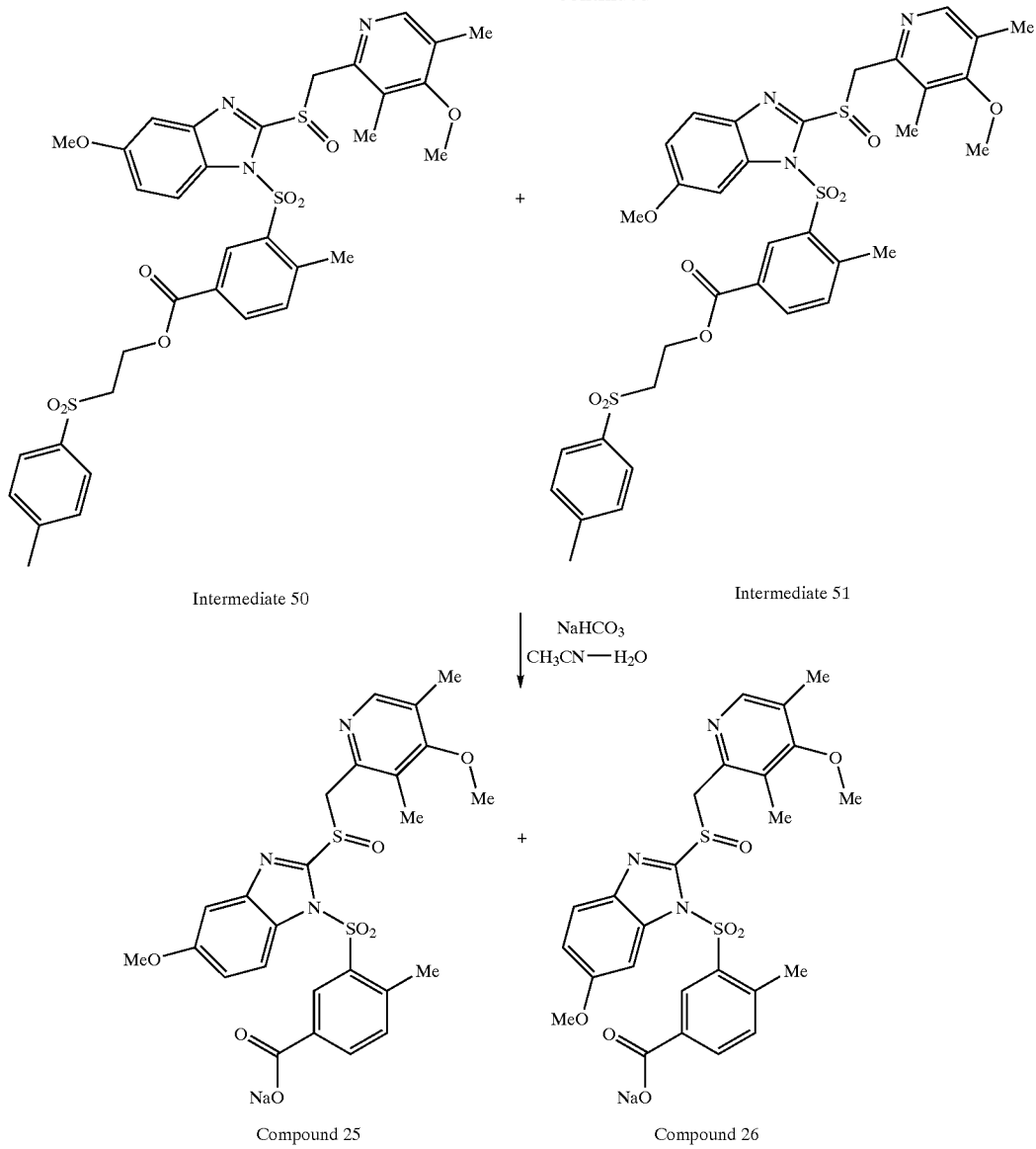

3-Chlorosulfonyl-4-methylbenzoic acid 2-(p-tolylsulfonyl)ethyl ester (Intermediate 49)

A heterogeneous mixture of 3-chlorosulfonyl-4-methylbenzoic acid (11.7 g, 50.0 mmol) in 18 mL of $SOCl_2$ was refluxed for 3 h. After the excess of $SOCl_2$ was removed, the residual brown oil was dissolved in 50 mL of $CH_3CN$, and then 2-(p-tolylsulfonyl)ethanol (9.4 g, 47.0 mmol, 0.95 eq.) was added. The mixture was heated to reflux temperature for 24 h. Thereafter most of $CH_3CN$ was removed, the resulting oil was purified by short column chromatography ($CH_2Cl_2$ to 1% MeOH in $CH_2Cl_2$) to give a light brown oil, which solidified on standing. The solid was dried further under vacuum to yield 19.5 g (99%) of 3-chlorosulfonyl-4-methylbenzoic acid 2-(p-tolylsulfonyl) ethyl ester (Intermediate 49).

$^1$H NMR ($CDCl_3$, 400 MHz) δ 2.33 (s, 3H), 2.84 (s, 3H), 3.50 (t, 2H), 4.70 (t, 2H), 7.29 (d, 2H), 7.46 (d, 1H), 7.79 (d, 2H), 8.03 (d, 1H), 8.42 (s, 1H).

Mixture of 3-[5-methoxy-2-(4-methoxy-3,5-dimethyl-pyridin-2-yl-methanesulfinyl)-benzimidazole-1-sulfonyl]-4-methylbenzoic acid 2-(toluene-4-sulfonyl)ethyl ester (Intermediate 50) and 3-[6-methoxy-2-(4-methoxy-3,5-dimethyl-pyridin-2-yl-methanesulfinyl)-benzimidazole-1-sulfonyl]-4-methylbenzoic acid 2-(toluene-4-sulfonyl)ethyl ester (Intermediate 51)

To a heterogeneous mixture of 5-methoxy-2-(4-methoxy-3,5-dimethyl-pyridin-2-yl-methanesulfinyl)-1H-benzimidazole (OMEPRAZOLE, 1.0 g, 2.90 mmol), 5 mL of $Et_3N$, and about 1 g of $NaHCO_3$ in $CH_2Cl_2$ (15 mL) was added the sulfonyl chloride (Intermediate 49, 1.45 g, 3.48 mmol, 1.2 eq) in $CH_2Cl_2$ (5 mL) at room temperature, and then the mixture was stirred for 0.5 h. Thereafter water was added, the mixture was extracted with $CH_2Cl_2$, and the organic layers were dried, and concentrated. The oil was purified by column chromatography ($CH_2Cl_2$ to 1% MeOH in $CH_2Cl_2$) to yield 1.5 g (71%) of mixture of 3-[5-methoxy-2-(4-methoxy-3,5-dimethyl-pyridin-2-yl-methanesulfinyl)-benzimidazole-1-sulfonyl]-4-methylbenzoic acid 2-(toluene-4-sulfonyl)ethyl ester (Intermediate 50) and 3-[6- methoxy-2-(4-methoxy-3,5-dimethyl-pyridin-2-yl-methanesulfinyl)-benzimidazole-1-sulfonyl]-4-methylbenzoic acid 2-(toluene-4-sulfonyl)ethyl ester (Intermediate 51) (1:1 ratio between 5- and 6-isomer) as a light brown foam.

$^1$H NMR (CDCl$_3$, 400 MHz) δ 2.25 and 2.26 (s, 3H, 5- and 6-isomers), 2.31 and 2.33 (s, 3H, 5- and 6-isomers), 2.56 and 2.59 (s, 3H, 5- and 6-isomers), 3.57 (m, 2H), 3.78 (s, 3H), 3.83 (s, 3H), 4.66 (m, 2H), 4.99 (dd, 2H), 7.02 (m, 1H), 7.26 (m, 5H), 7.61 and 7.71 (d, 1H, 5- and 6-isomers), 7.78 (d, 2H), 7.92 (m, 1H), 8.13 (s, 1H), 8.62 (s, 1H).

Mixture of 3-[5-methoxy-2-(4-methoxy-3,5-dimethyl-pyridin-2-yl-methanesulfinyl)-benzimidazole-1-sulfonyl]-4-methylbenzoic acid sodium salt (Compound 25) and 3-[6-methoxy-2-(4-methoxy-3,5-dimethyl-pyridin-2-yl-methanesulfinyl)-benzimidazole-1-sulfonyl]-4-methylbenzoic acid sodium salt (Compound 26)

To a solution of the mixture of 3-[5-methoxy-2-(4-methoxy-3,5-dimethyl-pyridin-2-yl-methanesulfinyl)-benzimidazole-1-sulfonyl]-4-methylbenzoic acid 2-(toluene-4-sulfonyl)ethyl ester (Intermediate 50) and 3-[6-methoxy-2-(4-methoxy-3,5-dimethyl-pyridin-2-methanesulfinyl)-benzimidazole-1-sulfonyl]-4-methylbenzoic acid 2-(toluene-4-sulfonyl)ethyl ester (Intermediate 51), 1.5 g (2.0 mmol), in 15 mL of CH$_3$CN was added a solution of NaHCO$_3$ (210 mg, 2.40 mmol, 1.2 eq) in 7 mL of H$_2$O at room temperature, and then the mixture was heated to 65° C. for 2.5 h. Thereafter the most of CH$_3$CN was removed, the mixture was extracted with EtOAc, and then aqueous layer was lyophilized overnight. The solid was dissolved in CH$_2$Cl$_2$, and then the mixture was filtered to remove insoluble solids. The filtrate was concentrated to near dryness. The residual oil was dissolved in about 2 mL of CH$_2$Cl$_2$ and EtOAc was added to the mixture to precipitate a white solid. The precipitate was collected by filtration, washed with EtOAc, and dried under vacuum to give 840 mg (74%) of mixture of 3-[5-methoxy-2-(4-methoxy-3,5-dimethyl-pyridin-2-yl-methanesulfinyl)-benzimidazole-1-sulfonyl]-4-methylbenzoic acid sodium salt (Compound 25) and of 3-[6-methoxy-2-(4-methoxy-3,5-dimethyl-pyridin-2-yl-methanesulfinyl)-benzimidazole-1-sulfonyl]-4-methylbenzoic acid sodium salt (Compound 26) (1:1 ratio between 5- and 6-isomer) as a white solid.

$^1$H NMR (D$_2$O, 400 MHz) δ 1.82 (m, 6H), 2.02 (s, 3H), 3.36 (s, 3H), 3.49 and 3.53 (s, 3H), 5- and 6-isomers), 4.66 (dd, 2H), 6.49 (m, 1H), 6.77 (s, 1H), 7.00 (m, 1H), 7.25–7.41 (d, 1H, 5- and 6-isomers), 7.57 (d, 1H), 7.82 (m, 1H), 8.34 and 8.40 (s, 1H, 5- and 6-isomers).

Reaction Scheme 21

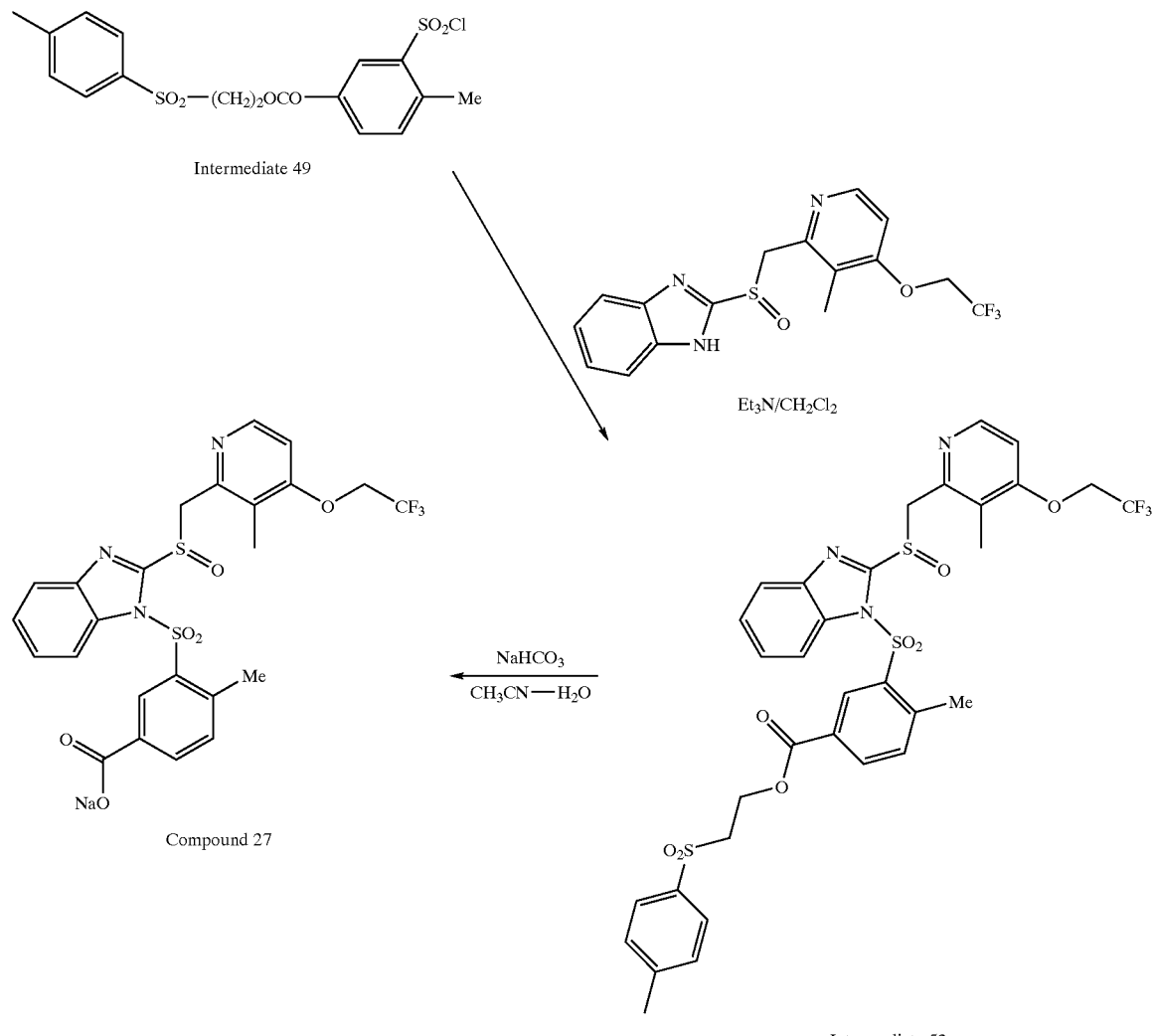

3-{2-[3-Methyl-4-(2,2,2-trifluoro-ethoxy)-pyridin-2-yl-methanesulfinyl]-benzimidazole-1-sulfonyl}-4-methylbenzoic acid 2-(toluene-4-sulfonyl)ethyl ester (Intermediate 52)

To a heterogeneous mixture of 2-[3-methyl-4-(2,2,2-trifluoroethoxy)pyridin-2-yl-methanesulfinyl]-1H-benzimidazole (LANSOPRAZOLE, 700 mg, 1.89 mmol), 3 mL of Et$_3$N, and about 1 g of NaHCO$_3$ in CH$_2$Cl$_2$ (15 mL) was added the sulfonyl chloride (Intermediate 49, 1.03 g, 2.47 mmol, 1.3 eq) in CH$_2$Cl$_2$ (5 mL) at room temperature, and then the mixture was stirred for 2 h. Thereafter water was added, the mixture was extracted with CH$_2$Cl$_2$, and the organic layers were dried, and concentrated. The resulting residual oil was purified by column chromatography (CH$_2$Cl$_2$ to 1% MeOH in CH$_2$Cl$_2$) to yield 1.1 g (78%) of 3-{2-[3-methyl-4-(2,2,2-trifluoro-ethoxy)-pyridin-2-yl-methanesulfinyl]-benzimidazole-1-sulfonyl}-4-methylbenzoic acid 2-(toluene-4-sulfonyl)ethyl ester (Intermediate 52) as a yellow foam.

$^1$H NMR (CDCl$_3$, 400 MHz) δ 2.31 (s, 3H), 2.33 (s, 3H), 2.58 (s, 3H), 3.57 (m, 2H), 4.38 (q, 2H), 4.67 (t, 2H), 4.80 (d, 1H), 4.97 (d, 1H), 6.61 (m, 1H), 7.31 (m, 3H), 7.42 (m, 2H), 7.50 (m, 1H), 7.79 (d, 2H), 7.83 (m, 1H), 7.93 (m, 1H), 8.17 (m, 1H), 8.65 (s, 1H).

3-{2-[3-Methyl-4-(2,2,2-trifluoro-ethoxy)-pyridin-2-yl-methanesulfinyl]-benzimidazole-1-sulfonyl}-4-methylbenzoic acid sodium salt (Compound 27)

To the solution of 3-{2-[3-methyl-4-(2,2,2-trifluoro-ethoxy)-pyridin-2-yl-methanesulfinyl]-benzimidazole-1-sulphonyl}-4-methylbenzoic acid 2-(toluene-4-sulfonyl) ethyl ester (Intermediate 52, 1.1 g, 1.46 mmol) in 8 mL of CH$_3$CN was added a solution of NaHCO$_3$ (160 mg, 1.91 mmol, 1.3 eq) in 4 mL of H$_2$O at room temperature, and then the mixture was heated to 65° C. for 2 h. Thereafter most of the CH$_3$CN was removed, the mixture was extracted with EtOAc, and then aqueous layer was lyophilized overnight. The solid was dissolved in CH$_2$Cl$_2$, and then the mixture was filtered to remove insoluble solids. The filtrate was concentrated to near dryness. The residual oil was dissolved in about 2 mL of CH$_2$Cl$_2$ and EtOAc was added to the mixture to precipitate a white solid. The precipitate was collected by filtration, washed with EtOAc, and dried under vacuum to give 540 mg (62%) of 3-{2-[3-methyl-4-(2,2,2-trifluoro-ethoxy)-pyridin-2-yl-methanesulfinyl]-benzimidazole-1-sulfonyl}-4-methylbenzoic acid sodium salt (Compound 27) as a light brown solid.

$^1$H NMR (D$_2$O, 400 MHz) ) δ 1.68 (s, 3H), 1.94 (s, 3H), 4.21 (m, 2H), 4.45 (d, 1H), 4.73 (d, 1H), 6.48 (d, 1H), 6.90 (d, 1H), 7.05 (m, 2H), 7.31 (m, 1H), 7.48 (m, 1H), 7.75 (m, 2H), 8.26 (s, 1H).

Reaction Scheme 22

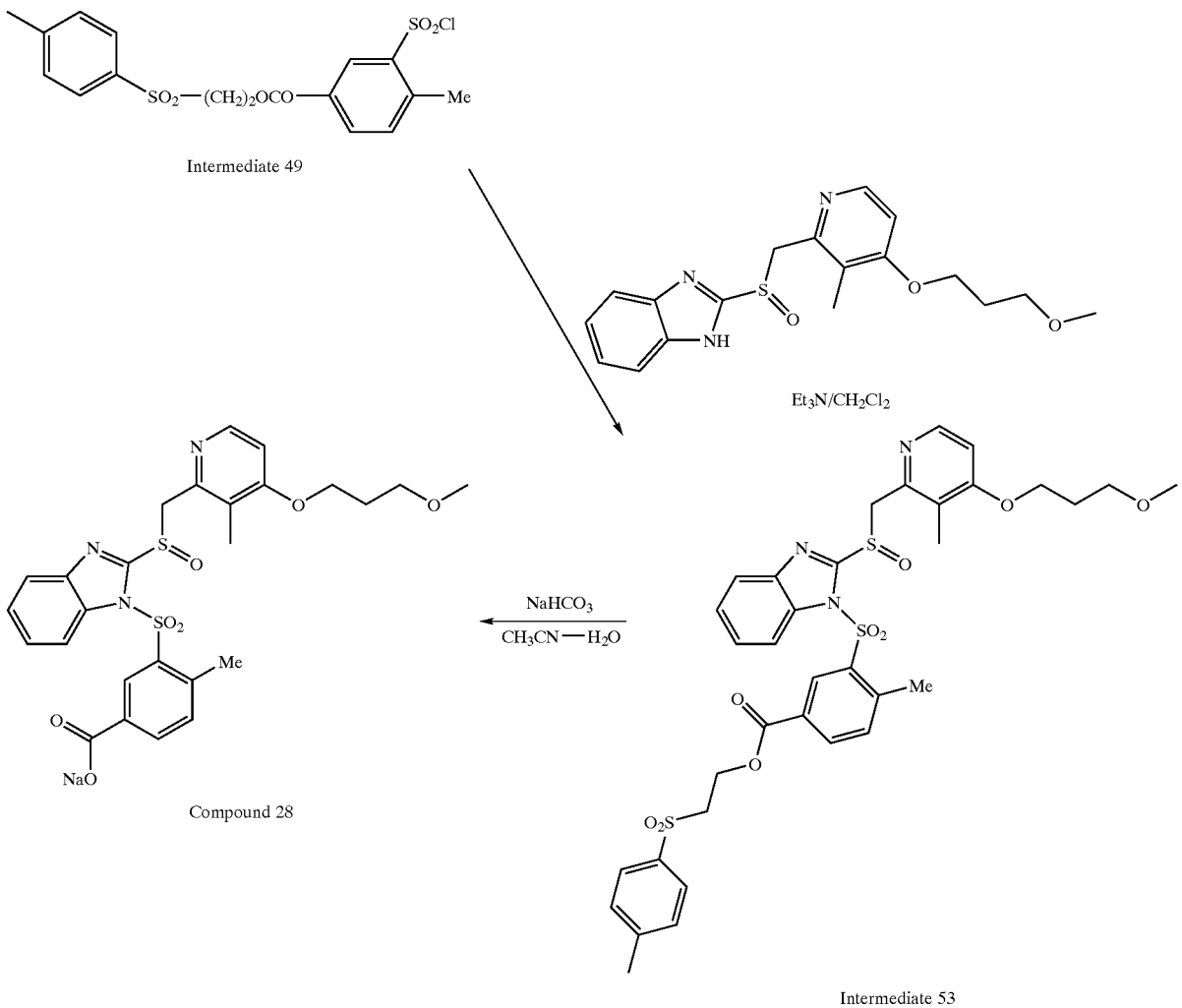

3-{2-[4-(3-Methoxy-propoxy)-3-methyl-pyridin-2-yl-methanesulfinyl]-benzimidazole-1-sulfonyl}-4-methylbenzoic acid 2-(toluene-4-sulfonyl)ethyl ester (Intermediate 53)

To a solution of 2-[4-(3-methoxy-propoxy)-3-methyl-pyridin-2-yl-methanesulfinyl]-1H-benzimidazole sodium salt (RABEPRAZOLE sodium salt, 1.0 g, 2.62 mmol), 5 mL of Et$_3$N, and about 1 g of NaHCO$_3$ in CH$_2$Cl$_2$ (15 mL) was added the sulfonyl chloride (Intermediate 49, 1.30 g, 3.15 mmol, 1.2 eq) in CH$_2$Cl$_2$ (5 mL) at room temperature, and then the mixture was stirred for 0.5 h. Thereafter water was added, the mixture was extracted with CH$_2$Cl$_2$, and the organic layers were dried, and concentrated. The residual oil was purified by column chromatography (CH$_2$Cl$_2$ to 1% MeOH in CH$_2$Cl$_2$) to yield 1.6 g (80%) of 3-{2-[4-(3-methoxy-propoxy)-3-methyl-pyridin-2-yl-methanesulfinyl]-benzimidazole-1-sulfonyl}-4-methylbenzoic acid 2-(toluene-4-sulfonyl)ethyl ester (Intermediate 53) as an off-white foam.

$^1$H NMR (CDCl$_3$, 400 MHz) δ 2.07 (t, 2H), 2.22 (s, 3H), 2.32 (s, 3H), 2.58 (s, 3H), 3.34 (s, 3H), 3.57 (m, 4H), 4.13 (t, 2H), 4.67 (t, 2H), 5.01 (dd, 2H), 6.74 (d, 1H), 7.30 (m, 3H), 7.40 (m, 2H), 7.79 (m, 5H), 8.19 (d, 1H), 8.64 (s, 1H).

3-{2-[4-(3-Methoxy-propoxy)-3-methyl-pyridin-2-yl-methanesulfinyl]-benzimidazole-1-sulfonyl}-4-methylbenzoic acid sodium salt (Compound 28)

To the solution of 3-{2-[4-(3-methoxy-propoxy)-3-methyl-pyridin-2-yl-methanesulfinyl]-benzimidazole-1-sulfonyl}-4-methylbenzoic acid 2-(toluene-4-sulfonyl)ethyl ester (Intermediate 53, 1.5 g, 1.97 mmol) in 15 mL of CH$_3$CN was added a solution of NaHCO$_3$ (200 mg, 2.36 mmol, 1.2 eq) in 7 mL of H$_2$O at room temperature, and then the mixture was heated to 65° C. for 2 h. Thereafter most of the CH$_3$CN was removed, the mixture was extracted with EtOAc, and the aqueous layer was lyophilized overnight. The solid was dissolved in CH$_2$Cl$_2$, and then the mixture was filtered to remove insoluble solids. The filtrate was concentrated to near dryness. The residual oil was dissolved in about 2 mL of CH$_2$Cl$_2$ and EtOAc-hexane (7:1) was added to precipitate a white solid. The precipitate was collected by filtration, washed with EtOAc-hexane (7:1), and dried under vacuum to give 950 mg (80%) of 3-{2-[4-(3-methoxy-propoxy)-3-methyl-pyridin-2-yl-methanesulfinyl]-benzimidazole-1-sulfonyl}-4-methylbenzoic acid sodium salt (Compound 28) as a white solid.

$^1$H NMR (D$_2$O, 400 MHz) ) δ 1.50 (s, 3H), 1.72 (t, 2H), 2.00 (s, 3H), 3.08 (s, 3H), 3.27 (t, 2H), 3.74 (m, 2H), 4.56 (d, 1H), 4.75 (d, 1H), 6.46 (d, 1H), 7.01 (d, 1H), 7.18 (m, 2H), 7.40 (m, 1H), 7.59 (m, 1H), 7.69 (d, 1H), 7.81 (d, 1H), 8.38 (s, 1H).

Reaction Scheme 23

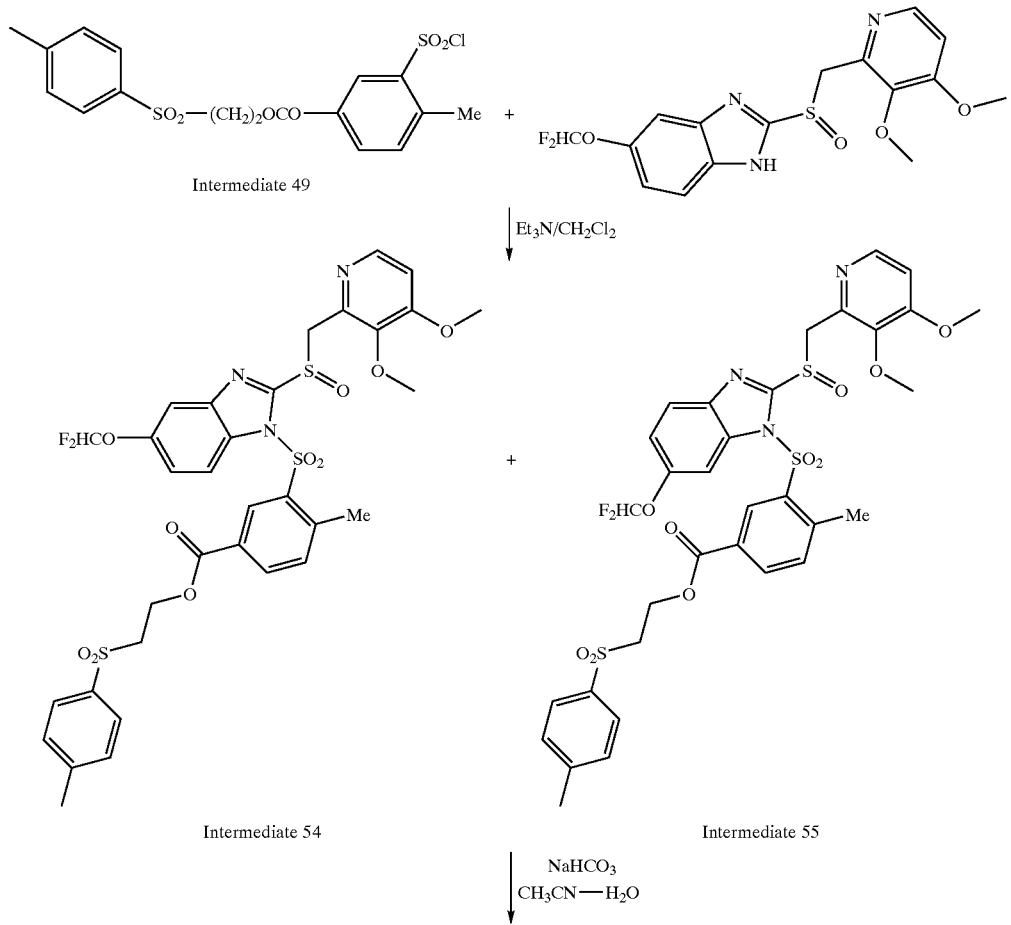

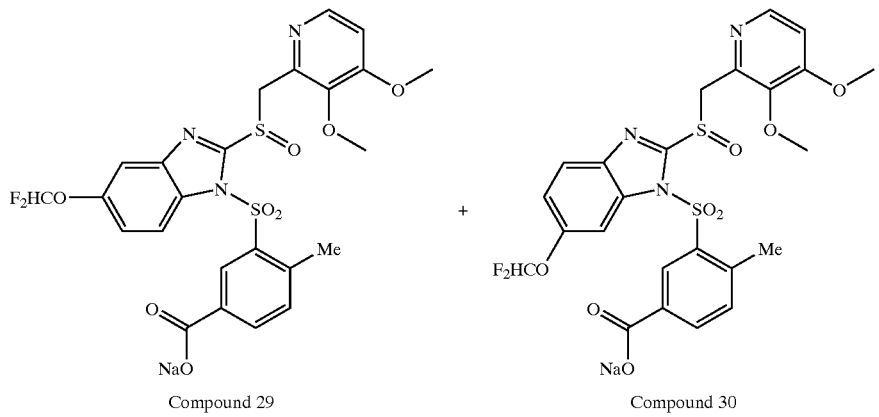

Compound 29      Compound 30

Mixture of 3-[5-difluoromethoxy-2-{(3,4-dimethoxy-pyridin-2-yl)-methanesulfinyl}-benzimidazole-1-sulfonyl]-4-methylbenzoic acid 2-(toluene-4-sulfonyl)ethyl ester (Intermediate 54) and 3-[6-difluoromethoxy-2-[(3,4-dimethoxy-pyridin-2-yl)-methanesulfinyl}benzimidazole-1-sulfonyl]-4-methylbenzoic acid 2-(toluene-4-sulfonyl)ethyl ester (Intermediate 55)

To a heterogeneous mixture of 5-difluoromethoxy-2-{(3,4-dimethoxy-pyridin-2-yl)-methanesulfinyl}-1H-benzimidazole sodium salt (LANSOPRAZOLE sodium salt, 1.0 g, 2.30 mmol), 2 mL of Et₃N, and about 1 g of NaHCO₃ in CH₂Cl₂ (15 mL) was added the sulfonyl chloride (Intermediate 49, 1.15 g, 2.76 mmol, 1.2 eq) in CH₂Cl₂ (5 mL) at room temperature, and then the mixture was stirred for 2 h. Thereafter water was added, the mixture was extracted with CH₂Cl₂, and the organic layers were dried, and concentrated. The oil was purified by column chromatography (CH₂Cl₂ to 1% MeOH in CH₂Cl₂) to yield 1.5 g (85%) of mixture of 3-[5-difluoromethoxy-2-{(3,4-dimethoxy-pyridin-2-yl)-methanesulfinyl}-benzimidazole-1-sulfonyl]-4-methylbenzoic acid 2-(toluene-4-sulfonyl) ethyl ester (Intermediate 54) and 3-[6-difluoromethoxy-2-{(3,4-dimethoxy-pyridin-2-yl)-methanesulfinyl}-benzimidazole-1-sulfonyl]-4-methylbenzoic acid 2-(toluene-4-sulfonyl)ethyl ester (Intermediate 55) as a light yellow foam (1:1 ratio between 5- and 6-isomer).

¹H NMR (CDCl₃, 400 MHz) δ 2.33 and 2.35 (3H), 2.58 (s, 3H), 3.58 (t, 2H), 3.90 (s, 3H), 3.91 (s, 3H), 4.68 (m, 2H), 4.89 (dd, 2H), 6.53 (t, J=73.4, 5-OCHF₂ or 6-OCHF₂, 1/2H), 6.54 (t, J=73.4, 5-OCHF₂ or 6-OCHF₂, 1/2H), 6.77 (d, 1H), 7.30 (m, 34H), 7.55 and 7.62 (s, 1H, 5- and 6-isomers), 7.81 (m, 3H), 7.97 (t, 1H), 7.06 (d, 1H), 8.61 and 8.68 (s, 1H), 5- and 6-isomers).

Mixture of 3-[5-difluoromethoxy-2-{(3,4-dimethoxy-pyridin-2-yl)-methanesulfinyl}-benzimidazole-1-sulfonyl]-4-methylbenzoic acid sodium salt (Compound 29) and 3-[6-difluoromethoxy-2-{(3,4-dimethoxy-pyridin-2-yl)-methanesulfinyl}-benzimidazole-1-sulfonyl]-4-methylbenzoic acid sodium salt (Compound 30)

To the solution of mixture of 3-[5-difluoromethoxy-2-{(3,4-dimethoxy-pyridin-2-yl)-methanesulfinyl}-benzimidazole-1-sulfonyl]-4-methylbenzoic acid 2-(toluene-4-sulfonyl)ethyl ester (Intermediate 54) and 3-[6-difluoromethoxy-2-{(3,4-dimethoxy-pyridin-2-yl)-methanesulfinyl}-benzimidazole-1-sulfonyl]-4-methylbenzoic acid 2-(toluene-4-sulfonyl)ethyl ester (Intermediate 55), 1.5 g (1.96 mmol), in 10 mL of CH₃CN was added a solution of NaHCO₃ (200 mg, 2.36 mmol, 1.2 eq) in 5 mL of H₂O at room temperature, and then the mixture was heated to 65° C. for 2 h. Thereafter most of the CH₃CN was removed, the mixture was extracted with EtOAc, and then aqueous layer was lyophilized overnight. The solid was dissolved in CH₂Cl₂, and then the mixture was filtered to remove insoluble solids. The filtrate was concentrated to near dryness. The residual oil was dissolved in about 2 mL of CH₂Cl₂ and EtOAc-ether (1:1) was added to the mixture to precipitate a white solid. The precipitate was collected by filtration, washed with EtOAc-ether (1:1) and dried under vacuum to give 850 mg (72%) of mixture of 3-[5-difluoromethoxy-2-{(3,4-dimethoxy-pyridin-2-yl)-methanesulfinyl}-benzimidazole-1-sulfonyl]-4-methylbenzoic acid sodium salt (Compound 29) and 3-[6-difluoromethoxy-2-{(3,4-dimethoxy-pyridin-2-yl)-methanesulfinyl}-benzimidazole-1-sulfonyl]-4-methylbenzoic acid sodium salt (Compound 30) as a white solid (1:1 ratio between 5- and 6-isomer). ¹H NMR (D₂O, 400 MHz) δ 2.51 (s, 3H), 3.74 (s, 3H), 3.83 (s, 3H), 4.50 (d, 1H), 4.67 (d, 1H), 6.93 (m), 7.07 (d), 7.12 (m), 7.33 (m), 7.55 (d), 7.70 (m), 8.90 (m), 8.13 (m), 8.28 and 8.40 (s, 5- and 6-isomers).

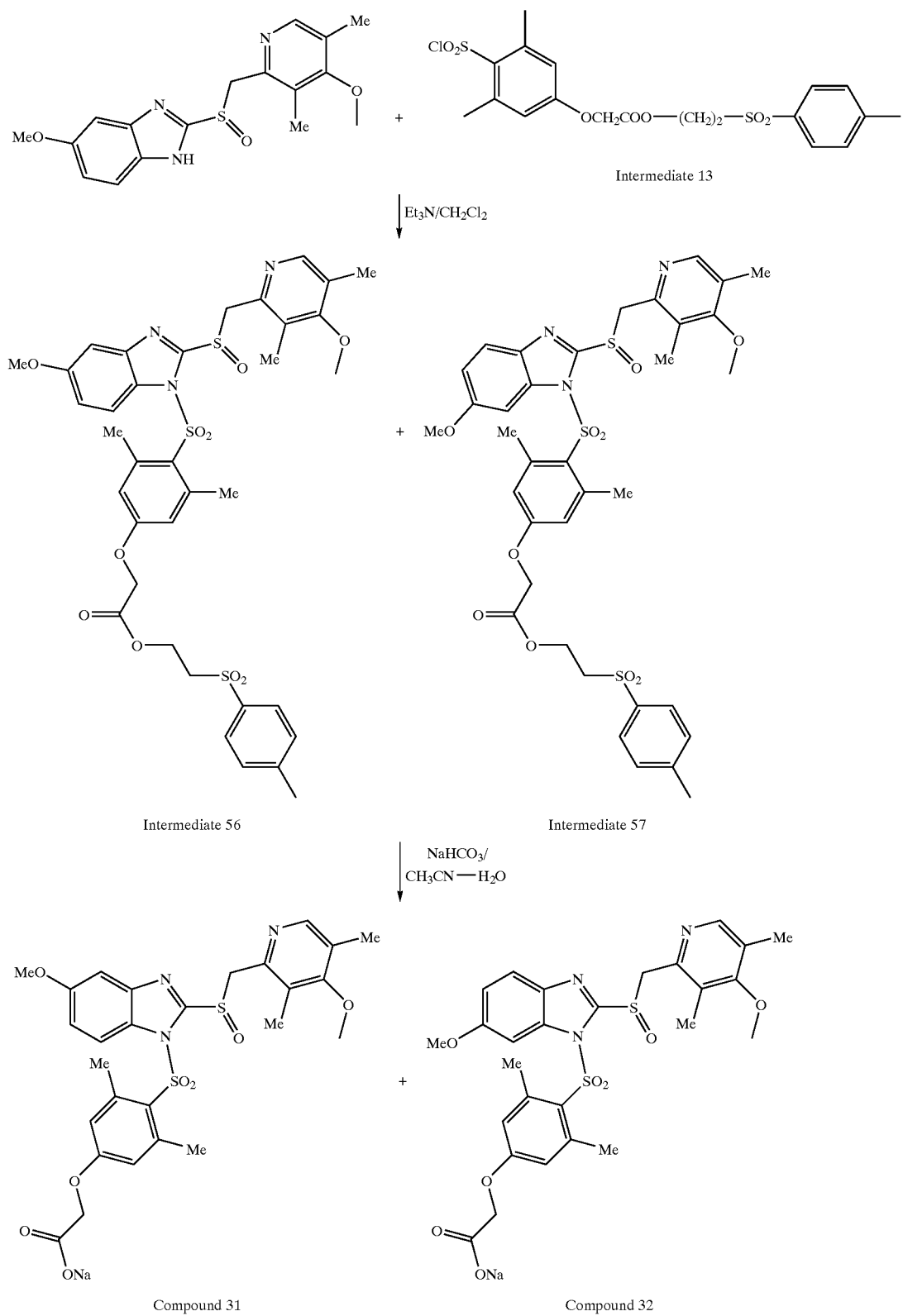

Mixture of 3,5-dimethyl-4-[5-methoxy-2-(4-methoxy-3,5-dimethyl-pyridin-2-yl-methanesulfinyl)-benzimidazole-1-sulfonyl]phenoxyacetic acid sodium salt (Compound 31) and 3,5-dimethyl-4-[6-methoxy-2-(4-methoxy-3,5-dimethyl-pyridin-2-yl-methanesulfinyl)-benzimidazole-1-sulfonyl]phenoxyacetic acid sodium salt (Compound 32)

To a heterogeneous solution of 5-methoxy-2-(4-methoxy-3,5-dimethyl-pyridin-2-ylmethanesulfinyl)-1H-benzimidazole (OMEPRAZOLE 4.0 g, 11.6 mmol) and 15 mL of Et$_3$N in 80 mL of CH$_2$Cl$_2$ was added the chlorosulfonyl ester (Intermediate 13, 6.94 g, 15.0 mmol, 1.3 eq). About 2 g of solid NaHCO$_3$ was added after the chlorosulfonyl ester has dissolved completely in the reaction mixture. The mixture was stirred at room temperature for 2 h. Thereafter the solvent was removed by evaporation and the residual oil was passed through a short column (silica gel, CH$_2$Cl$_2$) to remove an impurity and to give a mixture of Intermediates 56 and 57 as a brown oil. The oil (Intermediates 56 and 57, 9.5 g) was dissolved in 65 mL of CH$_3$CN and a solution of NaHCO$_3$ (1.07 g, 12.7 mmol, 1.1 eq) in 35 mL of H$_2$O was added. The mixture was heated to 65° C. for 2 h. Thereafter all volatile materials were removed under vacuum, the mixture was washed with EtOAc (2×), and then the aqueous layer was lyophilized overnight. The solid was dissolved in 150 mL of CH$_2$Cl$_2$, and then the mixture was filtered to remove insoluble material. The filtrate was concentrated and the resulting oil was dissolved in 10 mL of CH$_2$Cl$_2$. EtOAc was added to the mixture to precipitate a white solid. The precipitate was filtered, washed with EtOAc, and dried under vacuum to yield 5.1 g (72%) of mixture of 3,5-dimethyl-4-[5-methoxy-2-(4-methoxy-3,5-dimethyl-pyridin-2-yl-methanesulfinyl)-benzimidazole-1-sulfonyl]phenoxyacetic acid sodium salt (Compound 31) and 3,5-dimethyl-4-[6-methoxy-2-(4-methoxy-3,5-dimethyl-pyridin-2-yl-methanesulfinyl)-benzimidazole-1-sulfonyl]phenoxyacetic acid sodium salt (Compound 32) as a white solid (1:1 ratio between 5- and 6-isomer).

$^1$H NMR (D$_2$O, 400 MHz) δ 1.76 and 1.77 (s, 3H), 1.87 and 1.92 (s, 3H), 2.10 and 2.11 (s, 6H), 3.36 (s, 3H), 3.43 and 3.54 (s, 3H), 4.23 and 4.26 (s, 2H), 4.48 (d, 1H), 4.70 (d, 1H), 6.45–6.80 (m, 4H), 7.08 (m, 1H), 7.46 and 7.73 (m, 1H).

Reaction Scheme 25

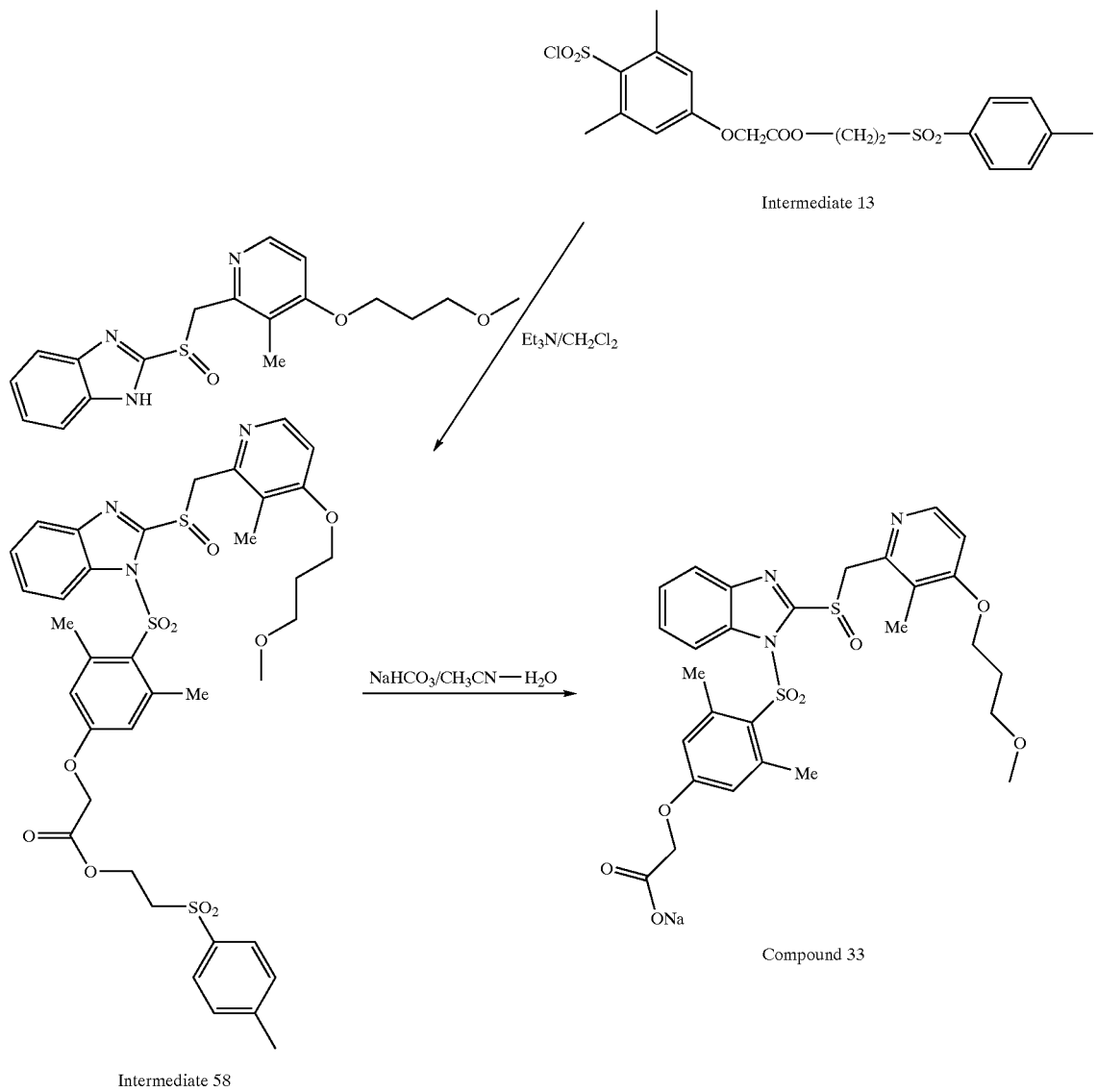

3,5-Dimethyl-4-{2-[4-(3-methoxy-propoxy)-3-methyl-pyridin-2-yl-methanesulfinyl]-benzimidazole-1-sulfonyl}phenoxyacetic acid 2-(toluene-4-sulfonyl)ethyl ester (Intermediate 58)

To a heterogeneous solution of 2-[4-(3-methoxy-propoxy)-3-methyl-pyridin-2-yl-methanesulfinyl]-1H-benzimidazole sodium salt (RABEPRAZOLE sodium salt, 1.0 g, 2.62 mmol) and 5 mL of Et$_3$N in 20 mL of CH$_2$Cl$_2$ was added the chlorosulfonyl ester (Intermediate 13, 1.57 g, 3.41 mmol, 1.3 eq). About 1 g of solid NaHCO$_3$ was added after the chlorosulfonyl ester has dissolved completely in the reaction mixture. The mixture was stirred at room temperature for 3 h. Thereafter the solvent was removed by evaporation and the residual oil was purified by column chromatography (silica gel, CH$_2$Cl$_2$ to 1% MeOH in CH$_2$Cl$_2$) to give 1.7 g (77%) of 3,5-dimethyl-4-{2-[4-(3-methoxy-propoxy)-3-methyl-pyridin-2-yl-methanesulfinyl]-benzimidazole-1-sulfonyl}phenoxyacetic acid 2-(toluene-4-sulfonyl)ethyl ester (Intermediate 58) as a white foam.

$^1$H NMR (CDCl$_3$, 400 MHz) δ 2.05 (m, 2H), 2.21 (s, 3H), 2.37 (s, 3H), 2.55 (s, 6H), 3.34 (s, 3H), 3.43 (t, 2H), 3.53 (m, 2H), 4.07 (t, 2H), 4.53 (m, 4H), 4.73 (dd, 2H), 6.66 (m, 2H), 7.36 (m, 4H), 7.57 (d, 1H), 7.75 (d, 2H), 7.89 (d, 1H), 7.99 (m, 1H), 8.18 (d, 1H).

3,5-Dimethyl-4-{2-[4-(3-methoxy-propoxy)-3-methyl-pyridin-2-yl-methanesulfinyl]-benzimidazole-1-sulfonyl}phenoxyacetic acid sodium salt (Compound 33)

To a solution of 3,5-dimethyl-4-{2-[4-(3-methoxy-propoxy)-3-methyl-pyridin-2-yl-methanesulfinyl]-benzimidazole-1-sulfonyl}phenoxyacetic acid 2-(toluene-4-sulfonyl)ethyl ester (Intermediate 58, 1.6 g, 1.90 mmol) in 10 mL of CH$_3$CN was added a solution of NaHCO$_3$ (208 mg, 2.47 mmol, 1.3 eq) in 5 mL of H$_2$O. The mixture was heated to 65° C. for 3 h. Thereafter all the volatile materials were removed under vacuum, the mixture was washed with EtOAc (2×), and then the aqueous layer was lyophilized overnight. The solid was dissolved in 80 mL of CH$_2$Cl$_2$, and then the mixture was filtered to remove insoluble material. The filtrate was concentrated and the residual oil was dissolved in 5 mL of CH$_2$Cl$_2$. EtOAc was added to the mixture to precipitate a white solid. The precipitate was collected by filtration, washed with EtOAc, and dried under vacuum to yield 800 mg (62%) of 3,5-dimethyl-4-{2-[4-(3-methoxy-propoxy)-3-methyl-pyridin-2-yl-methanesulfinyl]-benzimidazole-1-sulfonyl}phenoxyacetic acid sodium salt (Compound 33) as a white solid.

$^1$H NMR (D$_2$O, 400 MHz) δ 1.69 (m, 5H), 2.10 (s, 6H), 3.01 (s, 3H), 3.21 (m, 2H), 3.73 (m, 2H), 4.21 (s, 2H), 4.40 (m, 2H), 6.45 (s, 2H), 6.59 (m, 1H), 7.06–7.23 (m, 3H), 7.59 (m, 1H), 7.84 (m, 1H).

Reaction Scheme 26

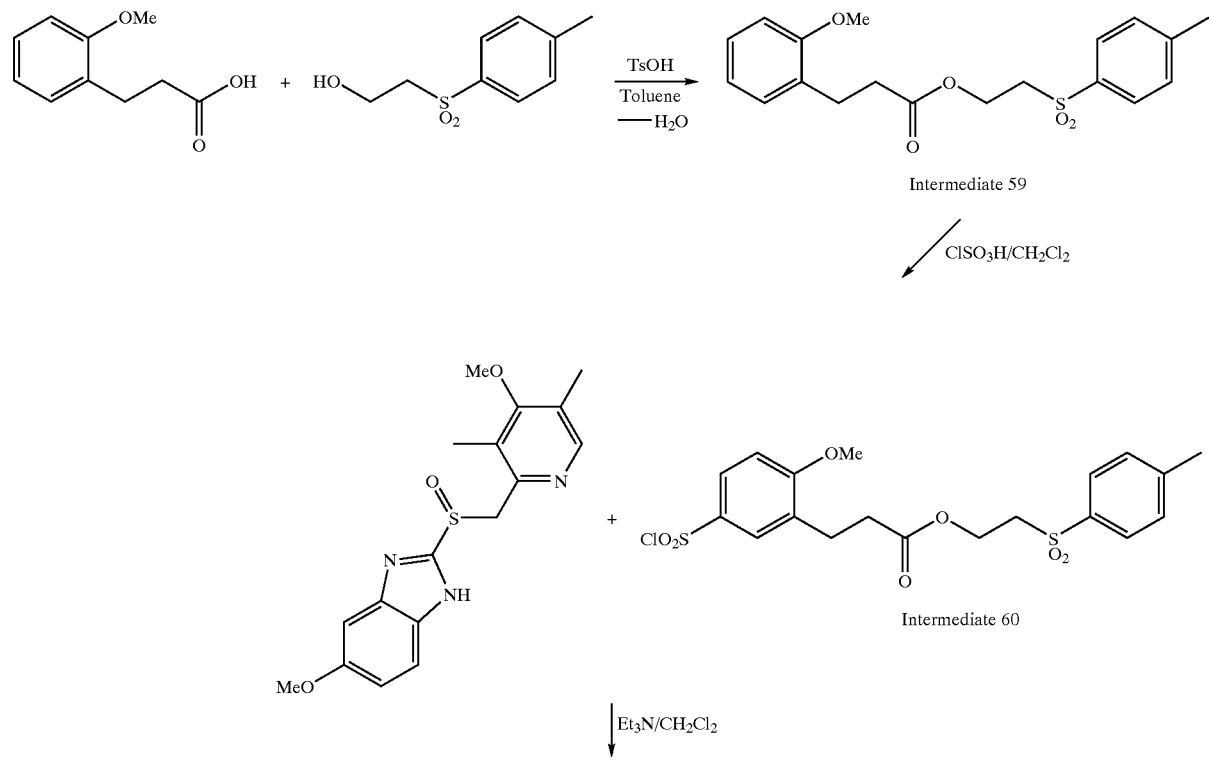

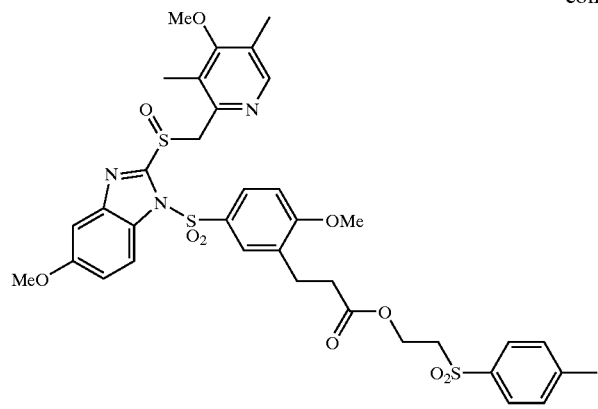

Intermediate 61

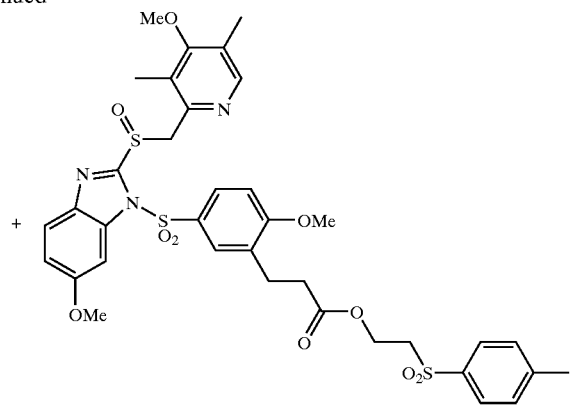

Intermediate 62

NaHCO₃/
CH₃CN—H₂O

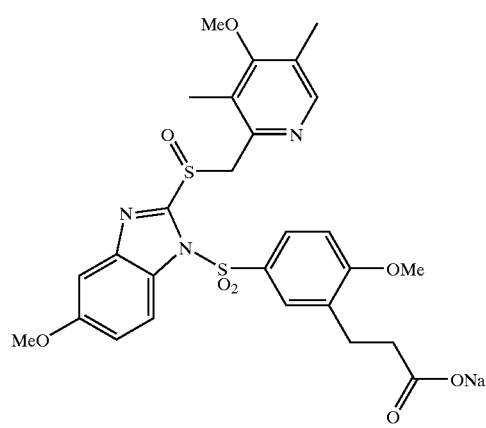

Compound 34

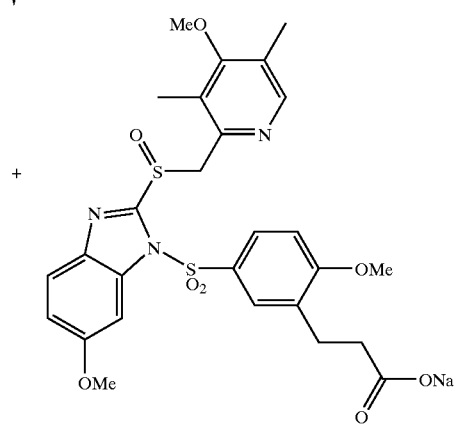

Compound 35

3-(2-Methoxyphenyl)propionic acid 2-(toluene-4-sulfonyl)ethyl ester (Intermediate 59)

A mixture of 3-(2-methoxyphenyl)propionic acid (5.0 g, 27.8 mmol), 2-(p-toluenesulfonyl)ethanol (5.5 g, 27.8 mmol), and p-toluenesulfonic acid hydrate (p-TsOH.H₂O) (0.5 g) in 100 mL of toluene was refluxed with Dean-Stark trap for 5 h. Then water was added and the mixture was extracted with CH₂Cl₂. The combined organic layers were washed with saturated NaHCO₃ solution (2×), dried over MgSO₄, and concentrated to give 3-(2-methoxyphenyl) propionic acid 2-(toluene-4-sulfonyl)ethyl ester (Intermediate 59, 5.5 g, 88%) as a light brown liquid.

$^1$H NMR (CDCl₃, 400 MHz) δ 2.39 (m, 5H), 2.79 (t, 2H), 3.40 (t, 2H), 3.81 (s, 3H), 4.37 (t, 2H), 6.87 (m, 2H), 7.07 (m, 1H), 7.17–7.35 (m, 3H), 7.78 (d, 2H).

3-(5-Chlorosulfonyl-2-methoxyphenyl)propionic acid 2-(toluene-4-sulfonyl)ethyl ester (Intermediate 60)

To a mixture of 3-(2-methoxyphenyl)propionic acid 2-(toluene-4-sulfonyl)ethyl ester (Intermediate 59, 5.0 g, 13.8 mmol) and 5 mL of CH₂Cl₂ was added dropwise chlorosulfonic acid (8.0 g, 69.0 mmol, 5.0 eq) with ice-bath cooling. The mixture was stirred at 0° C. for 30 min. The resulting thick oil was poured onto crushed ice with vigorous stirring. The mixture was extracted with EtOAc. The organic layer was dried over MgSO₄, and concentrated by evaporation to give a thick oil, which was purified by column chromatography (CH₂Cl₂) to yield 3-(5-chlorosulfonyl-2-methoxyphenyl)propionic acid 2-(toluene-4-sulfonyl)ethyl ester (Intermediate 60, 4.7 g, 74%) as a light brown oil.

$^1$H NMR (CDCl₃, 400 MHz) δ 2.40 (s, 3H), 2.47 (t, 2H), 2.89 (t, 2H), 3.42 (t, 2H), 3.94 (s, 3H), 4.40 (t, 2H), 6.98 (d, 1H), 7.36 (d, 2H), 7.75 (d, 1H), 7.80 (d, 2H), 7.91 (m, 1H).

Mixture of 3-[2-methoxy-5-{5-methoxy-2-(4-methoxy-3,5-dimethyl-pyridin-2-yl-methanesulfinyl)-benzimidazole-1-sulfonyl}phenyl] propionic acid 2-(toluene-4-sulfonyl)ethyl ester (Intermediate 61) and 3-[2-methoxy-5-{6-methoxy-2-(4-methoxy-3,5-dimethyl-pyridin-2-yl-methanesulfinyl)-benzimidazole-1-sulfonyl] phenyl}propionic acid 2-(toluene-4-sulfonyl) ethylester (Intermediate 62)

To a heterogeneous solution of 5-methoxy-2-(4-methoxy-3,5-dimethyl-pyridin-2-yl-methanesulfinyl)-1H-benzimidazole (OMEPRAZOLE, 1.7 g, 4.93 mmol) and 6 mL of Et₃N in 20 mL of CH₂Cl₂ was added the chlorosulfonyl ester (Intermediate 60, 2.8 g, 6.0 mmol, 1.3 eq). About 1 g of solid NaHCO₃ was added after the chlorosulfonyl ester has dissolved completely in the reaction mixture. The mixture was stirred at room temperature for 2 h. Thereafter the solvent was removed by evaporation and the residual oil was purified by column chromatography (silica gel, $CH_2Cl_2$ to 2% MeOH in $CH_2Cl_2$) to give a mixture of 3-[2-methoxy-5-{5-methoxy-2-(4-methoxy-3,5-dimethyl-pyridin-2-yl-methanesulfinyl)-benzimidazole-1-sulfonyl}phenyl] propionic acid 2-(toluene-4-sulfonyl)ethyl ester (Intermediate 61) and 3-[2-methoxy-5-{6-methoxy-2-(4-methoxy-3,5-dimethyl-pyridin-2-yl-methanesulfinyl)-benzimidazole-1-sulfonyl}phenyl]propionic acid 2-(toluene-4-sulfonyl)ethyl ester (Intermediate 62) (1.88 g, 50%) as an off-white foam (1:1 ratio between 5- and 6-isomer).

¹H NMR (CDCl₃, 400 MHz) δ 2.25 (s, 3H), 2.28 (m, 3H), 2.35 (m, 5H), 2.77 (m, 2H), 2.39 (m, 2H), 3.77–3.93 (m, 9H), 4.30 (m, 2H), 4.96 (m, 2H), 6.90 (t, 1H), 7.00 (m, 1H), 7.25–7.50 (m, 3H), 7.64–7.86 (m, 3H), 8.01 (m, 1H), 8.20 (s, 1H).

Mixture of 3-[2-methoxy-5-{5-methoxy-2-(4-methoxy-3,5-dimethyl-pyridin-2-yl-methanesulfinyl)-benzimidazole-1-sulfonyl}phenyl] propionic acid sodium salt (Compound 34) and 3-[2-methoxy-5-{6-methoxy-2-(4-methoxy-3,5-dimethyl-pyridin-2-yl-methanesulfinyl)-benzimidazole-1-sulfonyl}phenyl]propionic acid sodium salt (Compound 35)

To a solution of a mixture of 3-[2-methoxy-5-{5-methoxy-2-(4-methoxy-3,5-dimethyl-pyridin-2-yl-methanesulfinyl)-benzimidazole-1-sulfonyl}phenyl] propionic acid 2-(toluene-4-sulfonyl)ethyl ester (Intermediate 61) and 3-[2-methoxy-5-{6-methoxy-2-(4-methoxy-3,5-dimethyl-pyridin-2-yl-methanesulfinyl)-benzimidazole-1-sulfonyl}phenyl]propionic acid 2-(toluene-4-sulfonyl)ethyl ester (Intermediate 62), 1.7 g (2.21 mmol), in 17 mL of CH₃CN was added the solution of NaHCO₃ (205 mg, 2.43 mmol, 1.1 eq) in 8 mL of H₂O. The mixture was heated to 65° C. for 2 h. Thereafter all volatile materials were removed under vacuum, the mixture was washed with EtOAc (2x), and then the aqueous layer was lyophilized overnight. The solid was dissolved in 70 mL of CH₂Cl₂, and then the mixture was filtered to remove insoluble material. The filtrate was concentrated and the residual oil was dissolved in 3 mL of CH₂Cl₂. EtOAc was added to the mixture to precipitate a white solid. The precipitate was filtered, washed with EtOAc, and dried under vacuum to yield 1.0 g (75%) of mixture of 3-[2-methoxy-5-{5-methoxy-2-(4-methoxy-3,5-dimethyl-pyridin-2-yl-methanesulfinyl)-benzimidazole-1-sulfonyl}phenyl]propionic acid sodium salt (Compound 34) and 3-[2-methoxy-5-{6-methoxy-2-(4-methoxy-3,5-dimethyl-pyridin-2-yl-methanesulfinyl)benzimidazole-1-sulfonyl}phenyl]propionic acid sodium salt (Compound 35) as a white solid (1:1 ratio between 5- and 6-isomer).

¹H NMR (D₂O, 400 MHz) δ 1.53 (s, 6H), 2.08 (m, 2H), 2.52 (m, 2H), 3.35 (s, 3H), 3.42 (s, 3H), 3.49 and 3.62 (s, 3H, 5-OMe and 6-OMe), 4.60 (dd, 2H), 6.30 (m, 1H), 7.70 (m, 1H), 7.94 (m, 1H), 7.08–7.80 (m, 4H).

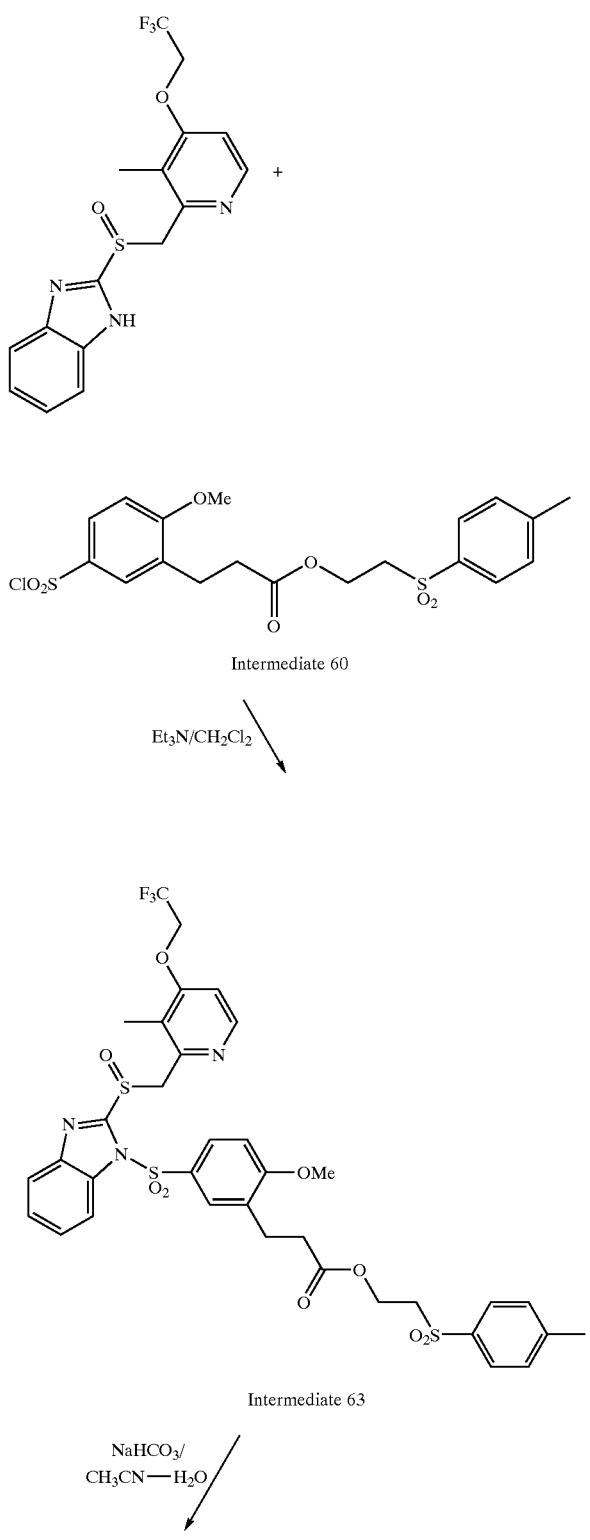

Reaction Scheme 27

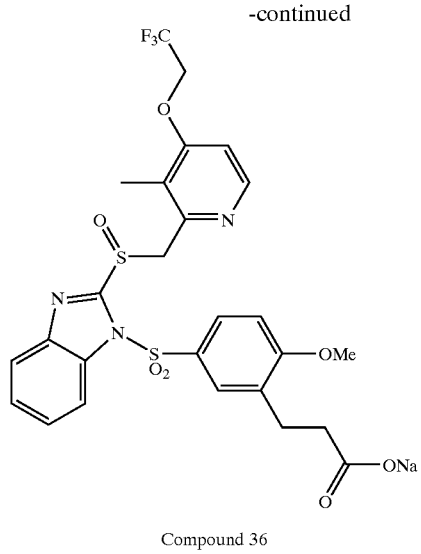

Compound 36

3-[2-Methoxy-5-{2-(3-methyl-4-(2,2,2-trifluoroethoxy)pyridin-2-yl-methanesulfinyl)-benzimidazole-1-sulfonyl}phenyl]propionic acid 2-(toluene-4-sulfonyl)ethyl ester (Intermediate 63)

To a heterogeneous solution of 2-[3-methyl-4-(2,2,2-trifluoroethoxy)pyridin-2-yl-methanesulfinyl]-1H-benzimidazole (LANSOPRAZOLE, 800 mg, 2.17 mmol) and 3 mL of $Et_3N$ in 20 mL of $CH_2Cl_2$ was added the chlorosulfonyl ester (Intermediate 60, 1.2 g, 2.60 mmol, 1.2 eq). About 1 g of solid $NaHCO_3$ was added after the chlorosulfonyl ester has dissolved completely in the reaction mixture. The mixture was stirred at room temperature 1 h. Thereafter the solvent was removed by evaporation and the residual oil was purified by column chromatography (silica gel, $CH_2Cl_2$ to 1% MeOH in $CH_2Cl_2$) to give Intermediate 63 (1.2 g, 70%) as an off-white foam.

$^1$H NMR ($CDCl_3$, 400 MHz) δ 2.32 (s, 3H), 2.39 (m, 5H), 2.78 (t, 2H), 3.39 (t, 2H), 3.85 (s, 3H), 4.32 (m, 2H), 4.40 (m, 2H), 4.90 (d, 1H), 5.03 (d, 1H), 6.68 (d, 1H), 6.89 (d, 1H), 7.35 (m, 4H), 7.80 (m, 4H), 7.99 (m, 2H), 8.27 (d, 1H).

3-[2-Methoxy-5-{2-(3-methyl-4-(2,2,2-trifluoroethoxy)pyridin-2-yl-methanesulfinyl)-benzimidazole-1-sulfonyl}phenyl]propionic acid sodium salt (Compound 36)

To a solution of 3-[2-methoxy-5-{2-(3-methyl-4-(2,2,2-trifluoroethoxy)pyridin-2-yl-methanesulfinyl)-benzimidazole-1-sulfonyl}phenyl]propionic acid 2-(toluene-4-sulfonyl)ethyl ester (Intermediate 63, 1.0 g, 1.26 mmol) in 10 mL of $CH_3CN$ was added the solution of $NaHCO_3$ (127 mg, 1.51 mmol, 1.2 eq) in 5 mL of $H_2O$. The mixture was heated to 65° C. for 4 h. Thereafter all the volatile materials were removed under vacuum, the mixture was washed with $Et_2O$-EtOAc (10:1)), and then the aqueous layer was lyophilized overnight. The solid was dissolved in 100 mL of $CH_2Cl_2$, and then the mixture was filtered to remove insoluble material. The filtrate was concentrated and the residual oil was dissolved in 5 mL of $CH_2Cl_2$. $Et_2O$ was added to the mixture to precipitate a white solid. The precipitate was filtered, washed with $Et_2O$, and dried under vacuum to yield 730 mg (91%) of 3-[2-methoxy-5-{2-(3-methyl-4-(2,2,2-trifluoroethoxy)pyridin-2-yl-methanesulfinyl)-benzimidazole-1-sulfonyl}phenyl]propionic acid sodium salt (Compound 36) as a white solid.

$^1$H NMR ($D_2O$, 400 MHz) δ 1.72 (s, 3H), 2.06 (t, 2H), 2.46 (t, 2H), 3.34 (s, 3H), 4.23 (m, 2H), 4.66 (d, 1H), 4.71 (d, 1H), 6.17 (m, 1H), 6.55 (d, 1H), 7.06 (m, 1H), 7.17 (m, 1H), 7.33 (m, 1H), 7.41 (m, 1H), 7.49 (m, 1H), 7.62 (m, 1H), 7.89 (m, 1H).

Reaction Scheme 28

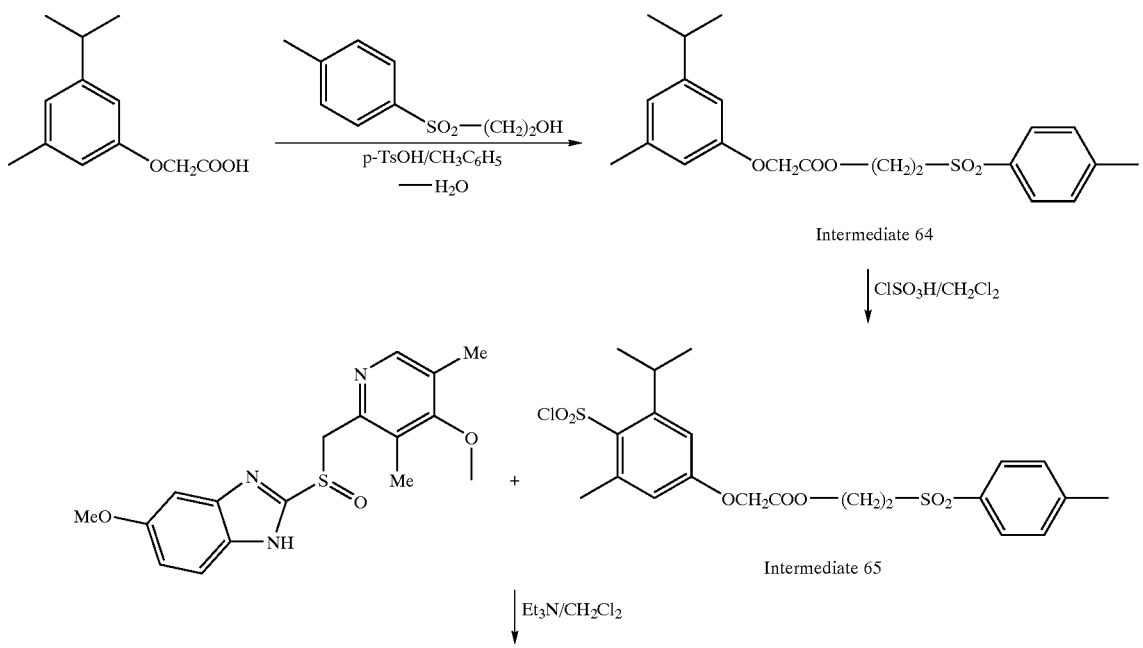

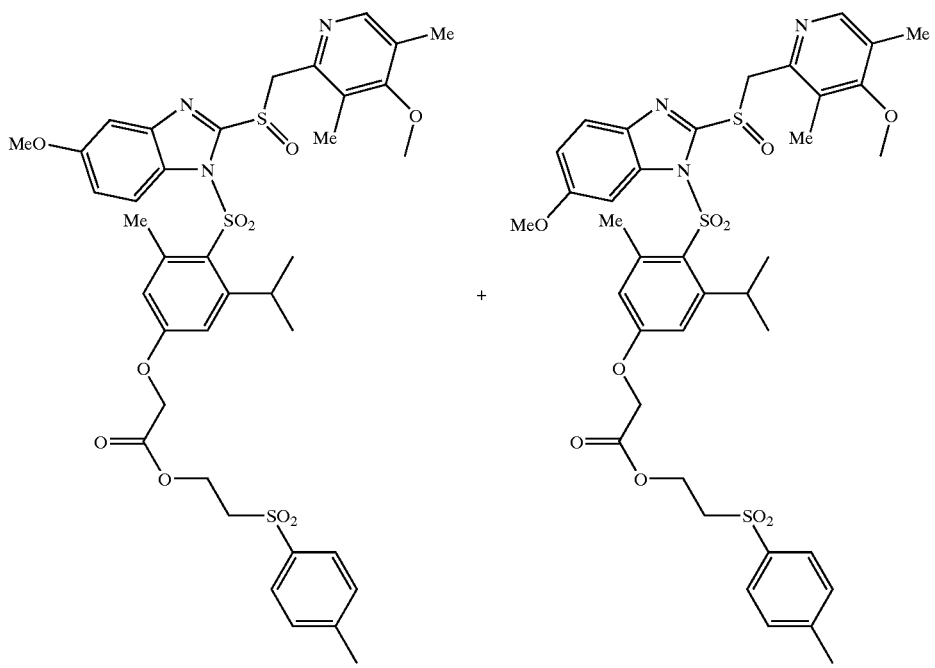

Intermediate 66    +    Intermediate 67

NaHCO₃/
CH₃CN—H₂O

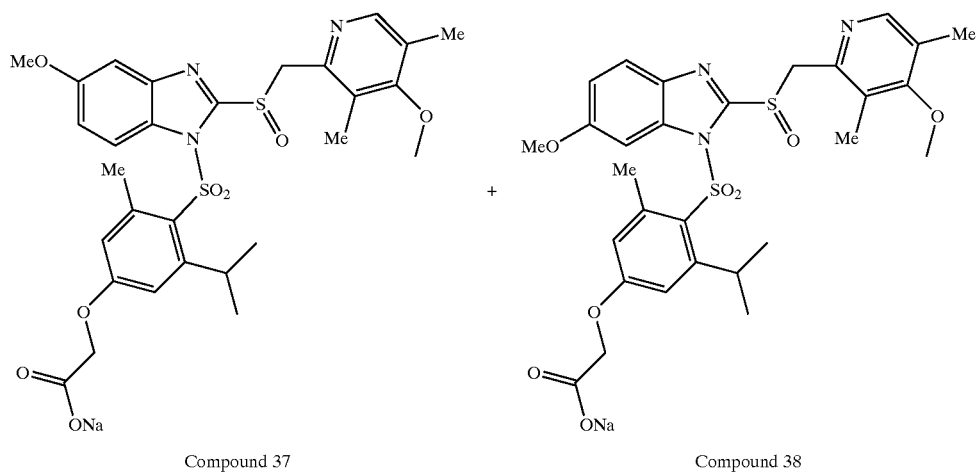

Compound 37    +    Compound 38

3-Isopropyl-5-methylphenoxyacetic acid 2-(toluene-4-sulfonyl)ethyl ester (Intermediate 64)

3-Isopropyl-5-methylphenoxyacetic acid was prepared, following a known method, as follows:

3-Isopropyl-5-methylphenol (44.0 g, 0.29 mol) and chloroacetic acid sodium salt (35.0 g, 0.3 mol) was dissolved in 180 mL of H₂O, and then KOH (86%, 20 g, 0.3 mol) was added slowly. The reaction mixture was refluxed overnight and thereafter concentrated by distillation. After cooling, the mixture was acidified to pH 1, and then extracted with EtOAc. The organic layer was washed H₂O, dried over MgSO4, and concentrated. The solid was recrystalized in 5% isopropanol in hexane to give pure 3-isopropyl-5-methylphenoxyacetic acid (38 g, 63%) as white crystals.

A mixture of 3-isopropyl-5-methylphenoxyacetic acid (prepared above, 6.0 g, 28.8 mmol), 2-(p-toluenesulfonyl) ethanol (5.77 g, 28.8 mmol), and p-toluenesulfonic acid hydrate (p-TsOH.H₂O) (0.5 g) in 100 mL of toluene was refluxed with Dean-Stark trap for 3 h. Then water was added and the mixture was extracted with CH₂Cl₂. The combined organic layers were washed with saturated NaHCO₃ solution (2×), dried over MgSO₄, and concentrated to give 3-isopropyl-5-methylphenoxyacetic acid 2-(toluene-4-sulfonyl)ethyl ester (Intermediate 64, 11.0 g, 98%) as a light brown oil.

$^1$H NMR (CDCl₃, 400 MHz) δ 1.21 (d, J=6.9 Hz, 6H), 2.30 (s, 3H), 2.41 (s, 3H), 2.83 (h, J=6.9 Hz, 1H), 3.47 (t, J=6.1 Hz, 2H), 4.38 (s, 3H), 4.53 (t, J=6.1 Hz, 2H), 6.46 (s, 1H), 6.56 (s, 1H), 6.69 (s, 1H), 7.35 (d, J=8.0 Hz, 2H), 7.80 (d, J=8.0 Hz, 2H).

4-Chlorosulfonyl-3-isopropyl-5-methylphenoxyacetic acid 2-(toluene-4-sulfonyl) ethyl ester (Intermediate 65)

To a mixture of 3-isopropyl-5-methylphenoxyacetic acid 2-(toluene-4-sulfonyl)ethyl ester (Intermediate 64, 5.5 g, 14.0 mmol) and 4 mL of CH₂Cl₂ was added dropwise chlorosulfonic acid (8.2 g, 70.0 mmol, 5.0 eq) with ice-bath cooling. The mixture was stirred at 0° C. for 3 h. The resulting thick oil was poured onto crushed ice with vigorous stirring. The mixture was extracted with EtOAc. The organic layer was washed with 1 N NaHCO₃ solution, dried over MgSO₄, and concentrated by evaporation to give crude product 4-chlorosulfonyl-3-isopropyl-5-methylphenoxyacetic acid 2-(toluene-4-sulfonyl)ethyl ester (Intermediate 65, 6.0 g, 87%) as light brown thick oil, which was purified by silica gel column chromatography.

$^1$H NMR (CDCl₃, 400 MHz) δ 1.15 (d, J=6.9 Hz, 6H), 2.21 (s, 3H), 2.42 (s, 3H), 2.83 (h, J=6.9 Hz, 1H), 3.14 (t, J=6.1 Hz, 2H), 3.82 (s, 3H), 4.20 (t, J=6.1 Hz, 2H), 6.60 (s, 1H), 6.82 (s, 1H), 7.31 (d, J=8.0 Hz, 2H), 7.70 (d, J=8.0 Hz, 2H).

Mixture of 3-isopropyl]-{5-methoxy-2-(4-methoxy-3,5-dimethyl-pyridin-2-yl-methanesulfinyl)-benzimidazole-1-sulfonyl}-5-methylphenoxy acid 2-(toluene-4-sulfonyl)ethyl ester (Intermediate 66) and 3-isopropyl-4-{6-methoxy-2-(4-methoxy-3,5-dimethyl-pyridin-2-yl-methanesulfinyl)-benzimidazole-1-sulfonyl}-5-methylphenoxy acid 2-(toluene-4-sulfonyl)ethyl ester (Intermediate 67)

To a heterogeneous solution of 5-methoxy-2-(4-methoxy-3,5-dimethyl-pyridin-2-yl-methanesulfinyl)-1H-benzimidazole (OMEPRAZOLE 2.9 g, 8.4 mmol) and 10 mL of Et₃N in 60 mL of CH₂Cl₂ was added 4-chlorosulfonyl-3-isopropyl-5-methylphenoxyacetic acid 2-(toluene-4-sulfonyl)ethyl ester (Intermediate 65, 5.5 g, 11.3 mmol, 1.3 eq). About 2 g of solid NaHCO₃ was added after the chlorosulfonyl ester has dissolved completely in the reaction mixture. The mixture was stirred at room temperature for 2 h. Thereafter the solvent was removed by evaporation and the residual oil was purified by column chromatography (silica gel, CH₂Cl₂ to 2% MeOH in CH₂Cl₂) to give a mixture of 3-isopropyl-4-{5-methoxy-2-(4-methoxy-3,5-dimethyl-pyridin-2-yl-methanesulfinyl)-benzimidazole-1-sulfonyl}-5-methylphenoxy acid 2-(toluene-4-sulfonyl) ethyl ester (Intermediate 66) and 3-isopropyl-4-{6-methoxy-2-(4-methoxy-3,5-dimethyl-pyridin-2-yl-methanesulfinyl)-benzimidazole-1-sulfonyl}-5-methylphenoxy acid 2-(toluene-4-sulfonyl)ethyl ester (Intermediate 67), 4.1 g (61%), as an off-white foam (1:1 ratio between 5- and 6-isomer).

$^1$H NMR (CDCl₃, 400 MHz) δ 1.14 (m, 6H), 2.22 (s, 3H), 2.25 (s, 3H), 2.43 (s, 3H), 2.83 (m, 4H), 3.15 (m, 2H), 3.72 (s, 3H), 3.82 and 3.84 (s, 3H), 4.19 (m, 2H), 4.44 (dd, 2H), 4.76 (m, 2H), 6.42 (s, 1H), 6.82 (s, 1H), 6.99 (m, 1H), 7.28 (d, 1H), 7.32 (d, 2H), 7.56 (d, 1H), 7.69 (d, 2H), 8.16 (s, 1H).

Mixture of 3-isopropyl-4-{5-methoxy-2-(4-methoxy-3,5-dimethyl-pyridin-2-yl-methanesulfinyl)-benzimidazole-1-sulfonyl}-5-methylphenoxy acid sodium salt (Compound 37) and 3-isopropyl-4-{6-methoxy-2-(4-methoxy-3,5-dimethyl-pyridin-2-yl-methanesulfinyl)-benzimidazole-1-sulfonyl}-5-methylphenoxy acid sodium salt (Compound 38)

To a solution of a mixture of 3-isopropyl-4-{5-methoxy-2-(4-methoxy-3,5-dimethyl-pyridin-2-yl-methanesulfinyl)-benzimidazole-1-sulfonyl}-5-methylphenoxy acid 2-(toluene-4-sulfonyl)ethyl ester (Intermediate 66) and 3-isopropyl-4-{6-methoxy-2-(4-methoxy-3,5-dimethyl-pyridin-2-yl-methanesulfinyl)-benzimidazole-1-sulfonyl}-5-methylphenoxy acid 2-(toluene-4-sulfonyl)ethyl ester (Intermediate 67), 4.0 g (5.02 mmol), in 40 mL of CH₃CN was added the solution of NaHCO₃ (500 mg, 6.02 mmol, 1.2 eq) in 20 mL of H₂O. The mixture was heated to 65° C. for 4 h. Thereafter all volatile materials were removed under vacuum, the mixture was washed with ether (2×), and then the aqueous layer was lyophilized overnight. The solid was dissolved in 80 mL of EtOAc, and then the mixture was filtered to remove insoluble material. The filtrate was concentrated and the residual oil was dissolved in 10 mL of EtOAc. Diethyl ether followed by hexane were added to the mixture to precipitate a white solid. The precipitate was filtered, washed with EtOAc, and dried under vacuum to yield 2.8 g (87%) of mixture of 3-isopropyl-4-{5-methoxy-2-(4-methoxy-3,5-dimethyl-pyridin-2-yl-methanesulfinyl)-benzimidazole-1-sulfonyl}-5-methylphenoxy acid sodium salt (Compound 37) and 3-isopropyl-4-{6-methoxy-2-(4-methoxy-3,5-dimethyl-pyridin-2-yl-methanesulfinyl)-benzimidazole-1-sulfonyl}-5-methylphenoxy acid sodium salt (Compound 38) as white solid (1:1 ratio between 5- and 6-isomer).

$^1$H NMR (D₂O, 400 MHz) δ 0.76 (m, 6H), 1.76 (m, 3H), 1.87 (s, 3H), 2.42 (m, 4H), 3.34–3.45 (m, 6H), 3.60–4.10 (m, 2H), 4.52 (m, 2H), 6.32 (s, 1H), 6.46 (d, 1H), 6.68 (m, 1H), 7.05 (m, 1H), 7.46 (d, 1H), 7.78 (s, 1H).

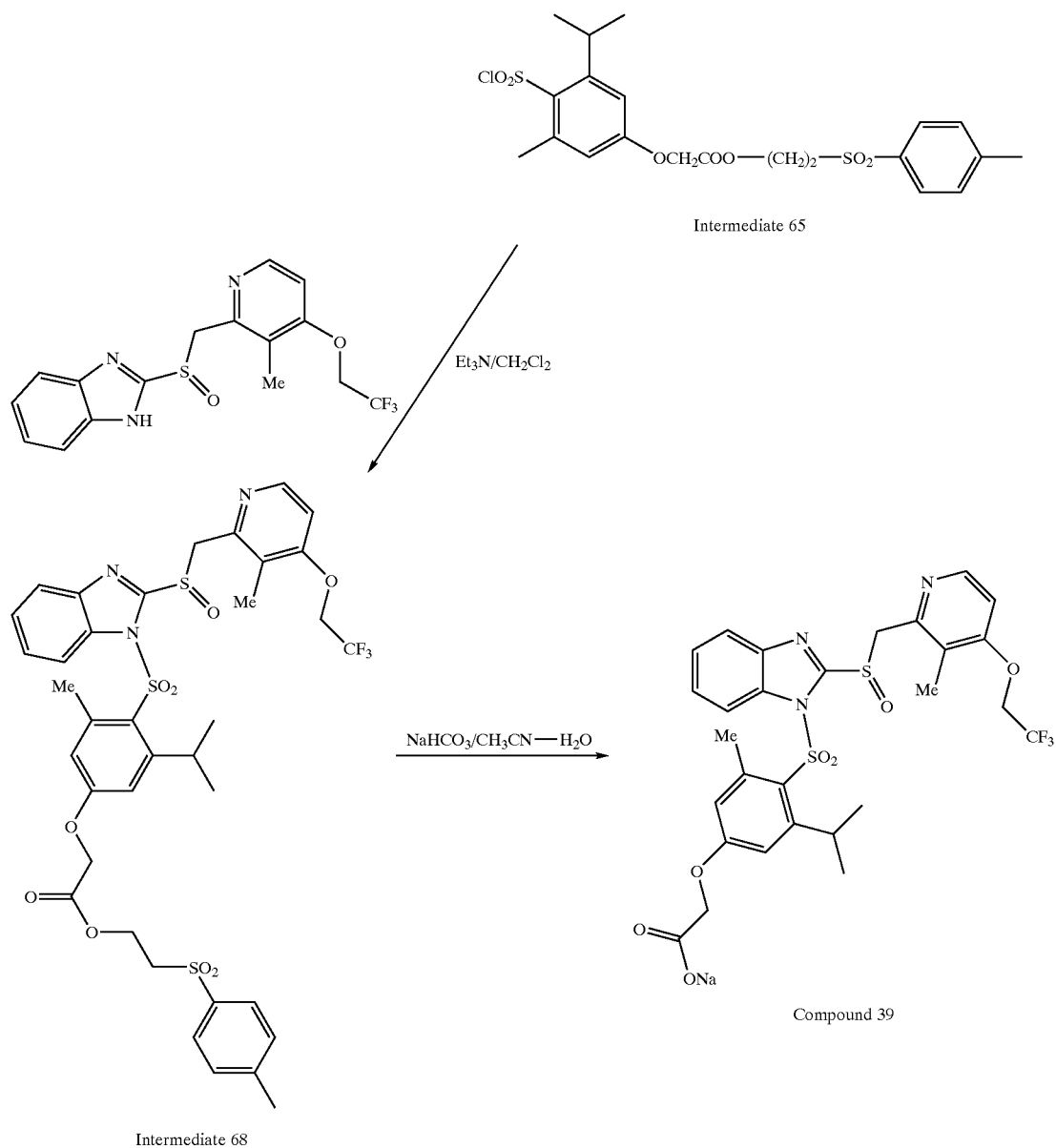

Reaction Scheme 29

Intermediate 65

Intermediate 68

Compound 39

4-[2-{3-Methyl-4-(2,2,2-trifluoroethoxy)pyridin-2-yl-methanesulfinyl}-benzimidazole-1-sulfonyl]-3-isopropyl-5-methylphenoxyacetic acid 2-(toluene-4-sulfonyl)ethyl ester (Intermediate 68)

To a heterogeneous solution of 2-[3-methyl-4-(2,2,2-trifluoroethoxy)pyridin-2-yl-methanesulfinyl]-1H-benzimidazole (LANSOPRAZOLE 1.0 g, 2.71 mmol) and 2 mL of Et₃N in 20 mL of CH₂Cl₂ was added 4-chlorosulfonyl-3-isopropyl-5-methylphenoxyacetic acid 2-(toluene-4-sulfonyl)ethyl ester the (Intermediate 65, 1.6 g, 3.25 mmol, 1.2 eq). About 1 g of solid NaHCO₃ was added after the chlorosulfonyl ester has dissolved completely in the reaction mixture. The mixture was stirred at room temperature for 2 h. Thereafter the solvent was removed by evaporation and the residual oil was purified by column chromatography (silica gel, CH₂Cl₂ to 1% MeOH in CH₂Cl₂) to give 4-[2-{3-methyl-4-(2,2,2-trifluoroethoxy)pyridin-2-yl-methanesulfinyl}-benzimidazole-1-sulfonyl]-3-isopropyl-5-methylphenoxyacetic acid 2-(toluene-4-sulfonyl)ethyl ester (Intermediate 68, 1.76 g, 79%) as a white foam.

$^1$H NMR (CDCl₃, 400 MHz) δ 1.13 (d, 6H), 2.26 (s, 3H), 2.42 (s, 3H), 2.78 (m, 1H), 2.86 (s, 3H), 3.08 (t, 2H), 4.14 (t, 2H), 4.35–4.51 (m, 4H), 4.82 (q, J=16.0 Hz, 2H), 6.43 (s, 1H), 6.64 (d, 1H), 6.84 (s, 1H), 7.35 (m, 4H), 7.68 (m, 3H), 7.78 (m, 1H), 8.27 (d, 1H).

4-[2-{3-Methyl-4-(2,2,2-trifluoroethoxy)pyridin-2-yl-methanesulfinyl}-benzimidazole-1-sulfonyl]-3-isopropyl-5-methylphenoxyacetic acid sodium salt (Compound 39)

To a solution of 4-[2-{3-methyl-4-(2,2,2-trifluoroethoxy)pyridin-2-yl-methanesulfinyl}-benzimidazole-1-sulfonyl]-

3-isopropyl-5-methylphenoxyacetic acid 2-(toluene-4-sulfonyl)ethyl ester (Intermediate 68, 1.6 g, 1.95 mmol) in 15 mL of CH₃CN was added the solution of NaHCO₃ (200 mg, 2.34 mmol, 1.2 eq) in 8 mL of H₂O. The mixture was heated to 65° C. for 1.5 h. Thereafter all volatile materials were removed under vacuum, the mixture was washed with ether (2×), and then the aqueous layer was lyophilized overnight. The solid was dissolved in 110 mL of ether-EtOAc (10:1), and then the mixture was filtered to remove insoluble material. The filtrate was concentrated and the residual oil was dissolved in 10 mL of ether-EtOAc (10:1).

Hexane was added to the mixture to precipitate a white solid. The precipitate was filtered, washed with hexane, and dried under vacuum to yield 1.0 g (77%) of 4-[2-{3-methyl-4-(2,2-trifluoroethoxy)pyridin-2-yl-methanesulfinyl}-benzimidazole-1-sulfonyl]-3-isopropyl-5-methylphenoxy-acetic acid sodium salt (Compound 39) as a white solid.

$^1$H NMR (D₂O, 400 MHz) ) δ 0.72 (m, 6H), 1.66 (s, 3H), 2.36 (s, 3H), 3.95 (q, J=19.7 Hz, 2H), 4.20 (s, 2H), 4.45 (dd, 2H), 6.25 (s, 1H), 6.40 (s, 1H), 6.53 (m, 1H), 6.89 (m, 1H), 7.04 (m, 1H), 7.17 (m, 1H), 7.55 (d, 1H), 7.90 (d, 1H).

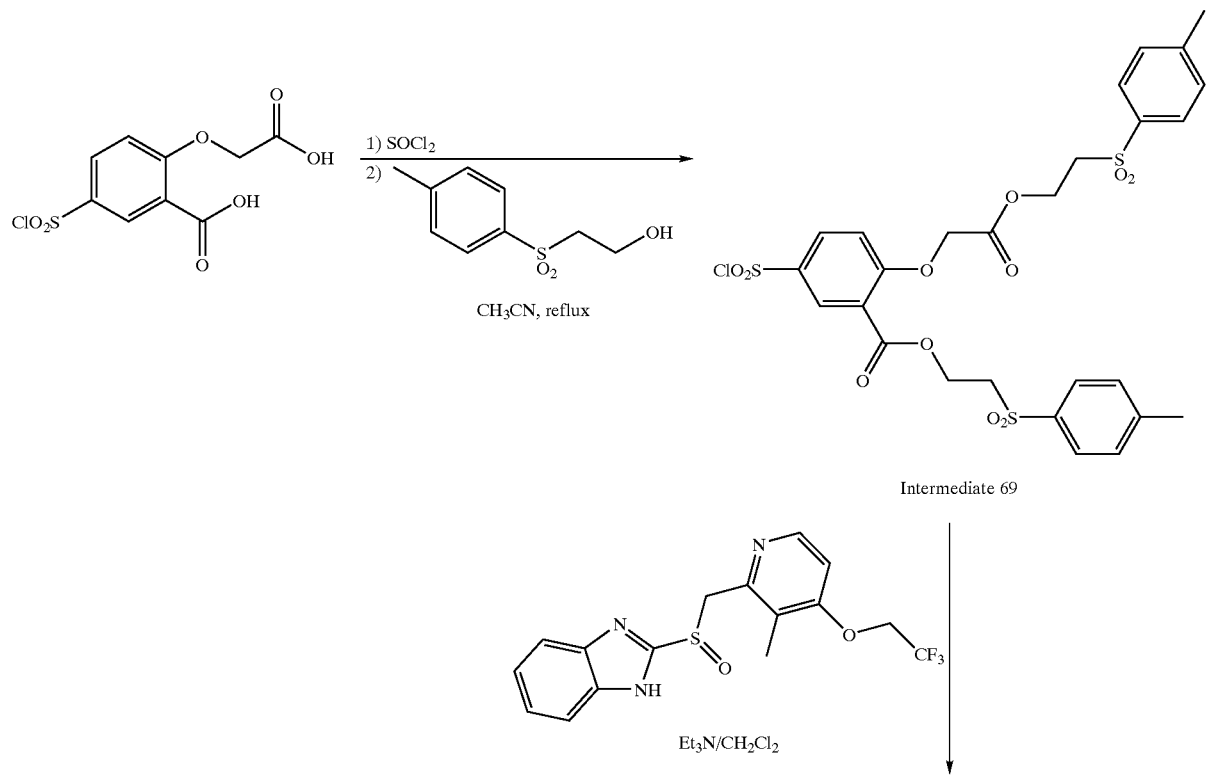

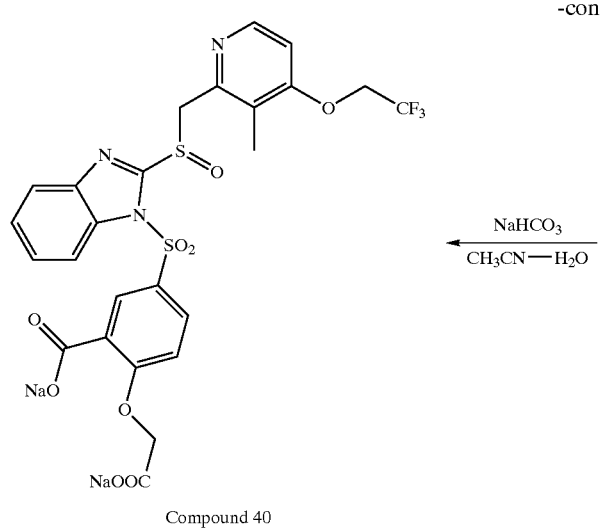

Compound 40

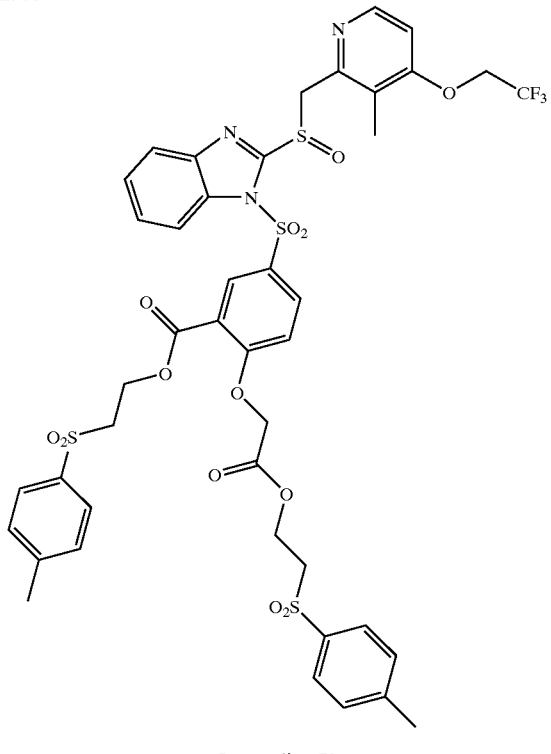

Intermediate 70

5-Chlorosulfonyl-2-[2-(toluene-4-sulfonyl)-ethoxycarbonylmethoxy]-benzoic acid 2-(toluene-4-sulfonyl)-ethyl ester (Intermediate 69)

2-(Carboxymethoxy)-5-chlorosulfonyl-benzoic acid was synthesized by the reaction of 2-carboxymethoxy benzoic acid with chlorosulfonic acid using a method similar to the synthesis of Intermediate 6.

A mixture of 2-(carboxymethoxy)-5chlorosulfonyl-benzoic acid (4.0 g, 13.5 mmol) and thionyl chloride (10 mL) was heated to reflux temperature for 2 h, and then the excess thionyl chloride was distilled off. The residual oil was dissolved in 15 mL of $CH_3CN$ and 2-(tolylsulfonyl)ethanol (5.0 g, 25.0 mmol) was added. The mixture was heated to reflux temperature for 40 h, then allowed to cool and water was added. The mixture was extracted with EtOAc and the organic layer was washed with 1 N $NaHCO_3$, dried, and concentrated to yield 7.7 g (93%) of a brown foam.

$^1$H NMR (DMSO-$d_6$, 400 MHz)) δ 2.44 (m, 6H), 3.46 (t, 2H), 3.59 (t, 2H), 4.57 (t, 2H), 4.64 (t, 2H), 4.76 (s, 2H), 7.30 (d, 1H), 8.07 (d, 1H), 8.28 (s, 1H).

2-(Carboxymethoxy)-5-{2-[3-methyl-4-(2,2,2-trifluoroethoxy)pyridin-2-yl-methanesulfinyl]-benzimidazole-1-sulfonyl}-benzoic acid disodium salt (Compound 40)

To a heterogeneous solution of 2-[3-methyl-4-(2,2,2-trifluoroethoxy)pyridin-2-yl-methanesulfinyl]-1H-benzimidazole (LANSOPRAZOLE, 3.0 g, 8.13 mmol) and 6 mL of $Et_3N$ in 70 ML of $CH_2Cl_2$ was added 5-chlorosulfonyl-2-[2-(toluene-4-sulfonyl)-ethoxycarbonylmethoxy]-benzoic acid 2-(toluene-4-sulfonyl)-ethyl ester (Intermediate 69, 7.0 g, 10.6 mmol, 1.3 eq). About 3 g of solid $NaHCO_3$ was added after the chlorosulfonyl ester has dissolved completely in the reaction mixture. The mixture was stirred at room temperature for 2 h. Thereafter the solvent was removed by evaporation and the residual oil was passed through a short column (silica gel, $CH_2Cl_2$ to 1% MeOH in $CH_2Cl_2$) to remove a colored impurity and $Et_3N$. Concentration of the eluent gave Intermediate 70 (about 9.0 g) as an off-white foam. To a solution of 2-(carboxymethoxy)-5-{2-[3-methyl-4-(2,2,2-trifluoroethoxy)pyridin-2-yl-methanesulfinyl]-benzimidazole-1-sulfonyl}-benzoic acid [bis{2-(toluene-4-sulfonyl)ethyl}ester] (Intermediate 70, 9.0 g, 8.13 mmol) in 80 mL of $CH_3CN$ was added the solution of $NaHCO_3$ (1.70 g, 20.3 mmol, 2.5 eq) in 40 mL of $H_2O$. The mixture was heated to 65° C. for 5 h. Thereafter all volatile materials were removed under vacuum, the mixture was washed with EtOAc (2×), and then the aqueous layer was lyophilized overnight. The solid was dissolved in 200 mL of $CH_2Cl_2$, and then the mixture was filtered to remove insoluble material. The filtrate was concentrated and the residual oil was dissolved in 20 mL of $CH_2Cl_2$. EtOAc-Ether (1:1) was added to the mixture to precipitate a white solid. The precipitate was collected by filtration, washed with diethyl ether, and dried under vacuum to yield 4.5 g (82%) of 2-(carboxymethoxy)-5-{2-[3-methyl-4-(2,2,2-trifluoroethoxy)pyridin-2-yl-methanesulfinyl]-benzimidazole-1-sulfonyl}-benzoic acid disodium salt (Compound 40) as a light brown solid.

$^1$H NMR ($D_2O$, 400 MHz) δ 1.96 (s, 3H), 4.48 (m, 4H), 4.70 (d, 1H), 4.87 (d, 1H), 6.68 (d, 1H), 6.80 (d, 1H), 7.25 (t, 1H), 7.32 (t, 1H), 7.53 (d, 1H), 7.63 (d, 1H), 7.83 (m, 2H), 7.97 (s, 1H).

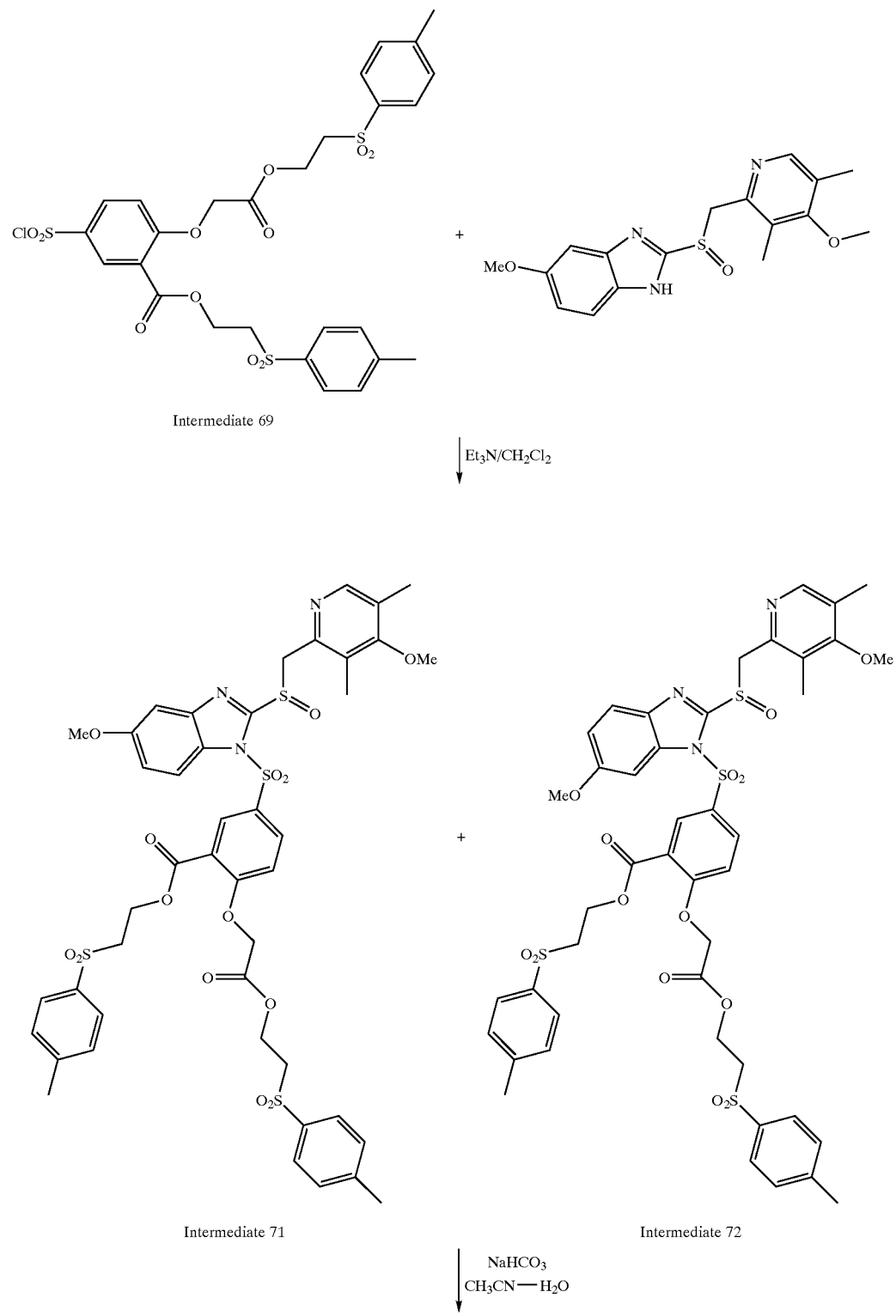

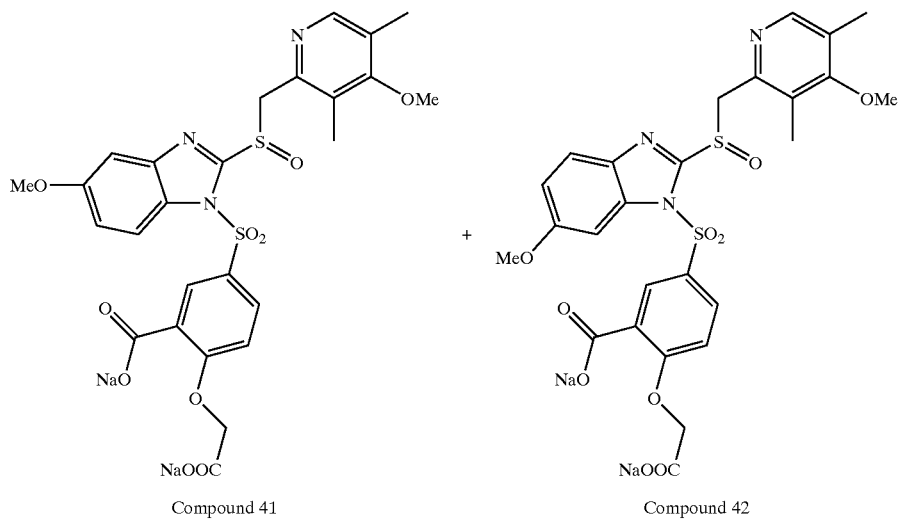

Compound 41 + Compound 42

Mixture of 2-(carboxymethoxy)-5-{5-methoxy-2-(4-methoxy-3,5-dimethyl-pyridin-2-yl-methanesulfinyl)benzimidazole-1-sulfonyl}-benzoic acid disodium salt (Compound 41) and 2-(carboxymethoxy)-5-{6-methoxy-2-(4-methoxy-3,5-dimethyl-pyridin-2-yl-methanesulfinyl)-benzimidazole-1-sulfonyl}-benzoic acid disodium salt (Compound 42)

To a heterogeneous solution of 5-methoxy-2-(4-methoxy-3,5-dimethyl-pyridin-2-yl-methanesulfinyl)-1H-benzimidazole (OMEPRAZOLE, 1.0 g, 3.03 mmol) and 4 mL of Et$_3$N in 20 mL of CH$_2$Cl$_2$ was added the chlorosulfonyl ester (Intermediate 69, 2.6 g, 3.95 mmol, 1.3 eq). About 1 g of solid NaHCO$_3$ was added after the chlorosulfonyl ester has dissolved completely in the reaction mixture. The mixture was stirred at room temperature for 2 h. Thereafter water was added and the mixture was extracted with EtOAc (2x). The combined organic layers were washed with water, dried, and concentrated to give a mixture of Intermediates 71 and 72 (about 2.9 g) as off-white foam, which were used without further purification.

To a solution of the mixture of Intermediates 71 and 72 (about 2.9 g) in 30 mL of CH$_3$CN was added the solution of NaHCO$_3$ (520 mg, 6.19 mmol, 2.2 eq) in 15 mL of H$_2$O. The mixture was heated to 65° C. for 3 h. Thereafter all volatile materials were removed under vacuum, the mixture was washed with EtOAc (2x), and the aqueous layer was lyophilized overnight. The solid was dissolved in 150 mL of CH$_2$Cl$_2$, and then the mixture was filtered to remove insoluble material. The filtrate was concentrated and the residual oil was dissolved in 5 mL of CH$_2$Cl$_2$. EtOAc was added to the mixture to precipitate a white solid. The precipitate was collected by filtration, washed with ether, and dried under vacuum to yield 1.86 g (95%) of mixture of 2-(carboxymethoxy)-5-{5-methoxy-2-(4-methoxy-3,5-dimethyl-pyridin-2-yl-methanesulfinyl)-benzimidazole-1-sulfonyl}-benzoic acid disodium salt (Compound 41) and 2-(carboxymethoxy)-5-{6-methoxy-2-(4-methoxy-3,5-dimethyl-pyridin-2-yl-methanesulfinyl)-benzimidazole-1-sulfonyl}-benzoic acid disodium salt (Compound 42) as a light brown solid (1:1 ratio between 5- and 6-isomer).

$^1$H NMR (D$_2$O, 400 MHz) δ 1.77 (m, 6H), 3.34 (m, 3H), 3.46 and 3.54 (s, 3H, 5- and 6-OMe isomer), 4.45 (m, 2H), 4.58 (d, 1H), 4.74 (d, 1H), 6.6–8.3 (m, 7H).

In the following reaction schemes and examples, as in the entire disclosure, unless it is expressly noted otherwise the reagents and/or starting materials are either available commercially or can be prepared in accordance with the chemical scientific and patent literature readily accessible to those of ordinary skill in the art.

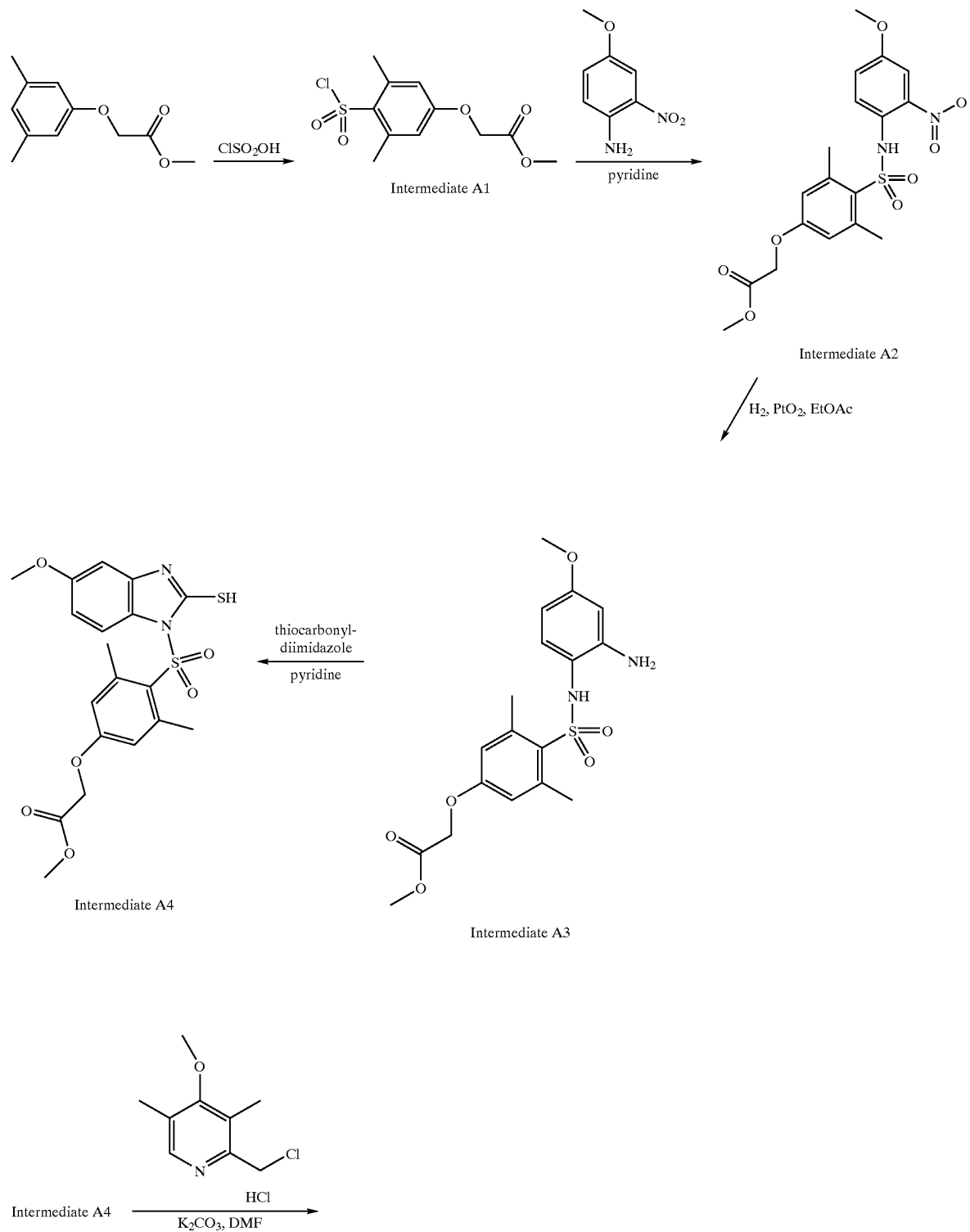

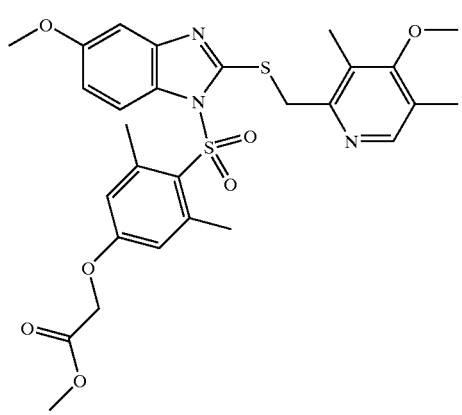

Intermediate A5

3-chloroperoxybenzoic acid
THF
→

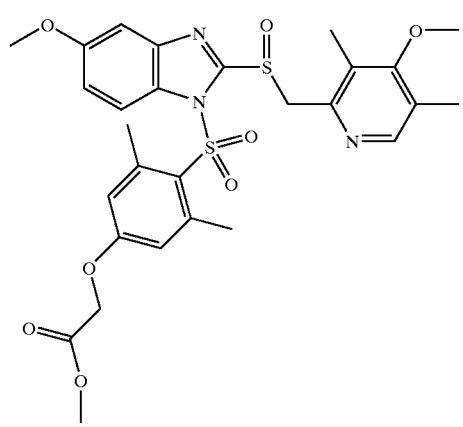

Intermediate A6

NaOH  H₂O, diimethoxyethane

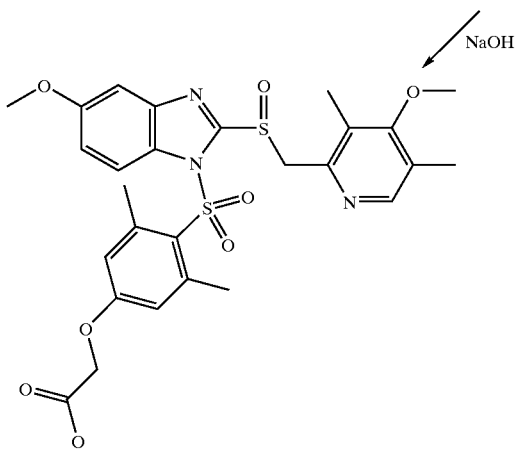

Compound 31
isomerically pure

Methyl (4-chlorosulfonyl-3,5-dimethylphenoxy) acetate (Intermediate A1)

Methyl (3,5-dimethylphenoxy)acetate (19.4 g, 0.10 mol) was added dropwise over ca. 30 min to rapidly stirred chlorosulfonic acid (58 g, 0.50 mol) that was cooled in a −20° C. bath. After an additional 20 min, the mixture was allowed to slowly warm to room temperature. After 2 hr, the mixture was poured slowly into 400 mL of ice/water. This suspension was extracted with 400 mL of dichloromethane, and the organic layer was washed with water and concentrated. The residue was purified by flash silica gel chromatography (hexanes→dichloromethane) to yield 7.6 g (27%) of the title compound.

Methyl [4-(4-methoxy-2-nitrophenyl)aminosulfonyl-3,5-dimethylphenoxy]acetate (Intermediate A2)

A mixture of methyl (4-chlorosulfonyl-3,5-dimethylphenoxy)acetate (Intermediate A1, 7.6 g, 0.026 mol), 4-methoxy-2-nitroaniline (4.0 g, 0.024 mol), and pyridine (50 mL) was stirred at room temperature for 16 hr, in a 90° C. bath for 5 hr, and in a 130° C. bath for 30 min. The mixture was cooled and stirred with toluene for 10 min. The resulting suspension was filtered, and the filtrate was concentrated, diluted with 150 mL toluene and 100 mL ethyl acetate, washed with 1 M hydrochloric acid and water, and concentrated to about 50 mL. The mixture was left overnight in a freezer. The solid was collected and washed with several portions of cold toluene. After drying, it weighed 8.2 g (74%). Another 0.45 g portion of the title compound was recovered from extraction of aqueous phases and crystallization of a second crop from the toluene filtrate.

Methyl [4-(2-amino-[4-methoxyphenyl) aminosulfonyl-3,5-dimethylphenoxy]acetate (Intermediate A3)

Methyl [4-(4-methoxy-2-nitrophenyl)aminosulfonyl-3,5-dimethylphenoxy]acetate (Intermediate A2, 8.1 g, 0.019 mol) in 200 mL ethyl acetate was stirred with Raney nickel (0.75 g) for 30 min and filtered through a celite pad with the aid of an additional 100 mL of ethyl acetate. The filtrate was mixed with platinum oxide (0.40 g, 0.0018 mol) and hydrogenated to give 7.8 g (100%) of the title compound.

Methyl {4-[(2-mercapto-5-methoxybenzimidazolyl) sulfonyl]-3,5-dimethylphenoxy}acetate (Intermediate A4)

Methyl [4-(2-amino-4-methoxyphenyl)aminosulfonyl-3,5-dimethylphenoxy]acetate (Intermediate A3, 7.5 g, 0.019 mol), thiocarbonyldiimidazole (5.1 g, 0.029 mol), and pyridine (100 mL) were mixed and stirred for 3 hr. The reaction mixture was poured into 1 L of rapidly stirring water. After 2 hr, the resulting solid was collected, washed with several portions of water, and air-dried to give 8.9 g (110%) of the desired title compound contaminated with some pyridine. The impure product was used in the alkylation step.

2-Chloromethyl-3,5-dimethyl-4-methoxypyridine hydrochloride

To a solution of 4-methoxy-3,5-dimethylpyridinemethanol (25.1 g, 0.15 mol) in dichloromethane (400 mL) was added a solution of thionyl chloride (18.8 g, 0.158 mol) in dichloromethane (100 mL) over 30 min at room temperature under argon. After an additional 30 min of stirring at room temperature, the solvent was removed under reduced pressure. The solid residue was suspended in hexanes (200 mL) and filtered. The solid was washed with hexanes (50 mL) and air-dried to give 33.3 g (100%) of the title compound as a white solid.

Methyl {4-[(5-methoxy-2{[4-methoxy, 3,5-dimethyl (2-pyridyl)methyl]thio}benzimidazolyl)sulfonyl]-3, 5-dimethylphenoxy}Acetate (Intermediate A5)

2-Chloromethyl-3,5-dimethyl-4-methoxypyridine hydrochloride (4.4 g, 0.020 mol) was added to a mixture of methyl {4-[(2-mercapto-5-methoxybenzimidazolyl)sulfonyl]-3,5-dimethylphenoxy}acetate (Intermediate A4, 8.2 g, 0.019 mol), potassium carbonate (5.7 g, 0.041 mol), and dimethylformamide (80 mL). The mixture was stirred for 1.5 hr and was then poured in 150 mL of rapidly stirring ice water containing 40 mL of 1.2 M hydrochloric acid. The resulting solid was collected and washed with several portions of water. After partial air-drying, the 10 g of solid was dissolved in 100 mL of dichloromethane. This solution was washed with saturated aqueous sodium bicarbonate, filtered through 1PS paper, and concentrated. The residue was mixed with boiling methanol and collected, yielding 8.9 g (80%) of the title compound.

Methyl {4-[(5-methoxy-2{[4-methoxy, 3,5-dimethyl (2-pyridyl)methyl]sulfinyl}benzimidazolyl) sulfonyl]-3,5-dimethylphenoxy}acetate (Intermediate A6)

Solutions of methyl {4-[(5-methoxy-2{[4-methoxy, 3,5-dimethyl(2-pyridyl)methyl]thio}benzimidazolyl)sulfonyl]-3,5-dimethylphenoxy}acetate (Intermediate A5, 7.1 g, 0.12 mol) in 100 mL of tetrahydrofuran and 3-chloroperoxybenzoic acid (2.6 g, 0.15 mol) in 20 mL of the same solvent were cooled in a freezer for 1 hr and then mixed. The solution was left in the freezer for about 16 hr, diluted with ethyl acetate, and washed with several portions each of 5% sodium metabisulfite, 5% sodium bicarbonate, and saturated sodium chloride. The organic phase was concentrated and then purified on flash silica gel (hexanes→ethyl acetate→1% methanol in ethyl acetate). The title compound recovered weighed 3.3 g (46%).

2-{4-[(5-methoxy-2-{[(4-methoxy-3,5-dimethyl(2-pyridyl))methyl]sulfinyl}benzimidazolyl)sulfonyl]-3,5-dimethylphenoxy}acetic acid sodium salt (Compound 31, isomerically pure)

A solution of methyl {4-[(5-methoxy-2{[4-methoxy, 3,5-dimethyl(2-pyridyl)methyl]sulfinyl}benzimidazolyl) sulfonyl]-3,5-dimethylphenoxy}acetate (Intermediate A6, 2.96 g, 0.493 mol) in 250 mL of dimethoxyethane was stirred rapidly as 49 mL of 0.100 N aqueous sodium hydroxide was added. The mixture was concentrated at aspirator pressure (bath temperature <22° C.). The residue was reconcentrated from 200 mL of dimethoxyethane, left briefly at high vacuum, and partitioned between ethyl acetate and water. The aqueous layer was washed with several portions of ethyl acetate and was then concentrated at high vacuum. The residue was partitioned between ethyl acetate and water at pH 3. The aqueous layer was extracted with an additional portion of ethyl acetate, and the combined organic layers were reduced in volume and diluted with hexanes. The resulting solid was collected and combined with a second crop recovered from the filtrate. This material was washed with 10:1 diethyl ether:tetrahydrofuran, dissolved in dimethoxyethane, neutralized with 0.0100 N sodium hydroxide, and washed with ethyl acetate. The product, title compound weighed 0.925 g (31%).

NMR (300 MHz) (D$_2$O) δ 7.9 (s, 1H); 7.2–6.6 (complex, 5H); 4.9–4.6 (AB, 2H); 4.4 (s, 2H); 3.7 (s, 3H); 3.5 (s, 3H); 2.2 (s, 6H); 2.0 (s, 3H); 1.9 (s, 3H).

Reaction Scheme 33

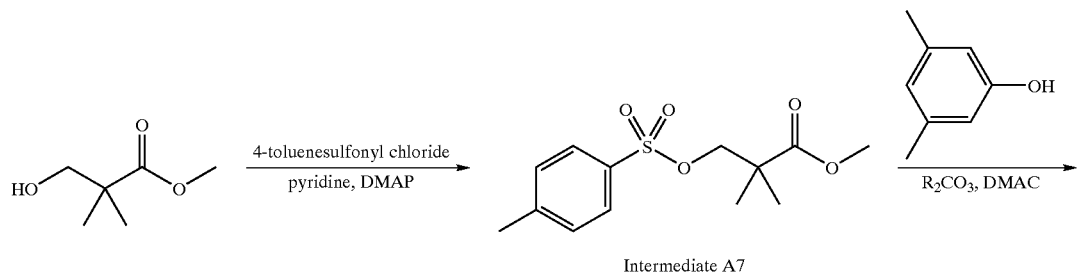

Intermediate A7

-continued
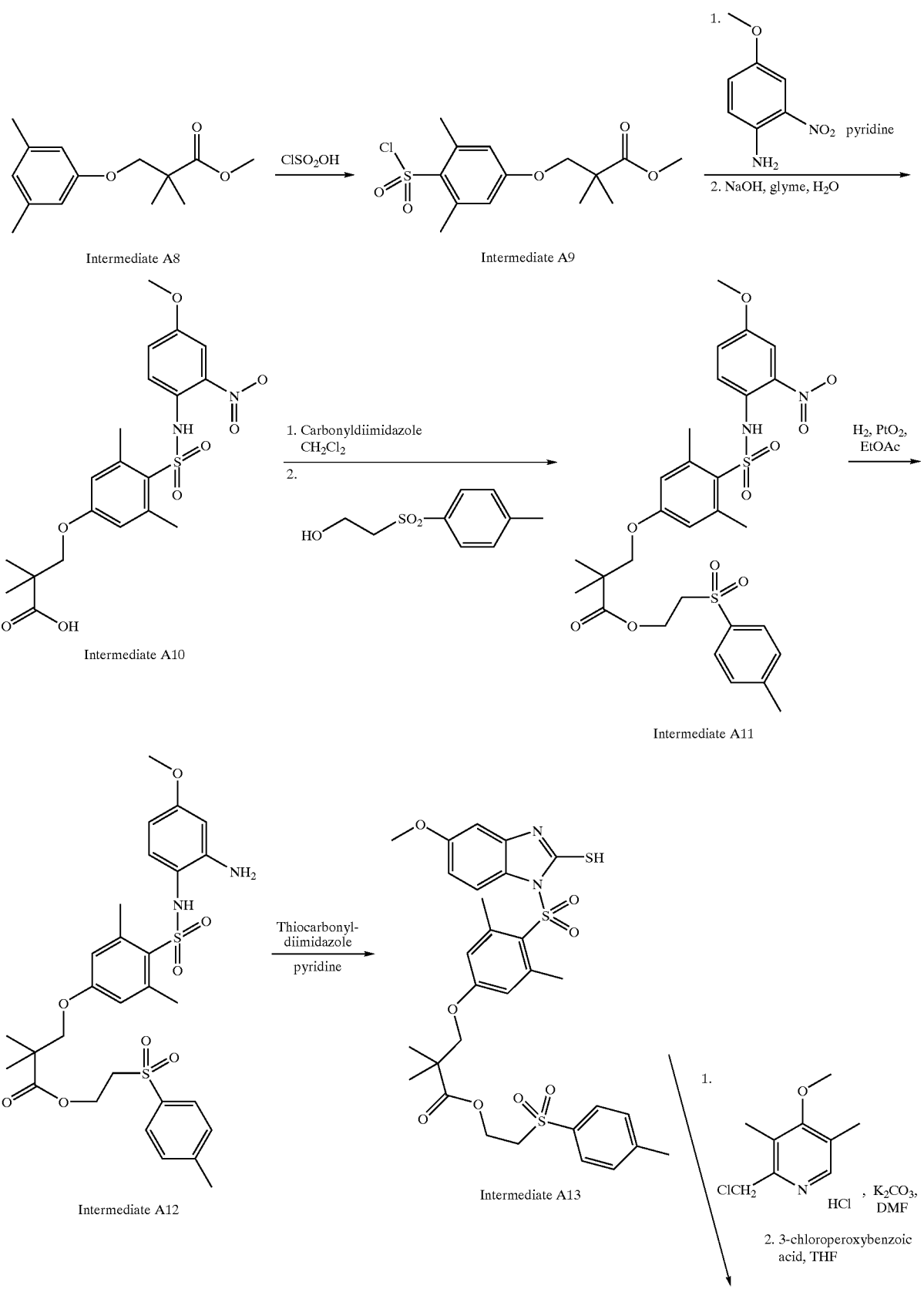

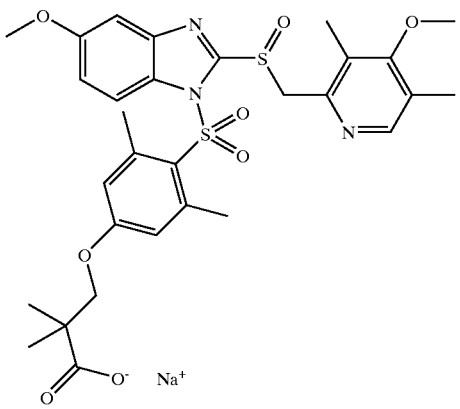

Compound 43

CH₃CN, i-PrOH,
NaHCO₃, H₂O

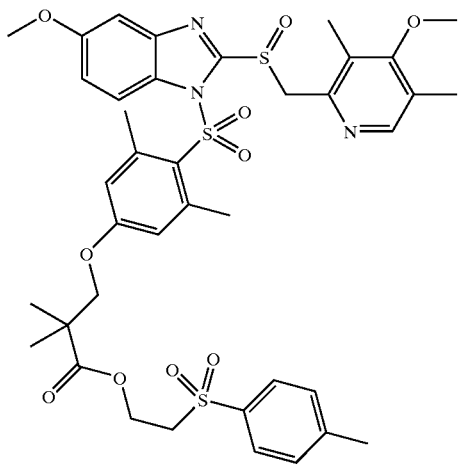

Intermediate A14

Methyl 2,2-dimethyl-3-(4-tolylsulfonyloxy) propionate (Intermediate A7)

A mixture of methyl 2,2-dimethyl-3-hydroxypropionate (100 g, 0.76 mol), 4-toluenesulfonyl chloride (151 g, 0.80 mol), 4-dimethylaminopyridine (4.6 g, 0.038 mol), and pyridine (200 mL) was stirred for 20 hrs and then was diluted with 200 mL toluene, stirred for 30 min and filtered. The filtrate was concentrated to 250 mL at aspirator pressure, diluted with 100 mL toluene, filtered, and concentrated. The residue was suspended in 200 mL hexanes, and the solvent was removed at aspirator pressure to yield the title compound (235 g, 100%) contaminated by a trace of toluenesulfonyl chloride.

Methyl 3-(3,4-dimethylphenyloxy)-2,2-dimethylpropionate (Intermediate A8)

A reaction vessel was charged with methyl 2,2-dimethyl-3-tosyloxypropionate (Intermediate A7, 100 g, 0.35 mol), 3,5-dimethylphenol (45 g, 0.37 mol), potassium carbonate (73 g, 0.53 mol), and dimethylacetamide (300 mL). The mixture was heated on a steam bath for 16 hr and in a 170° C. bath for 6 hr. The cooled reaction mixture was diluted with 1 L water and extracted with 2×200 mL portions of ethyl acetate. The combined organic layers were washed with water, 0.5 M sodium hydroxide (twice), water, and saturated aqueous sodium chloride. The solvent was removed at aspirator pressure and high vacuum. The residue was taken up in dichloromethane and washed with several portions of 1 M sodium hydroxide, water, and saturated sodium chloride. The solution was concentrated, and the residue was distilled at 2 torr to yield 43.5 g (52%) of the title compound.

Methyl 3-(4-chlorosulfonyl-3,5-dimethylphenyloxy)-2,2-dimethylpropionate (Intermediate A9)

Methyl 3-(3,4-dimethylphenyloxy)-2,2-dimethylpropionate (Intermediate A8, 23.6 g, 0.100 mol) was added dropwise over 30 min to rapidly stirred chlorosulfonic acid (46.6 g, 0.400 mol) while the reaction temperature was maintained at −2° C. The reaction mixture was then poured into a stirred mixture of 300 g ice and 300 mL of dichloromethane. The aqueous phase was extracted with additional dichloromethane, and the combined organic layers were washed with water, 0.5 M sodium bicarbonate (×2), and water. The solvent was removed at aspirator pressure and the residue was purified by several passes of flash chromatography (silica gel: hexanes→2% ethyl acetate in hexanes) to yield 9.6 g (29%) of the title compound.

Methyl 3-{4-[4-methoxy-2-nitrophenylaminosulfonyl}-3,5-dimethylphenoxy]-2,2-dimethylpropionate Methyl 3-(4-chlorosulfonyl-3,5-dimethylphenyloxy)-2,2-dimethylpropionate (Intermediate A9, 8.3 g, 0.025 mol), 3-methoxy-2-nitroaniniline (3.9 g, 0.023 mol), and pyridine (40 mL) were mixed and stirred while immersed in a 100° C. bath for 1.5 hr and for 4 days at room temperature. The mixture was diluted with 150 mL toluene and filtered. The filtrate was concentrated at aspirator pressure, and the residue was partitioned between 1.2 M hydrochloric acid and ethyl acetate. The organic layer was washed with water and concentrated. The foamy residue was stirred with 50 mL 2:1 hexanes:ethyl acetate. The resulting solid was collected and washed with several portions of the same solvent. After drying the product, title compound, weighed 9.1 g (85%).

3-{4-[4-Methoxy-2-nitrophenyl]aminosulfonyl}-3,5-dimethylphenoxy]-2,2-dimethylpropionic acid (Intermediate A10)

A 54 mL (0.054 mol) portion of 0.100 N sodium hydroxide was added to a dimethoxyethane solution of methyl 3-({4-[4-methoxy-2-nitrophenyl]aminosulfonyl}-3,5-dimethylphenoxy)-2,2-dimethylpropionate (8.5 g, 0.018 mol). After ca. 20 hr, the mixture was diluted with 60 mL of 1.2 M hydrochloric acid and 100 g ice. The resulting suspension was extracted with several portions of ethyl acetate, and the combined organic layers were washed with saturated aqueous sodium chloride and concentrated. The residue was stirred with hexanes for 1 hr and then collected with the aid of additional hexanes to yield 8.2 g (100%) of the title compound.

2-(4-Tolylsulfonyl)ethyl 3-{4-[4-methoxy-2-nitrophenylaminosulfonyl}-3,5-dimethylphenox]-2,2-dimethylpropionate (Intermediate A11)

A mixture of 3-{4-[4-methoxy-2-nitrophenylaminosulfonyl}-3,5-dimethylphenoxy]-2,2-dimethylpropionic acid (Intermediate A10, 24.2 g, 0.054 mol) and carbonyldiimidazole (9.5 g, 0.059 mol) was diluted with 45 mL dichloromethane and warmed in a 36° C. bath for 15 min. Then, 4-tolylsulfonylethanol was added, the bath temperature was raised to 55° C., and the solvent was blown off in a nitrogen stream. After 1.5 hr, the stream was stopped, and after 2.5 hr, the cooled reaction mixture was partitioned between ethyl acetate and 1.2 M hydrochloric acid. The aqueous layer was extracted with additional ethyl acetate, and the combined organic layers were washed with water and saturated sodium chloride, concentrated at aspirator pressure and high vacuum. The product, title compound, (34 g, 99%) was carried on without further purification.

2-(4-Tolylsulfonyl)ethyl 3-({4-[2-amino-4-methoxyphenyl]aminosulfonyl}-3,5-dimethylphenoxy)-2,2-dimethylpropionate (Intermediate A12)

2-(4-Tolylsulfonyl)ethyl 3-{4-[4-methoxy-2-nitrophenylaminosulfonyl}-3,5-dimethylphenoxy]-2,2-dimethylpropionate (Intermediate A11, 34 g, 0.54 mol) was hydrogenated in ethyl acetate using platinum oxide (1.7 g, 0.0075 mol) as catalyst. The product, title compound, was taken on without further purification.

2-(4-Tolylsulfonyl)ethyl 3-(4-[2-mercapto-5-methoxybenzimidazolyl}sulfonyl]-3,5-dimethylphenoxy)-2,2-dimethylpropionate (Intermediate A13)

2-(4-Tolylsulfonyl)ethyl 3-({4-[2-amino-4-methoxyphenyl]-aminosulfonyl}-3,5-dimethylphenoxy)-2,2-dimethylpropionate (Intermediate A12, 4.1 g, 0.0068 mol) and thiocarbonyldiimidazole (1.8 g, 0.010 mol) were dissolved in pyridine (40 mL). After ca. 16 hr, the mixture was poured into 400 mL of water. The suspension was extracted with several portions of ethyl acetate, and the combined organic layers were washed with 2 portions of 1.2 M hydrochloric acid and concentrated. The residue was reconcentrated from dichloromethane to yield 4.3 g (98%) of the title compound.

2-(4-Tolylsulfonyl)ethyl 3-(4-[(5-methoxy-2-{[(4-methoxy-3,5-dimethyl(2-pyridyl)) methylthio}benzimidazolyl)sulfonyl]-3,5-dimethylphenoxy}-2,2-dimethylpropionate 2-(4-Tolylsulfonyl)ethyl 3-(4-[{2-mercapto-5-methoxybenzimidazolyl}sulfonyl]-3,5-dimethylphenoxy)-2,2-dimethylpropionate (Intermediate A13, 4.2 g, 0.0065 mol) and potassium carbonate (1.97 g, 0.014 mol) were mixed in dimethylformamide (41 mL). Then, 2-(chloromethyl)-4-methoxy-3,5-dimethylpyridinium hydrochloride (1.5 g, 0.0068 mol) was added in a single portion. After 90 min, the reaction mixture was poured into a rapidly stirring mixture of 16 mL of 1.2 M hydrochloric acid and 45 g of ice. The resulting oily suspension began to crystallize upon extensive scratching with a glass rod. It was then stirred for several days. The product, title compound, was collected by filtration and washed with several portions of water. After drying, it weighed 4.8 g (93%)

2-(4-Tolylsulfonyl)ethyl 3-{4-[(5-methoxy-2-{[(4-methoxy-3,5-dimethyl(2-pyridyl) methylsulfinyl}benzimidazole)sulfonyl]-3,5-dimethylphenoxy}-2,2-dimethylpropionate (Intermediate A14)

2-(4-Tolylsulfonyl)ethyl 3-{4-[(5-methoxy-2-{[(4-methoxy-3,5-dimethyl(2-pyridyl))methylthio}benzimidazolyl)sulfonyl]-3,5-dimethylphenoxy}-2,2-dimethylpropionate (4.63 g, 0.00582 mol) and 70% 3-chloroperoxybenzoic acid (1.8 g, 0.00728 mol) were separately dissolved in 30 mL of tetrahydrofuran and cooled in a freezer for 40 min. The solutions were combined and left in a freezer for 16 hr. The reaction mixture was then poured into a mixture of ethyl acetate and 5% sodium metabisulfite. The organic layer was washed with an additional portion of bisulfite solution, with several portions of 5% sodium bicarbonate solution, and with saturated sodium chloride. After the solvent had been removed in vacuo, the residue was separated by flash chromatography (silica gel: 1:1 hexanes-:ethyl acetate→0.5% methanol in ethyl acetate) to yield 1.4 g (30%) of the title compound.

3-{4-[(5-methoxy-2-{[(4-methoxy-3,5-dimethyl(2-pyridyl))methylsulfinyl}benzimidazolyl)sulfonyl]-3,5-dimethylphenoxy}-2,2-dimethylpropionic acid sodium salt (Compound 43)

2-(4-Tolylsulfonyl)ethyl 3-{4-[(5-methoxy-2-{[(4-methoxy-3,5-dimethyl(2-pyridyl))methyl]sulfinyl}benzimidazolyl)sulfonyl]-3,5-dimethylphenoxy}-2,2-dimethylpropionate (Intermediate A14, 1.4 g, 0.0017 mol), dissolved in acetonitrile (9 mL), was mixed with isopropanol (3 mL) and 3 mL of water containing sodium bicarbonate (0.17 g, 0.0020 mol). The mixture was heated in a 70° C. bath for about 6 hr and was then concentrated at aspirator pressure and then high vacuum. The residue was washed with ethyl acetate, was then precipitated from a dichloromethane/isopropanol solution with ethyl acetate, and finally was concentrated from water at reduced pressure. The residue was redissolved in water and ethyl acetate. The pH was adjusted to 4, and the organic layer was filtered through a sodium sulfate plug and concentrated. After it had dried for several days at high vacuum, this acid was dissolved in dimethoxyethane and neutralized by the addition of a stoichiometric amount of 0.100 N sodium hydroxide. The solvents were removed at aspirator pressure and finally high vacuum, and the residue was collected with the aid of diethyl ether. After it had dried, the product, title compound, weighed 0.71 g (64%).

NMR (300 MHz) (D$_2$O) δ 7.9 (s, 1H); 7.2–6.5 (complex, 5H); 4.9–4.5 (AB, 2H); 3.9 (m, 2H); 3.7 (s, 3H); 3.5 (s, 3H), 2.2 (s, 6H); 2.0 (s, 3H); 1.9 (s, 3H); 1.0 (d, 6H).

Reaction Scheme 34

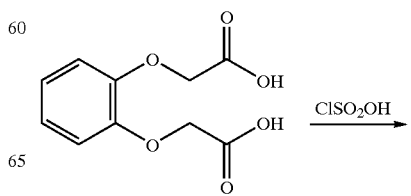

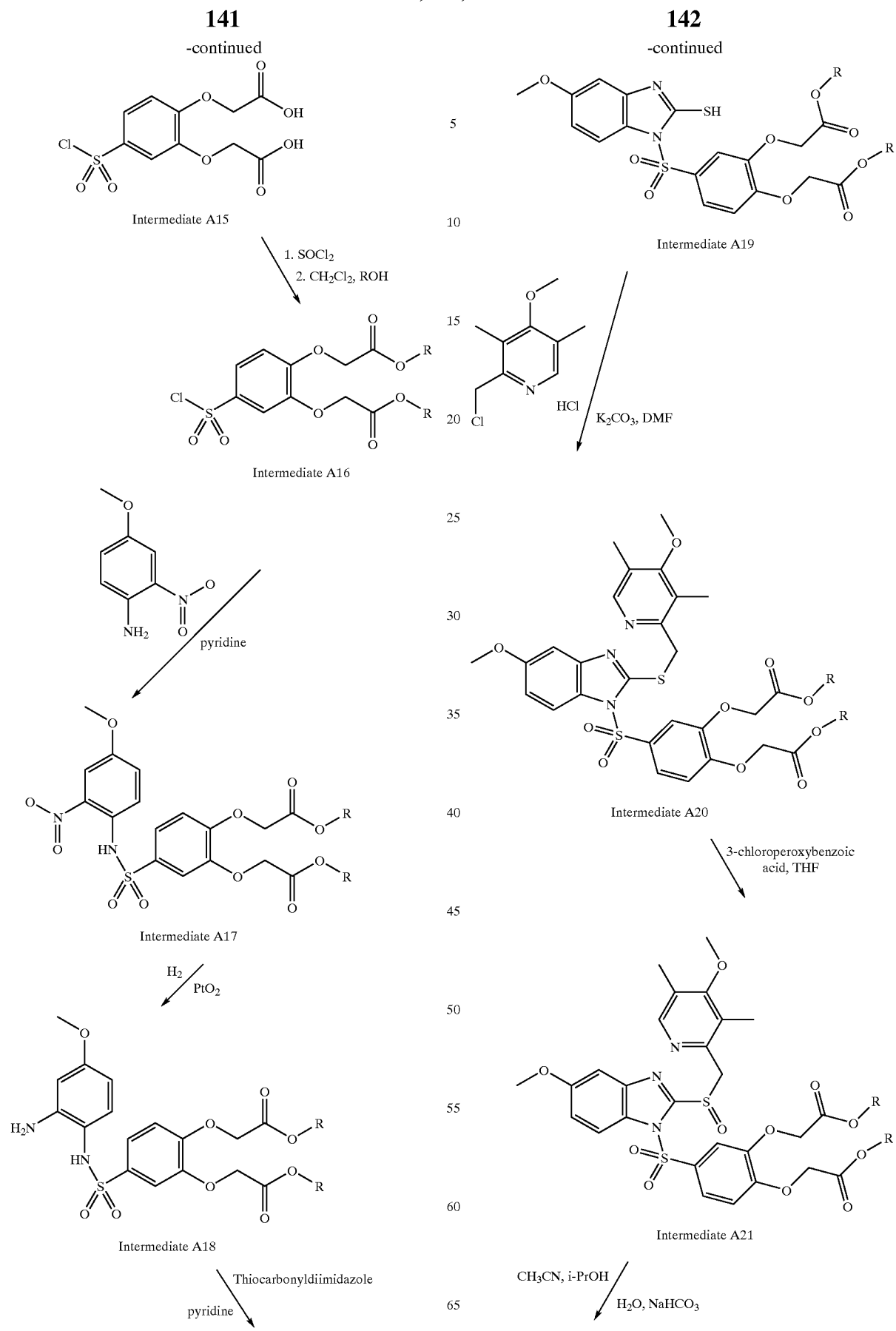

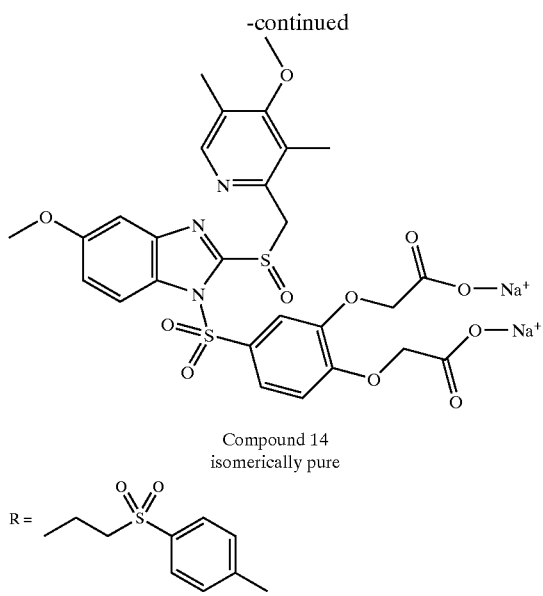

Compound 14
isomerically pure

2-Carboxymethoxy-4-chlorosulfonylphenoxyacetic acid (Intermediate A15)

2-Carboxymethoxyphenoxyacetic acid (15.3 g, 0.0675 mol) was added in portions over 30 min to stirred chlorosulfonic acid (59.0 g, 0.506 mol) that was cooled in an ice/methanol bath. The mixture was allowed to warm to room temperature over 2.5 hr and was then poured slowly into stirred ice water. The resulting solid was collected by filtration, washed with water, and dried at high vacuum over sodium hydroxide. The product, title compound, weighed 6.54 g (30%).

2(4-Tolylsulfonyl)ethyl 4-chlorosulfonyl-2-(2-[4-tolylsulfonyl]ethoxycarbonylmethoxy)phenoxyacetate (Intermediate A16, also known as Intermediate 36)

2-carboxymethoxy-4-chlorosulfonylphenoxyacetic acid (Intermediate A15, 6.54 g, 0.0202 mol) was heated at reflux with 15 mL (0.202 mol) of thionyl chloride. After 1 hr, the mixture was diluted with 20 mL toluene and concentrated to dryness at aspirator pressure and high vacuum. The crystalline residue was dissolved in 300 mL dichloromethane and mixed with 2-(4-tolylsulfonyl)ethanol (8.89 g, 0.044 mol). Pyridine (3.6 mL, 0.044 mol) in 100 mL dichloromethane was then added dropwise over 15 min. After an additional 1.75 hr, the reaction mixture was washed with 1 M sulfuric acid, dried over magnesium sulfate, and concentrated. The residue was purified on flash silica gel (dichloromethane→7.5% ethyl acetate in dichloromethane) to yield 9.74 g (70%) of the title compound.

2(4-Tolylsulfonyl)ethyl 4-(4-methoxy-2-nitrophenyl)aminosulfonyl-2-(2-[4-tolylsulfonyl]ethoxycarbonylmethoxy)phenoxyacetate (Intermediate A17)

4-Methoxy-2-nitroaniline (2.3 g, 0.014 mol) and 2-(4-tolylsulfonyl)ethyl-4-chlorosulfonyl-2-(2-[4-tolylsulfonyl]ethoxycarbonylmethoxy)phenoxyacetate (Intermediate A16, 9.6 g, 0.014 mol) were dissolved in 40 mL of pyridine and stirred under positive nitrogen pressure. After ca. 16 hr, the mixture was diluted with 50 mL of toluene and 20 mL of dichloromethane and was concentrated at aspirator pressure. The residue was purified on a flash silica gel column (dichloromethane→5:1 dichloromethane:ethyl acetate) to yield 6.7 g (58%) of the title compound.

2(4-Tolylsulfonyl)ethyl 4-(2-amino-4-methoxyphenyl)aminosulfonyl-2-(2-[4-tolylsulfonyl]-ethoxycarbonylmethoxy)phenoxyacetate (Intermediate A18)

2(4-Tolylsulfonyl)ethyl 4-(4-methoxy-2-nitro-phenyl)aminosulfonyl-2-(2-[4-tolylsulfonyl]ethoxycarbonylmethoxy)phenoxyacetate (Intermediate A17, 6.6 g, 0.0080 mol) was hydrogenated using platinum oxide as catalyst. The mixture was filtered and concentrated. After drying at high vacuum, the residual product, title compound, weighed 5.9 g (93%).

2-(4-Tolylsulfonyl)ethyl 4-[(2-mercapto-5-methoxybenzimidazolyl)sulfonyl]-2-(2-[4-tolylsulfonyl]ethoxycarbonylmethoxy)phenoxyacetate (Intermediate A19)

A mixture of 2-(4-tolylsulfonyl)ethyl 4-(2-amino-4-methoxy-phenyl)aminosulfonyl-2-(2-[4-tolylsulfonyl]ethoxycarbonylmethoxy)phenoxyacetate (Intermediate A18, 5.9 g, 0.0075 mol) and thiocarbonyldiimidazole (2.0 g, 0.011 mol) in 35 mL of pyridine was stirred under nitrogen for 4 hr. The mixture was then poured into 400 mL of rapidly stirring water. This suspension was stirred for ca. 16 hr, and was then extracted with toluene, diethyl ether, dichloromethane (2 portions) and 1:1 dichloromethane:methanol (3 portions). The extracts were washed, combined, and concentrated to yield 5.9 g (96%) of the title compound.

2-(4-Tolylsulfonyl)ethyl 4-[{5-methoxy-([4-methoxy-3,5-dimethyl(2-pyridyl)]methylthio)-benzimidazolyl}sulfonyl]-2-(2-[4-tolylsulfonyl]ethoxycarbonylmethoxy)phenoxyacetate (Intermediate A20)

2-(4-Tolylsulfonyl)ethyl 4-[(2-mercapto-5-methoxybenzimidazolyl)sulfonyl]-2-(2-[4-tolylsulfonyl]ethoxycarbonylmethoxy)phenoxyacetate (Intermediate A19, 5.9 g, 0.0072 mol) was dissolved in 50 mL of dimethylformamide and then mixed with potassium carbonate (2.2 g, 0.016 mol) ($N_2$ atmosphere). Then 2-(chloromethyl)-4-methoxy-3,5-dimethylpyridinium hydrochloride (1.7 g, 0.0076 mol) was added in 1 portion. After about 2.5 hr, the volume of the mixture was reduced to ca. 20 mL at high vacuum (bath temperature <22° C.). The residual solution was poured into a rapidly stirring mixture of 10 mL of 1.2 M hydrochloric acid in 200 mL of water and ice. The suspension was stirred until the precipitate was granular. The solid was then collected and washed with water and allowed to air-dry. The solid was then stirred for 14 hr with 1:1 isopropanol:water. The supernatant was decanted away, and the residue was taken up in dichloromethane and concentrated to dryness. The residue was purified on a flash silica gel column (4% ethyl acetate in dichloromethane→ethyl acetate) yielding 4.8 g (75%) of the title compound.

2-(4-Tolylsulfonyl)ethyl 4-[{5-methoxy-([4-methoxy-3,5-dimethyl(2-pyridyl)]methylsulfinyl)benzimidazolyl}sulfonyl]-2-(2-[4-tolylsulfonyl]ethoxycarbonylmethoxy)phenoxyacetate (Intermediate A21)

2-(4-Tolylsulfonyl)ethyl 4-[{5-methoxy-([4-methoxy-3,5-dimethyl(2-pyridyl)]methylthio)benzimidazolyl}sulfonyl]-2-(2-[4-tolylsulfonyl]ethoxycarbonyl-methoxy)phenoxyacetate (Intermediate A20, 4.8 g, 0.0054 mol) was dissolved in 20 mL of tetrahydrofuran, and the solution was left in a freezer for 40 min. A solution of 3-chloroperoxybenzoic acid (1.3 g, 0.0075 mol) in 6 mL of tetrahydrofuran was cooled for 30 min. The two were combined and left in the freezer for 16 hr. The mixture was then poured into a rapidly stirring mixture of 5% aqueous sodium metabisulfite and ethyl acetate. The layers were separated, and the organic layer was washed with 2 portions of 2.5% aqueous sodium bicarbonate and with saturated aqueous sodium chloride. The solution was filtered through 1PS paper and concentrated at aspirator pressure. The residue was separated on a column of flash silica gel (2:1 ethyl acetate:hexanes→ethyl acetate) to yield 2.0 g (41%) of the title compound.

2-Carboxymethoxy-4-[(5-methoxy-2-{[(4-methoxy-3,5-dimethyl(2-pyridyl))methylsulfinyl}benzimidazolyl)sulfonyl]phenoxy}acetic acid di-sodium salt (Compound 14)

2-(4-Tolylsulfonyl)ethyl 4-[{5-methoxy-([4-methoxy-3,5-dimethyl(2-pyridyl)]methylsulfinyl)benzimidazo-lyl}sulfonyl]-2-(2-[4-tolylsulfonyl]ethoxycarbonyl-methoxy)phenoxyacetate (Intermediate A21 2.0 g, 0.0033 mol) was dissolved in 15 mL acetonitrile and 5 mL isopropanol. This solution was mixed with sodium bicarbonate (0.61 g, 0.0072 mol) in 10 mL of water and heated, with stirring, in a 70° C. bath for 75 min. The solvents were removed at aspirator pressure (bath temperature <22° C.), and the residue was left overnight under high vacuum. It was then triturated with 2 portions of diethyl ether and 2 portions of ethyl acetate. The residue was dissolved in water and washed with 3 portions of ethyl acetate. The aqueous solution was then extracted with ethyl acetate at pH 5, 4, 3, and finally at pH 3 with increasing amounts of sodium chloride. The combined organic extracts were concentrated, and the product was collected with the aid of 1:1 dichloromethane:ethyl acetate. The filtrate was combined with similarly derived material and taken through the same neutral and acidic extract procedure. A total of 1.1 g (49% combined yield) of the title compound was obtained.

NMR (300 MHz) ($D_2O$) δ 7.7–6.8 (complex, 7H); 4.7 (AB, 2H), 4.4 (s, 2H); 4.3 (s, 2H); 3.9 (s, 3H); 3.8 (s, 3H); 2.0 (s, 6H).

Reaction Scheme 35

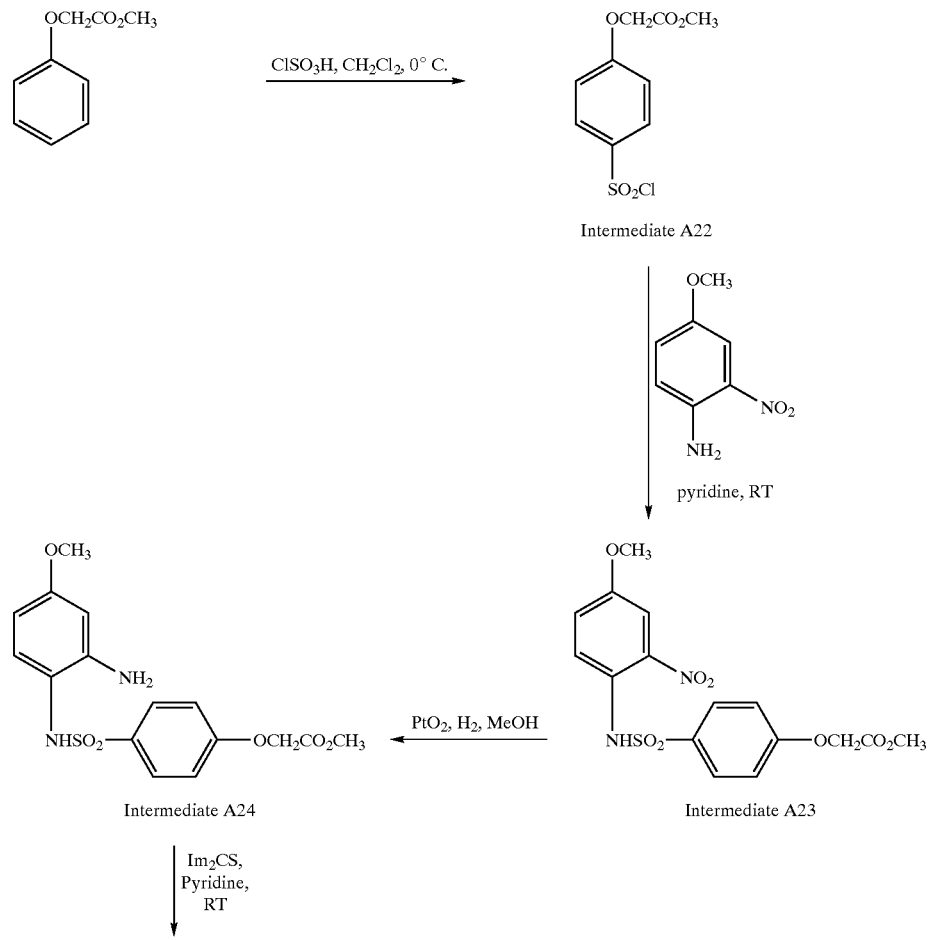

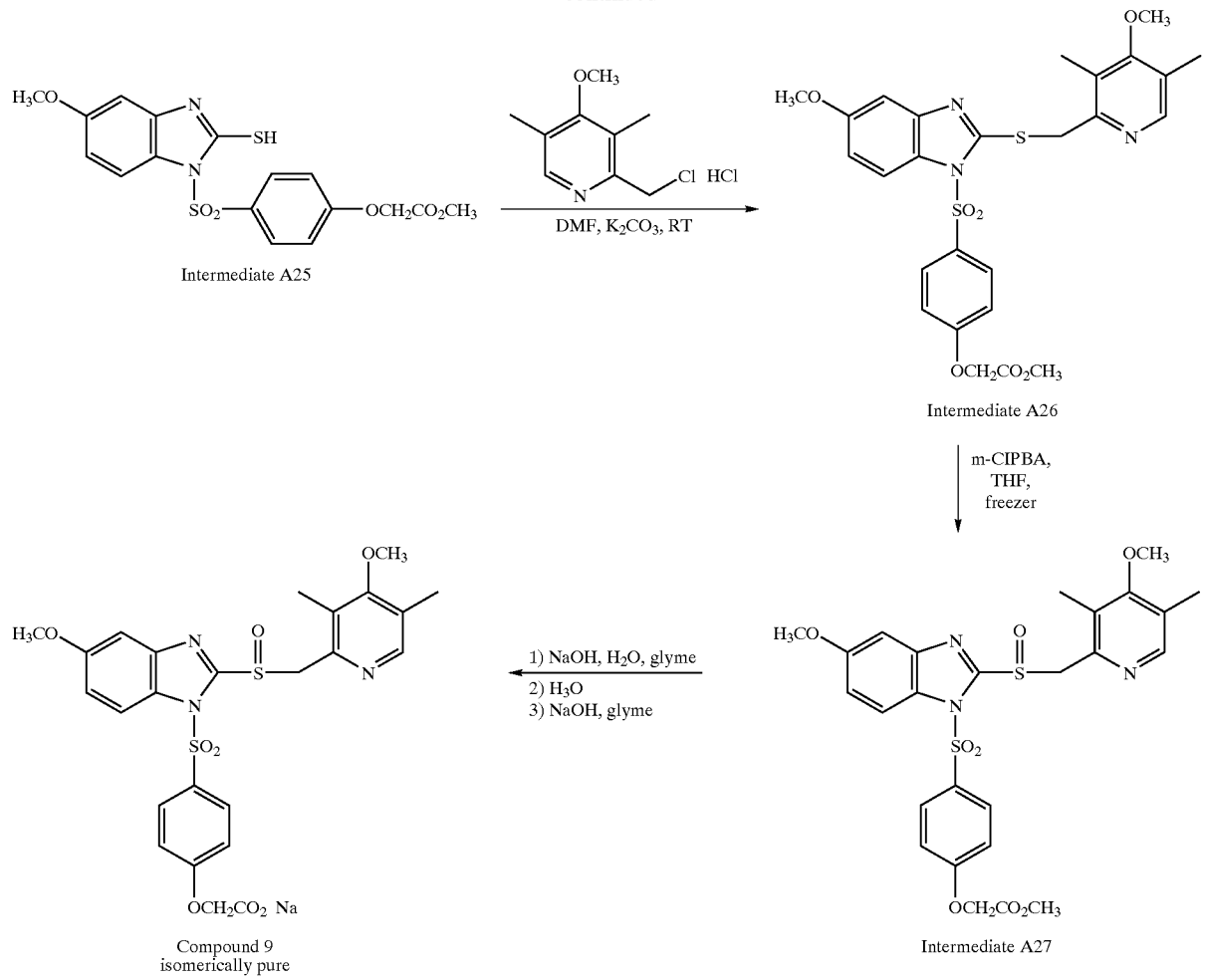

Methyl 2-[4-(chlorosulfonyl)phenoxy]acetate (Intermediate A22)

Methyl phenoxyacetate (99.9 g, 0.6 mol) was added dropwise to chlorosulfonic acid (279.6 g, 159.5 mL, 2.4 mol) at −5° C. at such a rate to maintain internal temperature between 0 to −5° C. (addition took about 60 min). Some solid formed during this addition. The cooling bath was removed and the reaction mixture was stirred at room temperature for an additional 1.5 hr. The reaction mixture was poured into a vigorously stirring mixture of dichloromethane (900 mL) and methanol (100 mL) at 0° C. After 15 min the cooling bath was removed and the resulting mixture was stirred at room temperature for 1 hr. The resulting mixture was washed with ice cold water (2×250 mL). The combined aqueous layers were back extracted with dichloromethane (1×250 mL). The combined organic layers were washed with brine (1×200 mL), dried over anhydrous magnesium sulfate (15 g) and concentrated under reduced pressure to give 132 g (83%) of the title compound as a white solid.

$^1$H NMR (60 Mhz) (CDCl$_3$) δ 8.2–7.2 (AB, 4H), 4.95 (s, 2H), 3.95 (s, 3H).

Methyl 2-(3-([4-methoxy-2-nitrophenyl)amino]sulfonyl)phenoxy)Acetate (Intermediate A23)

Solid methyl 2-[4-(chlorosulfonyl)phenoxy]acetate (Intermediate A22, 63.5 g, 0.24 mol) was added to a solution of 4-methoxy-2-nitroaniline (33.6 g, 0.2 mol) in pyridine (1 L) at room temperature under argon. The resulting mixture was stirred at room temperature overnight. The reaction mixture was then concentrated under reduced pressure. The residue was partitioned between 1.5 M hydrochloric acid (1000 mL) and ethyl acetate (500 mL). The aqueous layer was separated and extracted with ethyl acetate (2×250 mL). The combined organic layers were washed with brine (1×200 mL), dried over anhydrous magnesium sulfate (15 g) and concentrated under reduced pressure to give an orange solid. The solid was dissolved in boiling ethyl acetate (500 mL), placed at room temperature for 1 hr and in a freezer for 4 hr. Yellow crystals were collected and air dried to afford 64.2 g (81%) of the title compound.

$^1$H NMR (60 Mhz) (CDCl$_3$) δ 9.4 (s, 1H), 7.0–8.0 (m, 7H), 4.8 (s, 2H), 4.0 (s, 3H), 3.95 (s, 3H).

Methyl 2-(3-([2-amino-4-methoxyphenyl)amino]sulfonyl)phenoxy)Acetate (Intermediate A24)

A solution of methyl 2-(3-([4-methoxy-2-nitrophenyl)amino]sulfonyl)phenoxy)acetate (Intermediate A23, 22.57 g, 0.057 mol) in ethyl acetate (500 mL) was slurried with Raney nickel (3 g), filtered, and then hydrogenated over platinum(IV)oxide (0.5 g) until hydrogen uptake ceased. Upon completion the reaction mixture contained some solid product. The solid was collected and air dried to give 15.6 g crude product with 0.5 g catalyst in it. The filtrate was concentrated under reduced pressure to give an additional 3.1 g of product. The total weight of the product, title compound was 18.2 g (87%).

$^1$H NMR (60 Mhz) (d6-DMSO) δ 6–8.2 (m, 9H), 5.2 (br. s, 3H), 3.9 (s, 3H), 3.7 (s, 3H).

Methyl 2-{4-[(5-methoxy-2-sulfanylbenzimidazolyl) sulfonyl}Acetate (Intermediate A25)

The crude methyl 2-(3-([2-amino-4-methoxyphenyl) amino]sulfonyl)phenoxy)acetate (Intermediate A24, 17.93 g, ca. 0.05 mol) was dissolved in pyridine (200 mL) and filtered through glass fiber filter paper to remove catalyst from the previous preparation. This solution was charged with 1,1'-thiocarbonyldiimidazole (13.1 g, 0.0735 mol) and stirred at room temperature overnight under argon. Water (2.5 L) was then added to the reaction mixture and stirring continued an additional 1.5 hr. The resulting solid was collected, washed with 2 L water and air dried to give 20 g (100%) of the title compound.

$^1$H NMR (60 Mhz) (d6-DMSO) δ 7.0–8.8 (m, 8H), 5.1 (s, 2H), 3.9 (s, 3H), 3.8 (s, 3H).

Methyl 2-[4-({5-methoxy-2-[(4-methoxy-3,5-dimethyl(2-pyridyl)methylthio] benzimidazolyl}sulfonyl)phenoxy]acetate (Intermediate A26)

Anhydrous potassium carbonate (14.88 g, 0.108 mol) was ground in a mortar and pestle and added to a solution of methyl 2-{4-[(5-methoxy-2-sulfanylbenzimidazolyl) sulfonyl}acetate (Intermediate A25, 19.99 g, 0.049 mol) in N,N-dimethylformamide (150 mL). Then 2-chloromethyl-3,5-dimethyl-4-methoxypyridine hydrochloride (11.42 g, 0.051 mole) was added to the mixture and vigorously stirred under argon at room temperature. After 2 hr, HPLC analysis showed that the reaction was complete. A mixture of CH$_2$Cl$_2$/IPA (75:25) (800 mL) was added to the reaction mixture, followed by water (400 mL). After stirring for 10 min, the organic layer was separated, washed with water (400 mL) then with brine (400 mL) and dried over anhydrous magnesium sulfate. The solvent was removed on a rotary evaporator under aspirator pressure and finally under high vacuum to give a brown solid. This brown solid was triturated in a mixture of 35% ethyl acetate in hexane (250 mL) and stirred for 1 hr. The solid was collected, washed with a mixture of 35% ethyl acetate in hexane (100 mL) and air dried to give 21 g (77%) of the title compound.

$^1$H NMR (60 Mhz) (CDCl$_3$) δ 7.7–8.4 (m, 4H), 6.8–7.3 (m, 4H), 4.85 (s, 2H), 4.8 (s, 2H), 3.9 (s, 3H), 3.85 (s, 6H), 2.4 (s, 3H), 2.3 (s, 3H).

Methyl 2-{4-[(5-methoxy-2-{[(4-methoxy-3,5-dimethyl(2-pyridyl))methyl] sulfinyl}benzimidazolyl)sulfonyl]phenoxy}acetate (Intermediate A27)

A solution of 3-chloroperoxybenzoic acid (12.64 g of 70%, 0.051 mol) in THF (150 mL) was added to a cold solution of the sulfide (Intermediate A26, 22.84 g, 0.041 mol) in THF (500 mL). The resulting mixture was kept in a freezer overnight (19 hr). HPLC analysis showed 58% sulfoxide methyl ester, 6% unreacted starting sulfide, and two other unidentified impurities (8% and 24%). The reaction mixture was diluted with ethyl acetate (750 mL) and washed with: 5% sodium metabisulfite (2×200 mL), 5% sodium bicarbonate (2×200 mL), and brine (2×200 mL). The resulting solution was filtered through 1 PS filter paper and concentrated under reduced pressure to give 26 g of a foam. The foam was purified by flash chromatography (silica gel, ethyl acetate to 1% MeOH/ethyl acetate) to give 16.2 g of the crude product as a foam. This foam was triturated with 10% ethyl acetate/hexane (100 mL). The white solid was collected and air dried to give 15.25 g (65%) of the title compound, $^1$H NMR (60 Mhz) (CDCl$_3$) δ 8.0–8.7 (m, 4H), 7.7–7.3 (m, 4H), 5.2 (unresolved d, 4H), 3.95 (s, 3H), 3.8 (s, 3H), 3.75 (s, 3H), 2.4 (s, 3H), 2.2 (s, 3H).

2-{4-[(5-methoxy-2-{[(4-methoxy-3,5-dimethyl(2-pyridyl))methyl]sulfonyl}benzimidazolyl)sulfonyl] phenoxy}acetic acid (Compound 9)

A 3 L 3-necked flask equipped with a mechanical stirrer was charged with methyl 2-f{4-[(5-methoxy-2-{[(4-methoxy-3,5-dimethyl(2-pyridyl))methyl] sulfonyl}benzimidazolyl)sulfonyl]phenoxy}acetate (Intermediate A27, 13.75 g, 0.024 mol) in glyme (1200 mL). To this vigorously stirring solution was added 0.1 N NaOH solution (300 mL). The resulting mixture was concentrated under reduced pressure at 47° C. The residue was triturated with fresh ethyl acetate (100 mL) for a total of four times. The residue was placed under high vacuum for 1 hr to give 17 g of a gummy solid. In a 1 L 3-necked flask equipped with a mechanical stirrer was placed 16 g of this solid (equivalent to 13.3 g sodium salt, 0.0226 mol) in water (250 mL). The solution was washed by stirring with ethyl acetate (250 ML) for 1 hr and then the layers were separated. HPLC analysis of the ethyl acetate layer showed 64% omeprazole and 33% unreacted sulfoxide methyl ester. A fresh 250 mL of ethyl acetate was added to the aqueous layer. The resulting mixture was stirred and acidified to pH 3–4 with ca. 40 mL of 0.5 N hydrochloric acid. The ethyl acetate layer was separated quickly, because product started to crystallize, and placed in a freezer overnight. The crystals were collected and air dried to give 6.7 g (53%) of the methyl 2-{4-[(5-methoxy-2-{[(4-methoxy-3,5-dimethyl(2-pyridyl))methyl] sulfonyl}benzimidazolyl)sulfonyl]phenoxy}acetate.

Sodium salt of 2-{4-[(5-methoxy-2-{[(4-methoxy-3, 5-dimethyl(2-pyridyl))methyl] sulfonyl}benzimidaolyl)sulfonyl]phenoxy}acetic acid (Compound 9)

The sulfoxide acid (4.81 g, 0.0086 mol) was suspended in glyme (500 mL). The resulting mixture was stirred with a magnetic stir-bar and 1 N sodium hydroxide (8.6 mL, 0.0086 mol) was added over 20 min. Insoluble material was filtered and the filtrate concentrated in vacuo to give a tan solid. This solid was suspended in ethyl acetate (100 mL) and stirred for 1 hr. The solid was collected and air dried to give 4.1 g of the title compound.

$^1$H NMR (60 Mhz) (CDCl$_3$, d6-DMSO) δ 6.9–8.2 (m, 8H), 4.7–5.1 (dd, 2H), 4.3 (s, 2H), 3.8 (s, 3H), 3.7 (s, 3H), 2.25 (s, 3H), 2.15 (s, 3H).

Reaction Scheme 36
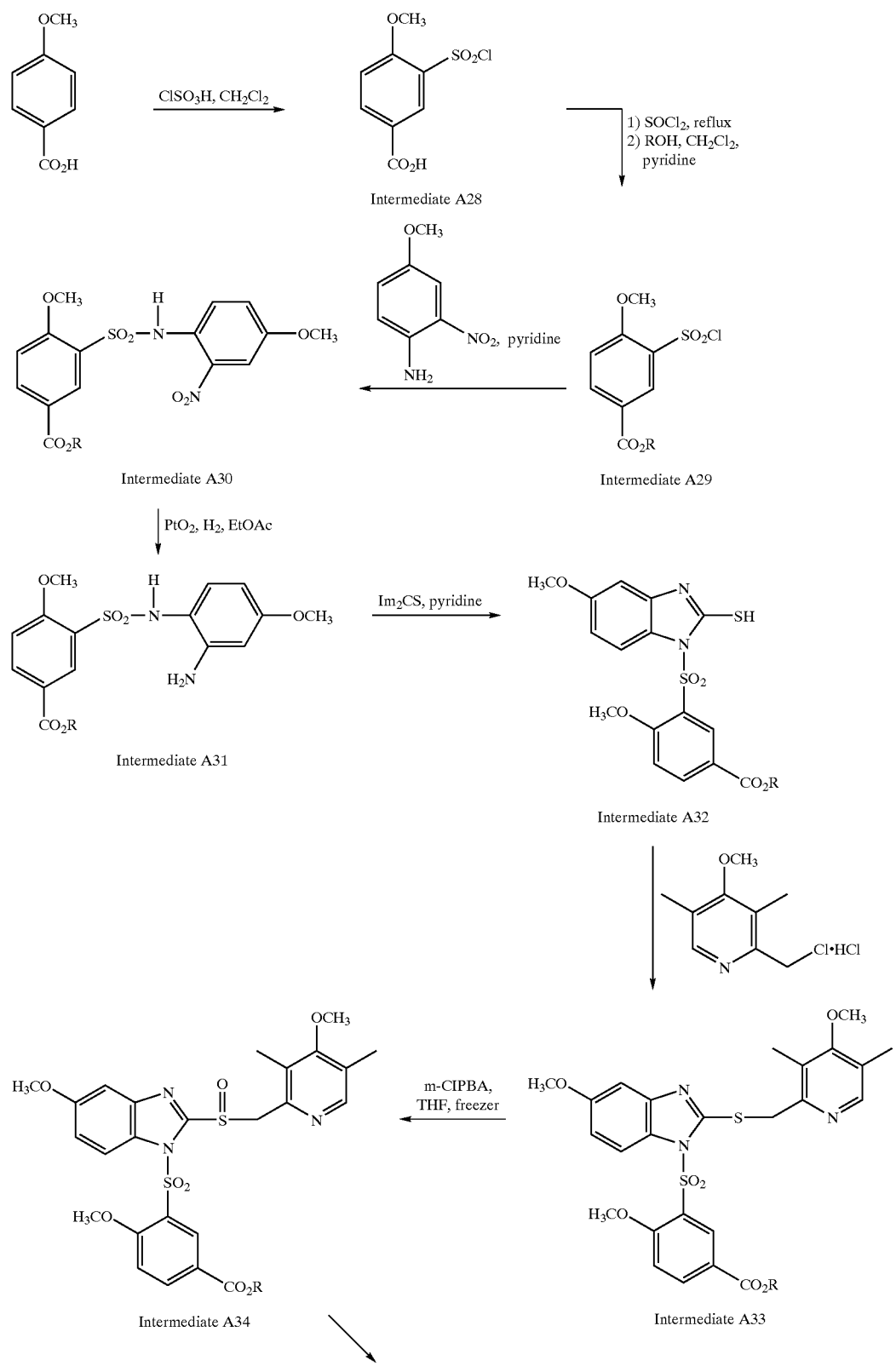

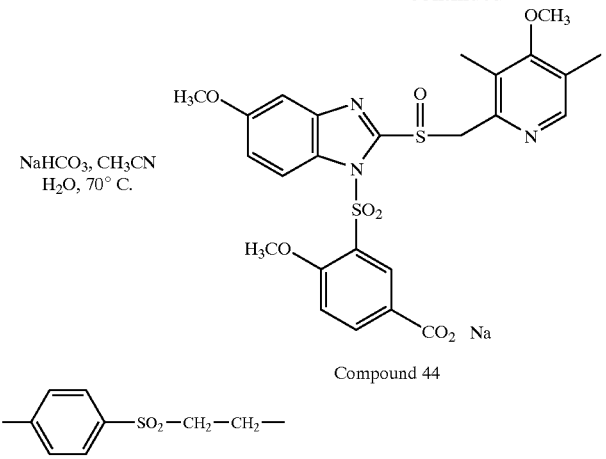

Compound 44

R = H$_3$C—⟨benzene⟩—SO$_2$—CH$_2$—CH$_2$—

3-(Chlorosulfonyl)-4-methoxybenzoic acid (Intermediate A28)

Solid 4-methoxy benzoic acid (45.6 g, 0.3 mol), in portions, was added to chlorosulfonic acid (139.8 g, 80 mL, 1.2 mol) at room temperature. After most of the bubbling had ceased, the reaction mixture was heated to 80° C. for 1 hr. The reaction mixture was then poured into vigorously stirring crushed-ice (500 g) and water was then added (500 mL). After 30 min, the white solid was collected, washed with water (2 L) and dried to give 50 g (66%) of the title compound.

3-Chlorosulfonyl-4-methoxy-benzoic acid 2-(toluene-4-sulfonyl)-ethyl ester (Intermediate A29)

A mixture of 3-(chlorosulfonyl)-4-methoxybenzoic acid (Intermediate A28, 13.78 g, 0.055 mol) and thionyl chloride (39.27 g, 25 mL, 0.33 mol) was refluxed for 1 hr. Excess thionyl chloride was distilled off at atmospheric pressure and finally at reduced pressure to give 15 g acid chloride as a light brown solid. To a mixture of acid chloride (15 g) and 2-(p-tolylsulfonyl)ethanol (10.46 g, 0.0522 mol) in dichloromethane (100 mL) was added triethylamine (5.56 g, 0.055 mol) at room temperature. TLC (ethyl acetate) showed the reaction was complete after 1 hr. The reaction mixture was washed with water (2×100 mL) and brine (1×100 mL), filtered through 1PS filter paper and concentrated under reduced pressure to give an oil. The oil was triturated with 15% ethyl acetate in hexane (100 mL) and solid was collected and dried to give 19.4 g, (81%) of the, title compound, sulfonyl chloride ester as a white solid.

4-Methoxy-3-(4-methoxy-2-nitro-phenylsulfamoyl)-benzoic acid 2-(toluene-4-sulfonyl)-ethyl ester (Intermediate A30)

The sulfonyl chloride (Intermediate A29, 18.17 g, 0.042 mol), 3-methoxy-2-nitroaniniline (7.06 g, 0.042 mol), and pyridine (100 mL) were mixed and stirred at room temperature overnight under argon. The reaction mixture was concentrated under reduced pressure. The residue was dissolved in ethyl acetate (250 mL), washed with 3 M hydrochloric acid (3×100 mL) and brine (1×100 mL), filtered through 1PS filter paper and concentrated under reduced pressure to give an orange-red oil. The oil was purified by flash chromatography (silica gel, 20% ethyl acetate in hexane to 50% ethyl acetate in hexane) to give 13.8 g (57%) of the title compound, nitro sulfonamide as a foam.

3-(2-Amino-4-methoxy-phenylsulfamoyl)-4-methoxy-benzoic acid 2-(toluene-4-sulfonyl)-ethyl ester (Intermediate A31)

A solution of nitro sulfonamide (Intermediate A30, 13.54 g, 0.024 mol) in ethyl acetate (400 mL) was stirred for 15 min with Raney nickel (3 g), filtered through a pad of celite, and hydrogenated over platinum(IV)oxide (1 g) overnight. The reaction mixture was filtered through glass fiber filter paper and concentrated under reduced pressure to give 11.8 g (92%) of the title compound, amine as a foam.

4-(2-Mercapto-5-methoxy-benzimidazole-1-sulfonyl)-3-methoxy-benzoic acid 2-(toluene-4-sulfonyl)-ethyl ester (Intermediate A32)

To a solution of the amino compound (Intermediate A31, 11.75 g, 0.022 mol) in pyridine (150 mL) was added 1,1'-thiocarbonyldiimidazole (5.88 g, 0.033 mol). The reaction mixture was stirred at room temperature for 2 hr and then water added (600 mL). After stirring for 1.5 hr, the solid was collected, washed with water (1 L), and dried to give 10.4 g (82%) of the title compound, benzimidazolethiol.

4-Methoxy-3-[5-methoxy-2-(4-methoxy-3,5-dimethyl-pyridin-2-ylmethylsulfanyl)-benzimidazole-1-sulfonyl]-benzoic acid 2-(toluene-4-sulfonyl)ethyl ester (Intermediate A33)

Anhydrous potassium carbonate (5.38 g, 0.039 mol) was ground in a mortar and pestle and added to a solution of the benzimidazolethiol (Intermediate A32, 10.2 g, 0.0177 mol) in N,N-dimethylformamide (100 mL). To this mixture 2-chloromethyl-3,5-dimethyl-4-methoxypyridine hydrochloride (4.13 g, 0.186 mol) was added. After 2 hr 150 mL of 25% isopropyl alcohol in dichloromethane was added to the reaction. The reaction was washed with water (2×75 mL) and brine (1×75 mL), filtered through 1PS filter paper and concentrated under reduced pressure to give a brown oil. The oil was purified by flash chromatography (silica gel, 40% ethyl acetate in hexane to ethyl acetate) to give 11 g (96%) of the title compound, sulfide as a foam.

4-Methoxy-3-[5-methoxy-2-(4-methoxy-3,5-dimethyl-pyridin-2-ylmethanesulfinyl)-benzimidazole-1-sulfonyl]-benzoic acid 2-(toluene-4-sulfonyl)-ethyl ester (Intermediate A34)

The sulfide (Intermediate A33, 10.77 g, 0.0166 mol) was dissolved in tetrahydrofuran (200 mL), and stored in a freezer for 1 hr. Following addition of a cold solution of m-chloroperoxybenzoic acid (5.1 g of 70%, 0.0207 mol) in tetrahydrofuran (100 mL), the reaction mixture was returned to the freezer and stored overnight. The reaction mixture was diluted with ethyl acetate (300 mL) and washed with: 5% sodium metabisulfite (3×100 mL), saturated sodium bicarbonate (2×100 mL) and brine (1×100 mL). The organic phase was filtered through 1PS filter paper, and concentrated under reduced pressure. The concentrate was purified by flash chromatography (silica gel, 50% ethyl acetate in hexane to 4% methanol in ethyl acetate), to give 5.7 g (52%) of the title compound, sulfoxide as a foam.

4-Methoxy-3-[(5-methoxy-2-{[(4-methoxy-3,5-dimethyl(2-pyridyl))methyl]sulfinyl}benzimidazolyl)sulfonyl]benzoic acid sodium salt (Compound 44)

To a solution of the sulfoxide (Intermediate A34, 5.52 g, 0.0083 mol) in a mixture of acetonitrile (45 mL), isopropyl alcohol (15 mL), water (30 mL) was added sodium bicarbonate (0.837 g, 0.00996 mol). The resulting mixture was heated at 78° C. for 45 min. The resulting mixture was concentrated under reduced pressure to give a foam. The foam was triturated with 2% methanol in dichloromethane and gave 4.5 g of a solid. The solid was dissolved in water (150 mL), a mixture of 4% methanol in chloroform (100 mL) was then added and acidified with 3 M hydrochloric acid (3 mL). The aqueous layer was extracted with 4% methanol in chloroform (2×100 mL). The combined organic layers were washed with water (1×100 mL) and concentrated under reduced pressure to a constant weight to give 3.6 g of a foam. The foam was dissolved in glyme (100 mL) and 0.2 N sodium hydroxide (7.45 mL) was added. The resulting mixture was concentrated under reduced pressure and triturated with ether (50 mL) to give 2.45 g of a solid after drying. The solid was dissolved in hot dichloromethane, hot filtered and concentrated under reduced pressure to give 1.8 g (43%) of the title compound $^1$H NMR (300 MHz) δ 9.15 (s, 1H), 8.55 (s, 1H), 8.25 (dd, 1H), 7.45–7.25 (m, 2H), 6.9 (m, 2H), 5.05 (q, 2H), 3.9 (s, 3H), 3.85 (s, 3H), 3.8 (s, 3H), 2.45 (s, 3H), 2.35 (s, 3H).

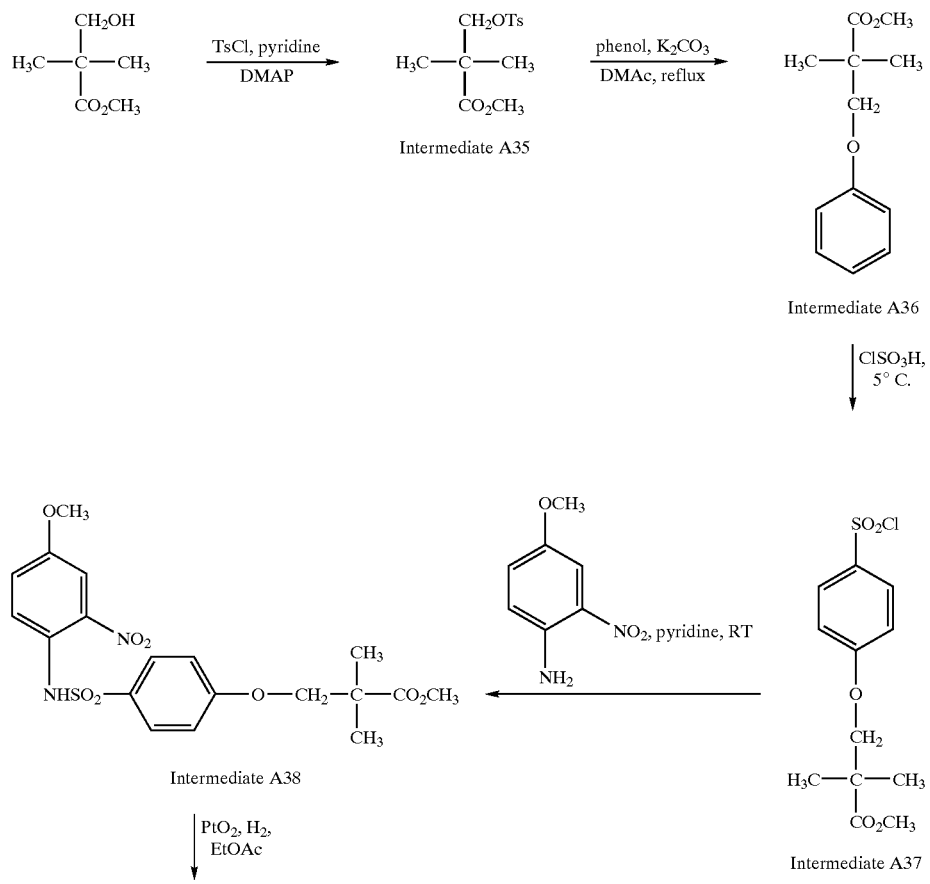

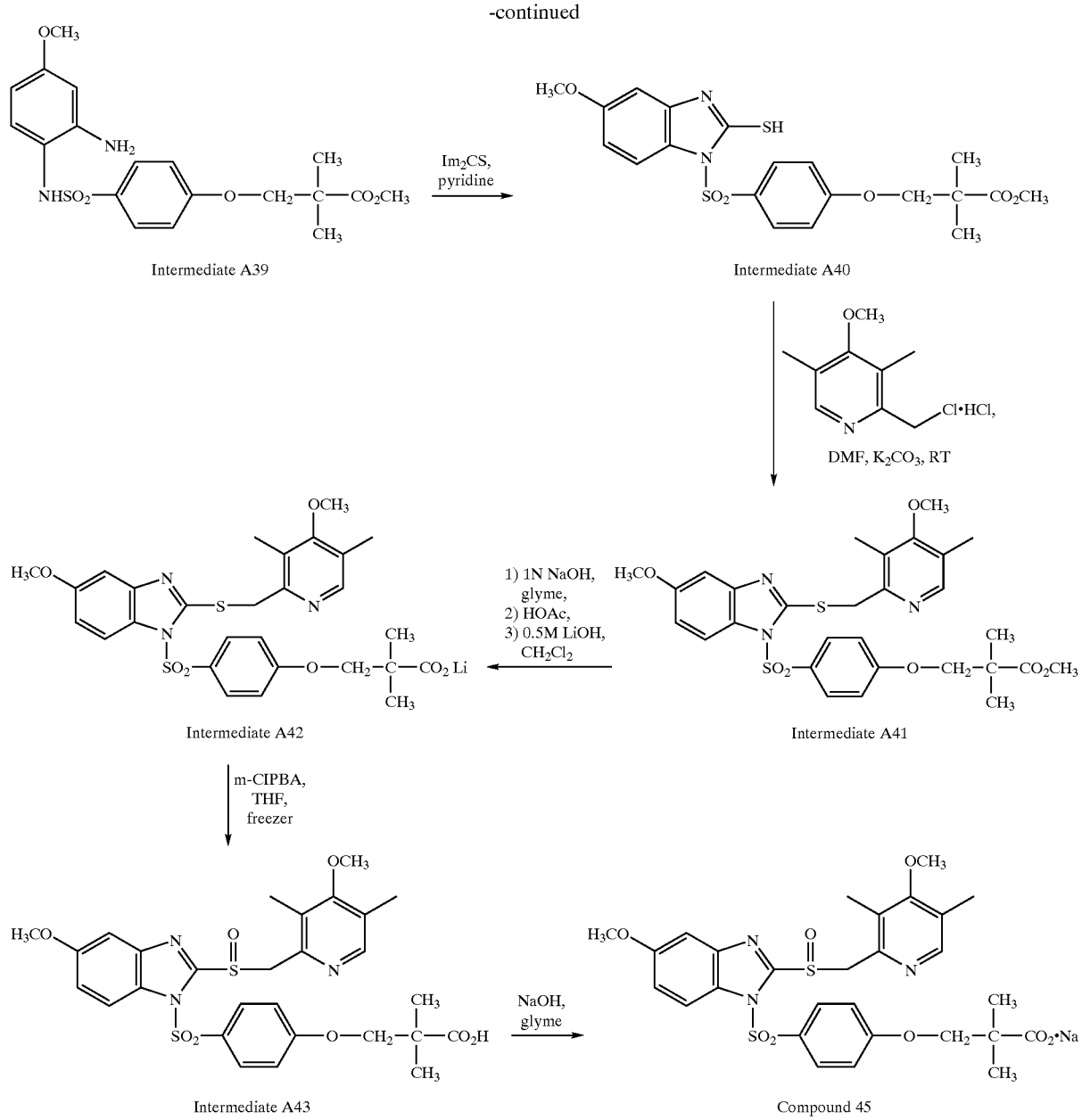

Methyl 2,2-dimethyl-3-(4-tolylsulfonyloxy) propionate (Intermediate A35)

A mixture of methyl 2,2-dimethyl-3-hydroxypropionate (100 g, 0.76 mol), 4-toluenesulfonyl chloride (151 g, 0.80 mol), 4-dimethylaminopyridine (4.6 g, 0.038 mol), and pyridine (200 mL) was stirred for 20 hrs and then was diluted with 200 mL toluene, stirred for 30 min, and filtered. The filtrate was concentrated to 250 mL under reduced pressure, diluted with 100 mL toluene, filtered, and concentrated. The residue was suspended in 200 mL hexanes, and the solvent was removed under reduced pressure to yield the title compound, desired product (235 g, 100%) contaminated by a trace of 4-toluenesulfonyl chloride.

Methyl 2,2-dimethyl-3-phenoxypioniate (Intermediate A36)

A mixture of methyl 2,2-dimethyl-3-(4-toluenesulfonyloxy)propionate (Intermediate A35, 80 g, 0.28 mol), phenol (28 g, 0.029 mol), potassium carbonate (58 g, 0.42 mol), and 250 mL N,N-dimethylacetamide was stirred and heated at reflux for 4 hr. The reaction mixture was cooled, diluted with ethyl acetate, and poured into water. The organic phase was washed with water and concentrated under reduced pressure. The residue was dissolved in hexanes and washed with water, 1 M sodium hydroxide, and a second portion of water. The concentrated solution was distilled at 15 torr (34–37° C.) to yield 25 g (42%) of the methyl 2,2-dimethyl-3-phenoxypropioniate.

3-(4-Chlorosulfonyl-phenoxy)-2,2-dimethyl-propionic acid methyl ester (Intermediate A37)

Methyl 2,2-dimethyl-3-phenoxypioniate (Intermediate A36, 36 g, 0.17 mol) was added dropwise over 60 min to rapidly stirred chlorosulfonic acid that was maintained at −5° C. The mixture was warmed to room temperature, stirred for an additional 90 min, and poured into a cooled, rapidly stirring mixture of dichloromethane (250 mL) and methanol (30 mL). The mixture was stirred for 30 min while being cooled and then for 60 min at room temperature. It was then washed with several portions of ice-water. The combined aqueous layers were extracted with a small portion of dichloromethane. The combined organic layers were washed with saturated aqueous sodium chloride and dried over sodium sulfate. The solvent was distilled off under reduced pressure, and the residue was stirred with hexanes and collected by filtration to yield 19 g (36%) of the title compound, sulfonyl chloride.

3-[4-(4-Methoxy-2-nitro-phenylsulfamoyl)-phenoxy]-2,2-dimethyl-propionic acid methyl ester (Intermediate A38)

The chlorosulfonyl compound (Intermediate A37, 18.4 g, 0.06 mol), 3-methoxy-2-nitroaniniline (8.4 g, 0.05 mol), and pyridine (500 mL) were mixed and stirred at room temperature overnight under argon. The reaction mixture was concentrated under reduced pressure, and the residue was partitioned between 1.5 M hydrochloric acid (300 mL) and ethyl acetate (300 mL). The aqueous layer was separated and extracted with ethyl acetate (2×150 mL). The combined organic layers were washed with brine (2×150 mL), dried over anhydrous magnesium sulfate and concentrated under reduced pressure to give an orange oily residue. The oil was purified by flash chromatography (silica gel, hexane to 35% ethyl acetate in hexane) to give 20.8 g (95%) of the title compound, nitro-sulfonamide as a creamy oil.

3-[4-(2-Amino-4-methoxy-phenylsulfamoyl)-phenoxy]-2,2-dimethyl-propionic acid methyl ester (Intermediate A39)

A solution of nitro sulfonamide (Intermediate A38 20.6 g, 0.047 mol) in ethyl acetate (300 mL) was stirred for 15 min with Raney nickel (1.5 g), filtered through a pad of celite, and hydrogenated over platinum(IV)oxide (0.5 g) overnight. The reaction mixture was filtered through glass fiber filter paper and concentrated under reduced pressure to give 16.3 g (85%) of the title compound, amine as a foam.

3-[4-(2-Mercapto-5-methoxy-benzimidazole-1-sulfonyl)-phenoxy]-2,2-dimethyl-propionic acid methyl ester (Intermediate A40)

To a solution of 3-[4-(2-mercapto-5-methoxy-benzimidazole-1-sulfonyl)-phenoxy]-2,2-dimethyl-propionic acid methyl ester (Intermediate A39, 16.1 g, 0.0395 mol) in pyridine (200 mL) was added 1,1'-thiocarbonyldiimidazole (10.56 g, 0.0592 mol). The reaction mixture was stirred at room temperature overnight and then water was added (2.5 L). After stirring for 1 hr, the solid was collected, washed with water (3 L), and dried to give 16.5 g (93%) of the title compound, benzimidazolethiol as a tan solid.

3-{4-[5-Methoxy-2-(4-methoxy-3,5-dimethyl-pyridin-2-ylmethylsulfanyl)-benzimidazole-1-sulfonyl]-phenoxy}-2,2-dimethyl-propionic acid methyl ester (Intermediate A41)

To a solution of benzimidazolethiol (Intermediate A40, 16.2 g, 0.036 mol) in N,N-dimethylformamide (150 mL) was added potassium carbonate (10.93 g, 0.079 mol). Solid 2-chloromethyl-3,5-dimethyl-4-methoxypyridine hydrochloride (8.39 g, 0.0378 mol) was added to this mixture.

After 1 hr a mixture of 800 mL of 25% isopropyl alcohol in dichloromethane was added to the reaction. The reaction was then washed with water (2×400 mL). The combined aqueous layers were back extracted with 100 mL of 25% isopropyl alcohol in dichloromethane. The combined organic layers were washed with brine (1×400 mL), dried over anhydrous magnesium sulfate (20 g) and concentrated under reduced pressure to give an oil. The oil solidified on standing and was triturated with 25% ethyl acetate in hexane (200 mL). The product, title compound (sulfide) was collected and dried to (20.2 g (93%)).

3-{4-[5-Methoxy-2-(4-methoxy-3,5-dimethyl-pyridin-2-ylmethylsulfanyl)-benzimidazole-1-sulfonyl]-phenoxy}-2,2-dimethyl-propionic acid lithium salt (Intermediate A42)

To a solution of sulfide (Intermediate A41, 9.58 g, 0.016 mol) in glyme (800 mL) was added 1 N sodium hydroxide solution (240 mL) over 30 min. After 3.5 hr, acetic acid (28.8 g) was added to get a pH of about 6.5. Most of the glyme was removed under reduced pressure. Water (250 mL) was added to the residue and the mixture was extracted with dichloromethane (2×125 mL). The combined organic layers were washed with water (1×100 mL) and brine (1×100 mL), filtered through 1PS filter paper and concentrated under reduced pressure. To a solution of residue (10 g) in dichloromethane was added 0.5 M lithium hydroxide solution (100 mL) followed by addition of brine (100 mL). The resulting mixture was stirred for 30 min and solid was collected, washed with water (50 mL) and dried to give 4.1 g (43%) lithium salt of the title compound, sulfide.

3-{4-[5-Methoxy-2-(4-methoxy-3,5-dimethyl-pyridin-2-ylmethanesulfinyl)-benzimidazole-1-sulfonyl]-phenoxy}-2,2-dimethyl-propionic acid (Intermediate A43)

Lithium salt of sulfide (Intermediate A42, 4.02 g, 0.0068 mol) was dissolved in tetrahydrofuran (250 mL) and cooled in a freezer for 1 hr. 3-Chloroperoxybenzoic acid (5.03 g, 0.0204 mol) was added and the resulting mixture was returned to the freezer and stored overnight. The reaction mixture was diluted with ethyl acetate (600 mL), washed with 5% sodium meta-bisulfite (3×150 mL), water (2×150 mL), brine (2×150 mL), filtered through 1PS filter paper and concentrated under reduced pressure to give a solid residue. The solid was purified by flash chromatography (silica gel, ethyl acetate) to give 1.3 g (29%) of the title compound, sulfoxide as a foam.

3-{4-[5-Methoxy-2-(4-methoxy-3,5-dimethyl-pyridin-2-ylmethanesulfinyl)-benzimidazole-1-sulfonyl]-phenoxy}-2,2-dimethyl-propionic acid sodium salt (Compound 45)

1 N sodium hydroxide (2 mL) was added to a solution of sulfoxide (Intermediate A43, 1.2 g, 0.002 mol) in glyme (25 mL). The resulting mixture was concentrated under reduced pressure to give a solid residue. The solid residue was triturated with ethyl acetate (25 mL). The product was collected and dried to give 1.05 g (85%) of the title compound as an off-white solid.

$^1$H NMR (300 MHz) (d6-DMSO) δ 8.1–7.9 (AB, 4H), 7.35 (d, 1H), 7.25(3d, 3H), 5.1–4.8 (AB, 2H), 3.9 (s, 2H), 3.8 (s, 3H), 3.7 (s, 3H), 2.25 (s, 3H), 2.15 (s, 3H), 1.1 (s, 6H).

Reaction Scheme 38
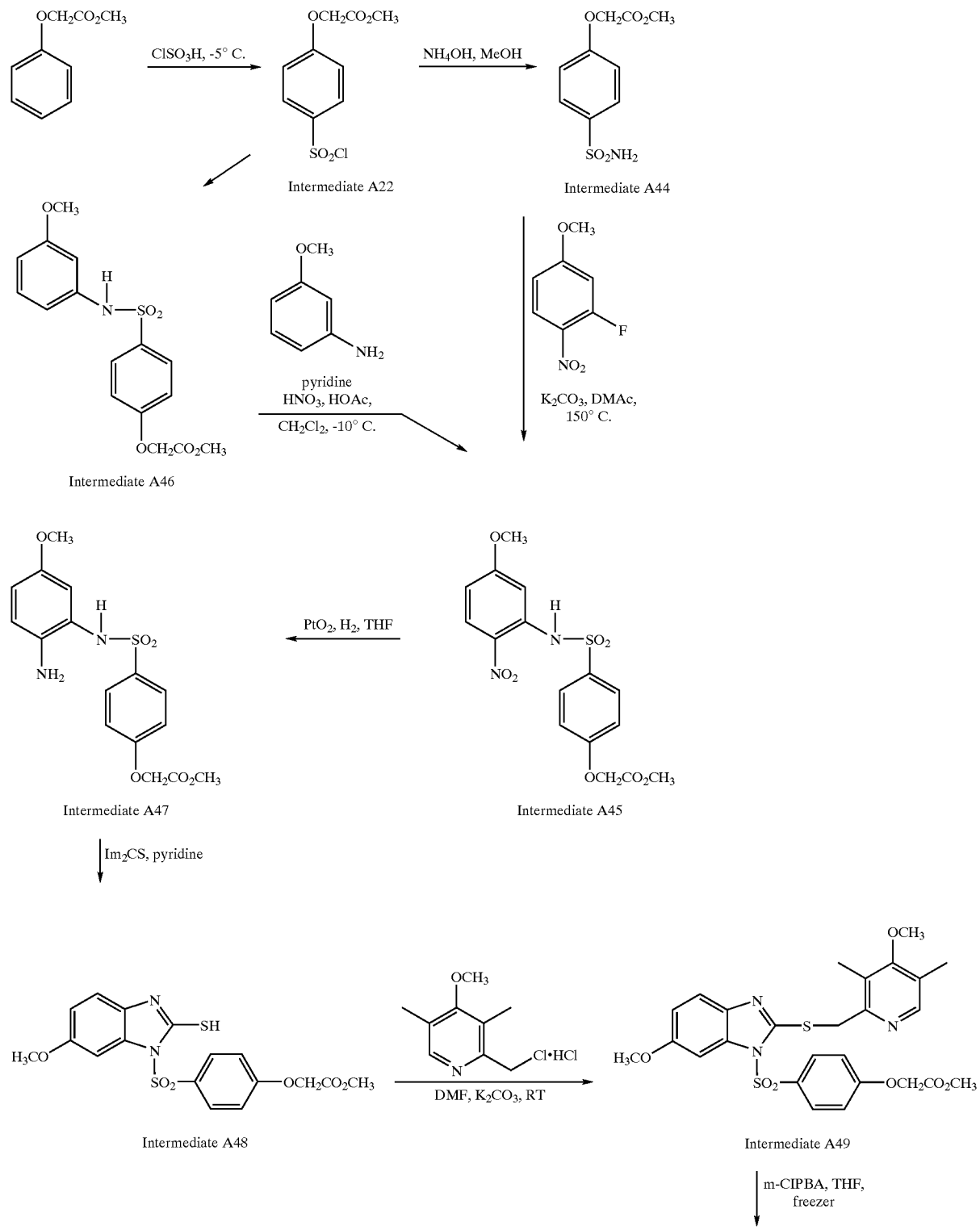

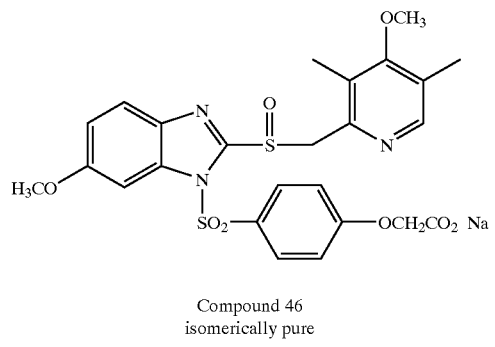

Compound 46
isomerically pure 1) 0–1N NaOH, glyme
2) HCl
3) NaHCO₃

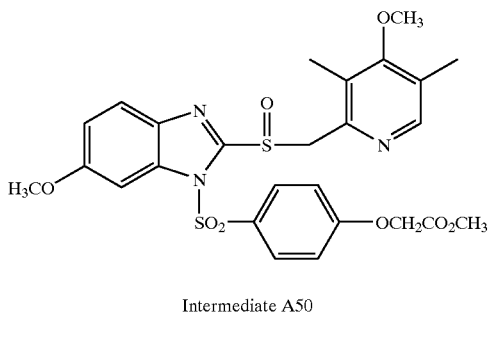

Intermediate A50

Procedure 1 for Making Nitro Sulfonamide Intermediate A45:

(4-Sulfamoyl-phenoxy)-acetic acid methyl ester (Intermediate A44)

In a 2 L 3-necked flask equipped with a mechanical stirrer and a thermometer was placed sulfonyl chloride (Intermediate A22, 68.77 g, 0.26 mol) in methanol (650 mL) and warmed to 30° C. to obtain a solution. To this solution was added methanolic ammonia (159 mL of 4.9 M). The reaction was stirred for 2 hr at room temperature and then stored in a refrigerator for 4 hr. The solid was collected, washed with methanol (100 mL), hexane (300 mL), and dried to give 55 g (86%) of the title compound, sulfonamide as a white solid.

3-Fluoro-4-nitroanisole

A solution of 3-fluoro-4-nitrophenol (75 g, 0.48 mol) in acetone (700 mL) was cooled in an ice-water bath. 1,8-Diazabicyclo[5,4,0]undec-7-ene (145 g, 0.96 mol) was then added over ca. 5 min. Finally, iodomethane (135 g, 0.96 mol) was added over 10 min. The mixture was stirred at room temperature for 16 hr. Additional 1,8-diazabicyclo[5,4,0]undec-7-ene (73 g, 0.48 mol) and iodomethane (68 g, 0.48 mol) were added, and the mixture was warmed to 50° C. for 1 hr. After a solid was removed by filtration, the concentrated filtrate was mixed with ethyl acetate and 1 M hydrochloric acid. The organic layer was washed with additional hydrochloric acid and aqueous sodium bicarbonate, concentrated, and stirred in 1% ethyl acetate in hexanes. The resulting solid was collected and dried to give 72 g (88%) of the title compound.

[4-(5-Methoxy-2-nitro-phenylsulfamoyl)-phenoxy]-acetic acid methyl ester (Intermediate A45)

Sulfonamide (Intermediate A44, 44.6 g, 0.18 mol), potassium carbonate (41.4 g, 0.3 mol), 3-fluoro-4-nitroanisole (25.65 g, 0.15 mol) and N,N-dimethylacetamide (250 mL) was heated at reflux for 2.5 hr. The reaction mixture was poured into a mixture of crushed-ice (800 g) and water (400 mL). The resulting mixture was extracted with ethyl acetate (3×500 mL). The combined organic layers were washed with brine (1×200 mL), filtered through 1PS filter paper and concentrated under reduced pressure to give an oil. The oil was purified by flash chromatography (silica gel, hexane to 50% ethyl acetate in hexane) to give 9.4 g (16%) of the title compound, nitro sulfonamide as a yellow solid.

Procedure 2 for Making Nitro Sulfonamide Intermediate A45:

[4-(3-Methoxy-phenylsulfamoyl)-phenoxy]-acetic acid methyl ester (Intermediate A46)

Solid sulfonyl chloride (Intermediate A22, 29.1 g, 0.11 mol) in several portions was added to a solution of m-anisidine (12.3 g, 0.1 mol) in pyridine (250 mL). The resulting mixture was stirred at room temperature overnight under argon. The reaction mixture was poured into a cold solution of 3 M hydrochloric acid (1 L) and stirred for 30 min. The pink solid was collected, washed with water and dried to give 33 g (94%) of the sulfonamide.

[4-(5-Methoxy-2-nitro-phenylsulfamoyl)-phenoxy]-acetic acid methyl ester (Intermediate A45)

A cold mixture of nitric acid (90 mL of 70%) and acetic acid (140 mL) was added to a solution of sulfonamide (Intermediate A46, 31.59 g, 0.09 mol) in dichloromethane (750 mL) at −10° C. over 15 min. After 3.5 hr, water (1 L) was added to the reaction mixture. The organic layer was separated, washed with water (1×300 mL), saturated sodium bicarbonate (1×300 mL), brine (1×300 mL), filtered through 1PS filter paper and concentrated under reduced pressure to give 40 g of a dark brown oil. The oil was purified by flash chromatography (silica gel, 30% ethyl acetate in hexane to ethyl acetate) to give 19.2 g of a residue which after trituration with ethyl acetate afforded 7.5 g (21%) of the title compound, nitro sulfonamide.

[4-(2-Amino-5-methoxy-phenylsulfamoyl)-phenoxy]-acetic acid methyl ester (Intermediate A47)

A solution of nitro sulfonamide (Intermediate A45, 17.5 g, 0.0044 mol) in tetrahydrofuran (700 mL) was treated with Raney nickel (2 g) for 15 min, filtered through a pad of celite, and hydrogenated over platinum(IV)oxide (1.5 g) until hydrogen uptake ceased. The reaction mixture was filtered through glass fiber filter paper and concentrated under reduced pressure to give 16.2 g (100%) of the title compound, amine as a tan solid.

[4-(2-Mercapto-6-methoxy-benzimidazole-1-sulfonyl)-phenoxy]-acetic acid methyl ester (Intermediate A48)

Amine (Intermediate A47, 16 g, 0.0437 mol) was dissolved in pyridine (200 mL). To this solution was added 1,1'-thiocarbonyldiimidazole (11.68 g, 0.0.655 mol) and stirred at room temperature overnight under argon. To the reaction mixture was added water (400 mL) and stirred for 1 hr. The resulting solid was collected, washed with water (600 mL) and dried to give 16.9 g (95%) of the title compound, benzimidazolethiol.

{4-[6-Methoxy-2-(4-methoxy-3,5-dimethyl-pyridin-2-ylmethylsulfanyl)-benzimidazole-1-sulfonyl]-phenoxy}-acetic acid methyl ester (Intermediate A49)

Anhydrous potassium carbonate (12.45 g, 0.09 mol) was ground in a mortar and pestle and added to a solution of thiol (Intermediate A48, 16.7 g, 0.041 mol) in N,N-dimethylformamide (275 mL). 2-Chloromethyl-3,5-dimethyl-4-methoxypyridine hydrochloride (9.56 g, 0.043 mole) was added to the reaction mixture. After 1 hr, water (1 L) was added and stirred at room temperature for an additional 15 min. The solid was collected, washed with water (1 L), and dried to give 20.3 g (89%) of the title compound, sulfide.

{4-[6-Methoxy-2-(4-methoxy-3,5-dimethyl-pyridin-2-ylmethanesulfinyl)-benzimidazole-1-sulfonyl]-phenoxy}-acetic acid methyl ester (Intermediate A50)

Sulfide (Intermediate A49, 20.05 g, 0.036 mol) was dissolved in tetrahydrofuran (350 mL), and stored in a freezer for 1 hr. Following addition of a cold solution of m-chloroperoxybenzoic acid (11.6 g of 70%, 0.047 mol) in tetrahydrofuran (150 mL), the reaction mixture was returned to the freezer and stored overnight. The reaction mixture was diluted with ethyl acetate (750 mL), washed with 5% sodium metabisulfite (2×200 mL), washed with saturated sodium bicarbonate (2×200 mL) and brine (2×200 mL), filtered through 1PS filter paper, and concentrated under reduced pressure. The concentrate was purified by flash chromatography (silica gel, hexane to ethyl acetate), to give 14.5 g of a foam. The foam was triturated with 35% ethyl acetate in hexane and gave 13 g (63%) of the title compound, sulfoxide as a white solid.

2-{4-[(6-methoxy-2-{[(4-methoxy-3,5-dimethyl-(2-pyridyl))methyl]sulfonyl}benzimidazolyl)sulfonyl]phenoxy}acetic acid sodium salt (Compound 46)

A solution of 0.1 N sodium hydroxide (2 mL) was added to a solution of sulfoxide (Intermediate A50, 11.46 g, 0.02 mol) in glyme (750 mL). The resulting mixture was extracted with ethyl acetate (2×400 mL). The combined organic layers were back extracted with water-brine, 1:1 (200 mL). The combined aqueous layers were acidified with 3 M hydrochloric acid (20 mL). After adding brine (200 mL), the resulting solution was extracted with ethyl acetate (5×250 mL). The combined organic layers were filtered through 1PS filter paper and concentrated under reduced pressure to give a solid residue. The solid residue was triturated with ethyl acetate (100 mL). The product collected and dried to give 4.5 g (40%) of 2-{4-[(6-methoxy-2-{[(4-methoxy-3,5-dimethyl(2-pyridyl))methyl]sulfinyl}benzimidazolyl)sulfonyl]phenoxy}acetic acid (sulfoxide acid).

To a suspension of the sulfoxide acid (4.47 g, 0.008 mol) in glyme (75 mL) was added a solution of sodium bicarbonate (0.672 g, 0.008 mol) in water (50 mL). The reaction mixture was extracted with ethyl acetate (4×50 mL). The combined organic layers were back extracted with water (2×25 mL). The combined aqueous layers were lyophilized to give 4.1 g (88%) of the title compound.

$^1$H NMR (300 Mhz) (D$_2$O) δ 7.65 (t, 3H), 7.25 (d, 1H), 6.95 (d, 1H), 6.7 (m, 3H), 4.7–4.5, (AB, 2H), 4.65 (water of crystallization), 4.15 (s, 2H), 3.5 (s, 3H), 3.35 (s, 3H), 1.5 (s, 3H), 1.75 (s, 3H).

Reaction Scheme 39

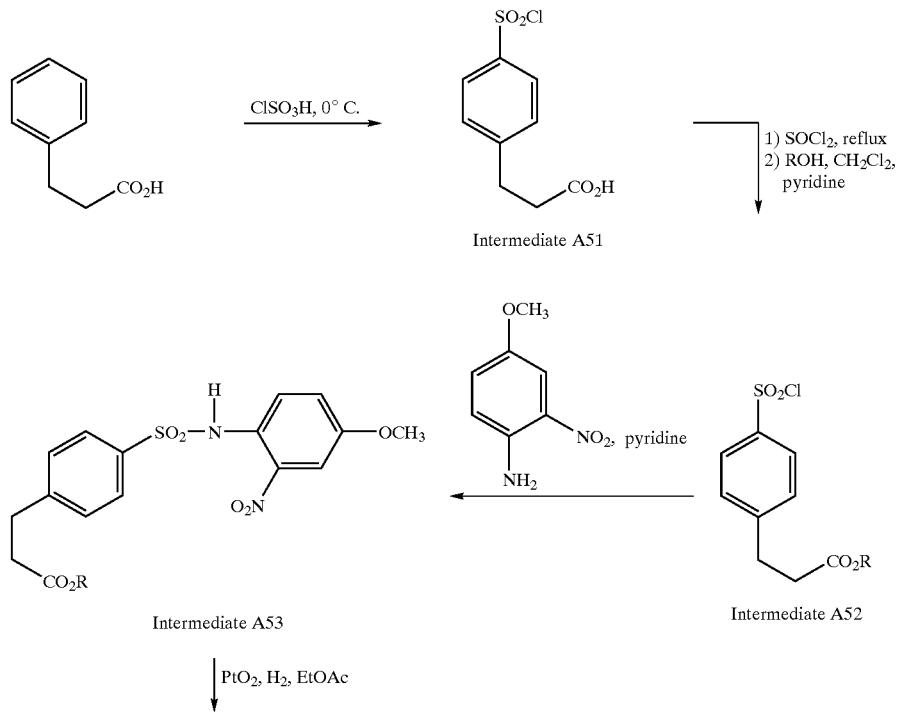

-continued
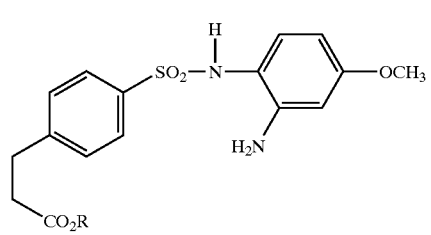
Intermediate A54
Im₂CS, pyridine →
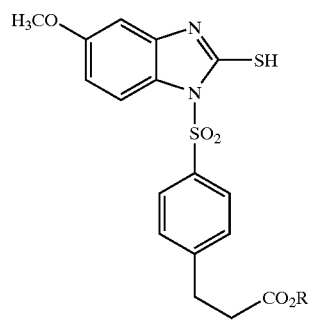
Intermediate A55
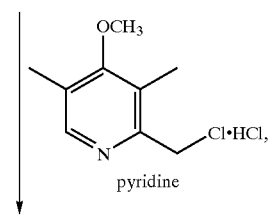
pyridine
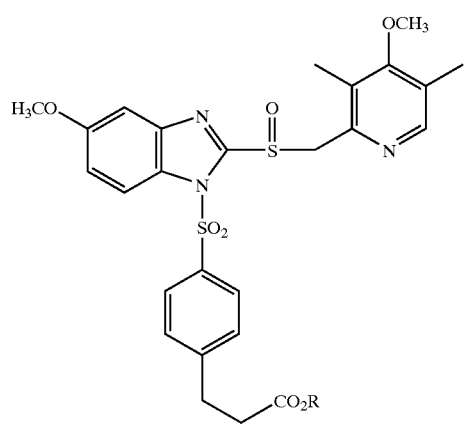
Intermediate A57
← m-ClPBA, THF, freezer
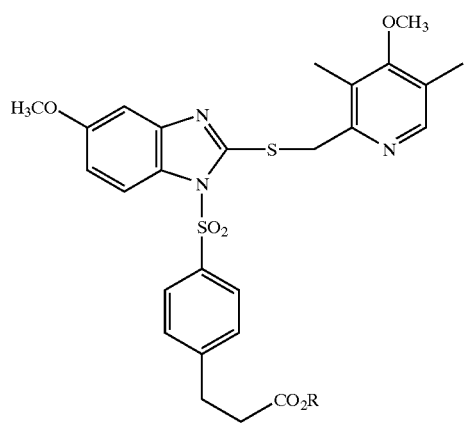
Intermediate A56
NaHCO₃, CH₃CN
H₂O 70° C.
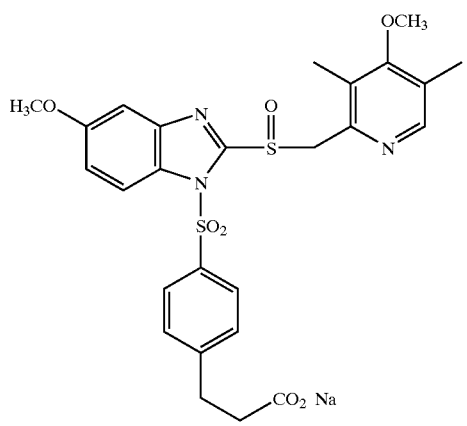
Compound 47
R = H₃C—⟨C₆H₄⟩—SO₂—CH₂—CH₂—

3-[4-(Chlorosulfonyl)phenyl]propionic acid (Intermediate A51)

Solid 3-phenylpropionic acid (45 g, 0.3 mol), in portions, was added to chlorosulfonic acid (174.75 g, 100 mL, 1.5 mol) at −5° C. to 0° C. over 45 min. After 1 hr, the reaction mixture was poured into vigorously stirred crushed-ice (500 g). After 30 min, the white solid was collected, washed with water (1.5 L) and dried to give 12 g of two isomers. The desired isomer was separated by flash chromatography (silica gel, 50% ethyl acetate in hexane to 1% methanol in ethyl acetate) to give 9 g (12%) of the title compound.

3-(4-Chlorosulfonyl-phenyl)-propionic acid 2-(toluene-4-sulfonyl)-ethyl ester (Intermediate A52)

A mixture of 3-[4-(chlorosulfonyl)phenyl]propionic acid (Intermediate A51, 8.2 g, 0.033 mol) and thionyl chloride (23.56 g, 0.198 mol) was refluxed for 1 hr. Excess thionyl chloride was distilled off at atmospheric pressure and finally at reduced pressure to give 9 g acid chloride as an oil. To a mixture of acid chloride (9 g) and 2-(p-tolylsulfonyl)ethanol (6.28 g, 0.0313 mol) in dichloromethane (25 mL) was added triethylamine (3.33 g, 0.033 mol) at room temperature. TLC (ethyl acetate) showed the reaction was complete after 1 hr. The reaction mixture was washed with water (2×50 mL) and brine (1×50 mL), filtered through 1PS filter paper and concentrated under reduced pressure to give an oil. The oil was purified by flash chromatography (silica gel, hexane to 50% ethyl acetate in hexane) to give 7.5 g, (56%) of the title compound, sulfonyl chloride ester as a white solid.

3-[4-(4-Methoxy-2-nitro-phenylsulfamoyl)-phenyl]-propionic acid 2-(toluene-4-sulfonyl)-ethyl ester (Intermediate A53)

Sulfonyl chloride (Intermediate A52, 7.75 g, 0.018 mol), 3-methoxy-2-nitroaniniline (3.02 g, 0.018 mol), and pyridine (60 mL) were mixed and stirred at room temperature overnight under argon. The reaction mixture was concentrated under reduced pressure. The residue was dissolved in ethyl acetate (100 mL), washed with 3 M hydrochloric acid (2×75 mL) and brine (1×100 mL), filtered through 1PS filter paper and concentrated under reduced pressure to give a red oil. The oil was purified by flash chromatography (silica gel, 15% ethyl acetate in hexane to ethyl acetate) to give 7.7 g (76%) of the title compound, nitro sulfonamide as a viscous red oil.

3-[4-(2-Amino-4-methoxy-phenylsulfamoyl)-phenyl]-propionic acid 2-(toluene-4-sulfonyl)-ethyl ester (Intermediate A54)

A solution of the nitro sulfonamide (Intermediate A53, 7.47 g, 0.0133 mol) in ethyl acetate (100 mL) was stirred for 15 min with Raney nickel (3 g), filtered through a pad of celite, and hydrogenated over platinum(IV)oxide (0.25 g) overnight. The reaction mixture was filtered through glass fiber filter paper and concentrated under reduced pressure to give 6.85 g (97%) of the title compound, amine as a light yellow foam.

3-[4-(2-Mercapto-5-methoxy-benzimidazole-1-sulfonyl)-phenyl]-propionic acid 2-(toluene-4-sulfonyl)-ethyl ester (Intermediate A55)

To a solution of the amine (Intermediate A54, 6.7 g, 0.0126 mol) in pyridine (100 mL) was added 1,1'-thiocarbonyldiimidazole (3.37 g, 0.0189 mol). The reaction mixture was stirred at room temperature for 2 hr. The reaction mixture was diluted with water (150 mL) and extracted with 3:1 dichloromethane/isopropyl alcohol (2×100 mL). The combined organic layers were washed with brine (1×100 mL), filtered through 1PS filter paper and concentrated under reduced pressure to give 8 g of a viscous oil. The oil was purified by flash chromatography (silica gel, 20% ethyl acetate in hexane to 75% ethyl acetate in hexane) to give 5.8 g (80%) of the title compound, benzimidazolethiol as a light yellow foam.

3-{4-[5-Methoxy-2-(4-methoxy-3,5-dimethyl-pyridin-2-ylmethylsulfanyl)-benzimidazole-1-sulfonyl]-phenyl}-propionic acid 2-(toluene-4-sulfonyl)-ethyl ester (Intermediate A56)

Anhydrous potassium carbonate (3.04 g, 0.022 mol) was ground in a mortar and pestle and added to a solution of the thiol (Intermediate A55, 5.74 g, 0.01 mol) in N,N-dimethylformamide (50 mL). 2-chloromethyl-3,5-dimethyl-4-methoxypyridine hydrochloride (2.33 g, 0.0.105 mol) was added. After 2 hr, 100 ml of 25% isopropyl alcohol in dichloromethane was added to the reaction mixture. The reaction was then washed with water (2×50 mL) and brine (1×50 mL), filtered through 1PS filter paper and concentrated under reduced pressure to give a light brown oil. The oil was purified by flash chromatography (silica gel, 20% ethyl acetate in hexane to 75% ethyl acetate) to give 6.47 g (100%) of the title compound, sulfide as a foam.

3-{4-[5-Methoxy-2-(4-methoxy-3,5-dimethyl-pyridin-2-ylmethanesulfinyl)-benzimidazole-1-sulfonyl]-phenyl}-propionic acid 2-(toluene-4-sulfonyl)-ethyl ester (Intermediate A57)

The sulfide (Intermediate A56, 6.47 g, 0.01 mol) was dissolved in tetrahydrofuran (100 mL), and stored in a freezer for 1 hr. Following addition of a cold solution of m-chloroperoxybenzoic acid (3.08 g of 70%, 0.0125 mol) in tetrahydrofuran (50 mL), the reaction mixture was returned to the freezer and stored overnight. The reaction mixture was then diluted with ethyl acetate (250 mL) and washed with: 5% sodium metabisulfite (2×100 mL), saturated sodium bicarbonate (2×100 mL) and brine (1×100 mL). The organic layer was filtered through 1PS filter paper, and concentrated under reduced pressure. The concentrate was purified by flash chromatography (silica gel, 25% ethyl acetate in hexane to 1% methanol in ethyl acetate), to give 3.8 g (57%) of the title compound, sulfoxide as a white foam.

3-{4-[(5-methoxy-2-{[(4-methoxy-3,5-dimethyl(2-pyridyl))methyl]sulfinyl}benzimidazolyl)sulfonyl]phenyl}propanoic acid sodium salt (Compound 47)

To a solution of the sulfoxide (Intermediate A57, 3.71 g, 0.005 mol) in acetonitrile (30 mL), isopropyl alcohol (10 mL), water (20 mL) was added sodium bicarbonate (0.5 g, 0.006 mol). The resulting mixture was heated at 78° C. for 60 min. The resulting mixture was concentrated under reduced pressure to give a glassy solid. The product was dissolved in 2% methanol in dichloromethane (75 mL), filtered to remove insoluble material, and concentrated under reduced pressure to give 34.5 g of a tan foam. This foam was dissolved in water (25 mL) and extracted with ethyl acetate (2×25 mL). The aqueous layer was concentrated under reduced pressure to give 1.35 g (54%) of the title compound as a tan solid.

$^1$H NMR (300 MHz) ($D_2O$) δ 7.75–7.5 (m, 4H), 7.15 (d, 2H), 6.9–6.75 (m, 2H), 4.8–4.6 (dd, 2H), 4.7 (s, water of crystallization), 3.6 (s, 3H), 3.4 (s, 3H), 2.65 (t, 2H), 2.2 (t, 2H), 1.9 (s, 3H), 1.85 (s, 3H).

Reaction Scheme 40

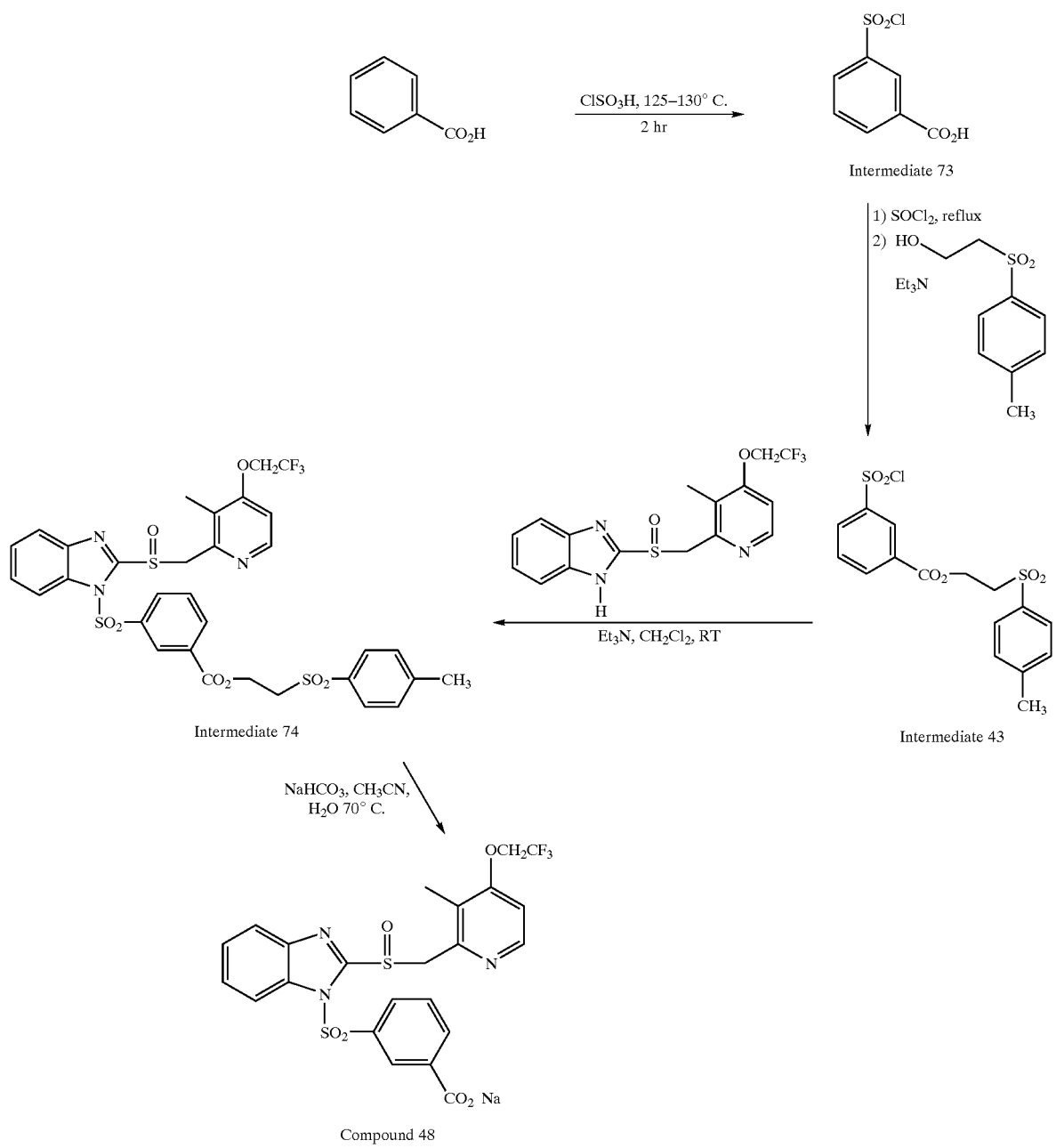

3-(Chlorosulfonyl)benzoic acid (Intermediate 73)

Solid benzoic acid (50 g, 0.41 mol) in portions was added to chlorosulfonic acid (348.7 g, 200 mL, 3 mol) at room temperature. The reaction mixture was heated to 125–130° C. for 2 hr and was then poured into vigorously stirred crushed-ice (1000 g). After 30 min, the white solid was collected, washed with water (1 L) and air dried to give 72.5 g (80%) of the title compound.

$^1$H NMR (CDCl$_3$:d4-MeOH 4:1, 60 MHz) δ 5.0 (s, 1H), 8.0–9.1 (m, 4H).

2-[(4-Methylphenyl)sulfonyl]ethyl 3-(chlorosulfonyl)benzoate (Intermediate 43)

A mixture of 3-(chlorosulfonyl) benzoic acid (Intermediate 73, 5.51 g, 0.025 mol) and thionyl chloride (17.85 g, 11 mL, 0.15 mol) was refluxed for 1 hr. Excess thionyl chloride was distilled off at atmospheric pressure and finally at reduced pressure to give crude acid chloride. To a mixture of the crude acid chloride and 2-(p-tolylsulfonyl) ethanol (4.8 g, 0.024 mol) in dichloromethane (50 mL) was added triethylamine (2.52 g, 0.025 mol) at room temperature. TLC showed the reaction mixture was complete after 1 hr. The reaction mixture was washed with water (2×25 mL), filtered through 1PS filter paper and concentrated under reduced pressure to give 10 g of a viscous oil. The oil was purified by flash chromatography (silica gel, 25 to 50% ethyl acetate in hexane) to give 6.1 g (63%) of the title compound as a white solid.

$^1$H NMR (CDCl$_3$, 60 MHz) δ 2.4 (s, 3H), 3.7 (t, 2H, J=6 Hz), 4.8 (t, 2H, J=6 Hz), 7.3–8.6 (m, 8H).

2-[(4-Methylphenyl)sulfonyl]ethyl 3-{[2-({[3-methyl-4-(2,2,2,-trifluoroethoxy)(2-pyridyl)]methyl}sulfinylbenzimidazolyl]sulfonyl}benzoate (Intermediate 74)

To a suspension of LANSOPRAZOLE (4.62 g, 0.0125 mol) and 2-[(4-methylphenyl)sulfonyl]ethyl 3-(chlorosulfonyl) benzoate (Intermediate 43, 6.04 g, 0.015 mol) in dichloromethane (50 mL) was added triethylamine (3.03 g, 0.03 mol). The resulting mixture was stirred at room temperature for 1 hr. The reaction was washed with water (2×25 mL) and brine (1×25 mL), filtered through 1PS filter paper and concentrated under reduced pressure to give 12 g of a yellow foam. The foam was purified by flash chromatography (silica gel, ethyl acetate) to give 8 g (87%) of the title compound as a yellow foam.

$^1$H NMR (CDCl$_3$, 60 MHz) δ 2.3 (s, 3H), 2.4 (s, 3H), 3.6 (t, 2H, J=6 Hz), 4.8–5.1 (complex, 6H), 6.7–8.7 (m, 13H).

3-{[2-({[3-methyl-4-(2,2,2-trifluoroethoxy)-2-pyridyl]methyl}sulfinyl)benzimidazolyl]sulfonyl}benzoic acid sodium salt (Compound 48)

To a solution of the ester (Intermediate 74, 4.78 g, 0.0065 mol) in a mixture of acetonitrile (30 mL), isopropyl alcohol (10 mL), water (20 mL), was added sodium bicarbonate (0.655 g, 0.0078 mol). After heating at 70° C. for 2 hr the reaction was concentrated under reduced pressure to give a tan solid. Ethyl acetate (50 mL) was added to this tan solid and stirred for 15 min. The resulting mixture was filtered to remove insoluble material and the filtrate was extracted with water (2×10 mL). The combined aqueous layers were back washed with ethyl acetate (1×10 mL) and concentrated under reduced pressure to give 2 g (53%) of the title compound as a tan solid.

$^1$H NMR (300 MHz) (d6-DMSO) δ 8.6 (s, 1H), 8.3–7.4 (m, 8H), 7.0 (d, 1H), 5.2 (d, 2H), 4.9 (m, 2H), 2.2 (s, 3H).

Reaction Scheme 41

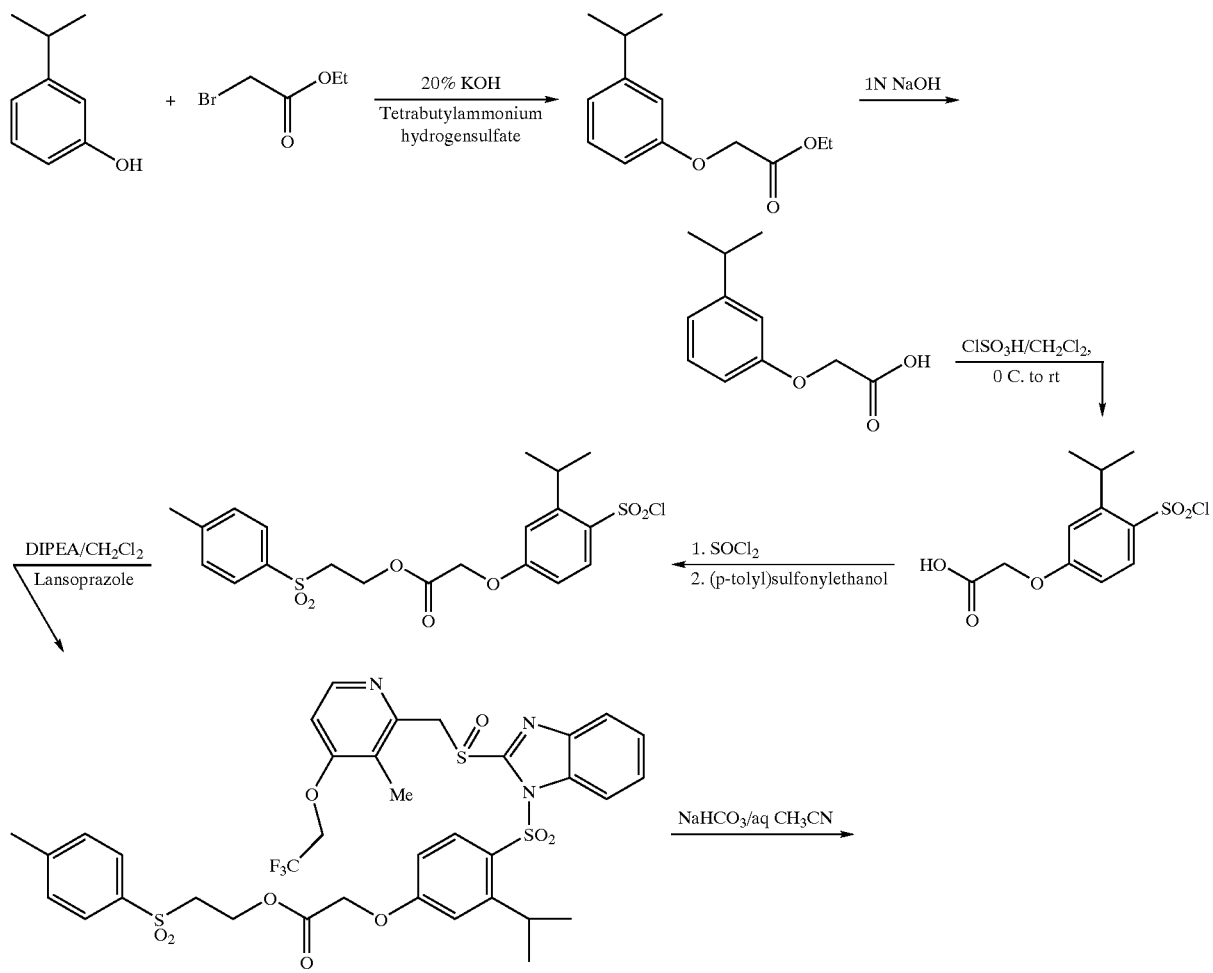

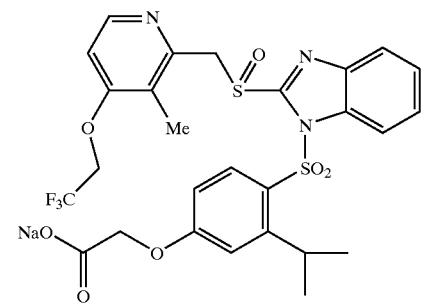

Compound 49

(3-Isopropyl-4-{2-[3-methyl-4-(2,2,2-trifluoro-ethoxy)-pyridin-2-ylmethanesulfinyl]-benzimidazole-1-sulfonyl}-phenoxy)-acetic acid sodium salt (Compound 49)

Compound 49 was prepared as shown in Reaction Scheme 41.

NMR (d6-DMSO) δ 8.1 (m, 2H), 7.85 (m, 1H), 7.65 (m, 1H), 7.5 (m, 2H), 7.0 (m, 2H), 6.9 (m, 2H), 4.9 (m, 4H), 4.4 (m, 2H), 3.6 (m, 1H), 2.2 (s, 3H), 1.0 (s, 3H).

Mass spectrum (negative ion) m/z for C27H25F3N3NaO7S2 Calc'd 647.62. Found 624 (M+ minus Na).

4-Methoxy-3-{2-[3-methyl-4-(2,2,2-trifluoro-ethoxy)-pyridin-2-ylmethanesulfinyl]-benzimidazole-1-sulfonyl}-benzoic acid sodium salt (Compound 50)

Compound 50 was prepared as shown in Reaction Scheme 42.

NMR (d6-DMSO) δ 8.7 (m, 1H), 8.2 (m, 1H), 7.8 (m, 1H), 7.65 (m, 1H), 7.25 (m, 1H), 7.0 (m, 1H), 4.8 (m, 4H), 3.75 (m, 3H), 2.2 (s, 3H).

Mass spectrum (negative ion) m/z for C24H19F3N3NaO7S2 Calc'd 605. Found 582 (M+ minus Na).

Reaction Scheme 42

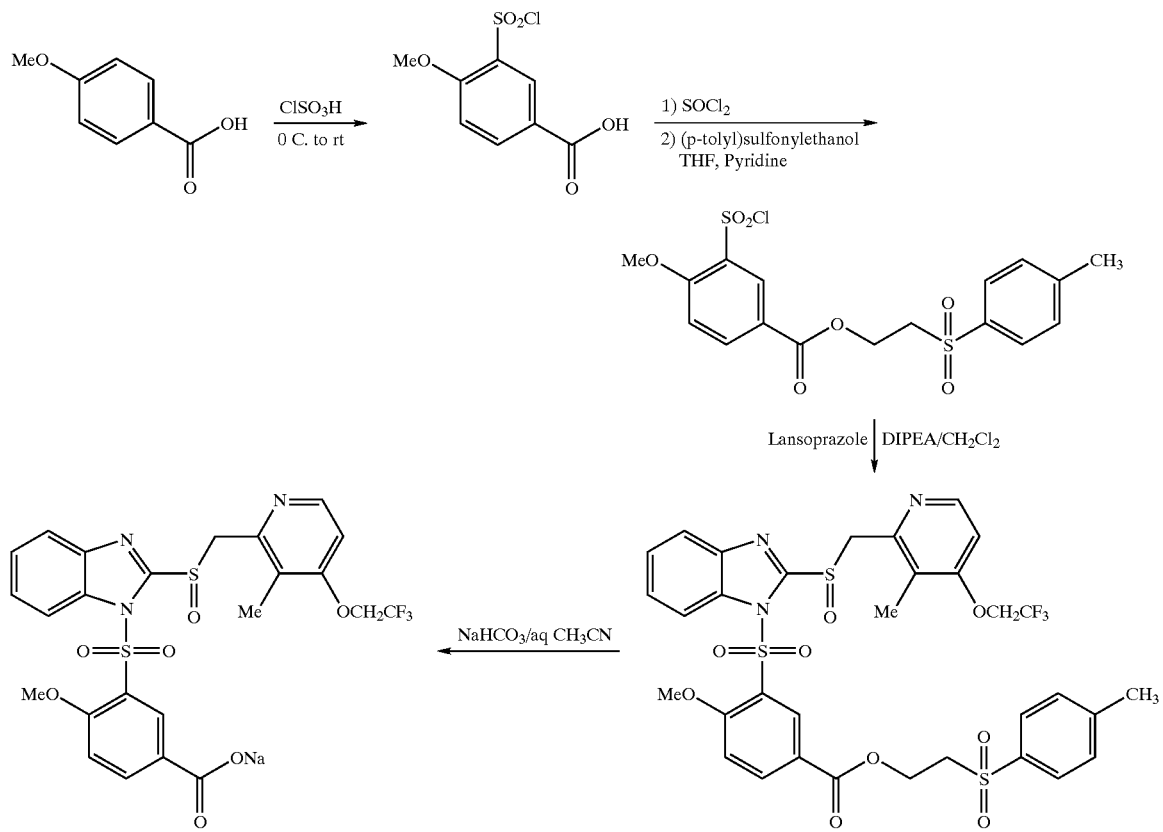

Compound 50

Reaction Scheme 43
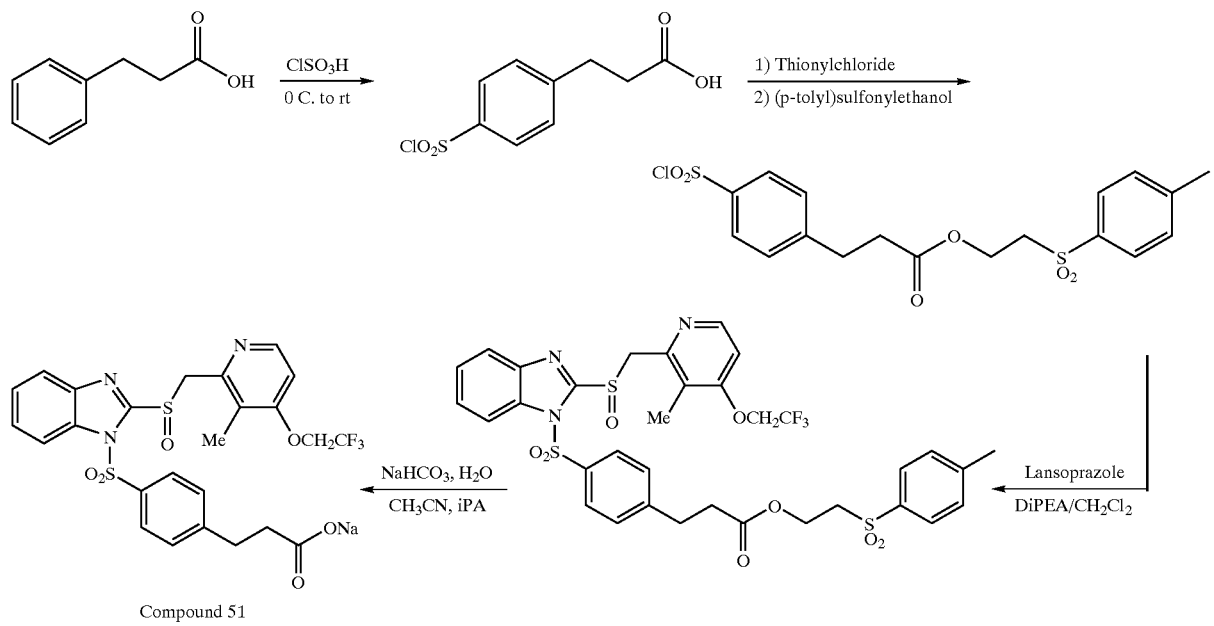
3-(4-{2-[3-Methyl-4-(2,2,2-trifluoro-ethoxy)-pyridin-2-ylmethanesulfinyl]-benzimidazole-1-sulfonyl}-phenyl)-propionic acid sodium salt (Compound 51)
Compound 51 was prepared as shown in Reaction Scheme 43.
NMR (d6-DMSO) δ 7.8 (m, 4H), 7.5 (m, 4H), 7.0 (m, 4H), 5.0 (m, 4H), 1.8–2.8 (m, 7H).
Mass spectrum (negative ion) m/z for C25H21F3N3NaO6S2 Calc'd 623. Found 580 (M+ minus Na).
Reaction Scheme 44
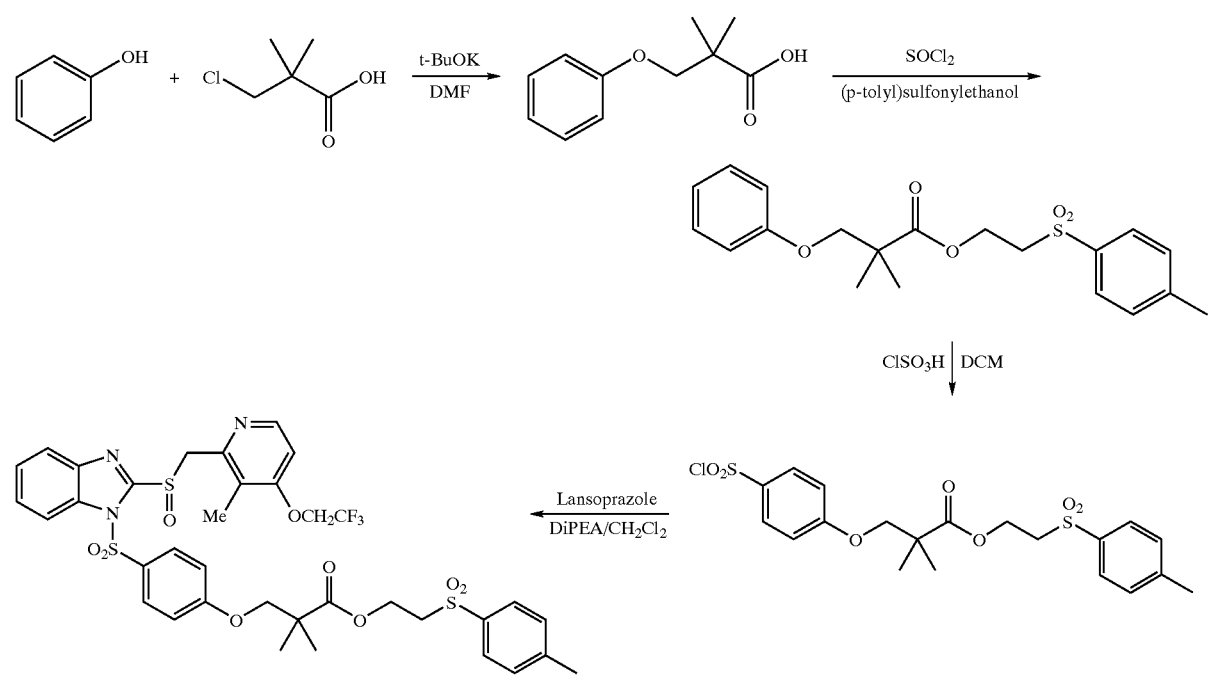

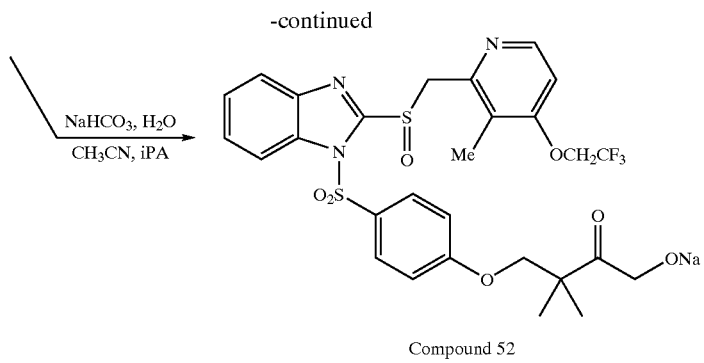

Compound 52

2,2-Dimethyl-3-(4-{2-[3-methyl-4-(2,2,2-trifluoro-ethoxy)-pyridin-2-ylmethanesulfinyl]-benzimidazole-1-sulfonyl}-phenoxy)-propionic acid sodium salt (Compound 52)

Compound 52 was prepared as shown in Reaction Scheme 44.

NMR (d6-DMSO) δ 8.2 (m, 2H), 8.0 (m, 2H), 7.8 (m, 1H), 7.5 (m, 2H), 7.2 (m, 2H), 7.0 (m, 1H), 5.0 (m, 4H), 4.0 (m, 2H), 2.4 (s, 3H), 1.2 (m, 6H).

Mass spectrum (negative ion) m/z for C27H25F3N3NaO7S2 Calc'd 647.62. Found 648 (M+), 625 (M+ minus Na).

What is claimed is:

1. A compound of Formula 1, Formula 2, Formula 3 or of Formula 4

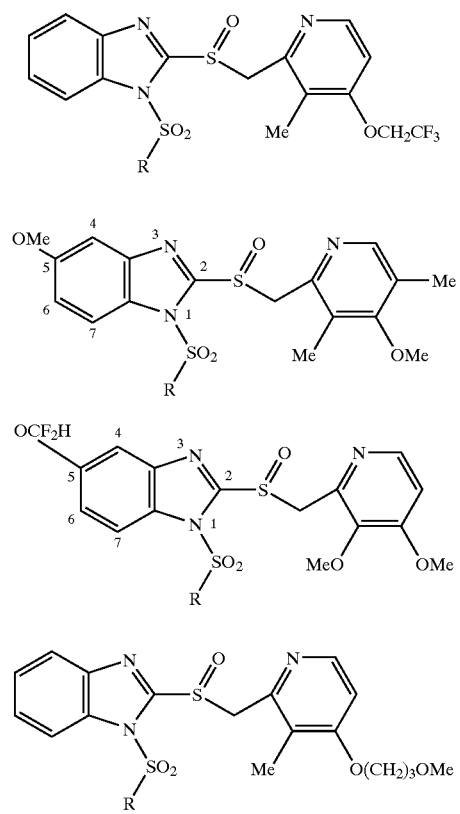

or isomers of the compounds of Formulas 2 and 3 where the OCH$_3$, and HF$_2$CO groups, respectively are linked to the 6 position of the benzimidazole ring, and wherein R represents the groups selected from Formulas (i) through (viii);

the dashed line represents the bond connecting the R group with the SO$_2$ group,

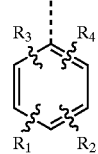

(i)

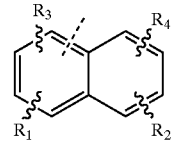

(iii)

$R_1$ and $R_2$ independently are H, a straight chained or branch-chained di- or trivalent alkyl group of 1 to 12 carbons including 1 or two $R_5$ groups, or a straight chained or branch-chained saturated hydrocarbon skeleton having no more than 12 carbons including 1 or two $R_5$ groups and optionally further including one to three X groups where X is independently selected from the group consisting of —O—, —S—, —NR$_6$—, —NHCO—, —CONH—, —CONHCO—, —COO—, —OCO— and a disubstituted phenyl group which can optionally be substituted with one or two halogen atoms or with one or two $R_3$ groups; or the $R_5$ group is directly attached without an intervening $R_1$ or $R_2$ group to the aromatic ring;

$R_3$ and $R_4$ independently are H, alkyl of 1 to 3 carbons, fluoroalkyl of 1 to 3 carbons, O-alkyl of 1 to 3 carbons, O-fluoroalkyl of 1 to 3 carbons, S-alkyl of 1 to 3 carbons, S-fluoroalkyl of 1 to 3 carbons;

$R_5$ is independently H, COOH or a tetrazole moiety;

$R_6$ is H or alkyl of 1 to 3 carbons;

with the provisos that one or more of the $R_1$ and $R_2$ groups is not H, and one or more $R_5$ is not H and no more than two $R_5$ groups are COOH or tetrazole whereby the compound has one but no more than two COOH or tetrazole groups;

or a pharmaceutically acceptable salt of said compound.

2. A compound in accordance with claim 1 which has the structure in accordance with Formula 1.

3. A compound in accordance with claim 1 which has the structure in accordance with Formula 2.

4. A compound in accordance with claim 1 which has the structure in accordance with Formula 3.

5. A compound in accordance with claim 1 which has the structure in accordance with Formula 4.

6. A compound in accordance with claim 1 where $R_5$ is independently selected from H and COOH, or a pharmaceutically acceptable salt of said compound.

7. A compound in accordance with claim 1 where the formula has one or more X groups.

8. A compound in accordance with claim 1 where one or more X is O.

9. A compound in accordance with claim 1 where one or more X is CONH.

10. A compound in accordance with claim 1 where R represents formula (i).

11. A compound of Formula 1a, Formula 2a, Formula 3a or of Formula 4a

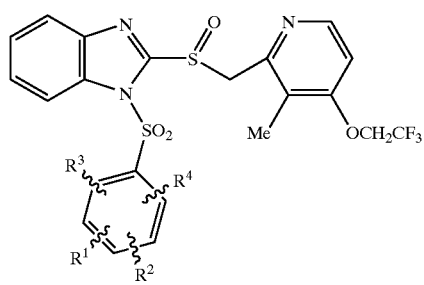

Formula 1a

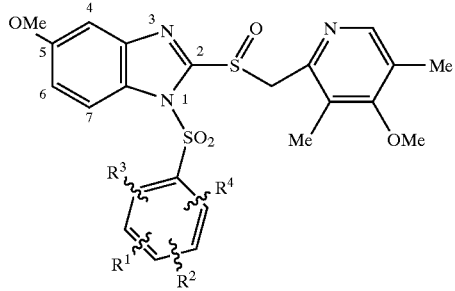

Formula 2a

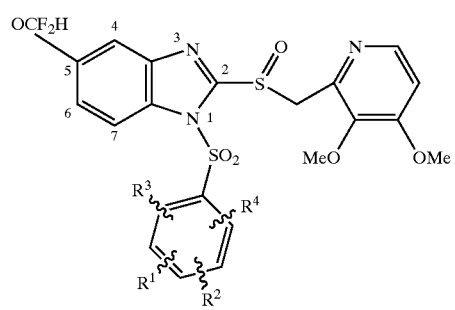

Formula 3a

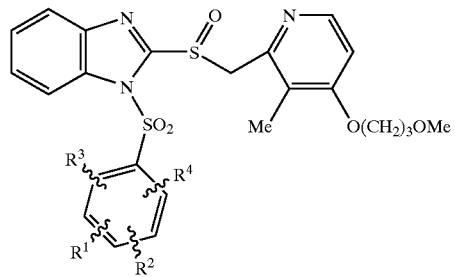

Fromula 4a or isomers of the compounds of Formulas 2a and 3a where the $OCH_3$, and $HF_2CO$ groups, respectively are linked to the 6 position of the benzimidazole ring, $R_1$ and $R_2$ independently are H, a straight chained or branch-chained di- or trisubstituted alkyl group of 1 to 12 carbons including 1 or two $R_5$ groups, or a straight chained or branch-chained saturated hydrocarbon skeleton having no more than 12 carbons including 1 or two $R_5$ groups and optionally further including one to three X groups where X is independently selected from the group consisting of —O—, —S—, —$NR_6$—, —NHCO—, —CONH—, —CONHCO—, —COO—, —OCO— and a disubstituted phenyl group which can optionally be substituted with one or two halogen atoms or with one or two $R_3$ groups; or the $R_5$ group is directly attached without an intervening $R_1$ or $R_2$ group to the aromatic ring;

$R_3$ and $R_4$ independently are H, alkyl of 1 to 3 carbons, fluoroalkyl of 1 to 3 carbons, O-alkyl of 1 to 3 carbons, O-fluoroalkyl of 1 to 3 carbons, S-alkyl of 1 to 3 carbons, S-fluoroalkyl of 1 to 3 carbons;

$R_5$ is independently H or COOH;

$R_6$ is H or alkyl of 1 to 3 carbons;

with the provisos that one or more of the $R_1$ and $R_2$ groups is not H, and one or more $R_5$ is not H and no more than two $R_5$ groups are COOH whereby the compound includes one but no more than two COOH groups;

or a pharmaceutically acceptable salt of said compound.

12. A compound in accordance with claim 11 that has Formula 1a.

13. A compound in accordance with claim 11 that has Formula 2a.

14. A compound in accordance with claim 13 where the $CH_3O$ group is in the 5 position of the benzimidazole moiety.

15. A compound in accordance with claim 11 that has Formula 3a.

16. A compound in accordance with claim 15 where the $HF_2CO$ group is in the 5 position of the benzimidazole moiety.

17. A compound in accordance with claim 11 that has Formula 4a.

18. A compound in accordance with claim 11 that has only one COOH group, or its pharmaceutically acceptable salt.

19. A compound in accordance with claim 11 that has only two COOH groups, or its pharmaceutically acceptable salt.

20. A compound in accordance with claim 11 where $R_2$, $R_3$ and $R_4$ are hydrogen and $R_1$ is $OCH_2COOH$ attached in the 4 position on the phenyl ring relative to the sulfonyl group, or its pharmaceutically acceptable salt.

21. A compound of Formula 1, Formula 2, Formula 3 or of Formula 4

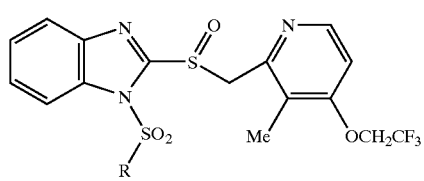

Formula 1

Formula 2
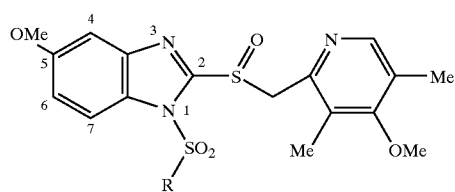
Formula 3
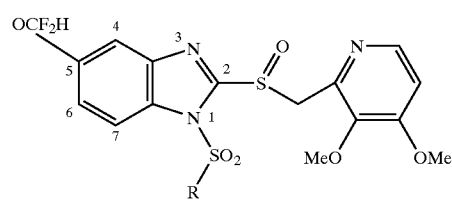
Formula 4
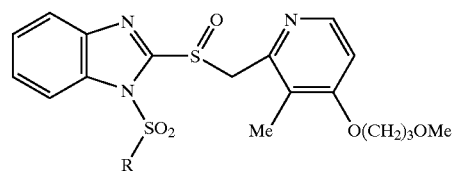
or isomers of the compounds of Formulas 2 and 3 where the OCH₃, and HF₂CO groups, respectively are linked to the 6 position of the benzimidazole ring, and
wherein R represents the groups selected from Formulas (a) through (s), the dashed line represents the bond connecting the R group with the SO₂ group,
(a)
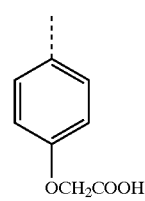
(b)
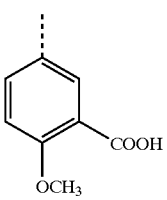
(c)
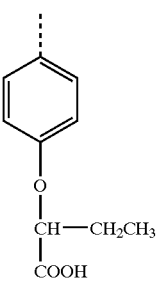
(d)
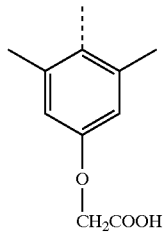
(e)
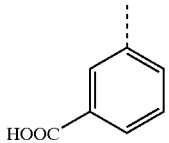
(f)
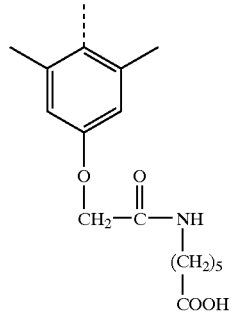
(g)
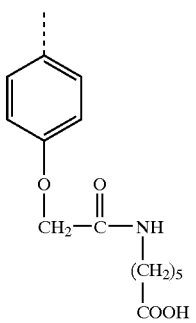
(h)
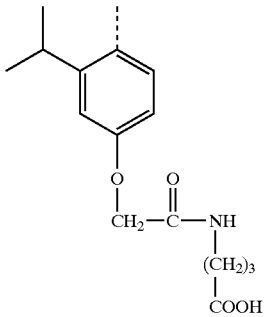
(i)
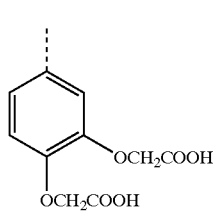

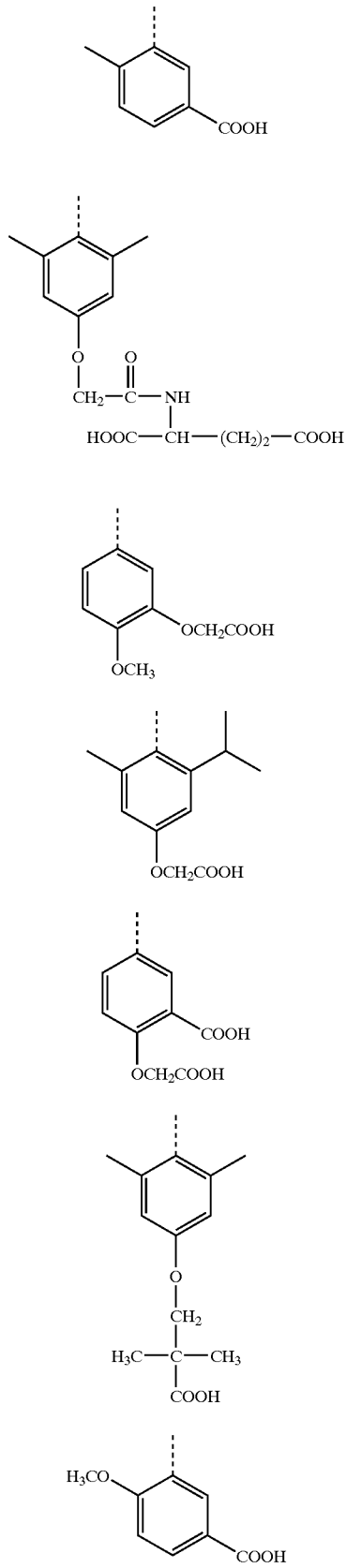
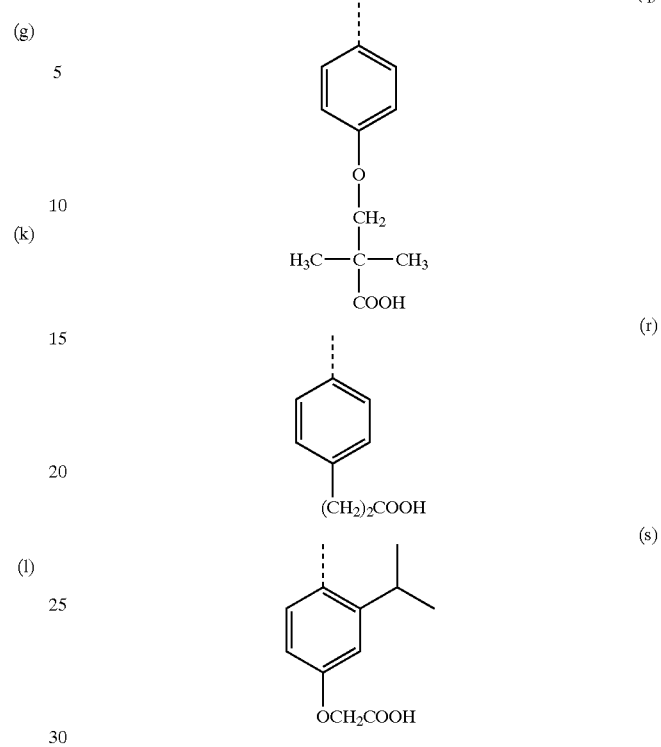

or a pharmaceutically acceptable salt of said compound.

22. A compound in accordance with claim 21 of Formula 1.

23. A compound in accordance with claim 21 of Formula 2.

24. A compound in accordance with claim 23 where the $CH_3O$ group is in the 5 position of the benzimidazole moiety.

25. A compound in accordance with claim 21 of Formula 3.

26. A compound in accordance with claim 25 where the $HF_2O$ group is in the 5 position of the benzimidazole moiety.

27. A compound in accordance with claim 21 of Formula 4.

28. A pharmaceutical composition comprising a pharmaceutically acceptable excipient and a compound in accordance with claim 1.

29. A pharmaceutical composition comprising a pharmaceutically acceptable excipient and a compound in accordance with claim 11.

30. A pharmaceutical composition comprising a pharmaceutically acceptable excipient and a compound in accordance with claim 21.

31. A compound in accordance with claim 1 having two $R_5$ groups which represents COOH, or a pharmaceutically acceptable salt of said compound.

32. A compound of the formula
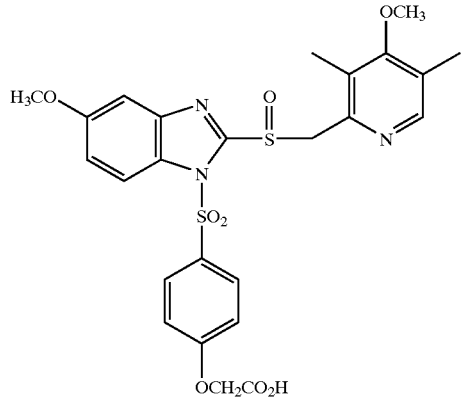
or a pharmaceutically acceptable salt thereof.
33. A compound of the formula
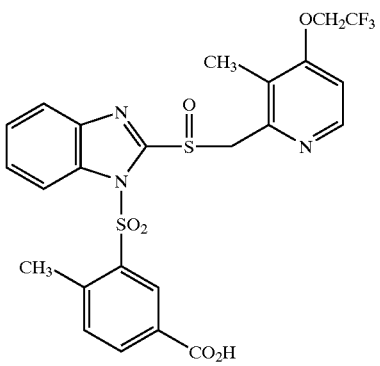
or a pharmaceutically acceptable salt thereof.
34. A pharmaceutical composition comprising a pharmaceutically acceptable excipient and a compound in accordance with claim 32.
* * * * *

UNITED STATES PATENT AND TRADEMARK OFFICE
CERTIFICATE OF CORRECTION

PATENT NO.   : 6,897,227 B2
DATED        : May 24, 2005
INVENTOR(S)  : Beard et al.

It is certified that error appears in the above-identified patent and that said Letters Patent is hereby corrected as shown below:

Column 29,
Line 40, "Compound 120 µmole/kg" should be -- Compound 1 20 µmole/k --.
Line 41, "Compound 320 µmole/kg" should be -- Compound 3 20 µmole/kg --.
Line 41, "Compound 420 µmole/kg" should be -- Compound 4 20 µmole/kg --.
Line 42, "Compound 620 µmole/kg" should be -- Compound 6 20 µmole/kg --.
Line 42, "Compound 940 µmole/kg" should be -- Compound 9 40 µmole/kg --.
Line 43, "Compound 1240 µmole/kg" should be -- Compound 12 40 µmole/kg --.
Line 49, "Compound 3640 µmole/kg" should be -- Compound 36 40 µmole/kg --.

Column 38,
Line 60, "$CH_2C_2$" should be -- $CH_2Cl_2$ --.

Column 71,
Line 40, "3,5-Dimethyl-42-3" should be -- 3,5-Dimethyl-4-{2-[3 --.

Column 111,
Line 21, "6.90 (t, 1H)" should be -- 6.90 (t, 1 HH) --.

Column 117,
Line 39, "3-isopropyl]-{5-methoxy" should be -- 3-isopropyl-4-{5-methoxy --.

Column 156,
Reaction Scheme 37, next to arrow below Intermediate A36, "5º C" should be -- -5ºC --.

UNITED STATES PATENT AND TRADEMARK OFFICE
CERTIFICATE OF CORRECTION

PATENT NO. : 6,897,227 B2
DATED : May 24, 2005
INVENTOR(S) : Beard et al.

It is certified that error appears in the above-identified patent and that said Letters Patent is hereby corrected as shown below:

<u>Column 180,</u>
Line 18, "(i) through (viii);" should be -- "(i) and (iii); --.
Line 37, "trivalant" should be -- trivalent --.

Signed and Sealed this

Fourteenth Day of March, 2006

JON W. DUDAS
*Director of the United States Patent and Trademark Office*

UNITED STATES PATENT AND TRADEMARK OFFICE
CERTIFICATE OF CORRECTION

PATENT NO. : 6,897,227 B2
APPLICATION NO. : 10/620252
DATED : May 24, 2005
INVENTOR(S) : Garst et al.

It is certified that error appears in the above-identified patent and that said Letters Patent is hereby corrected as shown below:

Column 29, line 40, "Compound 120 µmole/kg " should be
--Compound 1 20 µmole/k--

Column 29, line 41, "Compound 320 µmole/kg " should be
--Compound 3 20 µmole/kg--

Column 29, line 41, "Compound 420 µmole/kg " should be
--Compound 4 20 µmole/kg--

Column 29, line 42, "Compound 620 µmole/kg " should be
--Compound 6 20 µmole/kg--

Column 29, line 42, "Compound 940 µmole/kg " should be
--Compound 9 40 µmole/kg--

Column 29, line 43, "Compound 1240 µmole/kg " should be--Compound 12 40 µmole/kg--

Column 29, line 49, "Compound 3640 µmole/kg" should be
--Compound 36 40 µmole/kg--

Column 38, line 60, "$CH_2C_2$" should be-- $CH_2Cl_2$--

Column 71, line 40, "3,5-Dimethyl-42-3" should be
--3,5-Dimethyl-4-{2-[3 --

Column 111, line 21, "6.90 (t, 1H)" should be --6.90 (t, 1 HH)--

Column 117, line 39, "3-isopropyl]-{5-methoxy" should be--3-isopropyl-4-{5-methoxy--

Column 156, Reaction Scheme 37, next to arrow below Intermediate A36, "5° C" should be -- -5°C--

UNITED STATES PATENT AND TRADEMARK OFFICE
CERTIFICATE OF CORRECTION

PATENT NO. : 6,897,227 B2
APPLICATION NO. : 10/620252
DATED : May 24, 2005
INVENTOR(S) : Garst et al.

It is certified that error appears in the above-identified patent and that said Letters Patent is hereby corrected as shown below:

Column 180, line 18, "(i) through (viii);" should be --"(i) and (iii);--

Column 180, line 37, "trivalant" should be --trivalent--

Signed and Sealed this

Twenty-ninth Day of August, 2006

JON W. DUDAS
*Director of the United States Patent and Trademark Office*